US010023615B2

(12) United States Patent
Bonny

(10) Patent No.: US 10,023,615 B2
(45) **Date of Patent: *Jul. 17, 2018**

(54) EFFICIENT TRANSPORT INTO WHITE BLOOD CELLS

(75) Inventor: Christophe Bonny, Lausanne (CH)

(73) Assignee: Xigen Inflammation Ltd., Limassol (CY)

( * ) Notice: Subject to any disclaimer, the term of this patent is extended or adjusted under 35 U.S.C. 154(b) by 0 days.

This patent is subject to a terminal disclaimer.

(21) Appl. No.: 13/141,316

(22) PCT Filed: Dec. 22, 2009

(86) PCT No.: PCT/EP2009/009228

§ 371 (c)(1), (2), (4) Date: Nov. 14, 2011

(87) PCT Pub. No.: WO2010/072405

PCT Pub. Date: Jul. 1, 2010

(65) Prior Publication Data

US 2012/0058137 A1 Mar. 8, 2012

(30) Foreign Application Priority Data

Dec. 22, 2008 (WO) ................ PCT/EP2008/011003
Jun. 2, 2009 (WO) ................ PCT/EP2009/003927

(51) Int. Cl.

*C07K 7/06* (2006.01)
*C07K 14/005* (2006.01)
*A61K 47/64* (2017.01)
*A61K 38/00* (2006.01)

(52) U.S. Cl.

CPC ............ *C07K 14/005* (2013.01); *A61K 47/64* (2017.08); *A61K 47/645* (2017.08); *A61K 38/00* (2013.01); *C12N 2740/16322* (2013.01)

(58) Field of Classification Search

CPC .... C07K 2319/10; C07K 7/08; C07K 14/005; A61K 47/48315; A61K 47/48246; A61K 38/08; Y10S 530/81

See application file for complete search history.

(56) References Cited

U.S. PATENT DOCUMENTS 4,631,211 A 12/1986 Houghten
4,698,327 A 10/1987 Nagarajan et al.
4,732,890 A 3/1988 Bonelli et al.
5,169,933 A 12/1992 Anderson et al.
5,595,756 A 1/1997 Bally et al.
5,597,895 A 1/1997 Gaynor et al.
5,670,617 A 9/1997 Frankel et al.
5,672,479 A 9/1997 Johnson et al.
5,674,980 A 10/1997 Frankel et al.
5,686,264 A 11/1997 Gaynor et al.
5,747,641 A 5/1998 Frankel et al.
5,756,684 A 5/1998 Johnson et al.
5,804,604 A 9/1998 Frankel et al.
5,840,313 A 11/1998 Vahlne et al.
5,989,814 A 11/1999 Frankel et al.
5,994,108 A 11/1999 Gaynor et al.
5,994,109 A 11/1999 Woo et al.
6,043,083 A 3/2000 Davis et al.
6,117,632 A 9/2000 OMahony
6,284,456 B1 9/2001 Jones et al.
6,300,317 B1 10/2001 Szoka, Jr. et al.
6,316,003 B1 11/2001 Frankel et al.
6,348,185 B1 2/2002 Piwnica-Worms
6,420,031 B1 * 7/2002 Parthasarathy et al. ... 428/411.1
6,448,283 B1 9/2002 Ylikoski et al.
6,495,663 B1 12/2002 Rothbard et al.
6,586,403 B1 7/2003 Mathison et al.
6,610,820 B1 8/2003 Bonny
6,630,351 B1 10/2003 Monahan et al.
6,653,443 B2 11/2003 Zhang et al.
6,673,908 B1 1/2004 Stanton, Jr.
6,740,524 B1 5/2004 Akuta et al.
6,780,970 B2 8/2004 Bonny
6,881,825 B1 4/2005 Robbins et al.
6,960,648 B2 11/2005 Bonny
7,034,109 B2 4/2006 Bonny
7,148,215 B2 12/2006 Ratcliffe et al.
7,166,692 B2 * 1/2007 Karas ........................... 530/300
7,635,681 B2 * 12/2009 Bonny .......................... 514/1.1
7,943,574 B2 * 5/2011 Bonny .......................... 514/8.3
8,063,012 B2 11/2011 Watt et al.
8,236,924 B2 * 8/2012 Bonny .......................... 530/300
8,278,413 B2 * 10/2012 Bonny .......................... 530/300
8,748,395 B2 6/2014 Bonny
9,006,185 B2 4/2015 Bonny
9,150,618 B2 10/2015 Combette et al.
9,180,159 B2 11/2015 Bonny
2002/0042423 A1 4/2002 Richert et al.
2002/0103229 A1 8/2002 Bhagwat et al.
2003/0100549 A1 5/2003 Salituro et al.
2003/0104622 A1 6/2003 Robbins et al.
(Continued)

FOREIGN PATENT DOCUMENTS

CN 101263157 A 9/2008
EP 0084691 A1 8/1983
(Continued)

OTHER PUBLICATIONS

Tan et al. Cancer Research 2006, vol. 66, pp. 3764-3772.*
(Continued)

*Primary Examiner* — Bao Li
(74) *Attorney, Agent, or Firm* — Haug Partners LLP

(57) ABSTRACT

The present invention relates to the use of specific transporter cargo conjugate molecules for the transport of a substance of interest (cargo molecule) into white blood cells. Said transporter cargo conjugate molecules may be used for the treatment, prophylaxis, attenuation and/or amelioration of a disease and/or disorder involving white blood cells. The present invention also relates to manufacture of said transporter cargo conjugate molecules, to a method of transporting a substance of interest (cargo) into a white blood cell and to a white blood cell comprising said transporter cargo conjugate molecules or fragments thereof.

11 Claims, 35 Drawing Sheets

(56) References Cited

U.S. PATENT DOCUMENTS

| | | | |
|---|---|---|---|
| 2003/0108539 | A1 | 6/2003 | Bonny |
| 2003/0124113 | A1 | 7/2003 | Hillman et al. |
| 2003/0148395 | A1 | 8/2003 | Liu |
| 2003/0220480 | A1 | 11/2003 | Bonny |
| 2004/0058875 | A1 | 3/2004 | Gamache |
| 2004/0082509 | A1 | 4/2004 | Bonny |
| 2004/0265879 | A1 | 12/2004 | Iversen et al. |
| 2005/0019366 | A1 | 1/2005 | Zeldis |
| 2005/0059597 | A1 | 3/2005 | Tymianski |
| 2005/0106695 | A1 | 5/2005 | Bonny |
| 2006/0094753 | A1 | 5/2006 | Pang et al. |
| 2006/0258706 | A1 | 11/2006 | Saindane et al. |
| 2006/0270646 | A1 | 11/2006 | Graczyk et al. |
| 2007/0003531 | A1 | 1/2007 | Mukherji et al. |
| 2007/0015779 | A1 | 1/2007 | Griffin et al. |
| 2007/0060514 | A1 | 3/2007 | Bonny |
| 2008/0008749 | A1 | 1/2008 | Pearlman et al. |
| 2008/0051410 | A1 | 2/2008 | Watterson et al. |
| 2009/0305968 | A1 | 12/2009 | Bonny |
| 2011/0183888 | A1 | 7/2011 | Bonny |
| 2012/0058137 | A1 | 3/2012 | Bonny |
| 2012/0101046 | A1 | 4/2012 | Hirai et al. |
| 2012/0142584 | A1 | 6/2012 | Bonny |
| 2012/0258982 | A1 | 10/2012 | Cheung et al. |

FOREIGN PATENT DOCUMENTS

| | | | |
|---|---|---|---|
| EP | 0375040 | A2 | 6/1990 |
| EP | 0679716 | A1 | 11/1995 |
| EP | 0897002 | A3 | 2/1999 |
| EP | 1364949 | A1 | 11/2003 |
| EP | 1676574 | A | 7/2006 |
| EP | 2627346 | B1 | 3/2016 |
| FR | 2767323 | A1 | 2/1999 |
| JP | 1958-146538 | A | 9/1958 |
| JP | 2-221294 | A | 9/1990 |
| JP | 2002-221294 | A1 | 8/2002 |
| JP | 2002-534479 | A | 10/2002 |
| JP | 2003511071 | A | 3/2003 |
| JP | 2004-66595 | A1 | 3/2004 |
| JP | 2007-503617 | A1 | 2/2007 |
| WO | 9218138 | A1 | 10/1992 |
| WO | 9318759 | A1 | 9/1993 |
| WO | 9404562 | A1 | 3/1994 |
| WO | 9404686 | A1 | 3/1994 |
| WO | 9405311 | A1 | 3/1994 |
| WO | 9423751 | A1 | 10/1994 |
| WO | 9534295 | A1 | 12/1995 |
| WO | 9634093 | A1 | 10/1996 |
| WO | 9705265 | A1 | 2/1997 |
| WO | 9710836 | A1 | 3/1997 |
| WO | 9811907 | A1 | 3/1998 |
| WO | 9823781 | A1 | 6/1998 |
| WO | 9844106 | A1 | 10/1998 |
| WO | 9847913 | A3 | 10/1998 |
| WO | 9849188 | A1 | 11/1998 |
| WO | 9851325 | A3 | 11/1998 |
| WO | 9851825 | A1 | 11/1998 |
| WO | 9852614 | A3 | 11/1998 |
| WO | 9907728 | A3 | 2/1999 |
| WO | 9916787 | A1 | 4/1999 |
| WO | 9920624 | A1 | 4/1999 |
| WO | 9949879 | A1 | 10/1999 |
| WO | 9950282 | A3 | 10/1999 |
| WO | 9958561 | A1 | 11/1999 |
| WO | 9967284 | A3 | 12/1999 |
| WO | 0012587 | A3 | 3/2000 |
| WO | 0041719 | A1 | 7/2000 |
| WO | 0110888 | A1 | 2/2001 |
| WO | 0113957 | A2 | 3/2001 |
| WO | 0115511 | A3 | 3/2001 |
| WO | 0127268 | A3 | 4/2001 |
| WO | 01/43774 | A1 | 6/2001 |
| WO | 0139784 | A1 | 6/2001 |
| WO | 0182975 | A2 | 11/2001 |
| WO | 01/98324 | A1 | 12/2001 |
| WO | 0231109 | A3 | 4/2002 |
| WO | 0232437 | A1 | 4/2002 |
| WO | 02061105 | A3 | 8/2002 |
| WO | 02062396 | A3 | 8/2002 |
| WO | 02065986 | A3 | 8/2002 |
| WO | 02069930 | A1 | 9/2002 |
| WO | 02081504 | A3 | 10/2002 |
| WO | 02081505 | A3 | 10/2002 |
| WO | 03008553 | A2 | 1/2003 |
| WO | 03057725 | A2 | 7/2003 |
| WO | 03075917 | A1 | 9/2003 |
| WO | 03103698 | A1 | 12/2003 |
| WO | 03103718 | A3 | 12/2003 |
| WO | 03106491 | A2 | 12/2003 |
| WO | 2004022580 | A3 | 3/2004 |
| WO | 2004/026406 | A1 | 4/2004 |
| WO | 2004035793 | A1 | 4/2004 |
| WO | 2004037196 | A2 | 5/2004 |
| WO | 2004045535 | A3 | 6/2004 |
| WO | 2004054501 | A3 | 7/2004 |
| WO | 2004060318 | A2 | 7/2004 |
| WO | 2004070052 | A3 | 8/2004 |
| WO | 2004092339 | A3 | 10/2004 |
| WO | 2005084158 | A3 | 9/2005 |
| WO | 2005097116 | A1 | 10/2005 |
| WO | 2006001582 | A1 | 1/2006 |
| WO | 2006021458 | A2 | 3/2006 |
| WO | 2006050930 | A2 | 5/2006 |
| WO | 2007031098 | A1 | 3/2007 |
| WO | 2007031280 | A2 | 3/2007 |
| WO | 2008028860 | A1 | 3/2008 |
| WO | 2008094208 | A2 | 8/2008 |
| WO | 2008095943 | A1 | 8/2008 |
| WO | 2009137602 | A1 | 11/2009 |
| WO | 2009143864 | A1 | 12/2009 |
| WO | 2009143865 | A1 | 12/2009 |
| WO | 2009144037 | A1 | 12/2009 |
| WO | 2009144038 | A1 | 12/2009 |
| WO | 2010065850 | A2 | 6/2010 |
| WO | 2010072405 | A1 | 7/2010 |
| WO | 2010072406 | A1 | 7/2010 |
| WO | 2010091310 | A1 | 8/2010 |
| WO | 2011/082328 | A1 | 7/2011 |
| WO | 2011160653 | A1 | 12/2011 |
| WO | 2011160827 | A2 | 12/2011 |
| WO | 2012048721 | A1 | 4/2012 |
| WO | 2012048893 | A1 | 4/2012 |
| WO | 2013091670 | A1 | 6/2013 |
| WO | 2013091896 | A1 | 6/2013 |
| WO | 2014/206564 | A1 | 12/2014 |
| WO | 2014206426 | A1 | 12/2014 |
| WO | 2015/197193 | A1 | 12/2015 |

OTHER PUBLICATIONS

Vocero-Akbani et al. Nature Medicine, 1999, vol. 4, No. 11, pp. 29-33.*

Polyakov et al. (Bioconjugate Chem. 2000, vol. 11, pp. 762-771).*

Bowie, Deciphering the Message in Protein Sequences: Tolerance to Amino Acid Substitutions. Science Mar. 16, 1990;247(4948):1306-1310.

Ferrandi et al., Inhibition of c-Jun N-terminal kinase decreases cardiomyocyte apoptosis and infarct size after myocardial ischemia and reperfusion in anaesthetized rats. Br J Pharmacol. Jul. 2004;142(6):953-960.

Hirt et al., D-JNKI1, a Cell-Penetrating c-Jun-N-Terminal Kinase Inhibitor, Protects Against Cell Death in Severe Cerebral Ischemia, Stroke. Jul. 2004;35(7):1738-1743.

Kugler et al., MAP kinease pathways involved in glioblastoma response to erucylphosphocholine, Int J Oncol. Dec. 2004;25(6):1721-1727.

Wang et al., A Single Amino Acid Determines Lysophopholipid Specificity of the S1P1 (EDG1) and LPA1 (EDG2) Phospholipid Growth Factor Receptors. J Biol Chem. Dec. 28, 2001;276(52):49213-49220.

(56) References Cited

OTHER PUBLICATIONS

Wells, Additivity of Mutational Effects in Proteins. Biochemistry Sep. 18, 1990;29(37):8509-8517.
Zhang et al., Preparation of functionally active cell-permeable peptides by single-step ligation of two peptide modules. Proc. Natl. Acad. Sci. USA Aug. 4, 1998; 95(16): 9184-9189.
Zoukhri et al., c-Jun NH2-terminal kinase mediates interleukin-1 beta-induced inhibition of lacrimal gland secretion. J Neurochem Jan. 2006;96: 126-135.
International Search Report and Written Opinion dated Jun. 2, 2010 issued in PCT/EP2009/009228.
International Search Report and Written Opinion dated Apr. 27, 2010 issued in PCT/EP2009/009229.
133:204452, Interaction of native RNAs with Tat peptides. Chemical Abstracs Database Sep. 29, 2000:1-3.
AAD20443. islet-brain 1 [*Homo sapiens*]. GenBank Mar. 17, 1999: 1-2.
AAD22543. islet-brain 1 (Rattus norvegicus]. GenBank Mar. 1, 2006: 1-2.
Aarts et al., Treatment of Ischemic Brain Damage by Perturbing NMDA Receptor PSD-95 Protein Interactions. Science Oct. 25, 2002; 298(5594):846-850.
Abaza and Atassi, Effects of Amino Acid Substitutions Outside an Antigenic Site on Protein Binding to Monoclonal Antibodies of Predetermined Specificity Obtained by Peptide Immunization: Demonstration with Region 94-100 (Antigenic Site 3) of Myoglobin. Journal of Protein Chemistry Oct. 1992; 11(5):433-444.
Adle-Biassette et al., Neuronal apoptosis does not correlate with dementia in HIV infection but is related to microglial activation and axonal damage. Neuropathology and Applied Neurobiology Apr. 1999; 25(2): 123-133.
Adler et al., Regulation of JNK signaling by GSTp. The EMBO Journal Mar. 1, 1999;18(5): 1321-1334.
AF074091. *Homo sapiens* islet-brain 1 mRNA, complete cds. GenBank Mar. 17, 1999: 1-2.
AF108959. Rattus norvegicus islet-brain 1 (IBI) mRNA, complete cds. GenBank Mar. 1, 2006: 1-3.
AF218778. *Homo sapiens* islet-brain 2 mRNA, complete cds. GenBank Mar. 2, 2006: 1-2.
Aldrian-Herrada et al., A peptide nucleic acid {PNA) is more rapidly internalized in cultured neurons when coupled to a retro-inverso delivery peptide. The antisense activity depresses the target mRNA and protein in magnocellular oxytocin neurons. Nucleic Acids Research Nov. 1, l998; 26(21): 4910-4916.
Assi et al., The specific JNK inhibitor SP600125 targets tumour necrosis factor-alpha production and epithelial cell apoptosis in acute murine colitis. Immunology May 2006; 118:112-121.
Ausubel., Using Synthetic Oligonucleotides as Probes. Current Protocols in Molecular Biology 1988; suppl.: . 6.4.01-6.4.10.
Barr et al., Identification of the Critical Features of a Small Peptide Inhibitor of JNK Activity. The Journal of Biochemical Chemistry Mar. 29, 2002; 277(13):10987-10997.
Berendsen, A glimpse of the Holy Grail? Science Oct. 23, 1998; 282(5389): 642-643.
Bessalle et al., All-D-magainin: chirality, antimicrobial activity and proteolytic Resistance. FEBS Letters Nov. 12, 1990; 274 (1-2): 151-155.
Bonny et al., Cell-Permeable Peptide Inhibitors of JNK Novel Blockers of Beta-Cell Death. Diabetes Jan. 2001; 50:77-82.
Bonny et al., IB1, a JIP-1-related Nuclear Protein Present in Insulin-secreting Cells. The Journal of Biological Chemistry Jan. 23, 1998; 273(4): 1843-1846.
Bonny et al., Pancreatic-Specific Expression of the Glucose Transporter Type 2 Gene: Identification of cis-Elements and Islet-Specific trans-Acting Factors. Molecular Endocrinology 1995; 9(10): 1413-1426.
Bonny et al., Targeting the JNK Pathway as a Therapeutic Protective Strategy for Nervous System Diseases. Reviews in the Neurosciences 2005;16: 57-67.
Borsello and Bonny, Use of cell-permeable peptides to prevent neuronal degeneration. TRENDS in Molecular Medicine May 2004;10(5):239-244.
Borsello et al., A peptide inhibitor of c-Jun N-terminal kinase protects against excitotoxicity and cerebral ischemia. Nature Medicine Sep. 2003; 9(9):1180-1186.
Bradley and Barrick, Limits of Cooperativity in a Structurally Modular Protein: Response of the Notch Ankyrin Domain to Analogous Alanine Substitutions in Each Repeat. J. Mol. Biol. Nov. 22, 2002; 324(2): 373-386.
Brady and Dodson, Drug Design. Reflections on a peptide. Nature Apr. 21, 1994; 368(6473): 692-693.
Branden and Tooze, Prediction, Engineering and Design of Protein Structures. Introduction to Protein Structure, 1991:247.
Branden et al., A peptide nucleic acid-nuclear localization signal fusion that mediates nuclear transport of DNA. Nat Biotechnol Aug. 1999; 17(8):784-787.
Briand et al., A retro-inverso peptide corresponding to the GH loop of foot-and-mouth disease virus elicits high levels of long-lasting protective neutralizing antibodies. Proc Natl Acad Sci U S A. Nov. 11, 1997;94(23):12545-12450.
Brugidou et al., The Retro-Inverso Form of a Homeobox-Derived Short Peptide is Rapidly Internalised by Cultured Neurones: A New Basis for an Efficient Intracellular Delivery System. Biochem Biophys Res Commun Sep. 14, 1995; 214(2): 685-693.
Cardozo et al., Cell-permeable peptides induce dose- and length-dependent cytotoxic effects. Biochimica et Biophysica Acta 2007; 1768(9): 2222-2234.
Chaloin et al., Design of Carrier Peptide-Oligonucleotide Conjugates with Rapid Membrane Translocation and Nuclear Localization Properties. Biochem Biophys Res Commun Feb. 13, 1998; 243(2):601-608.
Chie et al., Identification of the Site of Inhibition of Oncogenic ras-p21-Induced Signal Transduction by a Peptide from a ras Effector Domain. Journal of Protein Chemistry Nov. 1999; 18(8): 881-884.
Chorev and Goodman, A Dozen Years of Retro-Inverso Peptidomimetics. Acc. Chem. Res. 1993; 26(5): 266-273.
Chorev and Goodman, Recent developments in retro peptides and proteins—an ongoing topochemical exploration. Trends Biotechnol Oct. 1995; 13(10):438-445.
Creighton, Protein—Protein Interactions. Encyclopedia of Molecular Biology vol. 1, 1999:2027-2033.
Dang and Lee, Nuclear and Nucleolar Targeting Sequences of c-erb-A, c-myb, N -myc, p53, HSP70, and HIV tat Proteins. THE Journal of Biological Chemistry Oct. 25, 1989; 264(30): 18019-18023.
Database WPI, 2010, Thomson Scientific, Table 1, 1-4_XP002643212.
Derossi et al., Cell Internalization of the Third Helix of the Antennapedia Homeodomain is Receptor-independent. The Journal of Biological Chemistry Jul. 26, 1996; 271(30): 18188-18193.
Designing Custom Peptides. Sigma Genosys website Dec. 2004: 1-2.
Dickens et al., A Cytoplasmic Inhibitor of the JNK Signal Transduction Pathway. Science Aug. 1, 1997;277(5326):693-696.
Dietz and Bahr, Delivery of bioactive molecules into the cell: the Trojan horse approach. Mol. Cell. Neurosci. Oct. 2004;27(2):85-131.
Dominguez-Bendala et al., TAT-Mediated Neurogenin 3 Protein Transduction Stimulates Pancreatic Endocrine Differentiation In Vitro. Diabetes Mar. 2005; 54(3): 720-726.
Elliott and Ohare, Intercellular Trafficking and Protein Delivery by a Herpesvirus Structural Protein. Cell Jan. 24, 1997; 88(2): 223-233.
Fawell et al., Tat-mediated delivery of heterologous proteins into cells. Proc. Natl. Acad. Sci. USA Jan. 18, 1994; 91(2):664-668.
Fornoni et al., The L-isoform but not D-isoforms of a JNK inhibitory peptide protects pancreatic Beta-cells. Biochem Biophys Res Commun Mar. 2, 2007;354:227-233.
Frankel and Pabo, Cellular Uptake of the Tat Protein from Human Immunodeficiency Virus. Cell Dec. 23, 1988; 55(6): 1189-1193.

(56) References Cited

OTHER PUBLICATIONS

Frankel et al., Activity of synthetic peptides from the Tat protein of human immunodeficiency virus type 1. Proc. Natl. Acad. Sci. USA Oct. 1989; 86(19):7397-7401.
Futaki et al., Arginine-rich Peptides: An Abundant Source of Membrane-Permeable Peptides Having Potential as Carriers for Intracellular Protein Delivery. The Journal of Biological Chemistry Feb. 23, 2001; 276(8): 5836-5840.
Gammon et al., Quantitative Analysis of Permeation Peptide Complexes Labeled with Technetium-99m: Chiral and Sequence-Specific Effects on Net Cell Uptake., Bioconjugate Chem. Mar.-Apr. 2003; 14(2): 368-376.
Giorello et al., Inhibition of Cancer Cell Growth and c-Myc Transcriptional Activityby a c-Myc Helix 1-Type Peptide Fused to an Internalization Sequence. Cancer Research Aug. 15, 1998; 58(16): 3654-3659.
Gotthardt et al., Interactions of the Low Density Lipoprotein Receptor Gene Family with Cytosolic Adaptor and Scaffold Proteins Suggest Diverse Biological Functions in Cellular Communication and Signal Transduction. The Journal of Biological Chemistry Aug. 18, 2000; 275(33):25616-25624.
Guichard et al., Antigenic mimicry of natural L-peptides with retro-inverso-peptidomimetics. Proc. Natl. Acad. Sci. USA Oct. 11, 1994; 91(21): 9765-9769.
Guichard et al., Partially Modified Retro-Inverso Pseudopeptides as Non-natural Ligands for the Human Class I Histocompatibility Molecule HLA-A2. Journal of Medicinal Chemistry May 10, 1996; 39(10): 2030-2039.
Gunaseelan et al., Synthesis of Poly( ethylene glycol)-Based Saquinavir Prodrug Conjugates and Assessment of Release and Anti-HIV-1 Bioactivity Using a Novel Protease Inhibition Assay. Bioconjugate Chem. Nov.-Dec. 2004; 15(6): 1322-1333.
Gura, Systems for Identifying New Drugs Are Often Faulty. Science Nov. 7, 1997; 278(5340):1041-1042.
Hauber et al., Mutational Analysis of the Conserved Basic Domain of Human Immunodeficiency Virus tat Protein. Journal of Virology Mar. 1989; 63(3): 1181-1187.
Hawiger, Noninvasive intracellular delivery of functional peptides and proteins. Current Opinion in Chemical Biology Feb. 1999; 3:89-94.
Hayashi et al., Development of oligoarginine-drug conjugates linked to new peptidic self-cleavable spacers toward effective intestinal absorption. Bioorganic & Medicinal Chemistry Letters Sep. 15, 2007; 17(18): 5129-5132.
Heemskerk et al., From chemical to drug: neurodegeneration drug screening and the ethics of clinical trials. Nat Neurosci Nov. 2002; 5 Suppl:1027-1029.
Herve et al., On the Immunogenic Properties of Retro-Inverso Peptides. Total Retro-Inversion of T-Cell Epitopes Causes a Loss of Binding to Mhc II Molecules. Molecular Immunology Feb. 1997; 34(2): 157-163.
Hillier et al, *Homo sapiens* cDNA clone. EMBL Sequence Database, 1995 R85141.
Ho et al., Synthetic Protein Transduction Domains: Enhanced Transduction Potential in Vitro and in Vivo. Cancer Research Jan. 15, 2001; 61(2): 474-477.
Holinger et al., Bak BH3 Peptides Antagonize Bcl-xL Function and Induce Apoptosis through Cytochrome c-independent Activation of Caspases. The Journal of Biological Chemistry, May 7, 1999; 274(19): 13298-13304.
Holzberg et al., Disruption of the c-JUN-JNK Complex by a Cell-permeable Peptide Containing the c-JUN delta Domain Induces Apoptosis and Affects a Distinct Set of Interleukin-1-induced Inflammatory Genes. The Journal of Biological Chemistry Oct. 10, 2003; 278(41): 40213-40223.
Houghten, General method for the rapid solid-phase synthesis of large numbers of peptides: Specificity of antigen-antibody interaction at the level of individual amino acids. Proc. Natl. Acad. Sci. USA Aug. 1985; 82(15): 5131-5135.
Hruby and Bonner, Chapter 11: Design of Novel Synthetic Peptides Including Cyclic Conformationally and Topgraphically Constrained Analogs. Peptide Synthesis Protocols, 1994 Humana Press Inc. :201-239.
Huq et al., Specific recognition of HIV-1 TAR RNA by a D-Tat peptide. Nature Structural Biology Nov. 1997; 4(11):881-882.
Inflammation. Stedman's Medical Dictionary 28th Edition, PDR® Electronic Library(TM): Stedman Definitions, (www .pdrel.com), Dec. 18, 2010:1-2.
Inhibit. Dictionary.com The American Heritage® Stedman's Medical Dictionary Copyright c. 2002, 2001, 1995 by Houghton Mifflin Company. Published by Houghton Mifflin Company.Oct. 10, 2007.
Jackson et al., Heat shock induces the release of fibroblast growth factor 1 from NIH 3T3 cells. Proc. Natl. Acad. Sci. USA Nov. 1992; 89: 10691-10695.
Jameson et al., A rationally designed CD4 analogue inhibits experimental allergic encephalomyelitis. Nature Apr. 21, 1994; 368(6473): 744-746.
Johnson and Nakamura, The c-jun kinase/stress-activated pathway: Regulation, function and role in human disease. Biochimica et Biophysica Acta 2007; 1773(8):1341-1348.
Kennedy and Davis, Role of JNK in Tumor Development. Cell Cycle May-Jun. 2003; 2(3); 199-201.
Kida et al., Design and synthesis of a Tat-related gene transporter: A tool for carrying the adenovirus vector into cells. Bioorganic & Medicinal Chemistry Letters Feb. 2006; 16(3): 743-745.
Kieber-Emmons et al., Therapeutic peptides and peptidomimetics. Current Opinion in Biotechnology Aug. 1997; 8(4):435-441.
Kisselev, Polypeptide Release Factors in Prokaryotes and Eukaryotes: Same Function, Different Structure. Structure Jan. 2002 ; 10:8-9.
Lebleu, Delivering information-rich drugs—prospects and challenges. Trends Biotechnol. Apr. 1996;14(4):109-10.
Lee et al., c-Jun N-terminal Kinase (JNK) Mediates Feedback Inhibition of the Insulin Signaling Cascade. The Journal of Biological Chemistry Jan. 31, 2003;278(5): 2896-2902.
Lewis et al., Lymphoma Cell Uptake of Radiometal- and Fluorescent-Labelled Bcl-2 Antisense Pna Conjugates is Mediated by a Retro-Inverso Delivery Peptide. J. Label Compd. Radiopharm. 2003; 46: S13.
Li, Specificity and versatility of SH3 and other proline-recognition domains: structural basis and implications for cellular signal transduction. Biochem. J. Sep. 15, 2005; 390(Pt 3): 641-653.
Lim et al., Penetration enhancement in mouse skin and lipolysis in adipocytes by TAT-GKH, a new cosmetic ingredient. ]ournal of Cosmetic Science Sep.-Oct. 2003; 54(5): 483-491.
Lin et al., Inhibition of Nuclear Translocation of Transcription Factor NF-kappa B by a Synthetic Peptide Containing a Cell Membrane-permeable Motif and Nuclear Localization Sequence. The Journal of Biological Chemistry Jun. 16, 1995; 270(24): 14255-14258.
Lloyd-Williams et al., Chapter 5: Formation of Disulfide Bridges. Chemical Approaches to the Synthesis of Peptides and Proteins. Library of Congress Cataloging-in-Publication Data c. 1997, CRC Press LLC: 209-236.
Lloyd-Williams et al., Chapter 6: Peptide Libraries. Chemical Approaches to the Synthesis of Peptides and Proteins. Library of Congress Cataloging-in-Publication Data c. 1997, CRC Press LLC: 237, 264-267.
Manheimer, PH0878; Ig kappa chain V region. NCB I Sequence Viewer v2., GenBank May 30, 1997.
Mann and Frankel, Endocytosis and targeting of exogenous HIV-1 Tat Protein. The EMBO Journal, Jul. 1991; 10(7): 1733-1739.
Marino et al., Inhibition of experimental autoimmune encephalomyelitis in SJL mice by oral administration of retro-inverso derivative of encephalitogenic epitope p. 87-99. Eur. J. Immunol. Aug. 1999; 29(8):2560-2566.
Marks et al., Protein Targeting by Tyrosine- and Di-leucine-based Signals: Evidence for Distinct Saturable Components. J Cell Biol. Oct. 1996; I35(2): 341-354.
Mayer, SH3 domains: complexity in moderation. Journal of Cell Science Apr. 2001; 114(Pt 7): 1253-1263.

(56) References Cited

OTHER PUBLICATIONS

Mazur and Perrino, Identification and Expression of the TREXI and TREX2 cDNA Sequences Encoding Mammalian 3'→5' Exonucleases. The Journal of Biological Chemistry Jul. 9, 1999; 274(28):19655-19660.
Melikov and Chernomordik, Arginine-rich cell penetrating peptides: from endosomaluptake to nuclear delivery. Cellular and Molecular Life Sciences Dec. 2005; 62(23):2739-2749.
Messer, Vasopressin and Oxytocin. http://www.neurosci.pharm.utoledo.edu/MBC3320/vasopressin.htm, Apr. 3, 2000:1-5.
Mi et al., Characterization of a Class of Cationic Peptides Able to Facilitate Efficient Protein Transduction in Vitro and in Vivo. Molecular Therapy Oct. 2000; 2(4):339-347.
Milano et al., A peptide inhibitor of c-Jun NH2-terminal kinase reduces myocardial•ischemia-reperfusion injury and infarct size in vivo. Am J Physiol Heart Circ Physiol Apr. 2007; 292(4): H 1828-H 1835.
Mooi et al., Regulation and structure of an *Escherichia coli* gene coding for an outer membrane protein involved in export of K88ab fimbrial subunits. Nucleic Acids Research Mar. 25, 1986; 14(6): 2443-2457.
Moon et al., Bcl-2 overexpression attenuates SP600125-induced apoptosis in human leukemia U937 cells. Cancer Letters Jun. 18, 2008; 264(2): 316-325.
Nagahara et al., Transduction of full-length TAT fusion proteins into mammalian cells: TAT-p27Kipl induces cell migration. Nature Medicine Dec. 1998; 4(12): 1449-1452.
Neori et al., Design of a Novel Peptide Inhibitor of the JNK Signaling Pathway. Diabetes 2001; 50 Supplement (2): A294 (1217-P).
Neundorf et al., Detailed Analysis Concerning the Biodistribution and Metabolism of Human Calcitonin-Derived Cell-Penetrating Peptides. Bioconjugate Chem. Aug. 2008; 19(8): 1596-1603.
Ngo et al., Computational Complexity, Protein Structure Prediction, and the Levinthal Paradox. The Protein Folding Problem and Tertiary Structure Prediction c. Birchuser Boston 1994; 491-495.
Noguchi et al., Regulation of c-Myc through Phosphorylation at Ser-62 and Ser-71 by c-Jun N-Terminal Kinase. J Biol Chem Nov. 12, 1999; 274(46): 32580-32587.
Nori and Kopecek, Intracellular targeting of polymer-bound drugs for cancer chemotherapy. Advanced Drug Delivery Reviews Feb. 28, 2005;57(4):609-636.
Nori et al., Tat-Conjugated Synthetic Macromolecules Facilitate Cytoplasmic Drug Delivery to Human Ovarian Carcinoma Cells. Bioconjugate Chem. Jan.-Feb. 2003; 14: 44-50.
Okitsu et al., Protein Transduction Domains Enable Isolated Islets to Efficiently Internalize the Target Protein. Transplantation Proceedings Feb. 2003; 35: 479.
Pan et al., Small peptide inhibitor of JNKs protects against MPTP-induced nigral dopaminergic injury via inhibiting the JNK-signaling pathway. Laboratory Investigation Feb. 2010; 90(2): 156-167.
Parkinson's Disease: Challenges, Progress, and Promise., NIH Publication No. 05-5595 NINDS. Dec. 2004: 1-22.
Penco et al., Identification of an import signal for, and the nuclear localization of, human lactoferrin. Biotechnol. Appl. Biochem, Dec. 2001; 34 (Pt 3): 151-159.
Pennington, Chapter 12: Solid-Phase Synthesis of Peptides Containing the CH2NH Reduced Bond Surrogate. Peptide Synthesis Protocols, 1994 Humana Press Inc. : 241-247.
Pinilla et al., Chap 5: The Versatility of Nonsupport-Bound Combinatorial Libraries. Combinatorial Peptide and Nonpeptide Libraries: A Handbook, ed. By G. Jung, VCH: 139-171.
Pirvola et al., Rescue of Hearing, Auditory Hair Cells, and Neurons by CEP-1347/KT7515, an Inhibitor of c-Jun N-Terminal Kinase Activation. The Journal of Neuroscience Jan. 1, 2000; 20: 43-50.
Prantner et al., Synthesis and Characterization of a Gd-DOTA-D-Permeation Peptide for Magnetic Resonance Relaxation Enhancement of Intracellular Targets. Molecular Imaging Oct. 2003; 2(4):333-341.
Q9WVI9, JIPI_MOUSE Standard; PRT; 707 AA. Database UniProt 2003.
Ramage and Epton, Peptides 1996: Proceedings of the Twenty-Fourth European Peptide Symposium. The European Peptide Society c. 1998: 447-451, 483-487.
Ramanathan et al., Targeting the Sodium-Dependent Multivitamin Transporter (SMVT) for Improving the Oral Absorption Properties of a Retro-Inverso Tat Nonapeptide. Pharmaceutical Research, Jul. 2001;18(7):950-956.
Ribeiro MM et al., Heme oxygenase-1 fused to a TAT peptide transduces and protects pancreatic beta-cells. Biochem Biophys Res Commun Jun. 13, 2003; 305(4):876-881.
Robinson et al., Properties and structure-activity studies of cyclic beta-hairpin peptidomimetics based on the cationic antimicrobial peptide protegrin I. Bioorg Med Chem Mar. 15, 2005; 13(6): 2055-2064.
Rojas et al., Controlling Epidermal Growth Factor (EGF)-stimulated Ras Activation in Intact Cells by a Cell-permeable Peptide Mimicking Phosphorylated EGF Receptor. J Biol Chem Nov. 1, 1996; 271(44): 27456-27461.
Roy et al., Role of the JNK signal transduction pathway in inflammatory bowel disease. World ]ournal of Gastroenterology Jan. 14, 2008; 14(2): 200-202.
Ruben et al., Structural and Functional Characterization of Human Immunodeficiency Virus tat Protein. Journal of Virology Jan. 1989; 63: 1-8.
Rudikoff et al., Single amino acid substitution altering antigen-binding specificity. Proc Natl Acad. Sci. USA Mar. 1982; 79(6):1979-1983.
Rudinger, Characteristics of the amino acids as components of a peptide hormone sequence. Peptide Hormones Jun. 1976:1-7.
Saito and Paterson, Contribution of Peptide Backbone Atoms to Binding of an Antigenic Peptide to Class I Major Histocompatibility Complex Molecule. Molecular Immunology Nov.-Dec. 1997; 34(16-17):1133-1145.
Schimmer AD et al., The BH3 domain of BAD fused to the Antennapedia peptide induces apoptosis via its alpha helical structure and independent of Bcl-2. Cell Death Differ Jul. 2001; 8(7): 725-733.
Schinzel and Drueckes, The phosphate recognition site of *Escherichia coli* maltodextrin phosphorylase. FEBS Lett Jul. 29, 1991; 286(1-2): 125-128.
Schwarze et al., In Vivo Protein Transduction: Delivery of a Biologically Active Protein into the Mouse. Science Sep. 3, 1999; 285(5433): 1569-1572.
Sebestyen et al., DNA vector chemistry: The covalent attachment of signal peptides to plasmid DNA. Nature Biotechnology Jan. 1998; 16:80-85.
Selective Dimerisation of Cysteines to form Heterodimers. NJE Feb. 3, 1997.
Shimonishi, Peptide Science—Present and Future: Proceedings of the 1st International Peptide Symposium. C. 1999 Kluwer Academic Publishers: 782-787, 805-807.
Smilek et al., A single amino acid change in a myelin basic protein peptide confers the capacity to prevent rather than induce experimental autoimmune encephalomyelitis. Proc. Natl. Acad. Sci. USA Nov. 1, 1991; 88(21):9633-9637.
Stevens et al., Efficient Generation of Major Histocompatibility Complex Class 1-Peptide Complexes Using Synthetic Peptide Libraries. The Journal of Biological Chemistry Jan. 30, 1998; 273(5): 2874-2884.
Stevens et al., Peptide length preferences for rat and mouse MHC class I molecules using random peptide libraries. Eur. J. Immunol. 1998;28(4): 1272-1279.
Torchilin, Fluorescence microscopy to follow the targeting of liposomes and micelles to cells and their intracellular fate. Advanced Drug Delivery Reviews Jan. 2, 2005;57: 95-109.
Torgerson et al., Regulation of NF-kappa B, AP-1, NFAT, and STATI Nuclear Import in T Lymphocytes by Noninvasive Delivery of Peptide Carrying the Nuclear Localization Sequence of NF-kappa B p50. The Journal of Immunology Dec. 1, 1998; 161(11):6084-6092.

(56) References Cited

OTHER PUBLICATIONS

Van Regenmortel and Muller, D•peptides as immunogens and diagnostic reagents. Current Opinion in Biotechnoloy Aug. 1998; 9(4):377-382.
Vives et al., A Truncated HIV-1 Tat Protein Basic Domain Rapidly Translocates through the Plasma Membrane and Accumulates in the Cell Nucleus. The Journal of Biological Chemistry Jun. 20, 1997; 272(25):16010-16017.
Vocero-Akbani et al., Killing HIV-infected cells by transduction with an HIV protease-activated caspase-3 protein. Nature Medicine Jan. 1999; 5: 29-33.
Voet and Voet, Abnormal Hemoglobins. Biochemistry Second Edition c. 1995; section 9.3:235-241.
Wadia et al., Delivery of Novel AntiCancer Peptides by Protein Transduction Domains. American Pharmaceutical Review 2004:65-69.
Waldmeier et al., Recent clinical failures in Parkinson's disease with apoptosis inhibitors underline the need for a paradigm shift in drug discovery for neurodegenerative diseases. Biochemical Pharmacology Nov. 15, 2006; 72(10): 1197-1206.
Walsh et al., Erythrocyte survival is promoted by plasma and suppressed by a Bak-derived BH3 peptide that interacts with membrane-associated Bcl-X(L). Blood May 1, 2002; 99(9): 3439-3448.
Wender et al., The design, synthesis, and evaluation of molecules that enable or enhance cellular uptake: Peptoid molecular transporters. Proc Natl Acad Sci USA Nov. 21, 2000; 97(24):13003-13008.
Whitmarsh and Davis, Transcription factor AP-1 regulation by mitogen-activated protein kinase signal transduction pathways. Journal of Molecular Medicine Oct. 1996; 74(10):589-607.
Whitmarsh et al., A Mammalian Scaffold Complex That Selectively Mediates MAP Kinase Activation. Science 1998 Seot 11; 281(5383):1671-1674.
Wilson, Preventing Nerve Cell Death in ALS. Internet http://www.als.ca/_news/57.aspx?print=1& Dec. 5, 2001: 1-2.
Wishart et al., A Single Mutation Converts a Novel Phosphotyrosine Binding Domain into a Dual-specificity Phosphatase. J Biol Chem Nov. 10, 1995;270(45):26782-26785.
Witkowski et al., Conversion of a Beta-Ketoacyl Synthase to a Malonyl Decarboxylase by Replacement of the Active-Site Cysteine with Glutamine. Biochemistry Sep. 7, 1999; 38(36): 11643-11650.
Yamamoto et al., Molecular Design of Bioconjugated Cell Adhesion Peptide with a Water-Soluble Polymeric Modifier for Enhancement of Antimetastatic Effect. Current Drug Targets Apr. 2002; 3(2):123-130.
Yang et al., Differential targeting of MAP kinases to the ETS-domain transcription factor Elk-1. The EMBO Journal Mar. 16, 1998; 17(6): 1740-1749.
Yasuda et al., The JIP Group of Mitogen-Activated Protein Kinase Scaffold Proteins. Molecular and Cellular Biology, Oct. 1999; 19(10): 7245-7254.
De Paiva et al., Essential Role for c-Jun N-Terminal Kinase 2 in Corneal Epithelial Response to Desiccating Stress. Arch Ophthalmol. Dec. 2009;127(12):1625-1631.
Hommes et al., Inhibition of Stress-Activated MAP Kinases Induces Clinical Improvement in Moderate to Severe Crohn's Disease. Gastroenterology. Jan. 2002;122(1):7-14.
Mitsuyama et al., Pro-inflammatory signaling by Jun-N-terminal kinase in inflammatory bowel disease. Int J Mol Med. Mar. 2006;17(3):449-455.
Qin and Qin, TAT Protein Transduction Domains: New Promise for Protein Therapy. Chin J Biochem Molec Biol. 2007;23(7):519-524—incl Engl transl abstract only.
Ahmed et al., Basal Cancer Cell Survival Involves JNK2 Suppression of a Novel JNK1 /c-Jun/Bcl-3 Apoptotic Network. PLoS One Oct. 6, 2009;4(10):e7305.
Asanuma et al., Protection against malonate-induced ischemic brain injury in rat by a cell-permeable peptidic c-Jun N-terminal kinase inhibitor, (L)-HIV-TAT48-57-PP-JBD20, observed by the apparent diffusion coefficient mapping magnetic resonance imaging method. Neurosci Lett. Apr. 8, 2004;359(1-2):57-60 (abstract only).
Bost et al., The Jun Kinase 2 Isoform is Preferentially Required for Epidermal Growth Factor-Induced Transformation of Human A549 Lung Carcinoma Cells. Mol Cell Biol. Mar. 1999;19(3):1938-1949.
Chang et al., JNK1 is Required for Maintenance of Neuronal Microtubules and Controls Phosphorylation of Microtubule-Associated Proteins. Dev Cell. Apr. 2003;4(4):521-533.
Hunot et al., JNK-mediated induction of cyclooxygenase 2 is required for neurodegeneration in a mouse model of Parkinson's disease. Proc Natl Acad Sci USA. Jan. 13, 2004;101(2):665-670.
Jaeschke et al., Disruption of the Jnk2 (Mapk9) gene reduces destructive insulitis and diabetes in a mouse model of type I diabetes. Proc Natl Acad Sci USA. May 10, 2005;102(19):6931-6935.
Kaneto et al., Possible novel therapy for diabetes with cell-permeable JNK-inhibitory peptide. Nat Med. Oct. 2004;10(10):1128-1132.
Kuan et al., A critical role of neural-specific JNK3 for ischemic apoptosis. Proc Natl Acad Sci USA., Dec. 9, 2003;100(25):15184-15189.
Saar et al., Cell-penetrating peptides: A comparative membrane toxicity study. Anal Biochem. Oct. 1, 2005;345(1):55-65.
Sabapathy, Role of the JNK Pathway in Human Diseases. Prog Mol Biol Transl Sci. 2012;106:145-169.
Salh, c-Jun N-terminal kinases as potential therapeutic targets. Expert Opin Ther Targets. Oct. 2007;11(10):1339-1353.
Seki et al., A Liver Full of JNK: Signaling in Regulation of Cell Function and Disease Pathogenesis, and Clinical Approaches. Gastroenterology. Aug. 2012;143(2):307-320.
Sumara et al., "Jnking" atherosclerosis. Cell Mol Life Sci. Nov. 2005;62(21):2487-2494.
Tachibana et al., JNK1 is required to preserve cardiac function in the early response to pressure overload. Biochem Biophys Res Commun. May 19, 2006;343(4):1060-1066.
Westwick et al., Activation of Jun Kinase Is an Early Event in Hepatic Regeneration. J Clin Invest. Feb. 1995;95(2):803-810.
Bogoyevitch et al, Taking the cell by stealth or storm? Protein transduction domains (PTDs) as versatile vectors for delivery. DNA Cell Biol. Dec. 2002;21(12):879-894.
Chemical Abstracts Accession No. 2004:27781 & CAS Registry File CN 647864-97-9 copyright 2014:2pp.
InVivoGen, Inc. SP600125 MAP Kinase Inhibitor—Autophagy Inhibitor—JNK inhibitor. Downloaded Jun. 9, 2014:2pp.
Kelekar and Thompson, Bcl-2-family proteins: the role of the BH3 domain in apoptosis. Trends Cell Biol. Aug. 1998;8(8):324-330.
Killick et al, Clusterin regulates β-amyloid toxicity via Dickkopf-1-driven induction of the wnt-PCP-JNK pathway. Mol Psychiatry. Jan. 2014;19(1):88-98.
Parenteau et al., Free uptake of cell-penetrating peptides by fission yeast. FEBS Lett. Aug. 29, 2005;579(21):4873-4878.
Patel et al., Getting into the Brain: Approaches to Enhance Brain Drug Delivery. CNS Drugs. 2009;23(1):35-58.
Du et al., JNK inhibition reduces apoptosis and neovascularization in a murine model of agerelated macular degeneration, Proc Natl Acad Sci USA. Feb. 5, 2013;110(6):2377-2382.
Iyer et al., RDP58, a rationally designed peptide, inhibits multiple forms of pathogenic inflammation through the inhibition of p38MAPK and JNK. Biopolymers Jan. 2013;71(3):298.
Noguchi et al., Cell Permeable Peptide of JNK Inhibitor Prevents Islet Apoptosis Immediately After Isolation and Improves Islet Graft Function. Am J Transplant. Aug. 2005;5(8):1848-1855.
Noguchi et al., Effect of JNK Inhibitor During Islet Isolation and Transplantation. Transplant Proc. Mar. 2008;40(2):379-381.
Tsuyoshi et al., Behcet's disease. NE J Med. 1999:1284-1291.
Cui et al., JNK pathway: diseases and therapeutic potential. Acta Pharmacol Sin. May 2007;28(5):601-608.
Josephson et al., High-Efficiency Intracellular Magnetic Labeling with Novel Superparamagnetic-Tat Peptide Conjugates. Bioconjug Chem. Mar.-Apr. 1999;10(2)186-191.
Moschos et al., Lung Delivery Studies Using siRNA Conjugated to TAT(48-60) and Penetratin Reveal Peptide Induced Reduction in

(56) References Cited

OTHER PUBLICATIONS

Gene Expression and Induction of Innate Immunity. Bioconjug Chem. Sep.-Oct. 2007;18(5):1450-1459.
Aisen et al., "A randomized controlled trial of prednisonhe in Alzheimer's disease," Neurology, 54(3):588-593 (2000).
Asanuma et al, "Protection against malonate-induced ischemic brain injury in rat by a cell-permeable peptidic c-Jun N-terminal kinase inhibitor, (L)-HIV-TAT48-57-PP-JBD20, observed by the apparent diffusion coefficient mapping magnetic resonance imaging method," Neurosci Lett., 359(1-2):57-60 (2004) (only abstract).
Bloch et al., "Increased ERK and JNK activation and decreased ERK/JNK ratio are associated with long-term organ damage in patients with systemic lupus erythematosus," Rheumatology, 53(6):1034-1042 (2014).
Cerbone et al., "AS601245, an anti-inflammatory JNK inhibitor, and clofibrate have a synergistic effect in inducing cell-responses and in affecting the gene expression profile in CaCo-2 colon cancer cells," PPAR Research, vol. 2012 (2012), Article ID 269751, 16 pages.
Chen et al., "The role of c-Jun N-terminal kinase (JNK) in apoptosis induced by ultraviolet C and gamma radiation. Duration of JNK activation may determine cell death and proliferation," The Journal of Biological Chemistry, 271 (50):31929-31936 (1996).
Negri et al., "Design of a Novel Peptide Inhibitor of the JNK Signaling Pathway," Diabetes, Abstract Book, 61st Scientific Sessions, Jun. 22-26, 2001, Pennsylvania Convention Center, Philadelphia, PA, vol. 50, Supplement No. 2, p. A294, 1217-P (2001).
Dugan et al., "Role of c-Jun N-terminal kinase (JNK) activation in micturition reflexes in cyclophosphamide (CYP)-induced cystitis in female rats," Journal of Molecular Neuroscience, 54(3):360-369 (2014).
Guichard et al.; Horvath et al.; Hruby et al, Peptides 1996: Proceedings of the twenty-fourth European Peptide Symposium, Sep. 8-13, 1996, Edinburgh, Scotland; Ramage/Epton (Eds.), The European Peptide Society, Mayflower Scientific Ltd., Kingswinford, pp. 447-450 and 483-486 (1996).
Hanyu et al., "Pioglitazone improved cognition in a pilot study on patients with Alzheimer's disease and mild cognitive impairment with diabetes mellitus," Journal of the American Geriatrics Society, 57(1):177-179 (2009).
Kumar, B. et al., A pharmacogenetics supported clinica trial to delay onset of mild cognitive impairment due to Alzheimer's desease using low dose pioglitazone: the tomorrow study, Neuropsychopharmacology, vol. 39, No. suppl.1, Dec. 2014 (Dec. 2014), p. S342.
Manning et al., "Targeting JNK for therapeutic benefit: from junk to gold?" Nature Reviews Drug Discovery, 2:554-565 (2003).
Melino et al., "The effect of the JNK inhibitor, JIP peptide, on human T lymphocyte proliferation and cytokine production," 181(10):7300-7306 (2008).
Mooser et al. "Genomic Organization, Fine-Mapping, and Expression of the Human Islet-Brain 1 (IB1)/C-Jun-Amino-Terminal Kinase Interacting Protein-1 (JIP-1) Gene," Genomics, 55:202-208 (1999).
Roduit et al., "MAP kinase pathways in UV-induced apoptosis of retinal pigment epithelium ARPE19 cells," Apoptosis, 13(3):343-353 (2008).
Shimazawa et al., "Inhibitor of double stranded RNA-dependent protein kinase protects against cell damage induced by ER stress," Neurosci Lett., 409(3):192-195 (2006).
Soejima et al., "Activation of MKK4 (SEK1), JNK, and C-Jun in Labial Salivary Infiltrating T Cells in Patients with Sjögren's Syndrome," Rheumatology International 27(4):329-333 (2006).
Spatola et al., "Cyclic Peptide Libraries: Recent Developments," Chapter 11, Combinatorial Peptide and Nonpeptide Libraries—A Handbook, Edited by Günther Jung, John Wiley & Sons, pp. 327-347 (1996).
Touchard et al., "A peptide inhibitor of c-Jun N-terminal kinase for the treatment of endotoxin-induced uveitis," nvestigative Ophthalmology & Visual Science, 51(9):4683-4693 (2010).
Vives et al., "Structure-activity relationship study of the plasma membrane translocating potential of a short peptide from HIV-1 Tat protein," Letters in Peptide Science, 4(4):429-436 (1997).
Weston et al., "The JNK signal transduction pathway," Curr. Opin. Cell Biol., 19(2):142-149, (2007).
Auerbach et al., "Angiogenesis assays: problems and pitfalls," Cancer and Metastasis Reviews, 19:167-172 (2000).
Chung et al., "Endogenous NGF Regulate Collagen Expression and Bladder Hypertrophy Through AKT and MAPK Pathways During Cystitis," Journal of Biological Chemistry, 285:4206-4212 (2010).
Conti et al., "Atherosclerosis: a chronic inflammatory disease mediated by mast cells," Central European Journal of Immunology, 40:380-386 (2015).
Donath et al., "Type 2 diabetes as an inflammatory disease," Nature Reviews Immunology, 11:98-107 (2011).
Jain, "Barriers to drug delivery in solid tumors," Scientific American, 271:58-65 (1994).
Multifocal choroiditis, "National Center of Advancing Translational Science," https://rarediseases.info.nih.gov/diseases/9824/multifocal-choroiditis (2013).
Murdoch et al., "Chronic inflammation and asthma," Mutation Research, 690:24-39 (2010).
Neidle ed., Cancer Drug Design and Discovery, 427-431 (2008).
Rovina et al., "Inflammation and Immune Response in COPD: Where Do We Stand?" Mediators of Inflammation, 2013:1-9 (2013).
Sporn et al., "Chemoprevention of cancer," Carcinogenesis, 21:525-530 (2000).
Theoretical pi/mw average of the amino acid sequence DQSRPVQPFLNLTTPRKPRPPRRRQRRKKRG; http://web.expasy.org/cgi-bin/compute_pi/pi_tool (2017).
Todd et al., "Genetic Protection from the Inflammatory Disease Type 1 Diabetes in Humans and Animal Models," Immunity, 15:387-395 (2011).
Branden et al., Introduction to Protein Structure, 382 (1999).
Nakamura et al., "Expression of mitogen activated protein kinases in labial salivary glands of patients with Sjogren's syndrome," Annals of the Rheumatic Diseases, 58:382-385 (1999).
Kaneto et al., "Possible novel therapy for diabetes with cell-permeable JNK-inhibitory peptide," Nature Medicine, 10:1128-1132 (2004).
Wang et al., "JNK inhibition as a potential strategy in treating Parkinson's disease," Drug News & Perspectives, 17:646-654 (2004).

* cited by examiner

D-TAT-FITC

XG-102, 1mg/kg iv, rat (40x)

CTL

| | MONOCYTES | NEUTROPHILS | T LYMPHO. | B LYMPHO. |
|---|---|---|---|---|
| D-TAT | 3510.30 | 1698.16 | 1551.66 | 1323.95 |
| r3L-TAT | 2952.56 | 1518.37 | 995.46 | 1051.82 |

FIG. 16

| | SEQ ID NO: | RAW* | J77*** | BMDM* |
|---|---|---|---|---|
| D-TAT | 4 | 100 | 100 | 100 |
| r3-L-TAT | 15 | 107 | 51 | 65 |
| 12 | 32 | 30 | 13 | 41 |
| 19 | 39 | 12 | 10 | 12 |
| 20 | 40 | 45 | 20 | 33 |
| 21 | 41 | 83 | 39 | 61 |
| 28 | 48 | 156 | 35 | 149 |
| 33 | 53 | 69 | 19 | 54 |
| 41 | 61 | 65 | 28 | 100 |
| 60 | 80 | 54 | 21 | 28 |
| 64 | 84 | 150 | 71 | 120 |
| 80 | 100 | 63 | 26 | 26 |
| 83 | 103 | 70 | 41 | 59 |
| 92 | 112 | 48 | 24 | 28 |
| 93 | 113 | 57 | 29 | 37 |
| 94 | 114 | 136 | 75 | 84 |
| 95 | 115 | 78 | 19 | 98 |
| 96 | 116 | 75 | 33 | 64 |

*FIG. 17*

| | SEQ ID NO: | RAW* | J77*** | BMBDM* |
|---|---|---|---|---|
| D-TAT | 4 | 94 | 196 | 154 |
| r3-L-TAT | 15 | 100 | 100 | 100 |
| 12 | 32 | 28 | 25 | 63 |
| 19 | 39 | 11 | 19 | 18 |
| 20 | 40 | 42 | 39 | 51 |
| 21 | 41 | 78 | 77 | 94 |
| 28 | 48 | 146 | 68 | 229 |
| 33 | 53 | 64 | 37 | 82 |
| 41 | 61 | 61 | 56 | 154 |
| 60 | 80 | 51 | 41 | 43 |
| 64 | 84 | 141 | 139 | 185 |
| 80 | 100 | 59 | 52 | 41 |
| 83 | 103 | 66 | 81 | 91 |
| 92 | 112 | 45 | 47 | 43 |
| 93 | 113 | 54 | 56 | 56 |
| 94 | 114 | 128 | 146 | 129 |
| 95 | 115 | 73 | 38 | 150 |
| 96 | 116 | 70 | 65 | 99 |

*FIG. 18*

FIG. 19C
H&E
XG-102 STAINING
SALINE
CFA SALINE
CFA XG-102 (10μg/kg) - 1h

SEQUENCE LISTING

```
<160> NUMBER OF SEQ ID NOS: 413

<210> SEQ ID NO 1
<211> LENGTH: 86
<212> TYPE: PRT
<213> ORGANISM: Human immunodeficiency virus type 1
<220> FEATURE:
<221> NAME/KEY: misc_feature
<223> OTHER INFORMATION: Description of sequence:  HIV-1 TAT sequence
      (aa 1-86)

<400> SEQUENCE: 1

Met Glu Pro Val Asp Pro Arg Leu Glu Pro Trp Lys His Pro Gly Ser
1               5                   10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Arg Pro Pro Gln Gly Ser Gln Thr
    50                  55                  60

His Gln Val Ser Leu Ser Lys Gln Pro Thr Ser Gln Ser Arg Gly Asp
65                  70                  75                  80

Pro Thr Gly Pro Lys Glu
                85


<210> SEQ ID NO 2
<211> LENGTH: 9
<212> TYPE: PRT
<213> ORGANISM: Artificial Sequence
<220> FEATURE:
<223> OTHER INFORMATION: Description of sequence:  trafficking sequence
      L-TAT (s1a) (see Table 1)

<400> SEQUENCE: 2

Arg Lys Lys Arg Arg Gln Arg Arg Arg
1               5


<210> SEQ ID NO 3
<211> LENGTH: 10
<212> TYPE: PRT
<213> ORGANISM: Artificial
<220> FEATURE:
<223> OTHER INFORMATION: Description of sequence:  trafficking sequence
      L-TAT (s1b) (see Table 1)

<400> SEQUENCE: 3

Gly Arg Lys Lys Arg Arg Gln Arg Arg Arg
1               5                   10


<210> SEQ ID NO 4
<211> LENGTH: 9
<212> TYPE: PRT
<213> ORGANISM: Artificial Sequence
<220> FEATURE:
<223> OTHER INFORMATION: Description of sequence:  trafficking sequence
      D-TAT (see Table 1)
<220> FEATURE:
<221> NAME/KEY: VARIANT
<222> LOCATION: (1)..(9)
<223> OTHER INFORMATION: /replace="D-amino acid"

<400> SEQUENCE: 4

Arg Arg Arg Gln Arg Arg Lys Lys Arg
1               5
```

<210> SEQ ID NO 5
<211> LENGTH: 10
<212> TYPE: PRT
<213> ORGANISM: Artificial Sequence
<220> FEATURE:
<223> OTHER INFORMATION: Description of sequence: trafficking sequence
D-TAT (see Table 1)
<220> FEATURE:
<221> NAME/KEY: VARIANT
<222> LOCATION: (1)..(10)
<223> OTHER INFORMATION: /replace="D-amino acid"

<400> SEQUENCE: 5

Arg Arg Arg Gln Arg Arg Lys Lys Arg Gly
1 5 10

<210> SEQ ID NO 6
<211> LENGTH: 11
<212> TYPE: PRT
<213> ORGANISM: Artificial
<220> FEATURE:
<223> OTHER INFORMATION: Description of sequence: trafficking sequence
L-generic-TAT (s) (see Table 1)
<220> FEATURE:
<221> NAME/KEY: misc_feature
<223> OTHER INFORMATION: General formula: NH2-Xnb-RKKRRQRRR-Xnb-COOH
(see Table 1)
<220> FEATURE:
<221> NAME/KEY: VARIANT
<222> LOCATION: (1)..(1)
<223> OTHER INFORMATION: Xaa is Xnb as defined in the general formula,
wherein Xaa represents an amino acid residue, preferably selected
from any (native) amino acid residue;
<220> FEATURE:
<221> NAME/KEY: REPEAT
<222> LOCATION: (1)..(1)
<223> OTHER INFORMATION: Xaa is Xnb as defined in the general formula,
wherein n is 0-5, 5-10, 10-15, 15-20, 20-30 or more for Xnb
<220> FEATURE:
<221> NAME/KEY: VARIANT
<222> LOCATION: (11)..(11)
<223> OTHER INFORMATION: Xaa is Xnb as defined in the general formula,
wherein Xaa represents an amino acid residue, preferably selected
from any (native) amino acid residue;
<220> FEATURE:
<221> NAME/KEY: REPEAT
<222> LOCATION: (11)..(11)
<223> OTHER INFORMATION: Xaa is Xnb as defined in the general formula,
wherein n is 0-5, 5-10, 10-15, 15-20, 20-30 or more for Xnb

<400> SEQUENCE: 6

Xaa Arg Lys Lys Arg Arg Gln Arg Arg Arg Xaa
1 5 10

<210> SEQ ID NO 7
<211> LENGTH: 11
<212> TYPE: PRT
<213> ORGANISM: Artificial Sequence
<220> FEATURE:
<223> OTHER INFORMATION: Description of sequence: trafficking sequence
D-generic-TAT (s) (see Table 1)
<220> FEATURE:
<221> NAME/KEY: MISC_FEATURE
<223> OTHER INFORMATION: General formula: NH2-Xnb-rrrqrrkkr-Xnb-COOH
(see Table 1)
<220> FEATURE:
<221> NAME/KEY: VARIANT
<222> LOCATION: (1)..(1)
<223> OTHER INFORMATION: Xaa is Xnb as defined in the general formula,
wherein Xaa represents an amino acid residue, preferably selected
from any (native) amino acid residue;
<220> FEATURE:
<221> NAME/KEY: REPEAT
<222> LOCATION: (1)..(1)
<223> OTHER INFORMATION: Xaa is Xnb as defined in the general formula,

```
      wherein n is 0-5, 5-10, 10-15, 15-20, 20-30 or more for Xnb
<220> FEATURE:
<221> NAME/KEY: VARIANT
<222> LOCATION: (11)..(11)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (11)..(11)
<223> OTHER INFORMATION: Xaa is Xnb as defined in the general formula,
      wherein n is 0-5, 5-10, 10-15, 15-20, 20-30 or more for Xnb

<400> SEQUENCE: 7

Xaa Arg Arg Arg Gln Arg Arg Lys Lys Arg Xaa
1               5                   10


<210> SEQ ID NO 8
<211> LENGTH: 36
<212> TYPE: PRT
<213> ORGANISM: Human immunodeficiency virus type 1
<220> FEATURE:
<221> NAME/KEY: misc_feature
<223> OTHER INFORMATION: Description of sequence:  HIV-1 TAT sequence
      (aa 37-72)

<400> SEQUENCE: 8

Cys Phe Ile Thr Lys Ala Leu Gly Ile Ser Tyr Gly Arg Lys Lys Arg
1               5                   10                  15

Arg Gln Arg Arg Arg Pro Pro Gln Gly Ser Gln Thr His Gln Val Ser
            20                  25                  30

Leu Ser Lys Gln
        35


<210> SEQ ID NO 9
<211> LENGTH: 22
<212> TYPE: PRT
<213> ORGANISM: Human immunodeficiency virus type 1
<220> FEATURE:
<221> NAME/KEY: misc_feature
<223> OTHER INFORMATION: Description of sequence:  HIV-1 TAT sequence
      (aa 37-58)

<400> SEQUENCE: 9

Cys Phe Ile Thr Lys Ala Leu Gly Ile Ser Tyr Gly Arg Lys Lys Arg
1               5                   10                  15

Arg Gln Arg Arg Arg Pro
            20


<210> SEQ ID NO 10
<211> LENGTH: 24
<212> TYPE: PRT
<213> ORGANISM: Human immunodeficiency virus type 1
<220> FEATURE:
<221> NAME/KEY: misc_feature
<223> OTHER INFORMATION: Description of sequence:  HIV-1 TAT sequence
      (aa 38-58) including an additional N-terminal GCC

<400> SEQUENCE: 10

Phe Ile Thr Lys Ala Leu Gly Ile Ser Tyr Gly Arg Lys Lys Arg Arg
1               5                   10                  15

Gln Arg Arg Arg Pro Gly Gly Cys
            20


<210> SEQ ID NO 11
<211> LENGTH: 15
<212> TYPE: PRT
```

<213> ORGANISM: Human immunodeficiency virus type 1
<220> FEATURE:
<221> NAME/KEY: misc_feature
<223> OTHER INFORMATION: Description of sequence: HIV-1 TAT sequence (aa 47-58) including an additional C-terminal GCC

<400> SEQUENCE: 11

```
Cys Gly Gly Tyr Gly Arg Lys Lys Arg Arg Gln Arg Arg Arg Pro
1               5                   10                  15
```

<210> SEQ ID NO 12
<211> LENGTH: 15
<212> TYPE: PRT
<213> ORGANISM: Human immunodeficiency virus type 1
<220> FEATURE:
<221> NAME/KEY: misc_feature
<223> OTHER INFORMATION: Description of sequence: HIV-1 TAT sequence (aa 47-58) including an additional N-terminal GCC

<400> SEQUENCE: 12

```
Tyr Gly Arg Lys Lys Arg Arg Gln Arg Arg Arg Pro Gly Gly Cys
1               5                   10                  15
```

<210> SEQ ID NO 13
<211> LENGTH: 56
<212> TYPE: PRT
<213> ORGANISM: Human immunodeficiency virus type 1
<220> FEATURE:
<221> NAME/KEY: misc_feature
<223> OTHER INFORMATION: Description of sequence: HIV-1 TAT sequence (aa 1-72) including a mutated Cys to Ala residue at position 37

<400> SEQUENCE: 13

```
Met Glu Pro Val Asp Pro Arg Leu Glu Pro Trp Lys His Pro Gly Ser
1               5                   10                  15

Gln Pro Lys Thr Ala Phe Ile Thr Lys Ala Leu Gly Ile Ser Tyr Gly
            20                  25                  30

Arg Lys Lys Arg Arg Gln Arg Arg Arg Pro Pro Gln Gly Ser Gln Thr
        35                  40                  45

His Gln Val Ser Leu Ser Lys Gln
    50                  55
```

<210> SEQ ID NO 14
<211> LENGTH: 11
<212> TYPE: PRT
<213> ORGANISM: Artificial Sequence
<220> FEATURE:
<223> OTHER INFORMATION: Description of sequence: trafficking sequence L-TAT (s1c) (see Table 1)

<400> SEQUENCE: 14

```
Tyr Asp Arg Lys Lys Arg Arg Gln Arg Arg Arg
1               5                   10
```

<210> SEQ ID NO 15
<211> LENGTH: 9
<212> TYPE: PRT
<213> ORGANISM: Artificial Sequence
<220> FEATURE:
<223> OTHER INFORMATION: Description of sequence: trafficking sequence r3-L-TAT (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)

```
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 15

Arg Lys Lys Arg Arg Gln Arg Arg Arg
1               5


<210> SEQ ID NO 16
<211> LENGTH: 9
<212> TYPE: PRT
<213> ORGANISM: Artificial Sequence
<220> FEATURE:
<223> OTHER INFORMATION: Description of sequence:  trafficking sequence
      r3-L-TATi (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 16

Arg Arg Arg Gln Arg Arg Lys Lys Arg
1               5


<210> SEQ ID NO 17
<211> LENGTH: 9
<212> TYPE: PRT
<213> ORGANISM: Artificial Sequence
<220> FEATURE:
<223> OTHER INFORMATION: Description of sequence:  trafficking sequence
      betaA-r3-L-TAT (see Table 1)
<220> FEATURE:
<221> NAME/KEY: Variant
<222> LOCATION: (1)..(1)
<223> OTHER INFORMATION: /replace="D-amino acid"
<220> FEATURE:
<221> NAME/KEY: Variant
<222> LOCATION: (5)..(5)
<223> OTHER INFORMATION: /replace="D-amino acid"
<220> FEATURE:
<221> NAME/KEY: Variant
<222> LOCATION: (9)..(9)
<223> OTHER INFORMATION: /replace="D-amino acid"

<400> SEQUENCE: 17

Arg Lys Lys Arg Arg Gln Arg Arg Arg
1               5


<210> SEQ ID NO 18
<211> LENGTH: 9
<212> TYPE: PRT
<213> ORGANISM: Artificial Sequence
<220> FEATURE:
<223> OTHER INFORMATION: Description of sequence:  trafficking sequence
      betaA-r3-L-TATi (see Table 1)
<220> FEATURE:
<221> NAME/KEY: Variant
<222> LOCATION: (1)..(1)
<223> OTHER INFORMATION: /replace="D-amino acid"
<220> FEATURE:
<221> NAME/KEY: Variant
<222> LOCATION: (5)..(5)
<223> OTHER INFORMATION: /replace="D-amino acid"
```

<220> FEATURE:
<221> NAME/KEY: Variant
<222> LOCATION: (9)..(9)
<223> OTHER INFORMATION: /replace="D-amino acid"

<400> SEQUENCE: 18

Arg Arg Arg Gln Arg Arg Lys Lys Arg
1 5

<210> SEQ ID NO 19
<211> LENGTH: 9
<212> TYPE: PRT
<213> ORGANISM: Artificial Sequence
<220> FEATURE:
<223> OTHER INFORMATION: Description of sequence: trafficking sequence FITC-betaA-r3-L-TAT (see Table 1)
<220> FEATURE:
<221> NAME/KEY: Variant
<222> LOCATION: (1)..(1)
<223> OTHER INFORMATION: /replace="D-amino acid"
<220> FEATURE:
<221> NAME/KEY: Variant
<222> LOCATION: (5)..(5)
<223> OTHER INFORMATION: /replace="D-amino acid"
<220> FEATURE:
<221> NAME/KEY: Variant
<222> LOCATION: (9)..(9)
<223> OTHER INFORMATION: /replace="D-amino acid"

<400> SEQUENCE: 19

Arg Lys Lys Arg Arg Gln Arg Arg Arg
1 5

<210> SEQ ID NO 20
<211> LENGTH: 9
<212> TYPE: PRT
<213> ORGANISM: Artificial Sequence
<220> FEATURE:
<223> OTHER INFORMATION: Description of sequence: trafficking sequence FITC-betaA-r3-L-TATi (see Table 1)
<220> FEATURE:
<221> NAME/KEY: Variant
<222> LOCATION: (1)..(1)
<223> OTHER INFORMATION: /replace="D-amino acid"
<220> FEATURE:
<221> NAME/KEY: Variant
<222> LOCATION: (5)..(5)
<223> OTHER INFORMATION: /replace="D-amino acid"
<220> FEATURE:
<221> NAME/KEY: Variant
<222> LOCATION: (9)..(9)
<223> OTHER INFORMATION: /replace="D-amino acid"

<400> SEQUENCE: 20

Arg Arg Arg Gln Arg Arg Lys Lys Arg
1 5

<210> SEQ ID NO 21
<211> LENGTH: 9
<212> TYPE: PRT
<213> ORGANISM: Artificial Sequence
<220> FEATURE:
<223> OTHER INFORMATION: Description of sequence: trafficking sequence TAT(s2-1) (see Table 1)
<220> FEATURE:
<221> NAME/KEY: variant
<222> LOCATION: (1)..(1)
<223> OTHER INFORMATION: /replace="D-amino acid"
<220> FEATURE:
<221> NAME/KEY: variant
<222> LOCATION: (5)..(5)
<223> OTHER INFORMATION: /replace="D-amino acid"
<220> FEATURE:

<221> NAME/KEY: variant
<222> LOCATION: (9)..(9)
<223> OTHER INFORMATION: /replace="D-amino acid"

<400> SEQUENCE: 21

Arg Ala Lys Arg Arg Gln Arg Arg Arg
1               5

<210> SEQ ID NO 22
<211> LENGTH: 9
<212> TYPE: PRT
<213> ORGANISM: Artificial Sequence
<220> FEATURE:
<223> OTHER INFORMATION: Description of sequence: trafficking sequence
      TAT(s2-2) (see Table 1)
<220> FEATURE:
<221> NAME/KEY: Variant
<222> LOCATION: (1)..(1)
<223> OTHER INFORMATION: /replace="D-amino acid"
<220> FEATURE:
<221> NAME/KEY: Variant
<222> LOCATION: (5)..(5)
<223> OTHER INFORMATION: /replace="D-amino acid"
<220> FEATURE:
<221> NAME/KEY: Variant
<222> LOCATION: (9)..(9)
<223> OTHER INFORMATION: /replace="D-amino acid"

<400> SEQUENCE: 22

Arg Lys Ala Arg Arg Gln Arg Arg Arg
1               5

<210> SEQ ID NO 23
<211> LENGTH: 9
<212> TYPE: PRT
<213> ORGANISM: Artificial Sequence
<220> FEATURE:
<223> OTHER INFORMATION: Description of sequence: trafficking sequence
      TAT(s2-3) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<220> FEATURE:
<221> NAME/KEY: VARIANT
<222> LOCATION: (9)..(9)

<400> SEQUENCE: 23

Arg Lys Lys Ala Arg Gln Arg Arg Arg
1               5

<210> SEQ ID NO 24
<211> LENGTH: 9
<212> TYPE: PRT
<213> ORGANISM: Artificial Sequence
<220> FEATURE:
<223> OTHER INFORMATION: Description of sequence: trafficking sequence
      TAT(s2-4) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 24

Arg Lys Lys Arg Arg Ala Arg Arg Arg
1               5

<210> SEQ ID NO 25
<211> LENGTH: 9
<212> TYPE: PRT
<213> ORGANISM: Artificial Sequence
<220> FEATURE:
<223> OTHER INFORMATION: Description of sequence: trafficking sequence
      TAT(s2-5) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 25

Arg Lys Lys Arg Arg Gln Ala Arg Arg
1               5

<210> SEQ ID NO 26
<211> LENGTH: 9
<212> TYPE: PRT
<213> ORGANISM: Artificial Sequence
<220> FEATURE:
<223> OTHER INFORMATION: Description of sequence: trafficking sequence
      TAT(s2-6) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 26

Arg Lys Lys Arg Arg Gln Arg Ala Arg
1               5

<210> SEQ ID NO 27
<211> LENGTH: 9
<212> TYPE: PRT
<213> ORGANISM: Artificial Sequence
<220> FEATURE:
<223> OTHER INFORMATION: Description of sequence: trafficking sequence
      TAT(s2-7) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 27

Arg Asp Lys Arg Arg Gln Arg Arg Arg
1               5

<210> SEQ ID NO 28
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-8) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 28

Arg Lys Asp Arg Arg Gln Arg Arg Arg
1               5

<210> SEQ ID NO 29
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-9) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 29

Arg Lys Lys Asp Arg Gln Arg Arg Arg
1               5

<210> SEQ ID NO 30
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-10) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 30

```
Arg Lys Lys Arg Arg Asp Arg Arg Arg
1               5


<210> SEQ ID NO 31
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-11)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 31

Arg Lys Lys Arg Arg Gln Asp Arg Arg
1               5


<210> SEQ ID NO 32
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-12)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 32

Arg Lys Lys Arg Arg Gln Arg Asp Arg
1               5


<210> SEQ ID NO 33
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-13)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 33
```

```
Arg Glu Lys Arg Arg Gln Arg Arg Arg
1               5


<210> SEQ ID NO 34
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-14)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 34

Arg Lys Glu Arg Arg Gln Arg Arg Arg
1               5


<210> SEQ ID NO 35
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-15)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 35

Arg Lys Lys Glu Arg Gln Arg Arg Arg
1               5


<210> SEQ ID NO 36
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-16)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 36

Arg Lys Lys Arg Arg Glu Arg Arg Arg
```

1 5

<210> SEQ ID NO 37
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-17) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 37

Arg Lys Lys Arg Arg Gln Glu Arg Arg
1 5

<210> SEQ ID NO 38
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-18) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 38

Arg Lys Lys Arg Arg Gln Arg Glu Arg
1 5

<210> SEQ ID NO 39
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-19) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 39

Arg Phe Lys Arg Arg Gln Arg Arg Arg
1 5

<210> SEQ ID NO 40
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-20) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 40

Arg Lys Phe Arg Arg Gln Arg Arg Arg
1 5

<210> SEQ ID NO 41
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-21) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 41

Arg Lys Lys Phe Arg Gln Arg Arg Arg
1 5

<210> SEQ ID NO 42
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-22) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 42

Arg Lys Lys Arg Arg Phe Arg Arg Arg
1 5

```
<210> SEQ ID NO 43
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-23)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 43

Arg Lys Lys Arg Arg Gln Phe Arg Arg
1               5


<210> SEQ ID NO 44
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-24)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 44

Arg Lys Lys Arg Arg Gln Arg Phe Arg
1               5


<210> SEQ ID NO 45
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-25)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 45

Arg Arg Lys Arg Arg Gln Arg Arg Arg
1               5
```

<210> SEQ ID NO 46
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-26) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 46

Arg Lys Arg Arg Arg Gln Arg Arg Arg
1 5

<210> SEQ ID NO 47
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-27) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 47

Arg Lys Lys Lys Arg Gln Arg Arg Arg
1 5

<210> SEQ ID NO 48
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-28) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 48

Arg Lys Lys Arg Arg Arg Arg Arg Arg
1 5

<210> SEQ ID NO 49

<211> LENGTH: 9
<212> TYPE: PRT
<213> ORGANISM: Artificial Sequence
<220> FEATURE:
<223> OTHER INFORMATION: Description of sequence: trafficking sequence
TAT(s2-29) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 49

Arg Lys Lys Arg Arg Gln Lys Arg Arg
1               5

<210> SEQ ID NO 50
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-30) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 50

Arg Lys Lys Arg Arg Gln Arg Lys Arg
1               5

<210> SEQ ID NO 51
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-31) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 51

Arg His Lys Arg Arg Gln Arg Arg Arg
1               5

<210> SEQ ID NO 52
<211> LENGTH: 9

```
<212> TYPE: PRT
<213> ORGANISM: Artificial Sequence
<220> FEATURE:
<223> OTHER INFORMATION: Description of sequence:  trafficking sequence
      TAT(s2-32)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 52

Arg Lys His Arg Arg Gln Arg Arg Arg
1               5


<210> SEQ ID NO 53
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-33)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 53

Arg Lys Lys His Arg Gln Arg Arg Arg
1               5


<210> SEQ ID NO 54
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-34)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 54

Arg Lys Lys Arg Arg His Arg Arg Arg
1               5


<210> SEQ ID NO 55
<211> LENGTH: 9
<212> TYPE: PRT
```

<213> ORGANISM: Artificial Sequence
<220> FEATURE:
<223> OTHER INFORMATION: Description of sequence: trafficking sequence
TAT(s2-35) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 55

Arg Lys Lys Arg Arg Gln His Arg Arg
1 5

<210> SEQ ID NO 56
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-36) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 56

Arg Lys Lys Arg Arg Gln Arg His Arg
1 5

<210> SEQ ID NO 57
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-37) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 57

Arg Ile Lys Arg Arg Gln Arg Arg Arg
1 5

<210> SEQ ID NO 58
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-38) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 58

Arg Lys Ile Arg Arg Gln Arg Arg Arg
1               5

<210> SEQ ID NO 59
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-39) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 59

Arg Lys Lys Ile Arg Gln Arg Arg Arg
1               5

<210> SEQ ID NO 60
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-40) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 60

Arg Lys Lys Arg Arg Ile Arg Arg Arg
1               5

<210> SEQ ID NO 61
<211> LENGTH: 9
<212> TYPE: PRT
<213> ORGANISM: Artificial Sequence
<220> FEATURE:

<223> OTHER INFORMATION: Description of sequence: trafficking sequence
TAT(s2-41) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 61

Arg Lys Lys Arg Arg Gln Ile Arg Arg
1 5

<210> SEQ ID NO 62
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-42) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 62

Arg Lys Lys Arg Arg Gln Arg Ile Arg
1 5

<210> SEQ ID NO 63
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-43) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 63

Arg Leu Lys Arg Arg Gln Arg Arg Arg
1 5

<210> SEQ ID NO 64
<211> LENGTH: 9
<212> TYPE: PRT
<213> ORGANISM: Artificial Sequence
<220> FEATURE:
<223> OTHER INFORMATION: Description of sequence: trafficking sequence

```
      TAT(s2-44)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 64

Arg Lys Leu Arg Arg Gln Arg Arg Arg
1               5


<210> SEQ ID NO 65
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-45)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 65

Arg Lys Lys Leu Arg Gln Arg Arg Arg
1               5


<210> SEQ ID NO 66
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-46)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 66

Arg Lys Lys Arg Arg Leu Arg Arg Arg
1               5


<210> SEQ ID NO 67
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-47)  (see Table 1)
```

```
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 67

Arg Lys Lys Arg Arg Gln Leu Arg Arg
1               5


<210> SEQ ID NO 68
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-48)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 68

Arg Lys Lys Arg Arg Gln Arg Leu Arg
1               5


<210> SEQ ID NO 69
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-49)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 69

Arg Met Lys Arg Arg Gln Arg Arg Arg
1               5


<210> SEQ ID NO 70
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-50)  (see Table 1)
<220> FEATURE:
```

<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 70

Arg Lys Met Arg Arg Gln Arg Arg Arg
1               5

<210> SEQ ID NO 71
<211> LENGTH: 9
<212> TYPE: PRT
<213> ORGANISM: Artificial Sequence
<220> FEATURE:
<223> OTHER INFORMATION: Description of sequence: trafficking sequence
      TAT(s2-51) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 71

Arg Lys Lys Met Arg Gln Arg Arg Arg
1               5

<210> SEQ ID NO 72
<211> LENGTH: 9
<212> TYPE: PRT
<213> ORGANISM: Artificial Sequence
<220> FEATURE:
<223> OTHER INFORMATION: Description of sequence: trafficking sequence
      TAT(s2-52) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 72

Arg Lys Lys Arg Arg Met Arg Arg Arg
1               5

<210> SEQ ID NO 73
<211> LENGTH: 9
<212> TYPE: PRT
<213> ORGANISM: Artificial Sequence
<220> FEATURE:
<223> OTHER INFORMATION: Description of sequence: trafficking sequence
      TAT(s2-53) (see Table 1)
<220> FEATURE:
<221> NAME/KEY: VARIANT

```
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 73

Arg Lys Lys Arg Arg Gln Met Arg Arg
1               5


<210> SEQ ID NO 74
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-54)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 74

Arg Lys Lys Arg Arg Gln Arg Met Arg
1               5


<210> SEQ ID NO 75
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-55)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 75

Arg Asn Lys Arg Arg Gln Arg Arg Arg
1               5


<210> SEQ ID NO 76
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-56)  (see Table 1)
<220> FEATURE:
<221> NAME/KEY: VARIANT
<222> LOCATION: (1)..(1)
```

<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 76

Arg Lys Asn Arg Arg Gln Arg Arg Arg
1               5

<210> SEQ ID NO 77
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-57) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 77

Arg Lys Lys Asn Arg Gln Arg Arg Arg
1               5

<210> SEQ ID NO 78
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-58) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 78

Arg Lys Lys Arg Arg Asn Arg Arg Arg
1               5

<210> SEQ ID NO 79
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-59) (see Table 1)
<220> FEATURE:
<221> NAME/KEY: VARIANT
<222> LOCATION: (1)..(1)
<223> OTHER INFORMATION: /replace="D-amino acid"

```
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 79

Arg Lys Lys Arg Arg Gln Asn Arg Arg
1               5


<210> SEQ ID NO 80
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-60)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 80

Arg Lys Lys Arg Arg Gln Arg Asn Arg
1               5


<210> SEQ ID NO 81
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-61)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 81

Arg Gln Lys Arg Arg Gln Arg Arg Arg
1               5


<210> SEQ ID NO 82
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-62)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
```

```
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 82

Arg Lys Gln Arg Arg Gln Arg Arg Arg
1               5


<210> SEQ ID NO 83
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-63)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 83

Arg Lys Lys Gln Arg Gln Arg Arg Arg
1               5


<210> SEQ ID NO 84
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-64)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 84

Arg Lys Lys Arg Arg Lys Arg Arg Arg
1               5


<210> SEQ ID NO 85
<211> LENGTH: 9
<212> TYPE: PRT
<213> ORGANISM: Artificial Sequence
<220> FEATURE:
<223> OTHER INFORMATION: Description of sequence:  trafficking sequence
      TAT(s2-65)  (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
```

<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 85

Arg Lys Lys Arg Arg Gln Gln Arg Arg
1 5

<210> SEQ ID NO 86
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-66) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 86

Arg Lys Lys Arg Arg Gln Arg Gln Arg
1 5

<210> SEQ ID NO 87
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-67) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 87

Arg Ser Lys Arg Arg Gln Arg Arg Arg
1 5

<210> SEQ ID NO 88
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-68) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)

<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 88

Arg Lys Ser Arg Arg Gln Arg Arg Arg
1 5

<210> SEQ ID NO 89
<211> LENGTH: 9
<212> TYPE: PRT
<213> ORGANISM: Artificial Sequence
<220> FEATURE:
<223> OTHER INFORMATION: Description of sequence: trafficking sequence TAT(s2-69) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 89

Arg Lys Lys Ser Arg Gln Arg Arg Arg
1 5

<210> SEQ ID NO 90
<211> LENGTH: 9
<212> TYPE: PRT
<213> ORGANISM: Artificial Sequence
<220> FEATURE:
<223> OTHER INFORMATION: Description of sequence: trafficking sequence TAT(s2-70) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 90

Arg Lys Lys Arg Arg Ser Arg Arg Arg
1 5

<210> SEQ ID NO 91
<211> LENGTH: 9
<212> TYPE: PRT
<213> ORGANISM: Artificial Sequence
<220> FEATURE:
<223> OTHER INFORMATION: Description of sequence: trafficking sequence TAT(s2-71) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"

<220> FEATURE:
<221> NAME/KEY: VARIANT
<222> LOCATION: (9)..(9)
<223> OTHER INFORMATION: /replace="D-amino acid"

<400> SEQUENCE: 91

Arg Lys Lys Arg Arg Gln Ser Arg Arg
1 5

<210> SEQ ID NO 92
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-72) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 92

Arg Lys Lys Arg Arg Gln Arg Ser Arg
1 5

<210> SEQ ID NO 93
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-73) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 93

Arg Thr Lys Arg Arg Gln Arg Arg Arg
1 5

<210> SEQ ID NO 94
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-74) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:

<221> NAME/KEY: VARIANT
<222> LOCATION: (9)..(9)
<223> OTHER INFORMATION: /replace="D-amino acid"

<400> SEQUENCE: 94

Arg Lys Thr Arg Arg Gln Arg Arg Arg
1 5

<210> SEQ ID NO 95
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-75) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 95

Arg Lys Lys Thr Arg Gln Arg Arg Arg
1 5

<210> SEQ ID NO 96
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-76) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 96

Arg Lys Lys Arg Arg Thr Arg Arg Arg
1 5

<210> SEQ ID NO 97
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-77) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 97

Arg Lys Lys Arg Arg Gln Thr Arg Arg
1               5

<210> SEQ ID NO 98
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-78) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 98

Arg Lys Lys Arg Arg Gln Arg Thr Arg
1               5

<210> SEQ ID NO 99
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-79) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 99

Arg Val Lys Arg Arg Gln Arg Arg Arg
1               5

<210> SEQ ID NO 100
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-80) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)

<223> OTHER INFORMATION: /replace="D-amino acid"

<400> SEQUENCE: 100

Arg Lys Val Arg Arg Gln Arg Arg Arg
1               5

<210> SEQ ID NO 101
<211> LENGTH: 9
<212> TYPE: PRT
<213> ORGANISM: Artificial Sequence
<220> FEATURE:
<223> OTHER INFORMATION: Description of sequence: trafficking sequence TAT(s2-81) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 101

Arg Lys Lys Val Arg Gln Arg Arg Arg
1               5

<210> SEQ ID NO 102
<211> LENGTH: 9
<212> TYPE: PRT
<213> ORGANISM: Artificial Sequence
<220> FEATURE:
<223> OTHER INFORMATION: Description of sequence: trafficking sequence TAT(s2-82) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 102

Arg Lys Lys Arg Arg Val Arg Arg Arg
1               5

<210> SEQ ID NO 103
<211> LENGTH: 9
<212> TYPE: PRT
<213> ORGANISM: Artificial Sequence
<220> FEATURE:
<223> OTHER INFORMATION: Description of sequence: trafficking sequence TAT(s2-83) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 103

Arg Lys Lys Arg Arg Gln Val Arg Arg
1 5

<210> SEQ ID NO 104
<211> LENGTH: 9
<212> TYPE: PRT
<213> ORGANISM: Artificial Sequence
<220> FEATURE:
<223> OTHER INFORMATION: Description of sequence: trafficking sequence TAT(s2-84) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 104

Arg Lys Lys Arg Arg Gln Arg Val Arg
1 5

<210> SEQ ID NO 105
<211> LENGTH: 9
<212> TYPE: PRT
<213> ORGANISM: Artificial Sequence
<220> FEATURE:
<223> OTHER INFORMATION: Description of sequence: trafficking sequence TAT(s2-85) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 105

Arg Trp Lys Arg Arg Gln Arg Arg Arg
1 5

<210> SEQ ID NO 106
<211> LENGTH: 9
<212> TYPE: PRT
<213> ORGANISM: Artificial Sequence
<220> FEATURE:
<223> OTHER INFORMATION: Description of sequence: trafficking sequence TAT(s2-86) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 106

Arg Lys Trp Arg Arg Gln Arg Arg Arg
1               5

<210> SEQ ID NO 107
<211> LENGTH: 9
<212> TYPE: PRT
<213> ORGANISM: Artificial Sequence
<220> FEATURE:
<223> OTHER INFORMATION: Description of sequence: trafficking sequence
      TAT(s2-87) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 107

Arg Lys Lys Trp Arg Gln Arg Arg Arg
1               5

<210> SEQ ID NO 108
<211> LENGTH: 9
<212> TYPE: PRT
<213> ORGANISM: Artificial Sequence
<220> FEATURE:
<223> OTHER INFORMATION: Description of sequence: trafficking sequence
      TAT(s2-88) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 108

Arg Lys Lys Arg Arg Trp Arg Arg Arg
1               5

<210> SEQ ID NO 109
<211> LENGTH: 9
<212> TYPE: PRT
<213> ORGANISM: Artificial Sequence
<220> FEATURE:
<223> OTHER INFORMATION: Description of sequence: trafficking sequence
      TAT(s2-89) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 109

Arg Lys Lys Arg Arg Gln Trp Arg Arg
1 5

<210> SEQ ID NO 110
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-90) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 110

Arg Lys Lys Arg Arg Gln Arg Trp Arg
1 5

<210> SEQ ID NO 111
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-91) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 111

Arg Tyr Lys Arg Arg Gln Arg Arg Arg
1 5

<210> SEQ ID NO 112
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-92) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 112

Arg Lys Tyr Arg Arg Gln Arg Arg Arg
1 5

<210> SEQ ID NO 113
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-93) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 113

Arg Lys Lys Tyr Arg Gln Arg Arg Arg
1 5

<210> SEQ ID NO 114
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-94) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 114

Arg Lys Lys Arg Arg Tyr Arg Arg Arg
1 5

<210> SEQ ID NO 115
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-95) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 115

Arg Lys Lys Arg Arg Gln Tyr Arg Arg 1 5

<210> SEQ ID NO 116
<211> LENGTH: 9
<212> TYPE: PRT
<213> ORGANISM: Artificial Sequence
<220> FEATURE:
<223> OTHER INFORMATION: Description of sequence: trafficking sequence
TAT(s2-96) (see Table 1)
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (5)..(5)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 116

Arg Lys Lys Arg Arg Gln Arg Tyr Arg
1 5

<210> SEQ ID NO 117
<211> LENGTH: 2953
<212> TYPE: DNA
<213> ORGANISM: Rattus norvegicus
<220> FEATURE:
<221> NAME/KEY: misc_feature
<223> OTHER INFORMATION: description of sequence: rat IB1 cDNA sequence

<400> SEQUENCE: 117
ccgccccagc tcagtccgaa ccccgcggcg gcggcggcct cctccacacg cctccacctc 60
cgccgccgcc gccgccgccg ccgcctcccg cgccgctctc cgcccggatg gccaggctga 120
gcccgggaat ggcggagcga gagagcggcc tgagcggggg tgccgcgtcc ccaccggccg 180
cttccccatt cctgggactg cacatcgcgt cgcctcccaa tttcaggctc acccatgata 240
tcagcctgga ggagtttgag gatgaagacc tttcggagat cactgatgag tgtggcatca 300
gcctgcagtg caaagacacc ttgtctctcc ggcccccgcg cgccgggcta ctgtctgcgg 360
gtagcagcgg tagcgcgggg agccggctgc aggcggagat gctgcagatg gacctgatcg 420
acgcggcaag tgacactccg ggcgccgagg acgacgaaga ggacgacgac gagctcgctg 480
cccaacggcc aggagtgggg ccttccaaag ccgagtctgg ccaggagccg gcgtctcgca 540
gccagggtca gggccagggc cccggcacag gctgcggaga cacctaccgg cccaagaggc 600
ctaccacgct caacctttc ccgcaggtgc cgcggtctca ggacacgctg aataataact 660
ctttaggcaa aaagcacagt tggcaggacc gtgtgtctcg atcatcctcc cctctgaaga 720
caggggagca gacgcctcca catgaacata tctgcctgag tgatgagctg ccgccccagg 780
gcagtcctgt tcccacccag gatcgtggca cttccaccga cagcccttgt cgccgtactg 840
cagccaccca gatggcacct ccaagtggtc cccctgccac tgcacctggt ggccggggcc 900
actcccatcg agatcggtcc atatcagcag atgtgcggct cgaggcgact gaggagatct 960
acctgacccc agtgcagagg cccccagacc ctgcagaacc cacctccacc ttcttgccac 1020
ccactgagag ccggatgtct gtcagctcgg atcctgaccc tgccgcttac tctgtaactg 1080
cagggcgacc gcacccttcc atcagtgaag aggatgaggg cttcgactgt ctgtcatccc 1140
cagagcaagc tgagccacca ggtggagggt ggcggggaag cctcggggag ccaccaccgc 1200

-continued

```
ctccacgggc ctcactgagc tcggacacca gcgcactgtc ctacgactct gtcaagtaca   1260
cactggtggt ggatgagcat gcccagcttg agttggtgag cctgcggcca tgttttggag   1320
attacagtga cgaaagcgac tctgccactg tctatgacaa ctgtgcctct gcctcctcgc   1380
cctacgagtc agccattggt gaggaatatg aggaggcccc tcaaccccgg cctcccacct   1440
gcctgtcaga ggactccaca ccggatgagc ctgacgtcca cttctctaag aagtttctga   1500
atgtcttcat gagtggccgc tctcgttcct ccagtgccga gtcctttggg ctgttctcct   1560
gtgtcatcaa tggggaggag catgagcaaa cccatcgggc tatattcagg tttgtgcctc   1620
ggcatgaaga tgaacttgag ctggaagtgg acgaccctct gctggtggag ctgcaggcag   1680
aagactattg gtatgaggcc tataacatgc gcactggagc ccgtggtgtc tttcctgcct   1740
actatgccat tgaggtcacc aaggagcctg agcacatggc agcccttgcc aaaaacagcg   1800
actggattga ccagttccgg gtgaagttcc tgggctctgt ccaggttcct tatcacaagg   1860
gcaatgatgt cctctgtgct gctatgcaaa agatcgccac cacccgccgg ctcaccgtgc   1920
actttaaccc gccctccagc tgtgtccttg aaatcagcgt taggggtgtc aagataggtg   1980
tcaaagctga tgaagctcag gaggccaagg gaaataaatg tagccacttt ttccagctaa   2040
aaaacatctc tttctgtggg taccatccaa agaacaacaa gtactttggg tttatcacta   2100
agcaccctgc tgaccaccgg tttgcctgcc atgtctttgt gtctgaagat tccaccaaag   2160
ccctggcaga gtctgtgggg cgtgcatttc agcagttcta caagcaattt gtggaatata   2220
cctgtcctac agaagatatc tacttggagt agcagcaacc cccctctctg cagcccctca   2280
gccccaggcc agtactagga cagctgactg ctgacaggat gttgtactgc cacgagagaa   2340
tgggggagtg agggctgttg gggtcggggg gcaggggttt ggggagaggc agatgcagtt   2400
tattgtaata tatggggtta gattaatcta tggaggacag tacaggctct ctcggggctg   2460
gggaagggca gggctggggt gggggtcagg catctggcca caaaggggtc ccctagggac   2520
agaggcgctg caccatcctg ggcttgtttc atactagagg ccctggcttt ctggctcttg   2580
ggtcctgcct tgacaaagcc cagccacctg gaagtgtcac cttcccttgt ccacctcacc   2640
cagtgccctg agctcatgct gagcccaagc acctccgaag gactttccag taaggaaatg   2700
gcaacatgtg acagtgagac cctgttctca tctgtggggc tccggcagct ccgaccccca   2760
gcctggccag cacgctgacc ctggcaagct tgtgtgttca aagaaggaga gggccacagc   2820
aagccctgcc tgccagggaa ggttccctct cagctggccc cagccaactg gtcactgtct   2880
tgtcacctgg ctactactat taaagtgcca tttcttgtct gaaaaaaaaa aaaaaaaaaa   2940
aaaaaaactc gag                                                      2953
```

<210> SEQ ID NO 118
<211> LENGTH: 714
<212> TYPE: PRT
<213> ORGANISM: Rattus norvegicus
<220> FEATURE:
<221> NAME/KEY: misc_feature
<223> OTHER INFORMATION: description of sequence: amino acid sequence encoded by of rat IB1 cDNA sequence

<400> SEQUENCE: 118

```
Met Ala Arg Leu Ser Pro Gly Met Ala Glu Arg Glu Ser Gly Leu Ser
1               5                   10                  15

Gly Gly Ala Ala Ser Pro Pro Ala Ala Ser Pro Phe Leu Gly Leu His
            20                  25                  30

Ile Ala Ser Pro Pro Asn Phe Arg Leu Thr His Asp Ile Ser Leu Glu
```

```
        35                  40                  45

Glu Phe Glu Asp Glu Asp Leu Ser Glu Ile Thr Asp Glu Cys Gly Ile
    50                  55                  60

Ser Leu Gln Cys Lys Asp Thr Leu Ser Leu Arg Pro Pro Arg Ala Gly
65                  70                  75                  80

Leu Leu Ser Ala Gly Ser Ser Gly Ser Ala Gly Ser Arg Leu Gln Ala
                85                  90                  95

Glu Met Leu Gln Met Asp Leu Ile Asp Ala Ala Ser Asp Thr Pro Gly
            100                 105                 110

Ala Glu Asp Asp Glu Glu Asp Asp Asp Glu Leu Ala Ala Gln Arg Pro
        115                 120                 125

Gly Val Gly Pro Ser Lys Ala Glu Ser Gly Gln Glu Pro Ala Ser Arg
    130                 135                 140

Ser Gln Gly Gln Gly Gln Gly Pro Gly Thr Gly Cys Gly Asp Thr Tyr
145                 150                 155                 160

Arg Pro Lys Arg Pro Thr Thr Leu Asn Leu Phe Pro Gln Val Pro Arg
                165                 170                 175

Ser Gln Asp Thr Leu Asn Asn Asn Ser Leu Gly Lys Lys His Ser Trp
            180                 185                 190

Gln Asp Arg Val Ser Arg Ser Ser Ser Pro Leu Lys Thr Gly Glu Gln
        195                 200                 205

Thr Pro Pro His Glu His Ile Cys Leu Ser Asp Glu Leu Pro Pro Gln
    210                 215                 220

Gly Ser Pro Val Pro Thr Gln Asp Arg Gly Thr Ser Thr Asp Ser Pro
225                 230                 235                 240

Cys Arg Arg Thr Ala Ala Thr Gln Met Ala Pro Pro Ser Gly Pro Pro
                245                 250                 255

Ala Thr Ala Pro Gly Gly Arg Gly His Ser His Arg Asp Arg Ser Ile
            260                 265                 270

Ser Ala Asp Val Arg Leu Glu Ala Thr Glu Glu Ile Tyr Leu Thr Pro
        275                 280                 285

Val Gln Arg Pro Pro Asp Pro Ala Glu Pro Thr Ser Thr Phe Leu Pro
    290                 295                 300

Pro Thr Glu Ser Arg Met Ser Val Ser Ser Asp Pro Asp Pro Ala Ala
305                 310                 315                 320

Tyr Ser Val Thr Ala Gly Arg Pro His Pro Ser Ile Ser Glu Glu Asp
                325                 330                 335

Glu Gly Phe Asp Cys Leu Ser Ser Pro Glu Gln Ala Glu Pro Pro Gly
            340                 345                 350

Gly Gly Trp Arg Gly Ser Leu Gly Glu Pro Pro Pro Pro Pro Arg Ala
        355                 360                 365

Ser Leu Ser Ser Asp Thr Ser Ala Leu Ser Tyr Asp Ser Val Lys Tyr
    370                 375                 380

Thr Leu Val Val Asp Glu His Ala Gln Leu Glu Leu Val Ser Leu Arg
385                 390                 395                 400

Pro Cys Phe Gly Asp Tyr Ser Asp Glu Ser Asp Ser Ala Thr Val Tyr
                405                 410                 415

Asp Asn Cys Ala Ser Ala Ser Ser Pro Tyr Glu Ser Ala Ile Gly Glu
            420                 425                 430

Glu Tyr Glu Glu Ala Pro Gln Pro Arg Pro Pro Thr Cys Leu Ser Glu
        435                 440                 445

Asp Ser Thr Pro Asp Glu Pro Asp Val His Phe Ser Lys Lys Phe Leu
    450                 455                 460
```

Asn Val Phe Met Ser Gly Arg Ser Arg Ser Ser Ser Ala Glu Ser Phe
465 470 475 480

Gly Leu Phe Ser Cys Val Ile Asn Gly Glu Glu His Glu Gln Thr His
485 490 495

Arg Ala Ile Phe Arg Phe Val Pro Arg His Glu Asp Glu Leu Glu Leu
500 505 510

Glu Val Asp Asp Pro Leu Leu Val Glu Leu Gln Ala Glu Asp Tyr Trp
515 520 525

Tyr Glu Ala Tyr Asn Met Arg Thr Gly Ala Arg Gly Val Phe Pro Ala
530 535 540

Tyr Tyr Ala Ile Glu Val Thr Lys Glu Pro Glu His Met Ala Ala Leu
545 550 555 560

Ala Lys Asn Ser Asp Trp Ile Asp Gln Phe Arg Val Lys Phe Leu Gly
565 570 575

Ser Val Gln Val Pro Tyr His Lys Gly Asn Asp Val Leu Cys Ala Ala
580 585 590

Met Gln Lys Ile Ala Thr Thr Arg Arg Leu Thr Val His Phe Asn Pro
595 600 605

Pro Ser Ser Cys Val Leu Glu Ile Ser Val Arg Gly Val Lys Ile Gly
610 615 620

Val Lys Ala Asp Glu Ala Gln Glu Ala Lys Gly Asn Lys Cys Ser His
625 630 635 640

Phe Phe Gln Leu Lys Asn Ile Ser Phe Cys Gly Tyr His Pro Lys Asn
645 650 655

Asn Lys Tyr Phe Gly Phe Ile Thr Lys His Pro Ala Asp His Arg Phe
660 665 670

Ala Cys His Val Phe Val Ser Glu Asp Ser Thr Lys Ala Leu Ala Glu
675 680 685

Ser Val Gly Arg Ala Phe Gln Gln Phe Tyr Lys Gln Phe Val Glu Tyr
690 695 700

Thr Cys Pro Thr Glu Asp Ile Tyr Leu Glu
705 710

<210> SEQ ID NO 119
<211> LENGTH: 711
<212> TYPE: PRT
<213> ORGANISM: Homo sapiens
<220> FEATURE:
<221> NAME/KEY: misc_feature
<223> OTHER INFORMATION: description of sequence: human IB1 protein sequence
<220> FEATURE:
<221> NAME/KEY: misc_feature
<223> OTHER INFORMATION: description of sequence: human IB1 protein sequence

<400> SEQUENCE: 119

Met Ala Glu Arg Glu Ser Gly Gly Leu Gly Gly Gly Ala Ala Ser Pro
1 5 10 15

Pro Ala Ala Ser Pro Phe Leu Gly Leu His Ile Ala Ser Pro Pro Asn
20 25 30

Phe Arg Leu Thr His Asp Ile Ser Leu Glu Glu Phe Glu Asp Glu Asp
35 40 45

Leu Ser Glu Ile Thr Asp Glu Cys Gly Ile Ser Leu Gln Cys Lys Asp
50 55 60

Thr Leu Ser Leu Arg Pro Pro Arg Ala Gly Leu Leu Ser Ala Gly Gly
65 70 75 80

-continued

```
Gly Gly Ala Gly Ser Arg Leu Gln Ala Glu Met Leu Gln Met Asp Leu
                85                  90                  95

Ile Asp Ala Thr Gly Asp Thr Pro Gly Ala Glu Asp Asp Glu Glu Asp
            100                 105                 110

Asp Asp Glu Glu Arg Ala Ala Arg Arg Pro Gly Ala Gly Pro Pro Lys
        115                 120                 125

Ala Glu Ser Gly Gln Glu Pro Ala Ser Arg Gly Gln Gly Gln Ser Gln
    130                 135                 140

Gly Gln Ser Gln Gly Pro Gly Ser Gly Asp Thr Tyr Arg Pro Lys Arg
145                 150                 155                 160

Pro Thr Thr Leu Asn Leu Phe Pro Gln Val Pro Arg Ser Gln Asp Thr
                165                 170                 175

Leu Asn Asn Asn Ser Leu Gly Lys Lys His Ser Trp Gln Asp Arg Val
            180                 185                 190

Ser Arg Ser Ser Ser Pro Leu Lys Thr Gly Glu Gln Thr Pro Pro His
        195                 200                 205

Glu His Ile Cys Leu Ser Asp Glu Leu Pro Pro Gln Ser Gly Pro Ala
    210                 215                 220

Pro Thr Thr Asp Arg Gly Thr Ser Thr Asp Ser Pro Cys Arg Arg Ser
225                 230                 235                 240

Thr Ala Thr Gln Met Ala Pro Pro Gly Gly Pro Pro Ala Ala Pro Pro
                245                 250                 255

Gly Gly Arg Gly His Ser His Arg Asp Arg Ile His Tyr Gln Ala Asp
            260                 265                 270

Val Arg Leu Glu Ala Thr Glu Glu Ile Tyr Leu Thr Pro Val Gln Arg
        275                 280                 285

Pro Pro Asp Ala Ala Glu Pro Thr Ser Ala Phe Leu Pro Pro Thr Glu
    290                 295                 300

Ser Arg Met Ser Val Ser Ser Asp Pro Asp Pro Ala Ala Tyr Pro Ser
305                 310                 315                 320

Thr Ala Gly Arg Pro His Pro Ser Ile Ser Glu Glu Glu Glu Gly Phe
                325                 330                 335

Asp Cys Leu Ser Ser Pro Glu Arg Ala Glu Pro Pro Gly Gly Gly Trp
            340                 345                 350

Arg Gly Ser Leu Gly Glu Pro Pro Pro Pro Pro Arg Ala Ser Leu Ser
        355                 360                 365

Ser Asp Thr Ser Ala Leu Ser Tyr Asp Ser Val Lys Tyr Thr Leu Val
    370                 375                 380

Val Asp Glu His Ala Gln Leu Glu Leu Val Ser Leu Arg Pro Cys Phe
385                 390                 395                 400

Gly Asp Tyr Ser Asp Glu Ser Asp Ser Ala Thr Val Tyr Asp Asn Cys
                405                 410                 415

Ala Ser Val Ser Ser Pro Tyr Glu Ser Ala Ile Gly Glu Glu Tyr Glu
            420                 425                 430

Glu Ala Pro Arg Pro Gln Pro Pro Ala Cys Leu Ser Glu Asp Ser Thr
        435                 440                 445

Pro Asp Glu Pro Asp Val His Phe Ser Lys Lys Phe Leu Asn Val Phe
    450                 455                 460

Met Ser Gly Arg Ser Arg Ser Ser Ser Ala Glu Ser Phe Gly Leu Phe
465                 470                 475                 480

Ser Cys Ile Ile Asn Gly Glu Glu Gln Glu Gln Thr His Arg Ala Ile
                485                 490                 495
```

```
Phe Arg Phe Val Pro Arg His Glu Asp Glu Leu Glu Leu Glu Val Asp
            500                 505                 510

Asp Pro Leu Leu Val Glu Leu Gln Ala Glu Asp Tyr Trp Tyr Glu Ala
        515                 520                 525

Tyr Asn Met Arg Thr Gly Ala Arg Gly Val Phe Pro Ala Tyr Tyr Ala
    530                 535                 540

Ile Glu Val Thr Lys Glu Pro Glu His Met Ala Ala Leu Ala Lys Asn
545                 550                 555                 560

Ser Asp Trp Val Asp Gln Phe Arg Val Lys Phe Leu Gly Ser Val Gln
                565                 570                 575

Val Pro Tyr His Lys Gly Asn Asp Val Leu Cys Ala Ala Met Gln Lys
            580                 585                 590

Ile Ala Thr Thr Arg Arg Leu Thr Val His Phe Asn Pro Pro Ser Ser
        595                 600                 605

Cys Val Leu Glu Ile Ser Val Arg Gly Val Lys Ile Gly Val Lys Ala
    610                 615                 620

Asp Asp Ser Gln Glu Ala Lys Gly Asn Lys Cys Ser His Phe Phe Gln
625                 630                 635                 640

Leu Lys Asn Ile Ser Phe Cys Gly Tyr His Pro Lys Asn Asn Lys Tyr
                645                 650                 655

Phe Gly Phe Ile Thr Lys His Pro Ala Asp His Arg Phe Ala Cys His
            660                 665                 670

Val Phe Val Ser Glu Asp Ser Thr Lys Ala Leu Ala Glu Ser Val Gly
        675                 680                 685

Arg Ala Phe Gln Gln Phe Tyr Lys Gln Phe Val Glu Tyr Thr Cys Pro
    690                 695                 700

Thr Glu Asp Ile Tyr Leu Glu
705                 710


<210> SEQ ID NO 120
<211> LENGTH: 2136
<212> TYPE: DNA
<213> ORGANISM: Homo sapiens
<220> FEATURE:
<221> NAME/KEY: misc_feature
<223> OTHER INFORMATION: description of sequence: nucleic acid sequence
      encoding human IB1 protein

<400> SEQUENCE: 120

atggcggagc gagaaagcgg cggcctggga ggggggggccg cgtccccgcc cgccgcctcc      60

ccgttcctgg ggctgcacat cgcttcgcct cccaatttca ggctcaccca tgacatcagc     120

ctggaggagt ttgaggatga agacctctcg gagatcactg atgagtgtgg catcagctta     180

cagtgcaaag acaccctgtc cttacggccc ccgcgcgccg ggctgctctc tgcgggcggc     240

ggcggcgcgg ggagccggtt gcaggccgag atgctgcaga tggacctgat cgacgcgacg     300

ggggacactc ccggggccga ggacgacgag gaggacgacg acgaggagcg cgcggcccgg     360

cggccgggag cggggccgcc caaggccgag tccggccagg agccggcgtc ccgcggccag     420

ggccagagcc aaggccagag ccagggcccg ggcagcgggg acacgtaccg gcccaagcgg     480

cccaccacgc tcaacctctt tccgcaggtg ccgcggtctc aggacacact gaataataat     540

tctctgggca aaaagcacag ttggcaggat cgggtgtctc gatcatcctc acccctgaag     600

acaggggagc agacaccacc gcatgaacac atctgcctga gcgatgagct gcccccccag     660

agcggccccg cccccaccac agatcgaggc acctccaccg acagcccttg ccgccgcagc     720

acagccaccc agatggcacc tccgggtggt ccccctgctg ccccgcctgg gggtcggggc     780
```

```
cactcgcatc gagaccgaat ccactaccag gccgatgtgc gactagaggc cactgaggag    840

atctacctga ccccagtgca gaggccccca gacgctgcag agcccacctc cgccttcctg    900

ccgcccactg agagccggat gtcagtcagc tccgatccag accctgccgc ctacccctcc    960

acggcagggc ggccgcaccc ctccatcagt gaagaggaag agggcttcga ctgcctgtcg   1020

tccccagagc gggctgagcc cccaggcgga gggtggcggg ggagcctggg ggagccgccg   1080

ccacctccac gggcctctct gagctcggac accagcgccc tgtcctatga ctctgtcaag   1140

tacacgctgg tggtagatga gcatgcacag ctggagctgg tgagcctgcg gccgtgcttc   1200

ggagactaca gtgacgagag tgactctgcc accgtctatg acaactgtgc ctccgtctcc   1260

tcgccctatg agtcggccat cggagaggaa tatgaggagg ccccgcggcc ccagcccccct  1320

gcctgcctct ccgaggactc cacgcctgat gaacccgacg tccatttctc caagaaattc   1380

ctgaacgtct tcatgagtgg ccgctcccgc tcctccagtg ctgagtcctt cgggctgttc   1440

tcctgcatca tcaacgggga ggagcaggag cagacccacc gggccatatt caggtttgtg   1500

cctcgacacg aagacgaact tgagctggaa gtggatgacc ctctgctagt ggagctccag   1560

gctgaagact actggtacga ggcctacaac atgcgcactg gtgcccgggg tgtctttcct   1620

gcctattacg ccatcgaggt caccaaggag cccgagcaca tggcagccct ggccaaaaac   1680

agtgactggg tggaccagtt ccgggtgaag ttcctgggct cagtccaggt tccctatcac   1740

aagggcaatg acgtcctctg tgctgctatg caaaagattg ccaccacccg ccggctcacc   1800

gtgcacttta acccgccctc cagctgtgtc ctggagatca gcgtgcgggg tgtgaagata   1860

ggcgtcaagg ccgatgactc ccaggaggcc aaggggaata aatgtagcca ctttttccag   1920

ttaaaaaaca tctctttctg cggatatcat ccaaagaaca acaagtactt tgggttcatc   1980

accaagcacc ccgccgacca ccggtttgcc tgccacgtct ttgtgtctga agactccacc   2040

aaagccctgg cagagtccgt ggggagagca ttccagcagt tctacaagca gtttgtggag   2100

tacacctgcc ccacagaaga tatctacctg gagtag                            2136
```

<210> SEQ ID NO 121
<211> LENGTH: 19
<212> TYPE: PRT
<213> ORGANISM: Artificial
<220> FEATURE:
<223> OTHER INFORMATION: Description of sequence: Peptide L-IB1(s) (see Table 3)

<400> SEQUENCE: 121

```
Arg Pro Lys Arg Pro Thr Thr Leu Asn Leu Phe Pro Gln Val Pro Arg
1               5                   10                  15

Ser Gln Asp
```

<210> SEQ ID NO 122
<211> LENGTH: 19
<212> TYPE: PRT
<213> ORGANISM: Artificial
<220> FEATURE:
<223> OTHER INFORMATION: Description of sequence: Peptide D-IB1(s) (see Table 3)
<220> FEATURE:
<221> NAME/KEY: MUTAGEN
<222> LOCATION: (1)..(19)
<223> OTHER INFORMATION: all amino acids are D-amino acids

<400> SEQUENCE: 122

```
Asp Gln Ser Arg Pro Val Gln Pro Phe Leu Asn Leu Thr Thr Pro Arg
```

```
1               5                   10                  15

Lys Pro Arg


<210> SEQ ID NO 123
<211> LENGTH: 19
<212> TYPE: PRT
<213> ORGANISM: Artificial
<220> FEATURE:
<223> OTHER INFORMATION: Description of sequence: Peptide L-IB (generic)
      (s) (see Table 3)
<220> FEATURE:
<221> NAME/KEY: misc_feature
<223> OTHER INFORMATION: Description of sequence: Description of
      sequence: general formula: NH2-Xnb-Xna-RPTTLXLXXXXXXXQD-Xnb-COOH
      (see Table 1)
<220> FEATURE:
<221> NAME/KEY: misc_feature
<223> OTHER INFORMATION: Description of sequence: Description of
      sequence: general formula: NH2-Xnb-Xna-RPTTLXLXXXXXXXQD-Xnb-COOH
      (see Table 3)
<220> FEATURE:
<221> NAME/KEY: VARIANT
<222> LOCATION: (1)..(1)
<223> OTHER INFORMATION: Xaa is Xnb as defined in the general formula,
      wherein Xaa represents an amino acid residue, preferably selected
      from any (native) amino acid residue;
<220> FEATURE:
<221> NAME/KEY: REPEAT
<222> LOCATION: (1)..(1)
<223> OTHER INFORMATION: Xaa is Xnb as defined in the general formula,
      wherein n is 0-5, 5-10, 10-15, 15-20, 20-30 or more for Xnb
<220> FEATURE:
<221> NAME/KEY: VARIANT
<222> LOCATION: (2)..(2)
<223> OTHER INFORMATION: Xaa is Xna as defined in the general formula,
      wherein Xaa represents an amino acid residue, preferably selected
      from any (native) amino acid residue residue except serine and
      threonine
<220> FEATURE:
<221> NAME/KEY: REPEAT
<222> LOCATION: (2)..(2)
<223> OTHER INFORMATION: Xaa is Xna as defined in the general formula,
      wherein n is 0 or 1
<220> FEATURE:
<221> NAME/KEY: VARIANT
<222> LOCATION: (8)..(8)
<223> OTHER INFORMATION: Xaa represents an amino acid residue,
      preferably selected from any (native) amino acid residue;
<220> FEATURE:
<221> NAME/KEY: VARIANT
<222> LOCATION: (10)..(16)
<223> OTHER INFORMATION: Xaa represents an amino acid residue,
      preferably selected from any (native) amino acid residue;
<220> FEATURE:
<221> NAME/KEY: REPEAT
<222> LOCATION: (19)..(19)
<223> OTHER INFORMATION: Xaa is Xnb as defined in the general formula,
      wherein n is 0-5, 5-10, 10-15, 15-20, 20-30 or more for Xnb
<220> FEATURE:
<221> NAME/KEY: VARIANT
<222> LOCATION: (19)..(19)
<223> OTHER INFORMATION: Xaa is Xnb as defined in the general formula,
      wherein Xaa represents an amino acid residue, preferably selected
      from any (native) amino acid residue;

<400> SEQUENCE: 123

Xaa Xaa Arg Pro Thr Thr Leu Xaa Leu Xaa Xaa Xaa Xaa Xaa Xaa Xaa
1               5                   10                  15

Gln Asp Xaa


<210> SEQ ID NO 124
<211> LENGTH: 19
<212> TYPE: PRT
<213> ORGANISM: Artificial
```

<220> FEATURE:
<223> OTHER INFORMATION: Description of sequence: Peptide D-IB (generic) (s) (see Table 3)
<220> FEATURE:
<221> NAME/KEY: misc_feature
<223> OTHER INFORMATION: Description of sequence: general formula: NH2-Xnb-DQXXXXXXXLXLTTPR-Xna-Xnb-COOH,
<220> FEATURE:
<221> NAME/KEY: MUTAGEN
<222> LOCATION: (1)..(19)
<223> OTHER INFORMATION: all amino acids are D-amino acids
<220> FEATURE:
<221> NAME/KEY: VARIANT
<222> LOCATION: (1)..(11)
<223> OTHER INFORMATION: Xaa is Xnb as defined in the general formula, wherein Xaa represents an amino acid residue, preferably selected from any (native) amino acid residue;
<220> FEATURE:
<221> NAME/KEY: REPEAT
<222> LOCATION: (1)..(1)
<223> OTHER INFORMATION: Xaa is Xnb as defined in the general formula, wherein n is 0-5, 5-10, 10-15, 15-20, 20-30 or more for Xnb
<220> FEATURE:
<221> NAME/KEY: VARIANT
<222> LOCATION: (4)..(10)
<223> OTHER INFORMATION: Xaa represents an amino acid residue, preferably selected from any (native) amino acid residue;
<220> FEATURE:
<221> NAME/KEY: VARIANT
<222> LOCATION: (12)..(12)
<223> OTHER INFORMATION: Xaa represents an amino acid residue, preferably selected from any (native) amino acid residue;
<220> FEATURE:
<221> NAME/KEY: REPEAT
<222> LOCATION: (18)..(18)
<223> OTHER INFORMATION: Xaa is Xna as defined in the general formula, wherein n is 0 or 1
<220> FEATURE:
<221> NAME/KEY: VARIANT
<222> LOCATION: (18)..(18)
<223> OTHER INFORMATION: Xaa is Xna as defined in the general formula, wherein Xaa represents an amino acid residue, preferably selected from any (native) amino acid residue residue except serine and Threonine
<220> FEATURE:
<221> NAME/KEY: VARIANT
<222> LOCATION: (18)..(18)
<223> OTHER INFORMATION: Xaa is Xna as defined in the general formula, wherein Xaa represents an amino acid residue, preferably selected from any (native) amino acid residue residue except serine and threonine
<220> FEATURE:
<221> NAME/KEY: REPEAT
<222> LOCATION: (19)..(19)
<223> OTHER INFORMATION: Xaa is Xnb as defined in the general formula, wherein n is 0-5, 5-10, 10-15, 15-20, 20-30 or more for Xnb
<220> FEATURE:
<221> NAME/KEY: VARIANT
<222> LOCATION: (19)..(19)
<223> OTHER INFORMATION: Xaa is Xnb as defined in the general formula, wherein Xaa represents an amino acid residue, preferably selected from any (native) amino acid residue;

<400> SEQUENCE: 124

```
Xaa Asp Gln Xaa Xaa Xaa Xaa Xaa Xaa Xaa Leu Xaa Leu Thr Thr Pro
1               5                   10                  15

Arg Xaa Xaa
```

<210> SEQ ID NO 125
<211> LENGTH: 29
<212> TYPE: PRT
<213> ORGANISM: Artificial
<220> FEATURE:
<223> OTHER INFORMATION: Description of sequence: peptide IB1-long (see Table 3)

<400> SEQUENCE: 125

Pro Gly Thr Gly Cys Gly Asp Thr Tyr Arg Pro Lys Arg Pro Thr Thr
1 5 10 15

Leu Asn Leu Phe Pro Gln Val Pro Arg Ser Gln Asp Thr
20 25

<210> SEQ ID NO 126
<211> LENGTH: 27
<212> TYPE: PRT
<213> ORGANISM: Artificial
<220> FEATURE:
<223> OTHER INFORMATION: Description of sequence: Peptide IB2-long (see Table 3)

<400> SEQUENCE: 126

Ile Pro Ser Pro Ser Val Glu Glu Pro His Lys His Arg Pro Thr Thr
1 5 10 15

Leu Arg Leu Thr Thr Leu Gly Ala Gln Asp Ser
20 25

<210> SEQ ID NO 127
<211> LENGTH: 29
<212> TYPE: PRT
<213> ORGANISM: Artificial
<220> FEATURE:
<223> OTHER INFORMATION: Description of sequence: Peptide derived from c-Jun (see Table 3)

<400> SEQUENCE: 127

Gly Ala Tyr Gly Tyr Ser Asn Pro Lys Ile Leu Lys Gln Ser Met Thr
1 5 10 15

Leu Asn Leu Ala Asp Pro Val Gly Asn Leu Lys Pro His
20 25

<210> SEQ ID NO 128
<211> LENGTH: 29
<212> TYPE: PRT
<213> ORGANISM: Artificial
<220> FEATURE:
<223> OTHER INFORMATION: Description of sequence: Peptide derived from ATF2 (see Table 3)

<400> SEQUENCE: 128

Thr Asn Glu Asp His Leu Ala Val His Lys His Lys His Glu Met Thr
1 5 10 15

Leu Lys Phe Gly Pro Ala Arg Asn Asp Ser Val Ile Val
20 25

<210> SEQ ID NO 129
<211> LENGTH: 23
<212> TYPE: PRT
<213> ORGANISM: Artificial
<220> FEATURE:
<223> OTHER INFORMATION: Description of sequence: Peptide L-IB1 (see Table 3)

<400> SEQUENCE: 129

Asp Thr Tyr Arg Pro Lys Arg Pro Thr Thr Leu Asn Leu Phe Pro Gln
1 5 10 15

Val Pro Arg Ser Gln Asp Thr
20

<210> SEQ ID NO 130
<211> LENGTH: 23

<212> TYPE: PRT
<213> ORGANISM: Artificial
<220> FEATURE:
<223> OTHER INFORMATION: Description of sequence: Peptide D-IB1 (see Table 3)
<220> FEATURE:
<221> NAME/KEY: MUTAGEN
<222> LOCATION: (1)..(23)
<223> OTHER INFORMATION: all amino acids are D-amino acids

<400> SEQUENCE: 130

Thr Asp Gln Ser Arg Pro Val Gln Pro Phe Leu Asn Leu Thr Thr Pro
1               5                   10                  15

Arg Lys Pro Arg Tyr Thr Asp
            20

<210> SEQ ID NO 131
<211> LENGTH: 19
<212> TYPE: PRT
<213> ORGANISM: Artificial
<220> FEATURE:
<223> OTHER INFORMATION: Description of sequence: Peptide L-IB (generic) (see Table 3)
<220> FEATURE:
<221> NAME/KEY: VARIANT
<222> LOCATION: (1)..(1)
<223> OTHER INFORMATION: Xaa is selected from any amino acid residue,
<220> FEATURE:
<221> NAME/KEY: VARIANT
<222> LOCATION: (7)..(7)
<223> OTHER INFORMATION: Xaa is selected from any amino acid residue,
<220> FEATURE:
<221> NAME/KEY: VARIANT
<222> LOCATION: (9)..(15)
<223> OTHER INFORMATION: Xaa is selected from any amino acid residue,
<220> FEATURE:
<221> NAME/KEY: VARIANT
<222> LOCATION: (18)..(18)
<223> OTHER INFORMATION: Xaa is selected from serine or threonine,
<220> FEATURE:
<221> NAME/KEY: VARIANT
<222> LOCATION: (19)..(19)
<223> OTHER INFORMATION: Xaa is selected from any amino acid residue,

<400> SEQUENCE: 131

Xaa Arg Pro Thr Thr Leu Xaa Leu Xaa Xaa Xaa Xaa Xaa Xaa Xaa Gln
1               5                   10                  15

Asp Xaa Xaa

<210> SEQ ID NO 132
<211> LENGTH: 19
<212> TYPE: PRT
<213> ORGANISM: Artificial
<220> FEATURE:
<223> OTHER INFORMATION: Description of sequence: Peptide D-IB (generic) (see Table 3)
<220> FEATURE:
<221> NAME/KEY: MUTAGEN
<222> LOCATION: (1)..(19)
<223> OTHER INFORMATION: all amino acids are D-amino acids
<220> FEATURE:
<221> NAME/KEY: VARIANT
<222> LOCATION: (1)..(1)
<223> OTHER INFORMATION: Xaa is selected from any amino acid residue
<220> FEATURE:
<221> NAME/KEY: VARIANT
<222> LOCATION: (2)..(2)
<223> OTHER INFORMATION: Xaa is selected from serine or threonine
<220> FEATURE:
<221> NAME/KEY: VARIANT
<222> LOCATION: (5)..(11)
<223> OTHER INFORMATION: Xaa is selected from any amino acid residue
<220> FEATURE:

<221> NAME/KEY: VARIANT
<222> LOCATION: (13)..(13)
<223> OTHER INFORMATION: Xaa is selected from any amino acid residue
<220> FEATURE:
<221> NAME/KEY: VARIANT
<222> LOCATION: (19)..(19)
<223> OTHER INFORMATION: Xaa is selected from any amino acid residue

<400> SEQUENCE: 132

Xaa Xaa Asp Gln Xaa Xaa Xaa Xaa Xaa Xaa Xaa Leu Xaa Leu Thr Thr
1 5 10 15

Pro Arg Xaa

<210> SEQ ID NO 133
<211> LENGTH: 13
<212> TYPE: PRT
<213> ORGANISM: Artificial
<220> FEATURE:
<223> OTHER INFORMATION: Description of sequence: L-IB1(s1) (see Table 3)

<400> SEQUENCE: 133

Thr Leu Asn Leu Phe Pro Gln Val Pro Arg Ser Gln Asp
1 5 10

<210> SEQ ID NO 134
<211> LENGTH: 13
<212> TYPE: PRT
<213> ORGANISM: Artificial
<220> FEATURE:
<223> OTHER INFORMATION: Description of sequence: L-IB1(s2) (see Table 3)

<400> SEQUENCE: 134

Thr Thr Leu Asn Leu Phe Pro Gln Val Pro Arg Ser Gln
1 5 10

<210> SEQ ID NO 135
<211> LENGTH: 13
<212> TYPE: PRT
<213> ORGANISM: Artificial
<220> FEATURE:
<223> OTHER INFORMATION: Description of sequence: L-IB1(s3) (see Table 3)

<400> SEQUENCE: 135

Pro Thr Thr Leu Asn Leu Phe Pro Gln Val Pro Arg Ser
1 5 10

<210> SEQ ID NO 136
<211> LENGTH: 13
<212> TYPE: PRT
<213> ORGANISM: Artificial
<220> FEATURE:
<223> OTHER INFORMATION: Description of sequence: L-IB1(s4) (see Table 3)

<400> SEQUENCE: 136

Arg Pro Thr Thr Leu Asn Leu Phe Pro Gln Val Pro Arg
1 5 10

<210> SEQ ID NO 137
<211> LENGTH: 13
<212> TYPE: PRT
<213> ORGANISM: Artificial
<220> FEATURE:
<223> OTHER INFORMATION: Description of sequence: L-IB1(s5) (see Table 3)

<400> SEQUENCE: 137

Lys Arg Pro Thr Thr Leu Asn Leu Phe Pro Gln Val Pro
1 5 10

<210> SEQ ID NO 138
<211> LENGTH: 13
<212> TYPE: PRT
<213> ORGANISM: Artificial
<220> FEATURE:
<223> OTHER INFORMATION: Description of sequence: L-IB1(s6) (see Table 3)

<400> SEQUENCE: 138

Pro Lys Arg Pro Thr Thr Leu Asn Leu Phe Pro Gln Val
1 5 10

<210> SEQ ID NO 139
<211> LENGTH: 13
<212> TYPE: PRT
<213> ORGANISM: Artificial
<220> FEATURE:
<223> OTHER INFORMATION: Description of sequence: L-IB1(s7) (see Table 3)

<400> SEQUENCE: 139

Arg Pro Lys Arg Pro Thr Thr Leu Asn Leu Phe Pro Gln
1 5 10

<210> SEQ ID NO 140
<211> LENGTH: 12
<212> TYPE: PRT
<213> ORGANISM: Artificial
<220> FEATURE:
<223> OTHER INFORMATION: Description of sequence: L-IB1(s8) (see Table 3)

<400> SEQUENCE: 140

Leu Asn Leu Phe Pro Gln Val Pro Arg Ser Gln Asp
1 5 10

<210> SEQ ID NO 141
<211> LENGTH: 12
<212> TYPE: PRT
<213> ORGANISM: Artificial
<220> FEATURE:
<223> OTHER INFORMATION: Description of sequence: L-IB1(s9) (see Table 3)

<400> SEQUENCE: 141

Thr Leu Asn Leu Phe Pro Gln Val Pro Arg Ser Gln
1 5 10

<210> SEQ ID NO 142
<211> LENGTH: 12
<212> TYPE: PRT
<213> ORGANISM: Artificial
<220> FEATURE:
<223> OTHER INFORMATION: Description of sequence: L-IB1(s10) (see Table 3)

<400> SEQUENCE: 142

Thr Thr Leu Asn Leu Phe Pro Gln Val Pro Arg Ser
1 5 10

<210> SEQ ID NO 143
<211> LENGTH: 12

<212> TYPE: PRT
<213> ORGANISM: Artificial
<220> FEATURE:
<223> OTHER INFORMATION: Description of sequence: L-IB1(s11) (see Table 3)

<400> SEQUENCE: 143

Pro Thr Thr Leu Asn Leu Phe Pro Gln Val Pro Arg
1 5 10

<210> SEQ ID NO 144
<211> LENGTH: 12
<212> TYPE: PRT
<213> ORGANISM: Artificial
<220> FEATURE:
<223> OTHER INFORMATION: Description of sequence: L-IB1(s12) (see Table 3)

<400> SEQUENCE: 144

Arg Pro Thr Thr Leu Asn Leu Phe Pro Gln Val Pro
1 5 10

<210> SEQ ID NO 145
<211> LENGTH: 12
<212> TYPE: PRT
<213> ORGANISM: Artificial
<220> FEATURE:
<223> OTHER INFORMATION: Description of sequence: L-IB1(s13) (see Table 3)

<400> SEQUENCE: 145

Lys Arg Pro Thr Thr Leu Asn Leu Phe Pro Gln Val
1 5 10

<210> SEQ ID NO 146
<211> LENGTH: 12
<212> TYPE: PRT
<213> ORGANISM: Artificial
<220> FEATURE:
<223> OTHER INFORMATION: Description of sequence: L-IB1(s14) (see Table 3)

<400> SEQUENCE: 146

Pro Lys Arg Pro Thr Thr Leu Asn Leu Phe Pro Gln
1 5 10

<210> SEQ ID NO 147
<211> LENGTH: 12
<212> TYPE: PRT
<213> ORGANISM: Artificial
<220> FEATURE:
<223> OTHER INFORMATION: Description of sequence: L-IB1(s15) (see Table 3)

<400> SEQUENCE: 147

Arg Pro Lys Arg Pro Thr Thr Leu Asn Leu Phe Pro
1 5 10

<210> SEQ ID NO 148
<211> LENGTH: 11
<212> TYPE: PRT
<213> ORGANISM: Artificial
<220> FEATURE:
<223> OTHER INFORMATION: Description of sequence: L-IB1(s16) (see Table 3)

<400> SEQUENCE: 148

Asn Leu Phe Pro Gln Val Pro Arg Ser Gln Asp 1 5 10

<210> SEQ ID NO 149
<211> LENGTH: 11
<212> TYPE: PRT
<213> ORGANISM: Artificial
<220> FEATURE:
<223> OTHER INFORMATION: Description of sequence: L-IB1(s17) (see Table 3)

<400> SEQUENCE: 149

Leu Asn Leu Phe Pro Gln Val Pro Arg Ser Gln
1 5 10

<210> SEQ ID NO 150
<211> LENGTH: 11
<212> TYPE: PRT
<213> ORGANISM: Artificial
<220> FEATURE:
<223> OTHER INFORMATION: Description of sequence: L-IB1(s18) (see Table 3)

<400> SEQUENCE: 150

Thr Leu Asn Leu Phe Pro Gln Val Pro Arg Ser
1 5 10

<210> SEQ ID NO 151
<211> LENGTH: 11
<212> TYPE: PRT
<213> ORGANISM: Artificial
<220> FEATURE:
<223> OTHER INFORMATION: Description of sequence: L-IB1(s19) (see Table 3)

<400> SEQUENCE: 151

Thr Thr Leu Asn Leu Phe Pro Gln Val Pro Arg
1 5 10

<210> SEQ ID NO 152
<211> LENGTH: 11
<212> TYPE: PRT
<213> ORGANISM: Artificial
<220> FEATURE:
<223> OTHER INFORMATION: Description of sequence: L-IB1(s20) (see Table 3)

<400> SEQUENCE: 152

Pro Thr Thr Leu Asn Leu Phe Pro Gln Val Pro
1 5 10

<210> SEQ ID NO 153
<211> LENGTH: 11
<212> TYPE: PRT
<213> ORGANISM: Artificial
<220> FEATURE:
<223> OTHER INFORMATION: Description of sequence: L-IB1(s21) (see Table 3)

<400> SEQUENCE: 153

Arg Pro Thr Thr Leu Asn Leu Phe Pro Gln Val
1 5 10

<210> SEQ ID NO 154
<211> LENGTH: 11
<212> TYPE: PRT
<213> ORGANISM: Artificial
<220> FEATURE:
<223> OTHER INFORMATION: Description of sequence: L-IB1(s22) (see Table

3)

<400> SEQUENCE: 154

Lys Arg Pro Thr Thr Leu Asn Leu Phe Pro Gln
1 5 10

<210> SEQ ID NO 155
<211> LENGTH: 11
<212> TYPE: PRT
<213> ORGANISM: Artificial
<220> FEATURE:
<223> OTHER INFORMATION: Description of sequence: L-IB1(s23) (see Table 3)

<400> SEQUENCE: 155

Pro Lys Arg Pro Thr Thr Leu Asn Leu Phe Pro
1 5 10

<210> SEQ ID NO 156
<211> LENGTH: 11
<212> TYPE: PRT
<213> ORGANISM: Artificial
<220> FEATURE:
<223> OTHER INFORMATION: Description of sequence: L-IB1(s24) (see Table 3)

<400> SEQUENCE: 156

Arg Pro Lys Arg Pro Thr Thr Leu Asn Leu Phe
1 5 10

<210> SEQ ID NO 157
<211> LENGTH: 10
<212> TYPE: PRT
<213> ORGANISM: Artificial
<220> FEATURE:
<223> OTHER INFORMATION: Description of sequence: L-IB1(s25) (see Table 3)

<400> SEQUENCE: 157

Leu Phe Pro Gln Val Pro Arg Ser Gln Asp
1 5 10

<210> SEQ ID NO 158
<211> LENGTH: 10
<212> TYPE: PRT
<213> ORGANISM: Artificial
<220> FEATURE:
<223> OTHER INFORMATION: Description of sequence: L-IB1(s26) (see Table 3)

<400> SEQUENCE: 158

Asn Leu Phe Pro Gln Val Pro Arg Ser Gln
1 5 10

<210> SEQ ID NO 159
<211> LENGTH: 10
<212> TYPE: PRT
<213> ORGANISM: Artificial
<220> FEATURE:
<223> OTHER INFORMATION: Description of sequence: L-IB1(s27) (see Table 3)

<400> SEQUENCE: 159

Leu Asn Leu Phe Pro Gln Val Pro Arg Ser
1 5 10

<210> SEQ ID NO 160

<211> LENGTH: 10
<212> TYPE: PRT
<213> ORGANISM: Artificial
<220> FEATURE:
<223> OTHER INFORMATION: Description of sequence: L-IB1(s28) (see Table 3)

<400> SEQUENCE: 160

Thr Leu Asn Leu Phe Pro Gln Val Pro Arg
1 5 10

<210> SEQ ID NO 161
<211> LENGTH: 10
<212> TYPE: PRT
<213> ORGANISM: Artificial
<220> FEATURE:
<223> OTHER INFORMATION: Description of sequence: L-IB1(s29) (see Table 3)

<400> SEQUENCE: 161

Thr Thr Leu Asn Leu Phe Pro Gln Val Pro
1 5 10

<210> SEQ ID NO 162
<211> LENGTH: 10
<212> TYPE: PRT
<213> ORGANISM: Artificial
<220> FEATURE:
<223> OTHER INFORMATION: Description of sequence: L-IB1(s30) (see Table 3)

<400> SEQUENCE: 162

Pro Thr Thr Leu Asn Leu Phe Pro Gln Val
1 5 10

<210> SEQ ID NO 163
<211> LENGTH: 10
<212> TYPE: PRT
<213> ORGANISM: Artificial
<220> FEATURE:
<223> OTHER INFORMATION: Description of sequence: L-IB1(s31) (see Table 3)

<400> SEQUENCE: 163

Arg Pro Thr Thr Leu Asn Leu Phe Pro Gln
1 5 10

<210> SEQ ID NO 164
<211> LENGTH: 10
<212> TYPE: PRT
<213> ORGANISM: Artificial
<220> FEATURE:
<223> OTHER INFORMATION: Description of sequence: L-IB1(s32) (see Table 3)

<400> SEQUENCE: 164

Lys Arg Pro Thr Thr Leu Asn Leu Phe Pro
1 5 10

<210> SEQ ID NO 165
<211> LENGTH: 10
<212> TYPE: PRT
<213> ORGANISM: Artificial
<220> FEATURE:
<223> OTHER INFORMATION: Description of sequence: L-IB1(s33) (see Table 3)

<400> SEQUENCE: 165

```
Pro Lys Arg Pro Thr Thr Leu Asn Leu Phe
1               5                   10


<210> SEQ ID NO 166
<211> LENGTH: 10
<212> TYPE: PRT
<213> ORGANISM: Artificial
<220> FEATURE:
<223> OTHER INFORMATION: Description of sequence: L-IB1(s34) (see Table
      3)

<400> SEQUENCE: 166

Arg Pro Lys Arg Pro Thr Thr Leu Asn Leu
1               5                   10


<210> SEQ ID NO 167
<211> LENGTH: 13
<212> TYPE: PRT
<213> ORGANISM: Artificial
<220> FEATURE:
<223> OTHER INFORMATION: Description of sequence: D-IB1(s1) (see Table
      3)
<220> FEATURE:
<221> NAME/KEY: VARIANT
<222> LOCATION: (1)..(13)
<223> OTHER INFORMATION: /replace="D-amino acid"

<400> SEQUENCE: 167

Gln Pro Phe Leu Asn Leu Thr Thr Pro Arg Lys Pro Arg
1               5                   10


<210> SEQ ID NO 168
<211> LENGTH: 13
<212> TYPE: PRT
<213> ORGANISM: Artificial
<220> FEATURE:
<223> OTHER INFORMATION: Description of sequence: D-IB1(s2) (see Table
      3)
<220> FEATURE:
<221> NAME/KEY: VARIANT
<222> LOCATION: (1)..(13)
<223> OTHER INFORMATION: /replace="D-amino acid"

<400> SEQUENCE: 168

Val Gln Pro Phe Leu Asn Leu Thr Thr Pro Arg Lys Pro
1               5                   10


<210> SEQ ID NO 169
<211> LENGTH: 13
<212> TYPE: PRT
<213> ORGANISM: Artificial
<220> FEATURE:
<223> OTHER INFORMATION: Description of sequence: D-IB1(s3) (see Table
      3)
<220> FEATURE:
<221> NAME/KEY: VARIANT
<222> LOCATION: (1)..(13)
<223> OTHER INFORMATION: /replace="D-amino acid"

<400> SEQUENCE: 169

Pro Val Gln Pro Phe Leu Asn Leu Thr Thr Pro Arg Lys
1               5                   10


<210> SEQ ID NO 170
<211> LENGTH: 13
<212> TYPE: PRT
<213> ORGANISM: Artificial
<220> FEATURE:
<223> OTHER INFORMATION: Description of sequence: D-IB1(s4) (see Table
      3)
```

```
<220> FEATURE:
<221> NAME/KEY: VARIANT
<222> LOCATION: (1)..(13)
<223> OTHER INFORMATION: /replace="D-amino acid"

<400> SEQUENCE: 170

Arg Pro Val Gln Pro Phe Leu Asn Leu Thr Thr Pro Arg
1               5                   10


<210> SEQ ID NO 171
<211> LENGTH: 13
<212> TYPE: PRT
<213> ORGANISM: Artificial
<220> FEATURE:
<223> OTHER INFORMATION: Description of sequence: D-IB1(s5) (see Table
      3)
<220> FEATURE:
<221> NAME/KEY: VARIANT
<222> LOCATION: (1)..(13)
<223> OTHER INFORMATION: /replace="D-amino acid"

<400> SEQUENCE: 171

Ser Arg Pro Val Gln Pro Phe Leu Asn Leu Thr Thr Pro
1               5                   10


<210> SEQ ID NO 172
<211> LENGTH: 13
<212> TYPE: PRT
<213> ORGANISM: Artificial
<220> FEATURE:
<223> OTHER INFORMATION: Description of sequence: D-IB1(s6) (see Table
      3)
<220> FEATURE:
<221> NAME/KEY: VARIANT
<222> LOCATION: (1)..(13)
<223> OTHER INFORMATION: /replace="D-amino acid"

<400> SEQUENCE: 172

Gln Ser Arg Pro Val Gln Pro Phe Leu Asn Leu Thr Thr
1               5                   10


<210> SEQ ID NO 173
<211> LENGTH: 13
<212> TYPE: PRT
<213> ORGANISM: Artificial
<220> FEATURE:
<223> OTHER INFORMATION: Description of sequence: D-IB1(s7) (see Table
      3)
<220> FEATURE:
<221> NAME/KEY: VARIANT
<222> LOCATION: (1)..(13)
<223> OTHER INFORMATION: /replace="D-amino acid"

<400> SEQUENCE: 173

Asp Gln Ser Arg Pro Val Gln Pro Phe Leu Asn Leu Thr
1               5                   10


<210> SEQ ID NO 174
<211> LENGTH: 12
<212> TYPE: PRT
<213> ORGANISM: Artificial
<220> FEATURE:
<223> OTHER INFORMATION: Description of sequence: D-IB1(s8) (see Table
      3)
<220> FEATURE:
<221> NAME/KEY: VARIANT
<222> LOCATION: (1)..(12)
<223> OTHER INFORMATION: /replace="D-amino acid"

<400> SEQUENCE: 174
```

Pro Phe Leu Asn Leu Thr Thr Pro Arg Lys Pro Arg
1 5 10

<210> SEQ ID NO 175
<211> LENGTH: 12
<212> TYPE: PRT
<213> ORGANISM: Artificial
<220> FEATURE:
<223> OTHER INFORMATION: Description of sequence: D-IB1(s9) (see Table 3)
<220> FEATURE:
<221> NAME/KEY: VARIANT
<222> LOCATION: (1)..(12)
<223> OTHER INFORMATION: /replace="D-amino acid"

<400> SEQUENCE: 175

Gln Pro Phe Leu Asn Leu Thr Thr Pro Arg Lys Pro
1 5 10

<210> SEQ ID NO 176
<211> LENGTH: 12
<212> TYPE: PRT
<213> ORGANISM: Artificial
<220> FEATURE:
<223> OTHER INFORMATION: Description of sequence: D-IB1(s10) (see Table 3)
<220> FEATURE:
<221> NAME/KEY: VARIANT
<222> LOCATION: (1)..(12)
<223> OTHER INFORMATION: /replace="D-amino acid"

<400> SEQUENCE: 176

Val Gln Pro Phe Leu Asn Leu Thr Thr Pro Arg Lys
1 5 10

<210> SEQ ID NO 177
<211> LENGTH: 12
<212> TYPE: PRT
<213> ORGANISM: Artificial
<220> FEATURE:
<223> OTHER INFORMATION: Description of sequence: D-IB1(s11) (see Table 3)
<220> FEATURE:
<221> NAME/KEY: VARIANT
<222> LOCATION: (1)..(12)
<223> OTHER INFORMATION: /replace="D-amino acid"

<400> SEQUENCE: 177

Pro Val Gln Pro Phe Leu Asn Leu Thr Thr Pro Arg
1 5 10

<210> SEQ ID NO 178
<211> LENGTH: 12
<212> TYPE: PRT
<213> ORGANISM: Artificial
<220> FEATURE:
<223> OTHER INFORMATION: Description of sequence: D-IB1(s12) (see Table 3)
<220> FEATURE:
<221> NAME/KEY: VARIANT
<222> LOCATION: (1)..(12)
<223> OTHER INFORMATION: /replace="D-amino acid"

<400> SEQUENCE: 178

Arg Pro Val Gln Pro Phe Leu Asn Leu Thr Thr Pro
1 5 10

<210> SEQ ID NO 179
<211> LENGTH: 12
<212> TYPE: PRT

<213> ORGANISM: Artificial
<220> FEATURE:
<223> OTHER INFORMATION: Description of sequence: D-IB1(s13) (see Table 3)
<220> FEATURE:
<221> NAME/KEY: VARIANT
<222> LOCATION: (1)..(12)
<223> OTHER INFORMATION: /replace="D-amino acid"

<400> SEQUENCE: 179

Ser Arg Pro Val Gln Pro Phe Leu Asn Leu Thr Thr
1 5 10

<210> SEQ ID NO 180
<211> LENGTH: 12
<212> TYPE: PRT
<213> ORGANISM: Artificial
<220> FEATURE:
<223> OTHER INFORMATION: Description of sequence: D-IB1(s14) (see Table 3)
<220> FEATURE:
<221> NAME/KEY: VARIANT
<222> LOCATION: (1)..(12)
<223> OTHER INFORMATION: /replace="D-amino acid"

<400> SEQUENCE: 180

Gln Ser Arg Pro Val Gln Pro Phe Leu Asn Leu Thr
1 5 10

<210> SEQ ID NO 181
<211> LENGTH: 12
<212> TYPE: PRT
<213> ORGANISM: Artificial
<220> FEATURE:
<223> OTHER INFORMATION: Description of sequence: D-IB1(s15) (see Table 3)
<220> FEATURE:
<221> NAME/KEY: VARIANT
<222> LOCATION: (1)..(12)
<223> OTHER INFORMATION: /replace="D-amino acid"

<400> SEQUENCE: 181

Asp Gln Ser Arg Pro Val Gln Pro Phe Leu Asn Leu
1 5 10

<210> SEQ ID NO 182
<211> LENGTH: 11
<212> TYPE: PRT
<213> ORGANISM: Artificial
<220> FEATURE:
<223> OTHER INFORMATION: Description of sequence: D-IB1(s16) (see Table 3)
<220> FEATURE:
<221> NAME/KEY: VARIANT
<222> LOCATION: (1)..(11)
<223> OTHER INFORMATION: /replace="D-amino acid"

<400> SEQUENCE: 182

Phe Leu Asn Leu Thr Thr Pro Arg Lys Pro Arg
1 5 10

<210> SEQ ID NO 183
<211> LENGTH: 11
<212> TYPE: PRT
<213> ORGANISM: Artificial
<220> FEATURE:
<223> OTHER INFORMATION: Description of sequence: D-IB1(s17) (see Table 3)
<220> FEATURE:
<221> NAME/KEY: VARIANT
<222> LOCATION: (1)..(11)

<223> OTHER INFORMATION: /replace="D-amino acid"

<400> SEQUENCE: 183

Pro Phe Leu Asn Leu Thr Thr Pro Arg Lys Pro
1 5 10

<210> SEQ ID NO 184
<211> LENGTH: 11
<212> TYPE: PRT
<213> ORGANISM: Artificial
<220> FEATURE:
<223> OTHER INFORMATION: Description of sequence: D-IB1(s18) (see Table 3)
<220> FEATURE:
<221> NAME/KEY: VARIANT
<222> LOCATION: (1)..(11)
<223> OTHER INFORMATION: /replace="D-amino acid"

<400> SEQUENCE: 184

Gln Pro Phe Leu Asn Leu Thr Thr Pro Arg Lys
1 5 10

<210> SEQ ID NO 185
<211> LENGTH: 11
<212> TYPE: PRT
<213> ORGANISM: Artificial
<220> FEATURE:
<223> OTHER INFORMATION: Description of sequence: D-IB1(s19) (see Table 3)
<220> FEATURE:
<221> NAME/KEY: VARIANT
<222> LOCATION: (1)..(11)
<223> OTHER INFORMATION: /replace="D-amino acid"

<400> SEQUENCE: 185

Val Gln Pro Phe Leu Asn Leu Thr Thr Pro Arg
1 5 10

<210> SEQ ID NO 186
<211> LENGTH: 11
<212> TYPE: PRT
<213> ORGANISM: Artificial
<220> FEATURE:
<223> OTHER INFORMATION: Description of sequence: D-IB1(s20) (see Table 3)
<220> FEATURE:
<221> NAME/KEY: VARIANT
<222> LOCATION: (1)..(11)
<223> OTHER INFORMATION: /replace="D-amino acid"

<400> SEQUENCE: 186

Pro Val Gln Pro Phe Leu Asn Leu Thr Thr Pro
1 5 10

<210> SEQ ID NO 187
<211> LENGTH: 11
<212> TYPE: PRT
<213> ORGANISM: Artificial
<220> FEATURE:
<223> OTHER INFORMATION: Description of sequence: D-IB1(s21) (see Table 3)
<220> FEATURE:
<221> NAME/KEY: VARIANT
<222> LOCATION: (1)..(11)
<223> OTHER INFORMATION: /replace="D-amino acid"

<400> SEQUENCE: 187

Arg Pro Val Gln Pro Phe Leu Asn Leu Thr Thr
1 5 10

<210> SEQ ID NO 188
<211> LENGTH: 11
<212> TYPE: PRT
<213> ORGANISM: Artificial
<220> FEATURE:
<223> OTHER INFORMATION: Description of sequence: D-IB1(s22) (see Table
3)
<220> FEATURE:
<221> NAME/KEY: VARIANT
<222> LOCATION: (1)..(11)
<223> OTHER INFORMATION: /replace="D-amino acid"

<400> SEQUENCE: 188

Ser Arg Pro Val Gln Pro Phe Leu Asn Leu Thr
1 5 10

<210> SEQ ID NO 189
<211> LENGTH: 11
<212> TYPE: PRT
<213> ORGANISM: Artificial
<220> FEATURE:
<223> OTHER INFORMATION: Description of sequence: D-IB1(s23) (see Table
3)
<220> FEATURE:
<221> NAME/KEY: VARIANT
<222> LOCATION: (1)..(11)
<223> OTHER INFORMATION: /replace="D-amino acid"

<400> SEQUENCE: 189

Gln Ser Arg Pro Val Gln Pro Phe Leu Asn Leu
1 5 10

<210> SEQ ID NO 190
<211> LENGTH: 11
<212> TYPE: PRT
<213> ORGANISM: Artificial
<220> FEATURE:
<223> OTHER INFORMATION: Description of sequence: D-IB1(s24) (see Table
3)
<220> FEATURE:
<221> NAME/KEY: VARIANT
<222> LOCATION: (1)..(11)
<223> OTHER INFORMATION: /replace="D-amino acid"

<400> SEQUENCE: 190

Asp Gln Ser Arg Pro Val Gln Pro Phe Leu Asn
1 5 10

<210> SEQ ID NO 191
<211> LENGTH: 10
<212> TYPE: PRT
<213> ORGANISM: Artificial
<220> FEATURE:
<223> OTHER INFORMATION: Description of sequence: D-IB1(s25) (see Table
3)
<220> FEATURE:
<221> NAME/KEY: VARIANT
<222> LOCATION: (1)..(10)
<223> OTHER INFORMATION: /replace="D-amino acid"

<400> SEQUENCE: 191

Asp Gln Ser Arg Pro Val Gln Pro Phe Leu
1 5 10

<210> SEQ ID NO 192
<211> LENGTH: 10
<212> TYPE: PRT
<213> ORGANISM: Artificial
<220> FEATURE:
<223> OTHER INFORMATION: Description of sequence: D-IB1(s26) (see Table 1)
<220> FEATURE:
<221> NAME/KEY: VARIANT
<222> LOCATION: (1)..(10)
<223> OTHER INFORMATION: /replace="D-amino acid"

<400> SEQUENCE: 192

Gln Ser Arg Pro Val Gln Pro Phe Leu Asn
1 5 10

<210> SEQ ID NO 193
<211> LENGTH: 10
<212> TYPE: PRT
<213> ORGANISM: Artificial
<220> FEATURE:
<223> OTHER INFORMATION: Description of sequence: D-IB1(s27) (see Table 3)
<220> FEATURE:
<221> NAME/KEY: VARIANT
<222> LOCATION: (1)..(10)
<223> OTHER INFORMATION: /replace="D-amino acid"

<400> SEQUENCE: 193

Ser Arg Pro Val Gln Pro Phe Leu Asn Leu
1 5 10

<210> SEQ ID NO 194
<211> LENGTH: 10
<212> TYPE: PRT
<213> ORGANISM: Artificial
<220> FEATURE:
<223> OTHER INFORMATION: Description of sequence: D-IB1(s28) (see Table 3)
<220> FEATURE:
<221> NAME/KEY: VARIANT
<222> LOCATION: (1)..(10)
<223> OTHER INFORMATION: /replace="D-amino acid"

<400> SEQUENCE: 194

Arg Pro Val Gln Pro Phe Leu Asn Leu Thr
1 5 10

<210> SEQ ID NO 195
<211> LENGTH: 10
<212> TYPE: PRT
<213> ORGANISM: Artificial
<220> FEATURE:
<223> OTHER INFORMATION: Description of sequence: D-IB1(s29) (see Table 3)
<220> FEATURE:
<221> NAME/KEY: VARIANT
<222> LOCATION: (1)..(10)
<223> OTHER INFORMATION: /replace="D-amino acid"

<400> SEQUENCE: 195

Pro Val Gln Pro Phe Leu Asn Leu Thr Thr
1 5 10

<210> SEQ ID NO 196
<211> LENGTH: 10
<212> TYPE: PRT
<213> ORGANISM: Artificial
<220> FEATURE:
<223> OTHER INFORMATION: Description of sequence: D-IB1(s30) (see Table 3)
<220> FEATURE:
<221> NAME/KEY: VARIANT
<222> LOCATION: (1)..(10)
<223> OTHER INFORMATION: /replace="D-amino acid"

<400> SEQUENCE: 196

```
Val Gln Pro Phe Leu Asn Leu Thr Thr Pro
1               5                   10


<210> SEQ ID NO 197
<211> LENGTH: 10
<212> TYPE: PRT
<213> ORGANISM: Artificial
<220> FEATURE:
<223> OTHER INFORMATION: Description of sequence: D-IB1(s31) (see Table
      3)
<220> FEATURE:
<221> NAME/KEY: VARIANT
<222> LOCATION: (1)..(10)
<223> OTHER INFORMATION: /replace="D-amino acid"

<400> SEQUENCE: 197

Gln Pro Phe Leu Asn Leu Thr Thr Pro Arg
1               5                   10


<210> SEQ ID NO 198
<211> LENGTH: 10
<212> TYPE: PRT
<213> ORGANISM: Artificial
<220> FEATURE:
<223> OTHER INFORMATION: Description of sequence: D-IB1(s32) (see Table
      3)
<220> FEATURE:
<221> NAME/KEY: VARIANT
<222> LOCATION: (1)..(10)
<223> OTHER INFORMATION: /replace="D-amino acid"

<400> SEQUENCE: 198

Pro Phe Leu Asn Leu Thr Thr Pro Arg Lys
1               5                   10


<210> SEQ ID NO 199
<211> LENGTH: 10
<212> TYPE: PRT
<213> ORGANISM: Artificial
<220> FEATURE:
<223> OTHER INFORMATION: Description of sequence: D-IB1(s33) (see Table
      3)
<220> FEATURE:
<221> NAME/KEY: VARIANT
<222> LOCATION: (1)..(10)
<223> OTHER INFORMATION: /replace="D-amino acid"

<400> SEQUENCE: 199

Phe Leu Asn Leu Thr Thr Pro Arg Lys Pro
1               5                   10


<210> SEQ ID NO 200
<211> LENGTH: 10
<212> TYPE: PRT
<213> ORGANISM: Artificial
<220> FEATURE:
<223> OTHER INFORMATION: Description of sequence: D-IB1(s34) (see Table
      3)
<220> FEATURE:
<221> NAME/KEY: VARIANT
<222> LOCATION: (1)..(10)
<223> OTHER INFORMATION: /replace="D-amino acid"

<400> SEQUENCE: 200

Leu Asn Leu Thr Thr Pro Arg Lys Pro Arg
1               5                   10


<210> SEQ ID NO 201
<211> LENGTH: 241
```

<212> TYPE: PRT
<213> ORGANISM: Homo sapiens
<220> FEATURE:
<221> NAME/KEY: MISC_FEATURE
<223> OTHER INFORMATION: Description of sequence: amino acid sequence of Bid (human) (transcript variant 1)

<400> SEQUENCE: 201

```
Met Cys Ser Gly Ala Gly Val Met Met Ala Arg Trp Ala Ala Arg Gly
1               5                   10                  15

Arg Ala Gly Trp Arg Ser Thr Val Arg Ile Leu Ser Pro Leu Gly His
            20                  25                  30

Cys Glu Pro Gly Val Ser Arg Ser Cys Arg Ala Ala Gln Ala Met Asp
        35                  40                  45

Cys Glu Val Asn Asn Gly Ser Ser Leu Arg Asp Glu Cys Ile Thr Asn
    50                  55                  60

Leu Leu Val Phe Gly Phe Leu Gln Ser Cys Ser Asp Asn Ser Phe Arg
65                  70                  75                  80

Arg Glu Leu Asp Ala Leu Gly His Glu Leu Pro Val Leu Ala Pro Gln
                85                  90                  95

Trp Glu Gly Tyr Asp Glu Leu Gln Thr Asp Gly Asn Arg Ser Ser His
            100                 105                 110

Ser Arg Leu Gly Arg Ile Glu Ala Asp Ser Glu Ser Gln Glu Asp Ile
        115                 120                 125

Ile Arg Asn Ile Ala Arg His Leu Ala Gln Val Gly Asp Ser Met Asp
    130                 135                 140

Arg Ser Ile Pro Pro Gly Leu Val Asn Gly Leu Ala Leu Gln Leu Arg
145                 150                 155                 160

Asn Thr Ser Arg Ser Glu Glu Asp Arg Asn Arg Asp Leu Ala Thr Ala
                165                 170                 175

Leu Glu Gln Leu Leu Gln Ala Tyr Pro Arg Asp Met Glu Lys Glu Lys
            180                 185                 190

Thr Met Leu Val Leu Ala Leu Leu Leu Ala Lys Lys Val Ala Ser His
        195                 200                 205

Thr Pro Ser Leu Leu Arg Asp Val Phe His Thr Thr Val Asn Phe Ile
    210                 215                 220

Asn Gln Asn Leu Arg Thr Tyr Val Arg Ser Leu Ala Arg Asn Gly Met
225                 230                 235                 240

Asp
```

<210> SEQ ID NO 202
<211> LENGTH: 168
<212> TYPE: PRT
<213> ORGANISM: Homo sapiens
<220> FEATURE:
<221> NAME/KEY: MISC_FEATURE
<223> OTHER INFORMATION: Description of sequence: amino acid sequence of Bad (human)

<400> SEQUENCE: 202

```
Met Phe Gln Ile Pro Glu Phe Glu Pro Ser Glu Gln Glu Asp Ser Ser
1               5                   10                  15

Ser Ala Glu Arg Gly Leu Gly Pro Ser Pro Ala Gly Asp Gly Pro Ser
            20                  25                  30

Gly Ser Gly Lys His His Arg Gln Ala Pro Gly Leu Leu Trp Asp Ala
        35                  40                  45

Ser His Gln Gln Glu Gln Pro Thr Ser Ser Ser His His Gly Gly Ala
    50                  55                  60
```

```
Gly Ala Val Glu Ile Arg Ser Arg His Ser Ser Tyr Pro Ala Gly Thr
65                  70                  75                  80

Glu Asp Asp Glu Gly Met Gly Glu Glu Pro Ser Pro Phe Arg Gly Arg
                85                  90                  95

Ser Arg Ser Ala Pro Pro Asn Leu Trp Ala Ala Gln Arg Tyr Gly Arg
            100                 105                 110

Glu Leu Arg Arg Met Ser Asp Glu Phe Val Asp Ser Phe Lys Lys Gly
        115                 120                 125

Leu Pro Arg Pro Lys Ser Ala Gly Thr Ala Thr Gln Met Arg Gln Ser
    130                 135                 140

Ser Ser Trp Thr Arg Val Phe Gln Ser Trp Trp Asp Arg Asn Leu Gly
145                 150                 155                 160

Arg Gly Ser Ser Ala Pro Ser Gln
                165


<210> SEQ ID NO 203
<211> LENGTH: 483
<212> TYPE: PRT
<213> ORGANISM: Homo sapiens
<220> FEATURE:
<221> NAME/KEY: misc_feature
<223> OTHER INFORMATION: Description of sequence: amino acid sequence
      of Noxa1 (human)

<400> SEQUENCE: 203

Met Ala Ser Leu Gly Asp Leu Val Arg Ala Trp His Leu Gly Ala Gln
1               5                   10                  15

Ala Val Asp Arg Gly Asp Trp Ala Arg Ala Leu His Leu Phe Ser Gly
            20                  25                  30

Val Pro Ala Pro Pro Ala Arg Leu Cys Phe Asn Ala Gly Cys Val His
        35                  40                  45

Leu Leu Ala Gly Asp Pro Glu Ala Ala Leu Arg Ala Phe Asp Gln Ala
    50                  55                  60

Val Thr Lys Asp Thr Cys Met Ala Val Gly Phe Phe Gln Arg Gly Val
65                  70                  75                  80

Ala Asn Phe Gln Leu Ala Arg Phe Gln Glu Ala Leu Ser Asp Phe Trp
                85                  90                  95

Leu Ala Leu Glu Gln Leu Arg Gly His Ala Ala Ile Asp Tyr Thr Gln
            100                 105                 110

Leu Gly Leu Arg Phe Lys Leu Gln Ala Trp Glu Val Leu His Asn Val
        115                 120                 125

Ala Ser Ala Gln Cys Gln Leu Gly Leu Trp Thr Glu Ala Ala Ser Ser
    130                 135                 140

Leu Arg Glu Ala Met Ser Lys Trp Pro Glu Gly Ser Leu Asn Gly Leu
145                 150                 155                 160

Asp Ser Ala Leu Asp Gln Val Gln Arg Arg Gly Ser Leu Pro Pro Arg
                165                 170                 175

Gln Val Pro Arg Gly Glu Val Phe Arg Pro His Arg Trp His Leu Lys
            180                 185                 190

His Leu Glu Pro Val Asp Phe Leu Gly Lys Ala Lys Val Val Ala Ser
        195                 200                 205

Ala Ile Pro Asp Asp Gln Gly Trp Gly Val Arg Pro Gln Gln Pro Gln
    210                 215                 220

Gly Pro Gly Ala Asn His Asp Ala Arg Ser Leu Ile Met Asp Ser Pro
225                 230                 235                 240
```

```
Arg Ala Gly Thr His Gln Gly Pro Leu Asp Ala Glu Thr Glu Val Gly
            245                 250                 255

Ala Asp Arg Cys Thr Ser Thr Ala Tyr Gln Glu Gln Arg Pro Gln Val
            260                 265                 270

Glu Gln Val Gly Lys Gln Ala Pro Leu Ser Pro Gly Leu Pro Ala Met
        275                 280                 285

Gly Gly Pro Gly Pro Gly Pro Cys Glu Asp Pro Ala Gly Ala Gly Gly
    290                 295                 300

Ala Gly Ala Gly Gly Ser Glu Pro Leu Val Thr Val Thr Val Gln Cys
305                 310                 315                 320

Ala Phe Thr Val Ala Leu Arg Ala Arg Arg Gly Ala Asp Leu Ser Ser
                325                 330                 335

Leu Arg Ala Leu Leu Gly Gln Ala Leu Pro His Gln Ala Gln Leu Gly
            340                 345                 350

Gln Leu Ser Tyr Leu Ala Pro Gly Glu Asp Gly His Trp Val Pro Ile
        355                 360                 365

Pro Glu Glu Glu Ser Leu Gln Arg Ala Trp Gln Asp Ala Ala Ala Cys
    370                 375                 380

Pro Arg Gly Leu Gln Leu Gln Cys Arg Gly Ala Gly Gly Arg Pro Val
385                 390                 395                 400

Leu Tyr Gln Val Val Ala Gln His Ser Tyr Ser Ala Gln Gly Pro Glu
                405                 410                 415

Asp Leu Gly Phe Arg Gln Gly Asp Thr Val Asp Val Leu Cys Glu Glu
            420                 425                 430

Pro Asp Val Pro Leu Ala Val Asp Gln Ala Trp Leu Glu Gly His Cys
        435                 440                 445

Asp Gly Arg Ile Gly Ile Phe Pro Lys Cys Phe Val Val Pro Ala Gly
    450                 455                 460

Pro Arg Met Ser Gly Ala Pro Gly Arg Leu Pro Arg Ser Gln Gln Gly
465                 470                 475                 480

Asp Gln Pro


<210> SEQ ID NO 204
<211> LENGTH: 193
<212> TYPE: PRT
<213> ORGANISM: Homo sapiens
<220> FEATURE:
<221> NAME/KEY: MISC_FEATURE
<223> OTHER INFORMATION: Description of sequence: amino acid sequence
      of Puma (human)

<400> SEQUENCE: 204

Met Ala Arg Ala Arg Gln Glu Gly Ser Ser Pro Glu Pro Val Glu Gly
1               5                   10                  15

Leu Ala Arg Asp Gly Pro Arg Pro Phe Pro Leu Gly Arg Leu Val Pro
            20                  25                  30

Ser Ala Val Ser Cys Gly Leu Cys Glu Pro Gly Leu Ala Ala Ala Pro
        35                  40                  45

Ala Ala Pro Thr Leu Leu Pro Ala Ala Tyr Leu Cys Ala Pro Thr Ala
    50                  55                  60

Pro Pro Ala Val Thr Ala Ala Leu Gly Gly Ser Arg Trp Pro Gly Gly
65                  70                  75                  80

Pro Arg Ser Arg Pro Arg Gly Pro Arg Pro Asp Gly Pro Gln Pro Ser
                85                  90                  95

Leu Ser Leu Ala Glu Gln His Leu Glu Ser Pro Val Pro Ser Ala Pro
            100                 105                 110
```

```
Gly Ala Leu Ala Gly Gly Pro Thr Gln Ala Ala Pro Gly Val Arg Gly
        115                 120                 125

Glu Glu Glu Gln Trp Ala Arg Glu Ile Gly Ala Gln Leu Arg Arg Met
    130                 135                 140

Ala Asp Asp Leu Asn Ala Gln Tyr Glu Arg Arg Arg Gln Glu Glu Gln
145                 150                 155                 160

Gln Arg His Arg Pro Ser Pro Trp Arg Val Leu Tyr Asn Leu Ile Met
                165                 170                 175

Gly Leu Leu Pro Leu Pro Arg Gly His Arg Ala Pro Glu Met Glu Pro
            180                 185                 190

Asn


<210> SEQ ID NO 205
<211> LENGTH: 198
<212> TYPE: PRT
<213> ORGANISM: Homo sapiens
<220> FEATURE:
<221> NAME/KEY: MISC_FEATURE
<223> OTHER INFORMATION: Description of sequence: amino acid sequence
      of Bim (human) (transcript variant 1)

<400> SEQUENCE: 205

Met Ala Lys Gln Pro Ser Asp Val Ser Ser Glu Cys Asp Arg Glu Gly
1               5                   10                  15

Arg Gln Leu Gln Pro Ala Glu Arg Pro Pro Gln Leu Arg Pro Gly Ala
            20                  25                  30

Pro Thr Ser Leu Gln Thr Glu Pro Gln Gly Asn Pro Glu Gly Asn His
        35                  40                  45

Gly Gly Glu Gly Asp Ser Cys Pro His Gly Ser Pro Gln Gly Pro Leu
    50                  55                  60

Ala Pro Pro Ala Ser Pro Gly Pro Phe Ala Thr Arg Ser Pro Leu Phe
65                  70                  75                  80

Ile Phe Met Arg Arg Ser Ser Leu Leu Ser Arg Ser Ser Ser Gly Tyr
                85                  90                  95

Phe Ser Phe Asp Thr Asp Arg Ser Pro Ala Pro Met Ser Cys Asp Lys
            100                 105                 110

Ser Thr Gln Thr Pro Ser Pro Pro Cys Gln Ala Phe Asn His Tyr Leu
        115                 120                 125

Ser Ala Met Ala Ser Met Arg Gln Ala Glu Pro Ala Asp Met Arg Pro
    130                 135                 140

Glu Ile Trp Ile Ala Gln Glu Leu Arg Arg Ile Gly Asp Glu Phe Asn
145                 150                 155                 160

Ala Tyr Tyr Ala Arg Arg Val Phe Leu Asn Asn Tyr Gln Ala Ala Glu
                165                 170                 175

Asp His Pro Arg Met Val Ile Leu Arg Leu Leu Arg Tyr Ile Val Arg
            180                 185                 190

Leu Val Trp Arg Met His
        195


<210> SEQ ID NO 206
<211> LENGTH: 160
<212> TYPE: PRT
<213> ORGANISM: Homo sapiens
<220> FEATURE:
<221> NAME/KEY: MISC_FEATURE
<223> OTHER INFORMATION: Description of sequence: amino acid sequence
      of Bik (human)
```

<400> SEQUENCE: 206

```
Met Ser Glu Val Arg Pro Leu Ser Arg Asp Ile Leu Met Glu Thr Leu
1               5                   10                  15

Leu Tyr Glu Gln Leu Leu Glu Pro Pro Thr Met Glu Val Leu Gly Met
            20                  25                  30

Thr Asp Ser Glu Glu Asp Leu Asp Pro Met Glu Asp Phe Asp Ser Leu
        35                  40                  45

Glu Cys Met Glu Gly Ser Asp Ala Leu Ala Leu Arg Leu Ala Cys Ile
    50                  55                  60

Gly Asp Glu Met Asp Val Ser Leu Arg Ala Pro Arg Leu Ala Gln Leu
65                  70                  75                  80

Ser Glu Val Ala Met His Ser Leu Gly Leu Ala Phe Ile Tyr Asp Gln
                85                  90                  95

Thr Glu Asp Ile Arg Asp Val Leu Arg Ser Phe Met Asp Gly Phe Thr
            100                 105                 110

Thr Leu Lys Glu Asn Ile Met Arg Phe Trp Arg Ser Pro Asn Pro Gly
        115                 120                 125

Ser Trp Val Ser Cys Glu Gln Val Leu Leu Ala Leu Leu Leu Leu Leu
    130                 135                 140

Ala Leu Leu Leu Pro Leu Leu Ser Gly Gly Leu His Leu Leu Leu Lys
145                 150                 155                 160
```

<210> SEQ ID NO 207
<211> LENGTH: 18
<212> TYPE: PRT
<213> ORGANISM: Homo sapiens
<220> FEATURE:
<221> NAME/KEY: misc_feature
<223> OTHER INFORMATION: Description of sequence: native L-amino acid sequence of the BH3-domain of Bik (Bik BH3)

<400> SEQUENCE: 207

```
Ala Leu Ala Leu Arg Leu Ala Cys Ile Gly Asp Glu Met Asp Val Ser
1               5                   10                  15

Leu Arg
```

<210> SEQ ID NO 208
<211> LENGTH: 18
<212> TYPE: PRT
<213> ORGANISM: Homo sapiens
<220> FEATURE:
<221> NAME/KEY: misc_feature
<223> OTHER INFORMATION: Description of sequence: native L-amino acid sequence of the BH3-domain of Bad (Bad BH3)

<400> SEQUENCE: 208

```
Arg Tyr Gly Arg Glu Leu Arg Arg Met Ser Asp Glu Phe Val Asp Ser
1               5                   10                  15

Phe Lys
```

<210> SEQ ID NO 209
<211> LENGTH: 18
<212> TYPE: PRT
<213> ORGANISM: Homo sapiens
<220> FEATURE:
<221> NAME/KEY: misc_feature
<223> OTHER INFORMATION: Description of sequence: native L-amino acid sequence of the BH3-domain of Bid (Bid BH3)

<400> SEQUENCE: 209

```
Asn Ile Ala Arg His Leu Ala Gln Val Gly Asp Ser Met Asp Arg Ser
```

1 5 10 15

Ile Pro

<210> SEQ ID NO 210
<211> LENGTH: 18
<212> TYPE: PRT
<213> ORGANISM: Homo sapiens
<220> FEATURE:
<221> NAME/KEY: misc_feature
<223> OTHER INFORMATION: Description of sequence: native L-amino acid sequence of the BH3-domain of Bmf (Bmf BH3)

<400> SEQUENCE: 210

Gln Ile Ala Arg Lys Leu Gln Cys Ile Ala Asp Gln Phe His Arg Leu
1 5 10 15

His Val

<210> SEQ ID NO 211
<211> LENGTH: 18
<212> TYPE: PRT
<213> ORGANISM: Homo sapiens
<220> FEATURE:
<221> NAME/KEY: misc_feature
<223> OTHER INFORMATION: Description of sequence: native L-amino acid sequence of the BH3-domain of DP5/Hrk (DP5Hrk BH3)

<400> SEQUENCE: 211

Leu Thr Ala Ala Arg Leu Lys Ala Ile Gly Asp Glu Leu His Gln Arg
1 5 10 15

Thr Met

<210> SEQ ID NO 212
<211> LENGTH: 18
<212> TYPE: PRT
<213> ORGANISM: Homo sapiens
<220> FEATURE:
<221> NAME/KEY: misc_feature
<223> OTHER INFORMATION: Description of sequence: native L-amino acid sequence of the BH3-domain of Bim (Bim BH3)

<400> SEQUENCE: 212

Trp Ile Ala Gln Glu Leu Arg Arg Ile Gly Asp Glu Phe Asn Ala Tyr
1 5 10 15

Tyr Ala

<210> SEQ ID NO 213
<211> LENGTH: 18
<212> TYPE: PRT
<213> ORGANISM: Homo sapiens
<220> FEATURE:
<221> NAME/KEY: misc_feature
<223> OTHER INFORMATION: Description of sequence: native L-amino acid sequence of the BH3-domain of Noxa (Noxa BH3)

<400> SEQUENCE: 213

Glu Cys Ala Thr Gln Leu Arg Arg Phe Gly Asp Lys Leu Asn Phe Arg
1 5 10 15

Gln Lys

<210> SEQ ID NO 214
<211> LENGTH: 18
<212> TYPE: PRT
<213> ORGANISM: Homo sapiens
<220> FEATURE:
<221> NAME/KEY: misc_feature
<223> OTHER INFORMATION: Description of sequence: native L-amino acid sequence of the BH3-domain of PUMA (PUMA BH3)

<400> SEQUENCE: 214

Glu Ile Gly Ala Gln Leu Arg Arg Met Ala Asp Asp Leu Asn Ala Gln
1 5 10 15

Tyr Glu

<210> SEQ ID NO 215
<211> LENGTH: 18
<212> TYPE: PRT
<213> ORGANISM: Homo sapiens
<220> FEATURE:
<221> NAME/KEY: misc_feature
<223> OTHER INFORMATION: Description of sequence: native L-amino acid sequence of the BH3-domain of Bax (Bax BH3)

<400> SEQUENCE: 215

Lys Leu Ser Glu Cys Leu Lys Arg Ile Gly Asp Glu Leu Asp Ser Asn
1 5 10 15

Met Glu

<210> SEQ ID NO 216
<211> LENGTH: 18
<212> TYPE: PRT
<213> ORGANISM: Homo sapiens
<220> FEATURE:
<221> NAME/KEY: misc_feature
<223> OTHER INFORMATION: Description of sequence: native L-amino acid sequence of the BH3-domain of Bak (Bak BH3)

<400> SEQUENCE: 216

Gln Val Gly Arg Gln Leu Ala Ile Ile Gly Asp Asp Ile Asn Arg Arg
1 5 10 15

Tyr Asp

<210> SEQ ID NO 217
<211> LENGTH: 18
<212> TYPE: PRT
<213> ORGANISM: Homo sapiens
<220> FEATURE:
<221> NAME/KEY: misc_feature
<223> OTHER INFORMATION: Description of sequence: native L-amino acid sequence of the BH3-domain of Bok (Bok BH3)

<400> SEQUENCE: 217

Glu Val Cys Thr Val Leu Leu Arg Leu Gly Asp Glu Leu Glu Gln Ile
1 5 10 15

Arg Pro

<210> SEQ ID NO 218
<211> LENGTH: 4
<212> TYPE: PRT
<213> ORGANISM: Artificial Sequence
<220> FEATURE:
<223> OTHER INFORMATION: Description of sequence: signal sequence or localisation sequence

<400> SEQUENCE: 218

Lys Asp Glu Leu
1

<210> SEQ ID NO 219
<211> LENGTH: 4
<212> TYPE: PRT

<213> ORGANISM: Artificial Sequence
<220> FEATURE:
<223> OTHER INFORMATION: Description of sequence: signal sequence or localisation sequence

<400> SEQUENCE: 219

Asp Asp Glu Leu
1

<210> SEQ ID NO 220
<211> LENGTH: 4
<212> TYPE: PRT
<213> ORGANISM: Artificial Sequence
<220> FEATURE:
<223> OTHER INFORMATION: Description of sequence: signal sequence or localisation sequence

<400> SEQUENCE: 220

Asp Glu Glu Leu
1

<210> SEQ ID NO 221
<211> LENGTH: 4
<212> TYPE: PRT
<213> ORGANISM: Artificial Sequence
<220> FEATURE:
<223> OTHER INFORMATION: Description of sequence: signal sequence or localisation sequence

<400> SEQUENCE: 221

Gln Glu Asp Leu
1

<210> SEQ ID NO 222
<211> LENGTH: 4
<212> TYPE: PRT
<213> ORGANISM: Artificial Sequence
<220> FEATURE:
<223> OTHER INFORMATION: Description of sequence: signal sequence or localisation sequence

<400> SEQUENCE: 222

Arg Asp Glu Leu
1

<210> SEQ ID NO 223
<211> LENGTH: 7
<212> TYPE: PRT
<213> ORGANISM: Artificial Sequence
<220> FEATURE:
<223> OTHER INFORMATION: Description of sequence: signal sequence or localisation sequence

<400> SEQUENCE: 223

Pro Lys Lys Lys Arg Lys Val
1               5

<210> SEQ ID NO 224
<211> LENGTH: 7
<212> TYPE: PRT
<213> ORGANISM: Artificial Sequence
<220> FEATURE:
<223> OTHER INFORMATION: Description of sequence: signal sequence or localisation sequence

<400> SEQUENCE: 224

Pro Gln Lys Lys Ile Lys Ser
1               5

<210> SEQ ID NO 225
<211> LENGTH: 5
<212> TYPE: PRT
<213> ORGANISM: Artificial Sequence
<220> FEATURE:
<223> OTHER INFORMATION: Description of sequence: signal sequence or localisation sequence

<400> SEQUENCE: 225

Gln Pro Lys Lys Pro
1               5

<210> SEQ ID NO 226
<211> LENGTH: 4
<212> TYPE: PRT
<213> ORGANISM: Artificial Sequence
<220> FEATURE:
<223> OTHER INFORMATION: Description of sequence: signal sequence or localisation sequence

<400> SEQUENCE: 226

Arg Lys Lys Arg
1

<210> SEQ ID NO 227
<211> LENGTH: 12
<212> TYPE: PRT
<213> ORGANISM: Artificial Sequence
<220> FEATURE:
<223> OTHER INFORMATION: Description of sequence: signal sequence or localisation sequence

<400> SEQUENCE: 227

Arg Lys Lys Arg Arg Gln Arg Arg Arg Ala His Gln
1               5                   10

<210> SEQ ID NO 228
<211> LENGTH: 16
<212> TYPE: PRT
<213> ORGANISM: Artificial Sequence
<220> FEATURE:
<223> OTHER INFORMATION: Description of sequence: signal sequence or localisation sequence

<400> SEQUENCE: 228

Arg Gln Ala Arg Arg Asn Arg Arg Arg Arg Trp Arg Glu Arg Gln Arg
1               5                   10                  15

<210> SEQ ID NO 229
<211> LENGTH: 19
<212> TYPE: PRT
<213> ORGANISM: Artificial Sequence
<220> FEATURE:
<223> OTHER INFORMATION: Description of sequence: signal sequence or localisation sequence

<400> SEQUENCE: 229

Met Pro Leu Thr Arg Arg Arg Pro Ala Ala Ser Gln Ala Leu Ala Pro
1               5                   10                  15

Pro Thr Pro

<210> SEQ ID NO 230
<211> LENGTH: 15
<212> TYPE: PRT
<213> ORGANISM: Artificial Sequence
<220> FEATURE:

```
<223> OTHER INFORMATION: Description of sequence: signal sequence or
      localisation sequence

<400> SEQUENCE: 230

Met Asp Asp Gln Arg Asp Leu Ile Ser Asn Asn Glu Gln Leu Pro
1               5                   10                  15


<210> SEQ ID NO 231
<211> LENGTH: 9
<212> TYPE: PRT
<213> ORGANISM: Artificial Sequence
<220> FEATURE:
<223> OTHER INFORMATION: Description of sequence:  trafficking sequence
      r3R6
<220> FEATURE:
<221> NAME/KEY: VARIANT
<222> LOCATION: (1)..(1)
<223> OTHER INFORMATION: /replace="D-amino acid"
<220> FEATURE:
<221> NAME/KEY: VARIANT
<222> LOCATION: (4)..(4)
<223> OTHER INFORMATION: /replace="D-amino acid"
<220> FEATURE:
<221> NAME/KEY: VARIANT
<222> LOCATION: (9)..(9)
<223> OTHER INFORMATION: /replace="D-amino acid"

<400> SEQUENCE: 231

Arg Arg Arg Arg Arg Arg Arg Arg Arg
1               5


<210> SEQ ID NO 232
<211> LENGTH: 3
<212> TYPE: PRT
<213> ORGANISM: Artificial Sequence
<220> FEATURE:
<223> OTHER INFORMATION: Trafficking control sequence

<400> SEQUENCE: 232

Asp Ala Lys
1


<210> SEQ ID NO 233
<211> LENGTH: 31
<212> TYPE: PRT
<213> ORGANISM: Artificial Sequence
<220> FEATURE:
<223> OTHER INFORMATION: D-TAT-IB1 (XG-102)
<220> FEATURE:
<221> NAME/KEY: VARIANT
<222> LOCATION: (1)..(31)
<223> OTHER INFORMATION: /replace="D-amino acid"

<400> SEQUENCE: 233

Asp Gln Ser Arg Pro Val Gln Pro Phe Leu Asn Leu Thr Thr Pro Arg
1               5                   10                  15

Lys Pro Arg Pro Pro Arg Arg Arg Gln Arg Arg Lys Lys Arg Gly
            20                  25                  30


<210> SEQ ID NO 234
<211> LENGTH: 31
<212> TYPE: PRT
<213> ORGANISM: Artificial Sequence
<220> FEATURE:
<223> OTHER INFORMATION: Description of sequence: L-TAT-IB1 (s)

<400> SEQUENCE: 234

Gly Arg Lys Lys Arg Arg Gln Arg Arg Arg Pro Pro Arg Pro Lys Arg
1               5                   10                  15
```

```
Pro Thr Thr Leu Asn Leu Phe Pro Gln Val Pro Arg Ser Gln Asp
            20                  25                  30


<210> SEQ ID NO 235
<211> LENGTH: 9
<212> TYPE: PRT
<213> ORGANISM: Artificial
<220> FEATURE:
<223> OTHER INFORMATION: Description of sequence: consensus sequence
      rXXXrXXXr
<220> FEATURE:
<221> NAME/KEY: misc
<222> LOCATION: (1)..(1)
<223> OTHER INFORMATION: Arg is D-enantiomeric Arg
<220> FEATURE:
<221> NAME/KEY: misc_feature
<222> LOCATION: (2)..(4)
<223> OTHER INFORMATION: Xaa can be any naturally occurring amino acid
<220> FEATURE:
<221> NAME/KEY: misc
<222> LOCATION: (5)..(5)
<223> OTHER INFORMATION: Arg is D-enantiomeric Arg
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc
<222> LOCATION: (9)..(9)
<223> OTHER INFORMATION: Arg is D-enantiomeric Arg

<400> SEQUENCE: 235

Arg Xaa Xaa Xaa Arg Xaa Xaa Xaa Arg
1               5


<210> SEQ ID NO 236
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 236

Lys Arg Ile Ile Gln Arg Ile Leu Ser Arg Asn Ser
1               5                   10


<210> SEQ ID NO 237
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 237

Lys Arg Ile His Pro Arg Leu Thr Arg Ser Ile Arg
1               5                   10


<210> SEQ ID NO 238
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 238

Pro Pro Arg Leu Arg Lys Arg Arg Gln Leu Asn Met
1               5                   10


<210> SEQ ID NO 239
```

<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 239

Pro Ile Arg Arg Arg Lys Lys Leu Arg Arg Leu Lys
1 5 10

<210> SEQ ID NO 240
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 240

Arg Arg Gln Arg Arg Thr Ser Lys Leu Met Lys Arg
1 5 10

<210> SEQ ID NO 241
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 241

Met His Lys Arg Pro Thr Thr Pro Ser Arg Lys Met
1 5 10

<210> SEQ ID NO 242
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 242

Arg Gln Arg Ser Arg Arg Arg Pro Leu Asn Ile Arg
1 5 10

<210> SEQ ID NO 243
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 243

Arg Ile Arg Met Ile Gln Asn Leu Ile Lys Lys Thr
1 5 10

<210> SEQ ID NO 244
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 244

Ser Arg Arg Lys Arg Gln Arg Ser Asn Met Arg Ile
1 5 10

<210> SEQ ID NO 245
<211> LENGTH: 12

<212> TYPE: PRT
<213> ORGANISM: Artificial
<220> FEATURE:
<223> OTHER INFORMATION: Description of sequence: Disclaimed sequence

<400> SEQUENCE: 245

Gln Arg Ile Arg Lys Ser Lys Ile Ser Arg Thr Leu
1 5 10

<210> SEQ ID NO 246
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 246

Pro Ser Lys Arg Leu Leu His Asn Asn Leu Arg Arg
1 5 10

<210> SEQ ID NO 247
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 247

His Arg His Ile Arg Arg Gln Ser Leu Ile Met Leu
1 5 10

<210> SEQ ID NO 248
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 248

Pro Gln Asn Arg Leu Gln Ile Arg Arg His Ser Lys
1 5 10

<210> SEQ ID NO 249
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 249

Pro Pro His Asn Arg Ile Gln Arg Arg Leu Asn Met
1 5 10

<210> SEQ ID NO 250
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 250

Ser Met Leu Lys Arg Asn His Ser Thr Ser Asn Arg
1 5 10

<210> SEQ ID NO 251
<211> LENGTH: 12
<212> TYPE: PRT

<213> ORGANISM: Artificial
<220> FEATURE:
<223> OTHER INFORMATION: Description of sequence: Disclaimed sequence

<400> SEQUENCE: 251

Gly Ser Arg His Pro Ser Leu Ile Ile Pro Arg Gln
1 5 10

<210> SEQ ID NO 252
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 252

Ser Pro Met Gln Lys Thr Met Asn Leu Pro Pro Met
1 5 10

<210> SEQ ID NO 253
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 253

Asn Lys Arg Ile Leu Ile Arg Ile Met Thr Arg Pro
1 5 10

<210> SEQ ID NO 254
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 254

His Gly Trp Glx Ile His Gly Leu Leu His Arg Ala
1 5 10

<210> SEQ ID NO 255
<211> LENGTH: 11
<212> TYPE: PRT
<213> ORGANISM: Artificial
<220> FEATURE:
<223> OTHER INFORMATION: Description of sequence: Disclaimed sequence

<400> SEQUENCE: 255

Ala Val Pro Ala Lys Lys Arg Glx Lys Ser Val
1 5 10

<210> SEQ ID NO 256
<211> LENGTH: 11
<212> TYPE: PRT
<213> ORGANISM: Artificial
<220> FEATURE:
<223> OTHER INFORMATION: Description of sequence: Disclaimed sequence

<400> SEQUENCE: 256

Pro Asn Thr Arg Val Arg Pro Asp Val Ser Phe
1 5 10

<210> SEQ ID NO 257
<211> LENGTH: 12
<212> TYPE: PRT
<213> ORGANISM: Artificial

<220> FEATURE:
<223> OTHER INFORMATION: Description of sequence: Disclaimed sequence

<400> SEQUENCE: 257

Leu Thr Arg Asn Tyr Glu Ala Trp Val Pro Thr Pro
1 5 10

<210> SEQ ID NO 258
<211> LENGTH: 13
<212> TYPE: PRT
<213> ORGANISM: Artificial
<220> FEATURE:
<223> OTHER INFORMATION: Description of sequence: Disclaimed sequence

<400> SEQUENCE: 258

Ser Ala Glu Thr Val Glu Ser Cys Leu Ala Lys Ser His
1 5 10

<210> SEQ ID NO 259
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 259

Tyr Ser His Ile Ala Thr Leu Pro Phe Thr Pro Thr
1 5 10

<210> SEQ ID NO 260
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 260

Ser Tyr Ile Gln Arg Thr Pro Ser Thr Thr Leu Pro
1 5 10

<210> SEQ ID NO 261
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 261

Ala Val Pro Ala Glu Asn Ala Leu Asn Asn Pro Phe
1 5 10

<210> SEQ ID NO 262
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 262

Ser Phe His Gln Phe Ala Arg Ala Thr Leu Ala Ser
1 5 10

<210> SEQ ID NO 263
<211> LENGTH: 12
<212> TYPE: PRT
<213> ORGANISM: Artificial
<220> FEATURE:

<223> OTHER INFORMATION: Description of sequence: Disclaimed sequence

<400> SEQUENCE: 263

Gln Ser Pro Thr Asp Phe Thr Phe Pro Asn Pro Leu
1 5 10

<210> SEQ ID NO 264
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 264

His Phe Ala Ala Trp Gly Gly Trp Ser Leu Val His
1 5 10

<210> SEQ ID NO 265
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 265

His Ile Gln Leu Ser Pro Phe Ser Gln Ser Trp Arg
1 5 10

<210> SEQ ID NO 266
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 266

Leu Thr Met Pro Ser Asp Leu Gln Pro Val Leu Trp
1 5 10

<210> SEQ ID NO 267
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 267

Phe Gln Pro Tyr Asp His Pro Ala Glu Val Ser Tyr
1 5 10

<210> SEQ ID NO 268
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 268

Phe Asp Pro Phe Phe Trp Lys Tyr Ser Pro Arg Asp
1 5 10

<210> SEQ ID NO 269
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 269

Phe Ala Pro Trp Asp Thr Ala Ser Phe Met Leu Gly
1 5 10

<210> SEQ ID NO 270
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 270

Phe Thr Tyr Lys Asn Phe Phe Trp Leu Pro Glu Leu
1 5 10

<210> SEQ ID NO 271
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 271

Ser Ala Thr Gly Ala Pro Trp Lys Met Trp Val Arg
1 5 10

<210> SEQ ID NO 272
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 272

Ser Leu Gly Trp Met Leu Pro Phe Ser Pro Pro Phe
1 5 10

<210> SEQ ID NO 273
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 273

Ser His Ala Phe Thr Trp Pro Thr Tyr Leu Gln Leu
1 5 10

<210> SEQ ID NO 274
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 274

Ser His Asn Trp Leu Pro Leu Trp Pro Leu Arg Pro
1 5 10

<210> SEQ ID NO 275
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 275

Ser Trp Leu Pro Tyr Pro Trp His Val Pro Ser Ser
1 5 10

<210> SEQ ID NO 276
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 276

Ser Trp Trp Thr Pro Trp His Val His Ser Glu Ser
1 5 10

<210> SEQ ID NO 277
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 277

Ser Trp Ala Gln His Leu Ser Leu Pro Pro Val Leu
1 5 10

<210> SEQ ID NO 278
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 278

Ser Ser Ser Ile Phe Pro Pro Trp Leu Ser Phe Phe
1 5 10

<210> SEQ ID NO 279
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 279

Leu Asn Val Pro Pro Ser Trp Phe Leu Ser Gln Arg
1 5 10

<210> SEQ ID NO 280
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 280

Leu Asp Ile Thr Pro Phe Leu Ser Leu Thr Leu Pro
1 5 10

<210> SEQ ID NO 281
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 281

Leu Pro His Pro Val Leu His Met Gly Pro Leu Arg
1 5 10

<210> SEQ ID NO 282
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 282

Val Ser Lys Gln Pro Tyr Tyr Met Trp Asn Gly Asn
1 5 10

<210> SEQ ID NO 283
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 283

Asn Tyr Thr Thr Tyr Lys Ser His Phe Gln Asp Arg
1 5 10

<210> SEQ ID NO 284
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 284

Ala Ile Pro Asn Asn Gln Leu Gly Phe Pro Phe Lys
1 5 10

<210> SEQ ID NO 285
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 285

Asn Ile Glu Asn Ser Thr Leu Ala Thr Pro Leu Ser
1 5 10

<210> SEQ ID NO 286
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 286

Tyr Pro Tyr Asp Ala Asn His Thr Arg Ser Pro Thr
1 5 10

<210> SEQ ID NO 287
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 287

Asp Pro Ala Thr Asn Pro Gly Pro His Phe Pro Arg
1 5 10

<210> SEQ ID NO 288
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 288

Thr Leu Pro Ser Pro Leu Ala Leu Leu Thr Val His
1 5 10

<210> SEQ ID NO 289
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 289

His Pro Gly Ser Pro Phe Pro Pro Glu His Arg Pro
1 5 10

<210> SEQ ID NO 290
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 290

Thr Ser His Thr Asp Ala Pro Pro Ala Arg Ser Pro
1 5 10

<210> SEQ ID NO 291
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 291

Met Thr Pro Ser Ser Leu Ser Thr Leu Pro Trp Pro
1 5 10

<210> SEQ ID NO 292
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 292

Val Leu Gly Gln Ser Gly Tyr Leu Met Pro Met Arg
1 5 10

<210> SEQ ID NO 293
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 293

Gln Pro Ile Ile Ile Thr Ser Pro Tyr Leu Pro Ser 1 5 10

<210> SEQ ID NO 294
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 294

Thr Pro Lys Thr Met Thr Gln Thr Tyr Asp Phe Ser
1 5 10

<210> SEQ ID NO 295
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 295

Asn Ser Gly Thr Met Gln Ser Ala Ser Arg Ala Thr
1 5 10

<210> SEQ ID NO 296
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 296

Gln Ala Ala Ser Arg Val Glu Asn Tyr Met His Arg
1 5 10

<210> SEQ ID NO 297
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 297

His Gln His Lys Pro Pro Pro Leu Thr Asn Asn Trp
1 5 10

<210> SEQ ID NO 298
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 298

Ser Asn Pro Trp Asp Ser Leu Leu Ser Val Ser Thr
1 5 10

<210> SEQ ID NO 299
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 299

Lys Thr Ile Glu Ala His Pro Pro Tyr Tyr Ala Ser
1 5 10

<210> SEQ ID NO 300
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 300

```
Glu Pro Asp Asn Trp Ser Leu Asp Phe Pro Arg Arg
1               5                   10
```

<210> SEQ ID NO 301
<211> LENGTH: 12
<212> TYPE: PRT
<213> ORGANISM: Artificial
<220> FEATURE:
<223> OTHER INFORMATION: Description of sequence: Disclaimed sequence

<400> SEQUENCE: 301

```
His Gln His Lys Pro Pro Pro Leu Thr Asn Asn Trp
1               5                   10
```

<210> SEQ ID NO 302
<211> LENGTH: 19
<212> TYPE: PRT
<213> ORGANISM: Artificial
<220> FEATURE:
<223> OTHER INFORMATION: Description of sequence: Disclaimed sequence

<400> SEQUENCE: 302

```
Gly Val Val Gly Lys Leu Gly Gln Arg Arg Thr Lys Lys Gln Arg Arg
1               5                   10                  15

Gln Lys Lys
```

<210> SEQ ID NO 303
<211> LENGTH: 31
<212> TYPE: PRT
<213> ORGANISM: Artificial
<220> FEATURE:
<223> OTHER INFORMATION: Description of sequence: Disclaimed sequence

<400> SEQUENCE: 303

```
Gly Arg Arg Thr Lys Lys Gln Arg Arg Gln Lys Lys Pro Pro Arg Tyr
1               5                   10                  15

Met Ile Leu Gly Leu Leu Ala Leu Ala Ala Val Cys Ser Ala Ala
            20                  25                  30
```

<210> SEQ ID NO 304
<211> LENGTH: 14
<212> TYPE: PRT
<213> ORGANISM: Artificial
<220> FEATURE:
<223> OTHER INFORMATION: Description of sequence: Disclaimed sequence

<400> SEQUENCE: 304

```
Gly Arg Arg Thr Lys Lys Gln Arg Arg Gln Lys Lys Pro Pro
1               5                   10
```

<210> SEQ ID NO 305
<211> LENGTH: 4
<212> TYPE: PRT
<213> ORGANISM: Artificial
<220> FEATURE:
<223> OTHER INFORMATION: Description of sequence: Cytokine conserved
      residues

<400> SEQUENCE: 305

Cys Cys Cys Cys
1

<210> SEQ ID NO 306
<211> LENGTH: 5
<212> TYPE: PRT
<213> ORGANISM: Artificial
<220> FEATURE:
<223> OTHER INFORMATION: Description of sequence: Cytokine conserved sequence motif
<220> FEATURE:
<221> NAME/KEY: misc_feature
<222> LOCATION: (3)..(3)
<223> OTHER INFORMATION: Xaa = any natural amino acid

<400> SEQUENCE: 306

Trp Ser Xaa Trp Ser
1               5

<210> SEQ ID NO 307
<211> LENGTH: 3
<212> TYPE: PRT
<213> ORGANISM: Artificial
<220> FEATURE:
<223> OTHER INFORMATION: Description of sequence: Sequence showing an example of its inverse

<400> SEQUENCE: 307

Arg Arg Arg
1

<210> SEQ ID NO 308
<211> LENGTH: 5
<212> TYPE: PRT
<213> ORGANISM: Artificial
<220> FEATURE:
<223> OTHER INFORMATION: Description of sequence: Linker sequence

<400> SEQUENCE: 308

Gly Gly Gly Gly Gly
1               5

<210> SEQ ID NO 309
<211> LENGTH: 4
<212> TYPE: PRT
<213> ORGANISM: Artificial
<220> FEATURE:
<223> OTHER INFORMATION: Description of sequence: Linker sequence

<400> SEQUENCE: 309

Gly Gly Gly Gly
1

<210> SEQ ID NO 310
<211> LENGTH: 3
<212> TYPE: PRT
<213> ORGANISM: Artificial
<220> FEATURE:
<223> OTHER INFORMATION: Description of sequence: Linker sequence

<400> SEQUENCE: 310

Gly Gly Gly
1

<210> SEQ ID NO 311

<211> LENGTH: 3
<212> TYPE: PRT
<213> ORGANISM: Artificial
<220> FEATURE:
<223> OTHER INFORMATION: Description of sequence: Linker sequence

<400> SEQUENCE: 311

Cys Gly Gly
1

<210> SEQ ID NO 312
<211> LENGTH: 3
<212> TYPE: PRT
<213> ORGANISM: Artificial
<220> FEATURE:
<223> OTHER INFORMATION: Description of sequence: Linker sequence

<400> SEQUENCE: 312

Gly Gly Cys
1

<210> SEQ ID NO 313
<211> LENGTH: 9
<212> TYPE: PRT
<213> ORGANISM: Artificial
<220> FEATURE:
<223> OTHER INFORMATION: Description of sequence: Sequence construct

<400> SEQUENCE: 313

Ala Arg Lys Lys Arg Gln Arg Arg Arg
1               5

<210> SEQ ID NO 314
<211> LENGTH: 10
<212> TYPE: PRT
<213> ORGANISM: Artificial
<220> FEATURE:
<223> OTHER INFORMATION: Description of sequence: Sequence construct

<400> SEQUENCE: 314

Ala Arg Arg Arg Gln Arg Arg Lys Lys Arg
1               5                   10

<210> SEQ ID NO 315
<211> LENGTH: 10
<212> TYPE: PRT
<213> ORGANISM: Artificial
<220> FEATURE:
<223> OTHER INFORMATION: Description of sequence: Sequence construct

<400> SEQUENCE: 315

Ala Arg Lys Lys Arg Arg Gln Arg Arg Arg
1               5                   10

<210> SEQ ID NO 316
<211> LENGTH: 4
<212> TYPE: PRT
<213> ORGANISM: Artificial
<220> FEATURE:
<223> OTHER INFORMATION: Description of sequence: Sequence construct

<400> SEQUENCE: 316

Ala Asp Ala Lys
1

<210> SEQ ID NO 317
<211> LENGTH: 9

```
<212> TYPE: PRT
<213> ORGANISM: Artificial
<220> FEATURE:
<223> OTHER INFORMATION: Description of sequence: Sequence construct
      with amino acid protecting groups

<400> SEQUENCE: 317

Arg Ala Lys Arg Arg Gln Arg Arg Arg
1               5


<210> SEQ ID NO 318
<211> LENGTH: 9
<212> TYPE: PRT
<213> ORGANISM: Artificial
<220> FEATURE:
<223> OTHER INFORMATION: Description of sequence: Sequence construct
      with amino acid protecting groups

<400> SEQUENCE: 318

Arg Lys Ala Arg Arg Gln Arg Arg Arg
1               5


<210> SEQ ID NO 319
<211> LENGTH: 9
<212> TYPE: PRT
<213> ORGANISM: Artificial
<220> FEATURE:
<223> OTHER INFORMATION: Description of sequence: Sequence construct
      with amino acid protecting groups

<400> SEQUENCE: 319

Arg Lys Lys Ala Arg Gln Arg Arg Arg
1               5


<210> SEQ ID NO 320
<211> LENGTH: 9
<212> TYPE: PRT
<213> ORGANISM: Artificial
<220> FEATURE:
<223> OTHER INFORMATION: Description of sequence: Sequence construct
      with amino acid protecting groups

<400> SEQUENCE: 320

Arg Lys Lys Arg Arg Ala Arg Arg Arg
1               5


<210> SEQ ID NO 321
<211> LENGTH: 9
<212> TYPE: PRT
<213> ORGANISM: Artificial
<220> FEATURE:
<223> OTHER INFORMATION: Description of sequence: Sequence construct
      with amino acid protecting groups

<400> SEQUENCE: 321

Arg Lys Lys Arg Arg Gln Ala Arg Arg
1               5


<210> SEQ ID NO 322
<211> LENGTH: 9
<212> TYPE: PRT
<213> ORGANISM: Artificial
<220> FEATURE:
<223> OTHER INFORMATION: Description of sequence: Sequence construct
      with amino acid protecting groups

<400> SEQUENCE: 322

Arg Lys Lys Arg Arg Gln Arg Ala Arg
```

1 5

<210> SEQ ID NO 323
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 323

Arg Asp Lys Arg Arg Gln Arg Arg Arg
1 5

<210> SEQ ID NO 324
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 324

Arg Lys Asp Arg Arg Gln Arg Arg Arg
1 5

<210> SEQ ID NO 325
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 325

Arg Lys Lys Asp Arg Gln Arg Arg Arg
1 5

<210> SEQ ID NO 326
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 326

Arg Lys Lys Arg Arg Asp Arg Arg Arg
1 5

<210> SEQ ID NO 327
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 327

Arg Lys Lys Arg Arg Gln Asp Arg Arg
1 5

<210> SEQ ID NO 328
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 328

Arg Lys Lys Arg Arg Gln Arg Asp Arg
1               5

<210> SEQ ID NO 329
<211> LENGTH: 9
<212> TYPE: PRT
<213> ORGANISM: Artificial
<220> FEATURE:
<223> OTHER INFORMATION: Description of sequence: Sequence construct
with amino acid protecting groups

<400> SEQUENCE: 329

Arg Glu Lys Arg Arg Gln Arg Arg Arg
1               5

<210> SEQ ID NO 330
<211> LENGTH: 9
<212> TYPE: PRT
<213> ORGANISM: Artificial
<220> FEATURE:
<223> OTHER INFORMATION: Description of sequence: Sequence construct
with amino acid protecting groups

<400> SEQUENCE: 330

Arg Lys Glu Arg Arg Gln Arg Arg Arg
1               5

<210> SEQ ID NO 331
<211> LENGTH: 9
<212> TYPE: PRT
<213> ORGANISM: Artificial
<220> FEATURE:
<223> OTHER INFORMATION: Description of sequence: Sequence construct
with amino acid protecting groups

<400> SEQUENCE: 331

Arg Lys Lys Glu Arg Gln Arg Arg Arg
1               5

<210> SEQ ID NO 332
<211> LENGTH: 9
<212> TYPE: PRT
<213> ORGANISM: Artificial
<220> FEATURE:
<223> OTHER INFORMATION: Description of sequence: Sequence construct
with amino acid protecting groups

<400> SEQUENCE: 332

Arg Lys Lys Arg Arg Glu Arg Arg Arg
1               5

<210> SEQ ID NO 333
<211> LENGTH: 9
<212> TYPE: PRT
<213> ORGANISM: Artificial
<220> FEATURE:
<223> OTHER INFORMATION: Description of sequence: Sequence construct
with amino acid protecting groups

<400> SEQUENCE: 333

Arg Lys Lys Arg Arg Gln Glu Arg Arg
1               5

<210> SEQ ID NO 334

<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 334

Arg Lys Lys Arg Arg Gln Arg Glu Arg
1 5

<210> SEQ ID NO 335
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 335

Arg Phe Lys Arg Arg Gln Arg Arg Arg
1 5

<210> SEQ ID NO 336
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 336

Arg Lys Phe Arg Arg Gln Arg Arg Arg
1 5

<210> SEQ ID NO 337
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 337

Arg Lys Lys Phe Arg Gln Arg Arg Arg
1 5

<210> SEQ ID NO 338
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 338

Arg Lys Lys Arg Arg Phe Arg Arg Arg
1 5

<210> SEQ ID NO 339
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 339

```
Arg Lys Lys Arg Arg Gln Phe Arg Arg
1               5


<210> SEQ ID NO 340
<211> LENGTH: 9
<212> TYPE: PRT
<213> ORGANISM: Artificial
<220> FEATURE:
<223> OTHER INFORMATION: Description of sequence: Sequence construct
      with amino acid protecting groups

<400> SEQUENCE: 340

Arg Lys Lys Arg Arg Gln Arg Phe Arg
1               5


<210> SEQ ID NO 341
<211> LENGTH: 9
<212> TYPE: PRT
<213> ORGANISM: Artificial
<220> FEATURE:
<223> OTHER INFORMATION: Description of sequence: Sequence construct
      with amino acid protecting groups

<400> SEQUENCE: 341

Arg Arg Lys Arg Arg Gln Arg Arg Arg
1               5


<210> SEQ ID NO 342
<211> LENGTH: 9
<212> TYPE: PRT
<213> ORGANISM: Artificial
<220> FEATURE:
<223> OTHER INFORMATION: Description of sequence: Sequence construct
      with amino acid protecting groups

<400> SEQUENCE: 342

Arg Lys Arg Arg Arg Gln Arg Arg Arg
1               5


<210> SEQ ID NO 343
<211> LENGTH: 9
<212> TYPE: PRT
<213> ORGANISM: Artificial
<220> FEATURE:
<223> OTHER INFORMATION: Description of sequence: Sequence construct
      with amino acid protecting groups

<400> SEQUENCE: 343

Arg Lys Lys Lys Arg Gln Arg Arg Arg
1               5


<210> SEQ ID NO 344
<211> LENGTH: 9
<212> TYPE: PRT
<213> ORGANISM: Artificial
<220> FEATURE:
<223> OTHER INFORMATION: Description of sequence: Sequence construct
      with amino acid protecting groups

<400> SEQUENCE: 344

Arg Lys Lys Arg Arg Arg Arg Arg Arg
1               5


<210> SEQ ID NO 345
<211> LENGTH: 9
<212> TYPE: PRT
<213> ORGANISM: Artificial
<220> FEATURE:
```

<223> OTHER INFORMATION: Description of sequence: Sequence construct
      with amino acid protecting groups

<400> SEQUENCE: 345

Arg Lys Lys Arg Arg Gln Lys Arg Arg
1               5

<210> SEQ ID NO 346
<211> LENGTH: 9
<212> TYPE: PRT
<213> ORGANISM: Artificial
<220> FEATURE:
<223> OTHER INFORMATION: Description of sequence: Sequence construct
      with amino acid protecting groups

<400> SEQUENCE: 346

Arg Lys Lys Arg Arg Gln Arg Lys Arg
1               5

<210> SEQ ID NO 347
<211> LENGTH: 9
<212> TYPE: PRT
<213> ORGANISM: Artificial
<220> FEATURE:
<223> OTHER INFORMATION: Description of sequence: Sequence construct
      with amino acid protecting groups

<400> SEQUENCE: 347

Arg Lys Lys Arg Arg Gln Arg Lys Arg
1               5

<210> SEQ ID NO 348
<211> LENGTH: 9
<212> TYPE: PRT
<213> ORGANISM: Artificial
<220> FEATURE:
<223> OTHER INFORMATION: Description of sequence: Sequence construct
      with amino acid protecting groups

<400> SEQUENCE: 348

Arg Lys His Arg Arg Gln Arg Arg Arg
1               5

<210> SEQ ID NO 349
<211> LENGTH: 9
<212> TYPE: PRT
<213> ORGANISM: Artificial
<220> FEATURE:
<223> OTHER INFORMATION: Description of sequence: Sequence construct
      with amino acid protecting groups

<400> SEQUENCE: 349

Arg Lys Lys His Arg Gln Arg Arg Arg
1               5

<210> SEQ ID NO 350
<211> LENGTH: 9
<212> TYPE: PRT
<213> ORGANISM: Artificial
<220> FEATURE:
<223> OTHER INFORMATION: Description of sequence: Sequence construct
      with amino acid protecting groups

<400> SEQUENCE: 350

Arg Lys Lys Arg Arg His Arg Arg Arg
1               5

<210> SEQ ID NO 351
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 351

Arg Lys Lys Arg Arg Gln His Arg Arg
1               5

<210> SEQ ID NO 352
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 352

Arg Lys Lys Arg Arg Gln Arg His Arg
1               5

<210> SEQ ID NO 353
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 353

Arg Ile Lys Arg Arg Gln Arg Arg Arg
1               5

<210> SEQ ID NO 354
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 354

Arg Lys Ile Arg Arg Gln Arg Arg Arg
1               5

<210> SEQ ID NO 355
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 355

Arg Lys Lys Ile Arg Gln Arg Arg Arg
1               5

<210> SEQ ID NO 356
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 356

Arg Lys Lys Arg Arg Ile Arg Arg Arg
1 5

<210> SEQ ID NO 357
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 357

Arg Lys Lys Arg Arg Gln Ile Arg Arg
1 5

<210> SEQ ID NO 358
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 358

Arg Lys Lys Arg Arg Gln Arg Ile Arg
1 5

<210> SEQ ID NO 359
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 359

Arg Leu Lys Arg Arg Gln Arg Arg Arg
1 5

<210> SEQ ID NO 360
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 360

Arg Lys Leu Arg Arg Gln Arg Arg Arg
1 5

<210> SEQ ID NO 361
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 361

Arg Lys Lys Leu Arg Gln Arg Arg Arg
1 5

<210> SEQ ID NO 362
<211> LENGTH: 9
<212> TYPE: PRT
<213> ORGANISM: Artificial

<220> FEATURE:
<223> OTHER INFORMATION: Description of sequence: Sequence construct with amino acid protecting groups

<400> SEQUENCE: 362

Arg Lys Lys Arg Arg Leu Arg Arg Arg
1               5

<210> SEQ ID NO 363
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 363

Arg Lys Lys Arg Arg Gln Leu Arg Arg
1               5

<210> SEQ ID NO 364
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 364

Arg Lys Lys Arg Arg Gln Arg Leu Arg
1               5

<210> SEQ ID NO 365
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 365

Arg Met Lys Arg Arg Gln Arg Arg Arg
1               5

<210> SEQ ID NO 366
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 366

Arg Lys Met Arg Arg Gln Arg Arg Arg
1               5

<210> SEQ ID NO 367
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 367

Arg Lys Lys Met Arg Gln Arg Arg Arg
1               5

<210> SEQ ID NO 368
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 368

Arg Lys Lys Arg Arg Met Arg Arg Arg
1 5

<210> SEQ ID NO 369
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 369

Arg Lys Lys Arg Arg Gln Met Arg Arg
1 5

<210> SEQ ID NO 370
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 370

Arg Lys Lys Arg Arg Gln Arg Met Arg
1 5

<210> SEQ ID NO 371
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 371

Arg Asn Lys Arg Arg Gln Arg Arg Arg
1 5

<210> SEQ ID NO 372
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 372

Arg Lys Asn Arg Arg Gln Arg Arg Arg
1 5

<210> SEQ ID NO 373
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 373

Arg Lys Lys Asn Arg Gln Arg Arg Arg
1 5

<210> SEQ ID NO 374
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 374

Arg Lys Lys Arg Arg Asn Arg Arg Arg
1 5

<210> SEQ ID NO 375
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 375

Arg Lys Lys Arg Arg Gln Asn Arg Arg
1 5

<210> SEQ ID NO 376
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 376

Arg Lys Lys Arg Arg Gln Arg Asn Arg
1 5

<210> SEQ ID NO 377
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 377

Arg Gln Lys Arg Arg Gln Arg Arg Arg
1 5

<210> SEQ ID NO 378
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 378

Arg Lys Gln Arg Arg Gln Arg Arg Arg
1 5

<210> SEQ ID NO 379
<211> LENGTH: 9
<212> TYPE: PRT

<213> ORGANISM: Artificial
<220> FEATURE:
<223> OTHER INFORMATION: Description of sequence: Sequence construct with amino acid protecting groups

<400> SEQUENCE: 379

Arg Lys Lys Gln Arg Gln Arg Arg Arg
1 5

<210> SEQ ID NO 380
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 380

Arg Lys Lys Arg Arg Lys Arg Arg Arg
1 5

<210> SEQ ID NO 381
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 381

Arg Lys Lys Arg Arg Gln Gln Arg Arg
1 5

<210> SEQ ID NO 382
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 382

Arg Lys Lys Arg Arg Gln Arg Gln Arg
1 5

<210> SEQ ID NO 383
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 383

Arg Ser Lys Arg Arg Gln Arg Arg Arg
1 5

<210> SEQ ID NO 384
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 384

Arg Lys Ser Arg Arg Gln Arg Arg Arg
1 5

<210> SEQ ID NO 385
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 385

Arg Lys Lys Ser Arg Gln Arg Arg Arg
1 5

<210> SEQ ID NO 386
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 386

Arg Lys Lys Arg Arg Ser Arg Arg Arg
1 5

<210> SEQ ID NO 387
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 387

Arg Lys Lys Arg Arg Gln Ser Arg Arg
1 5

<210> SEQ ID NO 388
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 388

Arg Lys Lys Arg Arg Gln Arg Ser Arg
1 5

<210> SEQ ID NO 389
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 389

Arg Thr Lys Arg Arg Gln Arg Arg Arg
1 5

<210> SEQ ID NO 390
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 390

Arg Lys Thr Arg Arg Gln Arg Arg Arg
1               5

<210> SEQ ID NO 391
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 391

Arg Lys Lys Thr Arg Gln Arg Arg Arg
1               5

<210> SEQ ID NO 392
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 392

Arg Lys Lys Arg Arg Thr Arg Arg Arg
1               5

<210> SEQ ID NO 393
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 393

Arg Lys Lys Arg Arg Gln Thr Arg Arg
1               5

<210> SEQ ID NO 394
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 394

Arg Lys Lys Arg Arg Gln Arg Thr Arg
1               5

<210> SEQ ID NO 395
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 395

Arg Val Lys Arg Arg Gln Arg Arg Arg
1               5

<210> SEQ ID NO 396
<211> LENGTH: 9

<212> TYPE: PRT
<213> ORGANISM: Artificial
<220> FEATURE:
<223> OTHER INFORMATION: Description of sequence: Sequence construct with amino acid protecting groups

<400> SEQUENCE: 396

Arg Lys Val Arg Arg Gln Arg Arg Arg
1               5

<210> SEQ ID NO 397
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 397

Arg Lys Lys Val Arg Gln Arg Arg Arg
1               5

<210> SEQ ID NO 398
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 398

Arg Lys Lys Arg Arg Val Arg Arg Arg
1               5

<210> SEQ ID NO 399
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 399

Arg Lys Lys Arg Arg Gln Val Arg Arg
1               5

<210> SEQ ID NO 400
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 400

Arg Lys Lys Arg Arg Gln Arg Val Arg
1               5

<210> SEQ ID NO 401
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 401

Arg Trp Lys Arg Arg Gln Arg Arg Arg 1 5

<210> SEQ ID NO 402
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 402

Arg Lys Trp Arg Arg Gln Arg Arg Arg
1 5

<210> SEQ ID NO 403
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 403

Arg Lys Lys Trp Arg Gln Arg Arg Arg
1 5

<210> SEQ ID NO 404
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 404

Arg Lys Lys Arg Arg Trp Arg Arg Arg
1 5

<210> SEQ ID NO 405
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 405

Arg Lys Lys Arg Arg Gln Trp Arg Arg
1 5

<210> SEQ ID NO 406
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 406

Arg Lys Lys Arg Arg Gln Arg Trp Arg
1 5

<210> SEQ ID NO 407
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 407

Arg Tyr Lys Arg Arg Gln Arg Arg Arg
1 5

<210> SEQ ID NO 408
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 408

Arg Lys Tyr Arg Arg Gln Arg Arg Arg
1 5

<210> SEQ ID NO 409
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 409

Arg Lys Lys Tyr Arg Gln Arg Arg Arg
1 5

<210> SEQ ID NO 410
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 410

Arg Lys Lys Arg Arg Tyr Arg Arg Arg
1 5

<210> SEQ ID NO 411
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 411

Arg Lys Lys Arg Arg Gln Tyr Arg Arg
1 5

<210> SEQ ID NO 412
<211> LENGTH: 9
<212> TYPE: PRT
<213> ORGANISM: Artificial
<220> FEATURE:
<223> OTHER INFORMATION: Description of sequence: Sequence construct with amino acid protecting groups

<400> SEQUENCE: 412

Arg Lys Lys Arg Arg Gln Arg Tyr Arg
1 5

<210> SEQ ID NO 413

-continued

```
<211> LENGTH: 9
<212> TYPE: PRT
<213> ORGANISM: Artificial
<220> FEATURE:
<223> OTHER INFORMATION: Description of sequence: Consensus sequence
<220> FEATURE:
<221> NAME/KEY: misc_feature
<222> LOCATION: (2)..(4)
<223> OTHER INFORMATION: Xaa = any natural amino acid
<220> FEATURE:
<221> NAME/KEY: misc_feature
<222> LOCATION: (6)..(8)
<223> OTHER INFORMATION: Xaa = any natural amino acid

<400> SEQUENCE: 413

Arg Xaa Xaa Xaa Arg Xaa Xaa Xaa Arg
1               5
```

EFFICIENT TRANSPORT INTO WHITE BLOOD CELLS

RELATED APPLICATIONS

This application is filed under 35 U.S.C. § 371 as the U.S. national phase of International Application PCT/EP2009/009228, filed Dec. 22, 2009, which designated the U.S. and claims the benefit of International Application PCT/EP2008/011003, filed Dec. 22, 2008, and International Application PCT/EP2009/003927, filed Jun. 2, 2009.

BACKGROUND OF THE INVENTION

The present invention relates to the use of specific transporter cargo conjugate molecules for the transport of a substance of interest (cargo molecule) into white blood cells. Said transporter cargo conjugate molecules may be used for the treatment, prophylaxis, attenuation and/or amelioration of a disease and/or disorder involving white blood cells. The present invention also relates to manufacture of said transporter cargo conjugate molecules, to a method of transporting a substance of interest (cargo) into a white blood cell and to a white blood cell comprising said transporter cargo conjugate molecules or fragments thereof.

Techniques enabling efficient transfer of a substance of interest from the external medium into tissue or cells, and particularly to cellular nuclei, such as nucleic acids, proteins or cytotoxic agents, but also of other compounds, are of considerable interest in the field of biotechnology. These techniques may be suitable for transport and translation of nucleic acids into cells in vitro and in vivo and thus for protein or (poly-)peptide production, for regulation of gene expression, for induction of cytotoxic or apoptotic effects, for analysis of intracellular processes and for the analysis of the effects caused by the transport of a variety of different cargos into a cell (or cell nucleus), etc.

One important application of such a transfer of a cargo of interest from the external medium into tissue or cells is targeted drug delivery. Targeted drug delivery relates to the tissue-/cell specific delivery of a pharmaceutically active drug. The intention is to achieve after (systemic) administration over time a high concentration of the pharmaceutically active drug at or in the cells and tissues of interest while at the same time the concentration of the pharmaceutically active drug in the remaining cells and tissues is kept at a low level. This improves efficacy of the therapy and reduces side effects. Such targeted drug delivery can be mediated for example by highly specific antibodies.

A further important application of such a transfer of a cargo of interest from the external medium into tissue or cells is gene therapy, wherein the cargo is typically a nucleic acid or a gene. Although this technique has shown some rather promising developments in the last decades, gene transfer is typically limited by the inability of the gene transfer vectors to effectively transfer the biologically active cargo into the cytoplasm or nuclei of cells in the host to be treated without affecting the host genome or altering the biological properties of the active cargo.

In this respect, several techniques have been developed in an effort to more efficiently transfect e.g. nucleic acids, such as DNA or RNA, into cells. Transfection of nucleic acids into cells or tissues of patients by methods of gene transfer is a central method of molecular medicine and plays a critical role in therapy and prevention of numerous diseases.

Representative examples of gene transfer methods include general (physical or physico-chemical) methods such as coprecipitating nucleic acids with calcium phosphate or DEAE-dextran, a method which enables nucleic acids to penetrate the plasma membrane and then enter the cell and/or nucleus. However, this technique suffers from low transfer efficiency and a high percentage of cell death. Additionally, this method is restricted to in vitro or ex vivo methods, but is not applicable to in vivo situations due to its very nature.

The same holds true for methods involving in vitro electroporation. In vitro electroporation is based on the use of high-voltage current to make cell membranes permeable to allow the introduction of new nucleic acids, e.g. DNA or RNA, into the cell. However, such methods are typically not suitable in vivo. Furthermore, this technique also suffers from low transfer efficiency and a high percentage of cell death.

Further well known physical or physico-chemical methods include (direct) injection of (naked) nucleic acids or biolistic gene transfer. Biolistic gene transfer (also known as biolistic particle bombardment) is a method developed at Cornell University that allows introducing genetic material into tissues or culture cells. Biolistic gene transfer is typically accomplished by surface coating metal particles, such as gold or silver particles, and shooting these metal particles, comprising the adsorbed DNA, into cells by using a gene gun. Similar as discussed above this method is restricted to in vitro or ex vivo methods, but is usually not applicable in in vivo situations.

Other methods utilize the transport capabilities of so called transporter molecules. Transporter molecules to be used in this context typically may be divided into viral vectors on the one hand, i.e. transporter molecules, which involve viral elements, and nonviral vectors on the other hand.

The most successful gene therapy strategies available today rely on viral vectors, such as adenoviruses, adeno-associated viruses, retroviruses, and herpes viruses. These viral vectors typically employ a conjugate of a virus-related substance with a strong affinity for DNA and a nucleic acid. Due to their infection properties, viruses or viral vectors have a very high transfection rate. The viral vectors typically used are genetically modified in a way that no functional infectious particles are formed in the transfected cell. In spite of this safety precaution, however, there are many problems associated with viral vectors related to immunogenicity, cytotoxicity, and insertional mutagenesis. As an example, the risk of uncontrolled propagation of the introduced therapeutically active genes or viral genes cannot be ruled out, e.g., because of possible recombination events. Additionally, the viral conjugates are difficult to use and typically require a long preparation prior to treatment (see, e. g., U.S. Pat. No. 5,521,291).

Nonviral vectors are not as efficient as viral vectors if it comes to gene therapy; however, many of them have been developed to provide a safer alternative in gene therapy. Some of the most common nonviral vectors include polyethylenimine, dendrimers, chitosan, polylysine, and (poly-)peptide based transporter systems, e.g. many types of (poly-)peptides, which are generally cationic in nature and able to interact with nucleic acids such as plasmid DNA through electrostatic interactions. Additionally, nonviral vectors allow also for delivery of drugs not based on nucleic acids.

For successful delivery, the nonviral vectors, in particular (poly-)peptide based transporter systems, must be able to overcome many barriers. Such barriers include protection of the cargo moiety, e.g. of DNA or other compounds, during transport and prevention of an early degradation or metabolisation of the cargo moiety in vivo. In case of nucleic acids, such as DNA and RNA molecules, the nonviral vectors must furthermore be capable to specifically deliver these molecules for efficient gene expression in target cells.

Especially with respect to nucleic acids such as DNA and RNA molecules there are presently 4 barriers nonviral vectors must overcome to achieve successful gene delivery (see e.g. Martin et al., The AAPS Journal 2007; 9 (1) Article 3). The nonviral vector must be able to 1) tightly compact and protect the nucleic acids, 2) it must able to target specific cell-surface receptors, 3) the nonviral vector must be capable to disrupt the endosomal membrane, and 4) it has to deliver the nucleic acid cargo to the nucleus and allow translation of an encoded protein or (poly-)peptide sequence.

Such nonviral vectors, particularly (poly-)peptide-based nonviral vectors, are advantageous over other nonviral strategies in that they are in general able to achieve all 4 of these goals, however, with different efficiency regarding the different barriers.

As an example, cationic (poly-)peptides rich in basic residues such as lysine and/or arginine are able to efficiently condense nucleic acids such as DNA into small, compact particles that can be stabilized in serum. Furthermore, attachment of a (poly-)peptide ligand to the polyplex allows targeting to specific receptors and/or specific cell types. Polyplexes or cationic polymers as mentioned above typically form a complex with negatively charged nucleic acids leading to a condensation of nucleic acids and protecting these nucleic acids against degradation. Transport into cells using polyplexes (cationic polymers) typically occurs via receptor mediated endocytosis. Thereby, the DNA is coupled to a distinct molecule, such as Transferrin, via e.g. the polyplex poly-L-lysine (PLL), which binds to a surface receptor and triggers endocytosis. Polyplexes (cationic polymers) include e.g. poly-L-lysine (PLL), chitosan, polyethylenimine (PEI), polydimethylaminoethylmethacrylate (PDMAEMA), polyamidoamine (PAMAM). Such effects are also known from nanoplexes (nanoparticular systems) or lipoplexes (liposomal systems). Nanoplexes (nanoparticular systems) typically involve the use of polyacrylates, polyamides, polystyrene, cyanoacrylates, polylactat (PLA), poly (lactic-co-glycolic acid) (PLGA), etc. Lipoplexes or liposomal systems typically involve the use of cationic lipids, which are capable to mimic a cell membrane. Thereby, the positively charged moiety of the lipid interacts with the negatively charged moiety of the nucleic acid and thus enables fusion with the cell membrane. Lipoplexes or liposomal systems include, e.g. DOTMA, DOPE, DOSPA, DOTAP, DC-Chol, EDMPC, etc.

In this context, receptor-mediated endocytosis is also widely exploited in experimental systems for the targeted delivery of cargos such as nucleic acids or therapeutic agents into cells. During receptor-mediated endocytosis the cargo-containing complexes are either selectively internalized by receptors located in the cell membrane which are specific for the cargos, or by specific antibodies located in membrane constituents. Endocytotic activity has been described for many receptors including IgG Fc, somatostatin, insulin, IGF-I and -II, transferrin, EGF, GLP-1, VLDL or integrin receptors, etc.

Different (poly-)peptide or protein sequences have been tested widely for their use in gene transfer methods via receptor-mediated endocytosis. Interestingly, the isolation of (poly-)peptide sequences that direct efficient receptor-mediated endocytosis have been profoundly boosted by the use of phage display technologies. Phage display libraries are extremely powerful tools that provide for an almost unlimited source of molecular variants including modifications of natural ligands or cargo moieties to cell receptors and short (poly-)peptides. Similar libraries have also been injected directly into mice and (poly-)peptide sequences have been successfully isolated that show a 13-fold selectivity for brain and kidney.

Proprotein convertases may serve as an example of (poly-)peptide or protein sequences that may be used for transport of molecules into cells. Proprotein convertases are an example of a cell surface receptor which gets internalized through receptor mediated endocytosis. These proteins have been shown to be responsible for conversion of precursors of (poly-)peptide hormones, neuropeptides, and many other proteins into their biologically active forms. All cleavage sites for the proprotein convertase family obey to the consensus R—X—X—R. The mammalian proprotein convertases can be classified into three groups on the basis of their tissue distribution. Furin, PACE4, PC5/PC6, and LPCIPC7/PC8/SPC7 are expressed in a broad range of tissues and cell lines. In contrast, expression of PC2 and PC1/PC3 is limited to neuroendocrine tissues, such as pancreatic islets, pituitary, adrenal medulla and many brain areas. Expression of PC4 is highly restricted to testicular spermatogenic cells. The neuroendocrine-specific convertases, PC2 and PC1/PC3, are mainly localized in secretory granules. PC5/PC6A has also been reported to be localized to secretory granules. Furthermore, indirect evidence has suggested that a proportion of proprotein convertases molecules is present on the cell surface, and it has been shown that furin cycles between the TGN and the cell surface. Taken together, these properties indicate that proprotein convertases transport extracellular ligands into the intracellular space.

Advantageous are also so called translocatory proteins or protein transduction domains (PTDs). (Poly-)peptide sequences derived from translocatory proteins or protein transduction domains (PTDs) are typically able to selectively lyse the endosomal membrane in its acidic environment leading to cytoplasmic release of the polyplex. Translocatory proteins are considered as a group of (poly-)peptides capable of effecting transport of macromolecules between cells (translocatory proteins), such as HIV-1 TAT (HIV), antennapedia (*Drosophila antennapedia*), HSV VP22 (Herpes simplex), FGF or lactoferrin, etc. In contrast, protein transduction domains (PTDs) are considered as a group of (poly-)peptides capable of directing proteins and (poly-)peptides covalently bound to these sequences into a cell via the cell membrane (Leifert and Whitton: Translocatory proteins and protein transduction domains: a critical analysis of their biological effects and the underlying mechanisms. Molecular Therapy Vol. 8 No. 1 2003). Common to translocatory proteins as well as to PTDs is a basic region, which is regarded as mainly responsible for transport of the fusion (poly-)peptides since it is capable of binding polyanions such as nucleic acids. Without being bound thereto, PTDs may act similar to cationic transfection reagents using receptor dependent non-saturatable adsorptive endocytosis. PTDs are typically coupled to proteins or (poly-)peptides in order to effect or enhance a CTL response when administering a (poly-)peptide based vaccine (see review: Melikov and Chernomordik, Arginine-rich cell penetrating (poly-)peptides: from endosomal uptake to nuclear delivery, Cell. Mol. Life Sci. 2005).

Although there are several techniques known in the art which enable transfer of a substance of interest from the external medium into tissue or cells in general, there is still a great need for techniques allowing for efficient transfer into specific tissue and cell types.

SUMMARY OF THE INVENTION

The object of the present invention was thus to provide new means to target a cargo, e.g. drugs and effector molecules, efficiently and with improved specificity into specific tissue and cell types.

This object is solved for white blood cells (WBC) by means of the subject-matter as set forth in the appended claims. In particular, the inventors of the present application surprisingly found, that certain types of (poly-)peptides provide for an efficient transfer of a cargo of interest into white blood cells.

The term "WBC targeting (poly-)peptide", as used herein refers to a (poly-)peptide which is capable to enter white blood cells (leukocytes) with increased specificity (compared to, e.g., HepG2 (human liver carcinoma cells) or HCT-116 cells (human colon carcinoma cells)) and which is derived from HIV TAT protein, i.e. comprises or consists of an amino acid sequence which is a fragment or variant (or variant of such fragment of HIV TAT protein (SEQ ID NO:1; described in U.S. Pat. Nos. 5,804,604 and 5,674,980, each of these references being incorporated herein by reference). In particular said fragments, variants and variants of such fragments are produced from TAT residues 49 to 57 (SEQ ID NO: 2) or 48 to 57 (SEQ ID NO: 3). Said amino acid sequence may comprise D-amino acids and/or L-amino acids.

The term "(poly-)peptides" as used herein is generally understood as in the art, i.e. refers to a chain of amino acids. However, the term shall not be construed as limiting the length of the amino acid chain. The chain also need not be linear but may be branched.

Preferably, a WBC targeting (poly-)peptide comprises less than 150, 100, 90, 80, 70, 60, 50, 40, 30, 20, or than 10 amino acid residues, more preferably a range of 5 to 150 amino acid residues, more preferably 5 to 100 amino acid residues, even more preferably 5 to 75 amino acid residues and most preferably a range of 9 to 50 amino acid residues, e.g. 9, 10, 11, 12, 13, 14, 15, 16, 17, 18, 19, 20, 30, 40, or 50 amino acid residues.

Examples for sequences said WBC targeting (poly-)peptides may comprise or consist of are given in Table 1.

TABLE 1

| SEQUENCE/ PEPTIDE NAME | SEQ ID NO | AA | SEQUENCE |
|---|---|---|---|
| TAT (1-86) | 1 | 86 | MEPVDPRLEP WKHPGSQPKT ACTNCYCKKC CFHCQVCFIT KALGISYGRK KRRQRRRPPQ GSQTHQVSLS KQPTSQSRGD PTGPKE |
| L-TAT (s1a) | 2 | 9 | RKKRRQRRR ($NH_2$-RKKRRQRRR-COOH) |
| L-TAT (s1b) | 3 | 9 | GRKKRRQRRR ($NH_2$-GRKKRRQRRR-COOH) |
| D-TAT | 4 | 9 | rrrqrrkkr ($NH_2$-RRRQRRKKR-COOH) |
| D-TAT | 5 | 10 | rrrqrrkkrg ($NH_2$-RRRQRRKKRG-COOH) |
| L-generic-TAT (s) | 6 | | $NH_2$-$X_n^b$-RKKRRQRRR-$X_n^b$-COOH |

TABLE 1-continued

| SEQUENCE/ PEPTIDE NAME | SEQ ID NO | AA | SEQUENCE |
|---|---|---|---|
| D-generic-TAT (s) | 7 | | $NH_2$-$X_n^b$-rrrqrrkkr-$X_n^b$-COOH |
| TAT (37-72) | 8 | 36 | CFITKALGIS YGRKKRRQRR RPPQGSQTHQ VSLSKQ |
| TAT (37-58) | 9 | 22 | CFITKALGIS YGRKKRRQRR RP |
| TAT (38-58)GGC | 10 | 24 | FITKALGISY GRKKRRQRRR PGGC |
| TAT CGG(47-58) | 11 | 15 | CGGYGRKKRR QRRRP |
| TAT (47-58)GGC | 12 | 15 | YGRKKRRQRR RPGGC |
| TAT (1-72) Mut Cys/Ala 72 | 13 | 56 | MEPVDPRLEP WKHPGSQPKT AFITKALGIS YGRKKRRQRR RPPQGSQTHQ VSLSKQ |
| L-TAT (s1c) | 14 | 11 | YDRKKRRQRRR |
| $r_3$-L-TAT | 15 | 9 | rKKRrQRRr |
| $r_3$-L-TATi | 16 | 9 | rRRQrRKKr |
| βA-$r_3$-L-TAT | 17 | 9 | βA-rKKRrQRRr |
| βA-$r_3$-L-TATi | 18 | 9 | βA-rRRQrRKKr |
| FITC-βA-$r_3$-L-TAT | 19 | 9 | FITC-βA-rKKRrQRRr |
| FITC-βA-$r_3$-L-TATi | 20 | 9 | FITC-βA-rRRQrRKKr |
| TAT(s2-1) | 21 | 9 | rAKRrQRRr |
| TAT(s2-2) | 22 | 9 | rKARrQRRr |
| TAT(s2-3) | 23 | 9 | rKKArQRRr |
| TAT(s2-4) | 24 | 9 | rKKRrARRr |
| TAT(s2-5) | 25 | 9 | rKKRrQARr |
| TAT(s2-6) | 26 | 9 | rKKRrQRAr |
| TAT(s2-7) | 27 | 9 | rDKRrQRRr |
| TAT(s2-8) | 28 | 9 | rKDRrQRRr |
| TAT(s2-9) | 29 | 9 | rKKDrQRRr |
| TAT(s2-10) | 30 | 9 | rKKRrDRRr |
| TAT(s2-11) | 31 | 9 | rKKRrQDRr |
| TAT(s2-12) | 32 | 9 | rKKRrQRDr |
| TAT(s2-13) | 33 | 9 | rEKRrQRRr |
| TAT(s2-14) | 34 | 9 | rKERrQRRr |
| TAT(s2-15) | 35 | 9 | rKKErQRRr |
| TAT(s2-16) | 36 | 9 | rKKRrERRr |
| TAT(s2-17) | 37 | 9 | rKKRrQERr |
| TAT(s2-18) | 38 | 9 | rKKRrQREr |
| TAT(s2-19) | 39 | 9 | rFKRrQRRr |
| TAT(s2-20) | 40 | 9 | rKFRrQRRr |
| TAT(s2-21) | 41 | 9 | rKKFrQRRr |

TABLE 1-continued

| SEQUENCE/ PEPTIDE NAME | SEQ ID NO | AA | SEQUENCE |
|---|---|---|---|
| TAT(s2-22) | 42 | 9 | rKKRrFRRr |
| TAT(s2-23) | 43 | 9 | rKKRrQFRr |
| TAT(s2-24) | 44 | 9 | rKKRrQRFr |
| TAT(s2-25) | 45 | 9 | rRKRrQRRr |
| TAT(s2-26) | 46 | 9 | rKRRrQRRr |
| TAT(s2-27) | 47 | 9 | rKKKrQRRr |
| TAT(s2-28) | 48 | 9 | rKKRrRRRr |
| TAT(s2-29) | 49 | 9 | rKKRrQKRr |
| TAT(s2-30) | 50 | 9 | rKKRrQRKr |
| TAT(s2-31) | 51 | 9 | rHKRrQRRr |
| TAT(s2-32) | 52 | 9 | rKHRrQRRr |
| TAT(s2-33) | 53 | 9 | rKKHrQRRr |
| TAT(s2-34) | 54 | 9 | rKKRrHRRr |
| TAT(s2-35) | 55 | 9 | rKKRrQHRr |
| TAT(s2-36) | 56 | 9 | rKKRrQRHr |
| TAT(s2-37) | 57 | 9 | rIKRrQRRr |
| TAT(s2-38) | 58 | 9 | rKIRrQRRr |
| TAT(s2-39) | 59 | 9 | rKKIrQRRr |
| TAT(s2-40) | 60 | 9 | rKKRrIRRr |
| TAT(s2-41) | 61 | 9 | rKKRrQIRr |
| TAT(s2-42) | 62 | 9 | rKKRrQRIr |
| TAT(s2-43) | 63 | 9 | rLKRrQRRr |
| TAT(s2-44) | 64 | 9 | rKLRrQRRr |
| TAT(s2-45) | 65 | 9 | rKKLrQRRr |
| TAT(s2-46) | 66 | 9 | rKKRrLRRr |
| TAT(s2-47) | 67 | 9 | rKKRrQLRr |
| TAT(s2-48) | 68 | 9 | rKKRrQRLr |
| TAT(s2-49) | 69 | 9 | rMKRrQRRr |
| TAT(s2-50) | 70 | 9 | rKMRrQRRr |
| TAT(s2-51) | 71 | 9 | rKKMrQRRr |
| TAT(s2-52) | 72 | 9 | rKKRrMRRr |
| TAT(s2-53) | 73 | 9 | rKKRrQMRr |
| TAT(s2-54) | 74 | 9 | rKKRrQRMr |
| TAT(s2-55) | 75 | 9 | rNKRrQRRr |
| TAT(s2-56) | 76 | 9 | rKNRrQRRr |
| TAT(s2-57) | 77 | 9 | rKKNrQRRr |
| TAT(s2-58) | 78 | 9 | rKKRrNRRr |
| TAT(s2-59) | 79 | 9 | rKKRrQNRr |

TABLE 1-continued

| SEQUENCE/ PEPTIDE NAME | SEQ ID NO | AA | SEQUENCE |
|---|---|---|---|
| TAT(s2-60) | 80 | 9 | rKKRrQRNr |
| TAT(s2-61) | 81 | 9 | rQKRrQRRr |
| TAT(s2-62) | 82 | 9 | rKQRrQRRr |
| TAT(s2-63) | 83 | 9 | rKKQrQRRr |
| TAT(s2-64) | 84 | 9 | rKKRrKRRr |
| TAT(s2-65) | 85 | 9 | rKKRrQQRr |
| TAT(s2-66) | 86 | 9 | rKKRrQRQr |
| TAT(s2-67) | 87 | 9 | rSKRrQRRr |
| TAT(s2-68) | 88 | 9 | rKSRrQRRr |
| TAT(s2-69) | 89 | 9 | rKKSrQRRr |
| TAT(s2-70) | 90 | 9 | rKKRrSRRr |
| TAT(s2-71) | 91 | 9 | rKKRrQSRr |
| TAT(s2-72) | 92 | 9 | rKKRrQRSr |
| TAT(s2-73) | 93 | 9 | rTKRrQRRr |
| TAT(s2-74) | 94 | 9 | rKTRrQRRr |
| TAT(s2-75) | 95 | 9 | rKKTrQRRr |
| TAT(s2-76) | 96 | 9 | rKKRrTRRr |
| TAT(s2-77) | 97 | 9 | rKKRrQTRr |
| TAT(s2-78) | 98 | 9 | rKKRrQRTr |
| TAT(s2-79) | 99 | 9 | rVKRrQRRr |
| TAT(s2-80) | 100 | 9 | rKVRrQRRr |
| TAT(s2-81) | 101 | 9 | rKKVrQRRr |
| TAT(s2-82) | 102 | 9 | rKKRrVRRr |
| TAT(s2-83) | 103 | 9 | rKKRrQVRr |
| TAT(s2-84) | 104 | 9 | rKKRrQRVr |
| TAT(s2-85) | 105 | 9 | rWKRrQRRr |
| TAT(s2-86) | 106 | 9 | rKWRrQRRr |
| TAT(s2-87) | 107 | 9 | rKKWrQRRr |
| TAT(s2-88) | 108 | 9 | rKKRrWRRr |
| TAT(s2-89) | 109 | 9 | rKKRrQWRr |
| TAT(s2-90) | 110 | 9 | rKKRrQRWr |
| TAT(s2-91) | 111 | 9 | rYKRrQRRr |
| TAT(s2-92) | 112 | 9 | rKYRrQRRr |
| TAT(s2-93) | 113 | 9 | rKKYrQRRr |
| TAT(s2-94) | 114 | 9 | rKKRrYRRr |
| TAT(s2-95) | 115 | 9 | rKKRrQYRr |
| TAT(s2-96) | 116 | 9 | rKKRrQRYr |
| r3 (generic) | 235 | 9 | rXXXrXXXr |

In Table 1 D-enantiomeric amino acids are indicated with a small character and L-enantiomeric amino acids are indicated with a capital letter. All sequences read from the N-Terminus to the C-Terminus (left to right). "βA" refers to beta alanine. For SEQ ID NO: 6 and 7, each X typically represents an amino acid residue, preferably selected from any (native) amino acid residue. $X_n^a$ typically represents one amino acid residue, preferably selected from any amino acid residue except serine or threonine, wherein n (the number of repetitions of X) is 0 or 1. Furthermore, each $X_n^b$ may be selected from any amino acid residue, wherein n (the number of repetitions of X) is 0-5, 5-10, 10-15, 15-20, 20-30 or more, provided that if n (the number of repetitions of X) is 0 for $X_n^a$, $X_n^b$ does preferably not comprise a serine or threonine at its C-terminus, in order to avoid a serine or threonine at this position. Preferably, $X_n^b$ represents a contiguous stretch of (poly-)peptide residues derived from SEQ ID NO: 1. $X_n^a$ and $X_n^b$ may represent either D or L amino acids.

The WBC targeting (poly-)peptide for use in the different embodiments of the present invention may be for example a (poly-)peptide comprising or consisting of the amino acid sequence of HIV TAT residues 49 to 57 (SEQ ID NO: 2), or a (chemical) derivative thereof, or a variant thereof, wherein the variant of SEQ ID NO:2 is selected from the group consisting of:

i) a (poly-)peptide comprising or consisting of at least one amino acid sequence according to SEQ ID NO: 235, (chemical) derivatives thereof, or reverse sequence thereof, and
ii) a (poly-)peptide comprising or consisting of at least one amino acid sequence according to any one of SEQ ID NOs: 2 to 116, (chemical) derivatives thereof, or reverse sequence thereof.

In a particularly preferred embodiment a variant of a fragment of HIV TAT protein is a (poly-)peptide comprising an amino acid sequence according to any one of SEQ ID NOs: 1 to 116, more preferably a (poly-)peptide comprising or consisting of the amino acid sequence of L-TAT (SEQ ID NO: 2), D-TAT (SEQ ID NO: 4), $r_3$-L-TAT (SEQ ID NO: 15), $r_3$-L-TATi (SEQ ID NO: 16), TAT(s2-28) (SEQ ID NO: 48), TAT(s2-64) (SEQ ID NO: 84), or TAT(s2-91) (SEQ ID NO: 111).

In a particular embodiment the WBC targeting (poly-)peptide comprises or consists of at least one sequence according to rXXXrXXXr (SEQ ID NO: 235), wherein:

r represents an D-enatiomeric arginine;

X is any L-amino acid;

and wherein each X may be selected individually and independently of any other X within SEQ ID NO: 252. Preferably at least 4 out of said 6 X L-amino acids within SEQ ID NO: 235 are K or R. In another embodiment the WBC targeting (poly-)peptide according to the present invention comprises or consists of the sequence $rX_1X_2X_3rX_4X_5X_6r$ (SEQ ID NO: 235), wherein $X_1$ is K, $X_2$ is K, $X_3$ is R and $X_4$, $X_5$, and $X_6$ are any L-amino acid selected independently from each other. Similarly, the transporter construct according to the present invention may comprise or consist of the sequence $rX_1X_2X_3rX_4X_5X_6r$ (SEQ ID NO: 235), wherein $X_4$ is Q, $X_5$ is R, $X_6$ is R and $X_1$, $X_2$, and $X_3$ are any L-amino acid selected independently from each other. The inventive transporter construct may also comprises or consist of the sequence $rX_1X_2X_3rX_4X_5X_6r$ (SEQ ID NO: 235), wherein one, two, three, four, five or six X amino acid residues are chosen from the group consisting of: $X_1$ is K, $X_2$ is K, $X_3$ is R, $X_4$ is Q, $X_5$ is R, $X_6$ is R, while the remaining X amino acid residues not selected from above group may be any L-amino acid and are selected independently from each other. $X_1$ is then preferably Y and/or $X_4$ is preferably K or R. Similarly considered are reverse sequences and/or chemical derivatives of the above mentioned sequences and embodiments of SEQ ID NO: 235.

Additionally, WBC targeting (poly-)peptides may be selected from fragments or variants of the above mentioned WBC targeting (poly-)peptides as denoted in Table 1, with the proviso that they retain the functionality/activity to enter WBCs with higher selectivity. In particular, variants of the sequences in Table 1 need not follow the same sequence of D and L amino acids, i.e. may be entirely composed of D-amino acids, entirely composed of L-amino acids or composed of a random mixture of D and L-amino acid.

In the context of the present invention, variants and/or fragments of (poly-)peptides preferably comprise or consist of a (poly-)peptide sequence having at least 10%, 20%, 30%, 40%, 50%, 60%, 70%, 80%, or 85%, preferably at least 90%, more preferably at least 95% and most preferably at least 99% sequence identity over the whole length to the sequence of the (poly-)peptide referred to. Additionally, a fragment of such a (poly-)peptide may furthermore comprise epitopes (also called "antigen determinants") of the full-length sequence. Epitopes in the context of the present invention are typically fragments located on the outer surface of a (native) protein or (poly-)peptide sequence as defined herein, preferably having 5 to 15 amino acids, more preferably having 5 to 12 amino acids, even more preferably having 6 to 9 amino acids, which may be recognized by antibodies, i.e. in their original form.

"Fragment", as used herein, in particular of a WBC targeting (poly-)peptide as disclosed in Table 1, is preferably to be understood as a truncated sequence thereof, i.e. an amino acid sequence, which is N-terminally, C-terminally and/or intrasequentially truncated compared to the amino acid sequence of the original sequence.

Furthermore, in the context of the present invention, a "variant" of a (poly-)peptide is preferably to be understood as a sequence wherein the amino acid sequence of the variant differs from the sequence of the (poly-)peptide (or a fragment thereof) referred to by one or more mutation(s), such as one or more substituted, (or, if necessary, inserted and/or deleted) amino acid(s). The variants have essentially the same biological function or specific activity compared to the full-length original sequence. For variants of WBC targeting (poly-)peptides this means that they still provide for transport into WBC cells. More preferably, a variant may comprise about 1 to 50, 1 to 20, even more preferably 1 to 10 and most preferably 1 to 5, 4, 3, 2 or 1 amino acid alterations within the above meaning. Variants may also comprise conservative amino acid substitutions. Conservative amino acid substitutions may include substitutions of amino acid residues by other amin acid residues with sufficiently similar physicochemical properties, so that a substitution will preserve the biological activity of the molecule (see e.g. Grantham, R. (1974), Science 785, 862-864). It is evident to the skilled person that amino acids may also be inserted and/or deleted in the above-defined sequences without altering their function, particularly if the insertions and/or deletions only involve a few amino acids, e.g. less than twenty, and preferably less than ten, and do not remove or displace amino acids which are critical to functional activity. Conservative amino acid substitutions are preferably substitutions in which the amino acids, which originate from the same class of amino acids (basic amino acids, acidic amino acids, polar amino acids, etc.), are exchanged for one another. Relevant aspects are aliphatic side chains, positively or negatively charged side chains, aromatic groups in the side chains of amino acids, side chains which can provide for hydrogen bridges, e.g. side chains which have a hydroxyl function. This means that e.g. an amino acid having a polar side chain is replaced by another amino acid having a likewise polar side chain, or, for example, an amino acid characterized by a hydrophobic side chain is substituted by another amino acid having a likewise hydrophobic side chain (e.g. serine (threonine) by threonine (serine) or leucine (isoleucine) by isoleucine (leucine)). Synonymous amino acid residues, which are classified into the same groups and which are typically exchangeable by conservative amino acid substitutions, are listed in Table 2.

TABLE 2

Preferred Groups of Synonymous Amino Acid Residues

| Amino Acid | Synonymous Residue |
|---|---|
| Ser | Ser, Thr, Gly, Asn |
| Arg | Arg, Gln, Lys, Glu, His |
| Leu | Ile, Phe, Tyr, Met, Val, Leu |
| Pro | Gly, Ala, (Thr), Pro |
| Thr | Pro, Ser, Ala, Gly, His, Gln, Thr |
| Ala | Gly, Thr, Pro, Ala |
| Val | Met, Tyr, Phe, Ile, Leu, Val |
| Gly | Ala, (Thr), Pro, Ser, Gly |
| Ile | Met, Tyr, Phe, Val, Leu, Ile |
| Phe | Trp, Met, Tyr, Ile, Val, Leu, Phe |
| Tyr | Trp, Met, Phe, Ile, Val, Leu, Tyr |
| Cys | Ser, Thr, Cys |
| His | Glu, Lys, Gln, Thr, Arg, His |
| Gln | Glu, Lys, Asn, His, (Thr), Arg, Gln |
| Asn | Gln, Asp, Ser, Asn |
| Lys | Glu, Gln, His, Arg, Lys |
| Asp | Glu, Asn, Asp |
| Glu | Asp, Lys, Asn, Gln, His, Arg, Glu |
| Met | Phe, Ile, Val, Leu, Met |
| Trp | Trp |

In a particular embodiment a variant is a variant of SEQ ID NO:2 selected from the group consisting of:

i) a (poly-)peptide comprising or consisting of at least one amino acid sequence according to SEQ ID NO: 235, (chemical) derivatives thereof, or reverse sequence thereof, and ii) a (poly-)peptide comprising or consisting of at least one amino acid sequence according to any one of SEQ ID NOs: 2 to 116, (chemical) derivatives thereof, or reverse sequence thereof.

Functionality/activity of fragments or variants may be tested by various tests, e.g. transfection efficacy, correct expression of proteins encoded by cargo nucleic acids, or by biophysical methods, e.g. spectroscopy, computer modeling, structural analysis, etc. They may be analyzed by hydrophilicity analysis (see e.g. Hopp and Woods, 1981. Proc Natl Acad Sci USA 78: 3824-3828) that can be utilized to identify the hydrophobic and hydrophilic regions of the (poly-) peptides, thus aiding in the design of substrates for experimental manipulation. Secondary structural analysis may also be performed to identify regions of the (poly-)peptides or of variants and/or fragments thereof, that assume specific structural motifs (see e.g. Chou and Fasman, 1974, Biochem 13: 222-223). Manipulation, translation, secondary structure prediction, hydrophilicity and hydrophobicity profiles, open reading frame prediction and plotting, and determination of sequence homologies can be accomplished using computer software programs available in the art. Other methods of structural analysis include, e.g. X-ray crystallography (see e.g. Engstrom, 1974. Biochem Exp Biol 11: 7-13), mass spectroscopy and gas chromatography (see e.g. METHODS IN PROTEIN SCIENCE, 1997, J. Wiley and Sons, New York, N.Y.). Computer modeling (see e.g. Fletterick and Zoller, eds., 1986. Computer Graphics and Molecular Modeling. In: CURRENT COMMUNICATIONS IN MOLECULAR BIOLOGY, Cold Spring Harbor Laboratory Press, Cold Spring Harbor, N.Y.) may also be employed.

For (amino acid or nucleic acid) sequences without exact correspondence, a "% identity" of a first sequence may be determined with respect to a second sequence. In general, these two sequences to be compared are aligned to give a maximum correlation between the sequences. This may include inserting "gaps" in either one or both sequences, to enhance the degree of alignment. A % identity may then be determined over the whole length of each of the sequences being compared (so-called global alignment), that is particularly suitable for sequences of the same or similar length, or over shorter, defined lengths (so-called local alignment), that is more suitable for sequences of unequal length. In the above context, an amino acid sequence having a "sequence identity" of at least, for example, 95% to a query amino acid sequence, is intended to mean that the sequence of the subject amino acid sequence is identical to the query sequence except that the subject amino acid sequence may include up to five amino acid alterations per each 100 amino acids of the query amino acid sequence. In other words, to obtain an amino acid sequence having a sequence of at least 95% identity to a query amino acid sequence, up to 5% (5 of 100) of the amino acid residues in the subject sequence may be inserted or substituted with another amino acid or deleted, preferably within the above definitions of variants or fragments.

What has been set out above for variants and fragments of (poly-)peptides applies mutatis mutandis to nucleic acid sequences.

Methods for comparing the identity and homology of two or more sequences are well known in the art. The percentage to which two sequences are identical can e.g. be determined using a mathematical algorithm. A preferred, but not limiting, example of a mathematical algorithm which can be used is the algorithm of Karlin et al. (1993), PNAS USA, 90:5873-5877. Such an algorithm is integrated in the BLAST family of programs, e.g. BLAST or NBLAST program (see also Altschul et al, 1990, J. Mol. Biol. 215, 403-410 or Altschul et al. (1997), Nucleic Acids Res, 25:3389-3402), accessible through the home page of the NCBI at world wide web site ncbi.nlm.nih.gov and FASTA (Pearson (1990), Methods Enzymol. 183, 63-98; Pearson and Lipman (1988), Proc. Natl. Acad. Sci. U.S.A 85, 2444-2448.). Sequences which are identical to other sequences to a certain extent can be identified by these programmes. Furthermore, programs available in the Wisconsin Sequence Analysis Package, version 9.1 (Devereux et al., 1984, Nucleic Acids Res., 387-395), for example the programs BESTFIT and GAP, may be used to determine the % identity between two polynucleotides and the % identity and the % homology or identity between two polypeptide sequences. BESTFIT uses the "local homology" algorithm of Smith and Waterman ((1981), J. Mol. Biol. 147, 195-197), and finds the best single region of similarity between two sequences.

In the context of the present invention L-amino acids, also termed L-enantiomeric amino acids, are preferably amino acids selected from naturally occurring amino acids or their derivatives. Naturally occurring amino acids are typically selected from the standard (proteinogenic) amino acids alanine, arginine, asparagine, aspartic acid, cysteine, glutamine, glutaminic acid, glycine, histidine, isoleucine, leucine, lysine, methionine, phenyl alanine, proline, serine, threonine, tryptophane, tyrosine, and valine, as well as from non-standard amino acids such as ornithine, citrulline, homocysteine, S-adenosyl methionione, hydroxyproline, selenocysteine, pyrrolysine, lanthionine, 2-aminoisobutyric acid, dehydroalanine, gamma-aminobutyric acid, etc.

The term (Chemical) "Derivatives" as used herein refers to the (chemical) modification of amino acids/amino acid chains at the N-Terminus, the C-Terminus, the backbone, peptide bonds and/or the side chain residues. The term does not intend to refer to any addition, substitution or deletion of amino acids in an amino acid chain. (Chemical) Derivatives from such L-amino acids or L-enantiomeric amino acids typically comprise any naturally or non-naturally occurring derivative of these amino acids, including, without being limited thereto, amino acids as defined above comprising post-translational modifications or synthetic modifications, including acetylation (at the N-terminus of the (poly-) peptide sequence, at lysine residues, etc.), deacetylation, alkylation, such as methylation, ethylation, etc. (preferably at lysine or arginine residues within the (poly-)peptide sequence), dealkylation, such as demethylation, deethylation, etc., amidation (preferably at the C-terminus of the (poly-)peptide sequence), formylation, gamma-carboxylation, glutamylation, glycosylation (preferably at asparagine, lysine, hydroxylysine, serine or threonine residues, etc., within the (poly-)peptide sequence), addition of a heme or haem moiety, hydroxylation, iodination, isoprenylation addition of an isoprenoid moiety such as farnesyl or geranylgeraniol, etc.), lipoylation (attachment of lipoate functionality), such as prenylation, formation of a GPI anchor, including myristoylation, farnesylation, geranylgernaylation, etc., oxidation, phosphorylation (e.g. to a serine, tytosine, threonine or a histidine moiety, etc., within the (poly-)peptide sequence), sulfation (e.g. of tyrosine), selenoylation, sulfation, etc.

(Chemical) Derivatives of L-amino acids also include, without being limited thereto, modified L-amino acids, which have been modified by introducing one of the following labels:

(i) radioactive labels, i.e. radioactive phosphorylation or a radioactive label with sulphur, hydrogen, carbon, nitrogen, etc.;
(ii) colored dyes (e.g. digoxygenin, etc.);
(iii) fluorescent groups (e.g. fluorescein, rhodamine, flourochrome proteins as defined below, etc.);
(iv) chemoluminescent groups;
(v) a combination of labels of two or more of the labels mentioned under (i) to (iv).

Particularly specific examples of derivatives of L-amino acids include, without being limited thereto, AMC (aminomethylcoumarin), Dabcyl (dimethylaminophenylazobenzoyl), Dansyl (dimethylaminonaphtalenesulfonyl), FAM (carboxyfluoroscein), Mca (methoxycoumarin acetyl), Xan (xanthyl), Abu (aminobutyric acid), Beta-Ala (beta-alanine), E-Ahx (6-aminohexanoic acid), Alpha-Aib (alpha-aminoisobutyric acid), Ams (aminoserine), Cha (cyclohexylamine), Dab (diaminobutyric acid), Hse (homoserine), Hyp (hydroxyproline), Mpr (mercaptopropionic acid), NaI (naphtylalanine), Nva (Norvaline), Orn (ornithine), Phg (phenylglycine), Sar (sarcosine), Sec (selenocysteine), Thi (thienylalanine), etc.

Furthermore, L-enantiomeric amino acids selected may be selected from specific combinations of the above defined L-enantiomeric amino acids or derivatives thereof. Such combinations may comprise 1, 2, 3, 4, 5, 6, 7, 8, 9 or 10 or even more of the above defined L-enantiomeric amino acids or derivatives thereof. Combinations are also possible between any of the above defined L-enantiomeric amino acids or derivatives thereof and any of the above D-enantiomeric amino acids or derivatives thereof defined further below. Such specific combinations of amino acids may exhibit a higher or a lower stability towards peptidases and thus may provide a further possibility to render the in vivo or in vitro stability of the, e.g., WBC targeting (poly-) peptide towards a higher or a lower stability. As an example, the WBC targeting (poly-)peptide may contain the dipeptide sequence Arg-Lys in D- and/or L-form (i.e. both as D-enantiomeric amino acids or as L-enantiomeric amino acids or mixed D- and L-enantiomeric amino acids), preferably in L-form, which exhibits a lower stability towards peptidases and thus may be used to destabilize the (poly-) peptide sequence of the WBC targeting (poly-)peptide and therefore to decrease its half life in vivo to a further extent.

In the context of the present invention D-amino acids, also termed D-enantiomeric amino acids, are preferably non-native (non-proteinogenic) amino acids, wherein these non-native (non-proteinogenic) amino acids are preferably derived from naturally occurring L-amino acids and/or their derivatives as defined above. "D-amino acids" refers to an isomer of a naturally occurring L-amino acid as defined above (and (poly-)peptides made therefrom) in which the chirality of the naturally occurring L-amino acid residue is inverted in the corresponding D-amino acid (see e.g. Jameson et al, Nature, 368,744-746 (1994); Brady et al, Nature, 368,692-693 (1994)). In other words, in the (poly-)peptide bonds of D-amino acids the positions of carbonyl and amino groups are exchanged, while the position of the side-chain groups at each alpha carbon is preserved. Accordingly, D-amino acids may be inserted into a (poly-)peptide sequence consisting of or comprising L-amino acids and therefore may be conjugated with L-amino acids as defined above by methods known in the art. Such methods known in the art include e.g., without being limited thereto, liquid phase (poly-)peptide synthesis methods or solid (poly-) peptide synthesis methods, e.g. solid (poly-)peptide synthesis methods according to Merrifield, t-Boc solid-phase (poly-)peptide synthesis, Fmoc solid-phase (poly-)peptide synthesis, BOP (Benzotriazole-1-yl-oxy-tris-(dimethyl-amino)-phosphonium hexafluorophosphate) based solid-phase (poly-)peptide synthesis, etc. The content of D-amino acids provides a further variety of useful properties. For example, such (poly-)peptides are more stable (especially in vivo) and show lower immunogenicity than corresponding L-amino-acid-sequence based WBC targeting (poly-)peptides. However, they are not as persistent in the cell as WBC targeting (poly-)peptides entirely made of D-amino acids, particularly due to the fact that almost all decomposition enzymes, like proteases or peptidases, cleave (poly-)peptide bonds between adjacent L-amino acids. Consequently, (poly-)peptides composed of D-enantiomeric amino acids and L-enantiomeric amino acids are largely resistant towards a fast proteolytic breakdown without leading to an accumulation in the cell due to a missing degradation by proteases.

The WBC targeting (poly-)peptide preferably comprises L-amino acids and D-amino acids or their derivatives as defined above. Such derivatives may be contained in the entire WBC targeting (poly-)peptide in a content of about 0%, about 10%, about 20%, about 30%, about 40%, about 50%, about 60%, about 70%, about 80%, about 90%, or even about 100%. In other words, the entire WBC targeting (poly-)peptide may contain about 1, 2, 3, 4, 5, 6, 7, 8, 9, 10, 11, 12, 13, 14, 15, 16, 17, 18, 19, 20, 21, 22, 23, 24, 25, 26, or even more, of such derivatives.

The WBC targeting (poly-)peptide for use in the present invention does not consist of the following sequences: KRIIQRILSRNS (SEQ ID NO: 236); KRIHPRLTRSIR (SEQ ID NO: 237); PPRLRKRRQLNM (SEQ ID NO: 238); PIRRRKKLRRLK (SEQ ID NO: 239); RRQRRTSKLMKR (SEQ ID NO: 240); MHKRPTTPSRKM (SEQ ID NO: 241); RQRSRRRPLNIR (SEQ ID NO: 242); RIRMIQNLIKKT (SEQ ID NO: 243); SRRKRQRSNMRI (SEQ ID NO: 244); QRIRKSKISRTL (SEQ ID NO: 245); PSKRLLHNNLRR (SEQ ID NO: 246); HRHIRRQSLIML (SEQ ID NO: 247); PQNRLQIRRHSK (SEQ ID NO: 248); PPHNRIQRRLNM (SEQ ID NO: 249); SMLKRNHSTSNR (SEQ ID NO: 250); GSRHPSLIIPRQ (SEQ ID NO: 251); SPMQKTMNLPPM (SEQ ID NO: 252); NKRILIRIMTRP (SEQ ID NO: 253); HGWZIHGLLHRA (SEQ ID NO: 254); AVPAKKRZKSV (SEQ ID NO: 255); PNTRVRPDVSF (SEQ ID NO: 256); LTRNYEAWVPTP (SEQ ID NO: 257); SAETVESCLAKSH (SEQ ID NO: 258); YSHIATLPFTPT (SEQ ID NO: 259); SYIQRTPSTTLP (SEQ ID NO: 260); AVPAENALNNPF (SEQ ID NO: 261); SFHQFARATLAS (SEQ ID NO: 262); QSPTDFTFPNPL (SEQ ID NO: 263); HFAAWGGWSLVH (SEQ ID NO: 264); HIQLSPFSQSWR (SEQ ID NO: 265); LTMPSDLQPVLW (SEQ ID NO: 266); FQPYDHPAEVSY (SEQ ID NO: 267); FDPFFWKYSPRD (SEQ ID NO: 268); FAPWDTASFMLG (SEQ ID NO: 269); FTYKNFFWLPEL (SEQ ID NO: 270); SATGAPWKMWVR (SEQ ID NO: 271); SLGWMLPFSPPF (SEQ ID NO: 272); SHAFTWPTYLQL (SEQ ID NO: 273); SHNWLPLWPLRP (SEQ ID NO: 274); SWLPYPWHVPSS (SEQ ID NO: 275); SWWTPWHVHSES (SEQ ID NO: 276); SWAQHLSLPPVL (SEQ ID NO: 277); SSSIFPPWLSFF (SEQ ID NO: 278); LNVPPSWFLSQR (SEQ ID NO: 279); LDITPFLSLTLP (SEQ ID NO: 280); LPHPVLHMGPLR (SEQ ID NO: 281); VSKQPYYMWNGN (SEQ ID NO: 282); NYTTYKSHFQDR (SEQ ID NO: 283); AIPNNQLGFPFK (SEQ ID NO: 284); NIENSTLATPLS (SEQ ID NO: 285); YPYDANHTRSPT (SEQ ID NO: 286); DPATNPGPHFPR (SEQ ID NO: 287); TLPSPLALLTVH (SEQ ID NO: 288); HPGSPFPPEHRP (SEQ ID NO: 289); TSHTDAPPARSP (SEQ ID NO: 290); MTPSSLSTLPWP (SEQ ID NO: 291); VLGQSGYLMPMR (SEQ ID NO: 292); QPIIITSPYLPS (SEQ ID NO: 293); TPKTMTQTYDFS (SEQ ID NO: 294); NSGTMQSASRAT (SEQ ID NO: 295); QAASRVENYMHR (SEQ ID NO: 296); HQHKPPPLTNNW (SEQ ID NO: 297); SNPWDSLLSVST (SEQ ID NO: 298); KTIEAHPPYYAS (SEQ ID NO: 299); EPDNWSLDFPRR (SEQ ID NO: 300); HQHKPPPLTNNW (SEQ ID NO: 301); GVVGKLGQRRTKKQRRQKK (SEQ ID NO: 302); GRRTKKQRRQKKPPRYMILGLLALAAVCSAA (SEQ ID NO: 303); GRRTKKQRRQKKPP (SEQ ID NO: 304). In a particular embodiment the WBC targeting (poly-)peptide for use in the embodiments of the present invention does not comprise or consist of SEQ ID NO:1.

The underlying object of the present invention is solved by coupling one, two or more of the WBC targeting (poly-)peptides mentioned above to at least one further substance (cargo). The combination of WBC targeting (poly-)peptide and cargo will in the following be referred to as "transporter cargo conjugate molecule". Thus, the present invention relates also to a transporter cargo conjugate molecule comprising as a component (A) at least one WBC targeting (poly-)peptide according to the present invention, and as a component (B) a further substance (cargo). Of course, said transporter cargo conjugate molecule may also comprise any number of further components (C), (D), (E) etc. In the following, component (B) will be described in more detail; however, these features may also apply to any other further component (C), (D), (E) etc.

A person skilled in the art will understand that a contribution of the inventors of the present invention to the art is—primarily—that a general means allowing for efficient delivery of cargo to white blood cells is provided. Thus, the actual component (B) of the transporter cargo conjugate molecule according to the present invention may—in principle—be any substance the person skilled in the art wants to introduce into white blood cells for whatever reason. Without being limited thereto, such reasons comprise therapeutic reasons (such as treating, preventing, attenuating or ameliorating a disease), diagnostic reasons, scientific reasons, technical reasons, commercial reasons etc. In the following some examples are given for component (B). However, said examples shall not be construed as limiting the scope of the present invention.

For example, the cargo molecule (component (B)) may be selected from:
a) proteins or (poly-)peptides, including therapeutically active proteins and/or (poly-)peptides,
b) protein kinase inhibitors, including inhibitors of the protein kinase c-Jun amino terminal kinase or factors,
c) antigens,
d) antibodies,
e) apoptotic factors,
f) proteases implicated in pathological states, including peptidic protease inhibitors,
g) BH3-domains,
h) BH3-only proteins,
i) DNAs,
j) RNAs, including siRNAs, antisense RNAs, microRNAs,
k) cytotoxic agents,
l) small organic compounds,
m) small molecule pharmaceuticals,
n) gold particles,
o) fluorescent dyes,
p) antibiotics, and/or
q) virustatics etc.

In the context of the present invention, a therapeutically active protein or (poly-)peptide suitable as the effector molecule for component (B) of the inventive transporter cargo conjugate molecule may be selected from, without being limited thereto, proteins, capable of stimulating or inhibiting the signal transduction in the cell, e.g. cytokines, antibodies, etc. Therapeutically active proteins may thus comprise cytokines of class I of the family of cytokines, having 4 positionally conserved cysteine residues (CCCC) (SEQ ID NO:305) and comprising a conserved sequence motif Trp-Ser-X-Trp-Ser (WSXWS) (SEQ ID NO:306), wherein X is a non-conserved amino acid. Cytokines of class I of the family of cytokines comprise the GM-CSF subfamily, e.g. IL-3, IL-5, GM-CSF, the IL-6-subfamily, e.g. IL-6, IL-11, IL-12, or the IL-2-subfamily, e.g. IL-2, IL-4, IL-7, IL-9, IL-15, etc., or the cytokines IL-1 alpha, IL-1 beta, IL-10 etc. Therapeutically active proteins may also comprise cytokines of class II of the family of cytokines, which also comprise 4 positionally conserved cystein residues (CCCC) (SEQ ID NO:305), but no conserved sequence motif Trp-Ser-X-Trp-Ser (WSXWS) (SEQ ID NO:306). Cytokines of class II of the family of cytokines comprise e.g. IFN-alpha, IFN-beta, IFN-gamma, etc. Therapeutically active proteins may additionally comprise cytokines of the family of tumor necrose factors, e.g. TNF-alpha, TNF-beta, etc., or cytokines of the family of chemokines, which comprise 7 transmembrane helices and interact with G-protein, e.g. IL-8, MIP-1, RANTES, CCR5, CXR4, etc., or cytokine specific receptors, such as TNF-RI, TNF-RII, CD40, OX40 (CD134), Fas, or from fragments or variants thereof. Preferably, such fragments as well as variants exhibit a sequence homology or identity as defined above.

Therapeutically active proteins suitable as component (B) of the transporter cargo conjugate molecule according to the present invention may also be selected from any of the proteins given in the following non-exhaustive list: 0ATL3, 0FC3, 0PA3, 0PD2, 4-1BBL, 5T4, 6Ckine, 707-AP, 9D7, A2M, AA, AAAS, AACT, AASS, ABAT, ABCA1, ABCA4, ABCB1, ABCB11, ABCB2, ABCB4, ABCB7, ABCC2, ABCC6, ABCC8, ABCD1, ABCD3, ABCG5, ABCG8, ABL1, ABO, ABR ACAA1, ACACA, ACADL, ACADM, ACADS, ACADVL, ACAT1, ACCPN, ACE, ACHE, ACHM3, ACHM1, ACLS, ACPI, ACTA1, ACTC, ACTN4, ACVRL1, AD2, ADA, ADAMTS13, ADAMTS2, ADFN, ADH1B, ADH1C, ADLDH3A2, ADRB2, ADRB3, ADSL, AEZ, AFA, AFD1, AFP, AGA, AGL, AGMX2, AGPS, AGS1, AGT, AGTR1, AGXT, AH02, AHCY, AHDS, AHHR, AHSG, AIC, AIED, AIH2, AIH3, AIM-2, AIPL1, AIRE, AK1, ALAD, ALAS2, ALB, HPG1, ALDH2, ALDH3A2, ALDH4A1, ALDH5A1, ALDH1A1, ALDOA, ALDOB, ALMS1, ALPL, ALPP, ALS2, ALX4, AMACR, AMBP, AMCD, AMCD1, AMCN, AMELX, AMELY, AMGL, AMH, AMHR2, AMPD3, AMPD1, AMT, ANC, ANCR, ANK1, ANOP1, AOM, AP0A4, AP0C2, AP0C3, AP3B1, APC, aPKC, APOA2, APOA1, APOB, APOC3, APOC2, APOE, APOH, APP, APRT, APS1, AQP2, AR, ARAF1, ARG1, ARHGEF12, ARMET, ARSA, ARSB, ARSC2, ARSE, ART-4, ARTC1/m, ARTS, ARVD1, ARX, AS, ASAH, ASAT, ASD1, ASL, ASMD, ASMT, ASNS, ASPA, ASS, ASSP2, ASSP5, ASSP6, AT3, ATD, ATHS, ATM, ATP2A1, ATP2A2, ATP2C1, ATP6B1, ATP7A, ATP7B, ATP8B1, ATPSK2, ATRX, ATXN1, ATXN2, ATXN3, AUTS1, AVMD, AVP, AVPR2, AVSD1, AXIN1, AXIN2, AZF2, B2M, B4GALT7, B7H4, BAGE, BAGE-1, BAX, BBS2, BBS3, BBS4, BCA225, BCAA, BCH, BCHE, BCKDHA, BCKDHB, BCL10, BCL2, BCL3, BCL5, BCL6, BCPM, BCR, BCR/ABL, BDC, BDE, BDMF, BDMR, BEST1, beta-Catenin/m, BF, BFHD, BFIC, BFLS, BFSP2, BGLAP, BGN, BHD, BHR1, BING-4, BIRC5, WS, BLM, BLMH, BLNK, BMPR2, BPGM, BRAF, BRCA1, BRCA1/m, BRCA2, BRCA2/m, BRCD2, BRCD1, BRDT, BSCL, BSCL2, BTAA, BTD, BTK, BUB1, BWS, BZX, C0L2A1, C0L6A1, C1NH, C1QA, C1QB, C1QG, C1S, C2, C3, C4A, C4B, C5, C6, C7, C7orf2, C8A, C8B, C9, CA125, CA15-3/CA 27-29, CA195, CA19-9, CA72-4, CA2, CA242, CA50, CABYR, CACD, CACNA2D1, CACNA1A, CACNA1F, CACNA1S, CACNB2, CACNB4, CAGE, CA1, CALB3, CALCA, CALCR, CALM, CALR, CAM43, CAMEL, CAP-1, CAPN3, CARD15, CASP-5/m, CASP-8, CASP-8/m, CASR, CAT, CATM, CAV3, CB1, CBBM, CBS, CCA1, CCAL2, CCAL1, CCAT, CCL-1, CCL-11, CCL-12, CCL-13, CCL-14, CCL-15, CCL-16, CCL-17, CCL-18, CCL-19, CCL-2, CCL-20, CCL-21, CCL-22, CCL-23, CCL-24, CCL-25, CCL-27, CCL-3, CCL-4, CCL-5, CCL-7, CCL-8, CCM1, CCNB1, CCND1, CCO, CCR2, CCR5, CCT, CCV, CCZS, CD1, CD19, CD20, CD22, CD25, CD27, CD27L, cD3, CD30, CD30, CD3OL, CD33, CD36, CD3E, CD3G, CD3Z, CD4, CD40, CD40L, CD44, CD44v, CD44v6, CD52, CD55, CD56, CD59, CD80, CD86, CDAN1, CDAN2, CDAN3, CDC27, CDC27/m, CDC2L1, CDH1, CDK4, CDK4/m, CDKN1C, CDKN2A, CDKN2A/m, CDKN1A, CDKN1C, CDL1, CDPD1, CDR1, CEA, CEACAM1, CEACAM5, CECR, CECR9, CEPA, CETP, CFNS, CFTR, CGF1, CHAC, CHED2, CHED1, CHEK2, CHM, CHML, CHR39C, CHRNA4, CHRNA1, CHRNB1, CHRNE, CHS, CHS1, CHST6, CHX10, CIAS1, CIDX, CKN1, CLA2, CLA3, CLA1, CLCA2, CLCN1, CLCN5, CLCNKB, CLDN16, CLP, CLN2, CLN3, CLN4, CLN5, CLN6, CLN8, C1QA, C1QB, C1QG, C1R, CLS, CMCWTD, CMDJ, CMD1A, CMD1B, CMH2, MH3, CMH6, CMKBR2, CMKBR5, CML28, CML66, CMM, CMT2B, CMT2D, CMT4A, CMT1A, CMTX2, CMTX3, C-MYC, CNA1, CND, CNGA3, CNGA1, CNGB3, CNSN, CNTF, COA-1/m, COCH, COD2, COD1, COH1, COL10A, COL2A2, COL11A2, COL17A1, COL1A1, COL1A2, COL2A1, COL3A1, COL4A3, COL4A4, COL4A5, COL4A6, COL5A1, COL5A2, COL6A1, COL6A2, COL6A3, COL7A1, COL8A2, COL9A2, COL9A3, COL11A1, COL1A2, COL23A1, COL1A1, COLQ, COMP, COMT, CORDS, CORD1, COX10, COX-2, CP, CPB2, CPO, CPP, CPS1, CPT2, CPT1A, CPX, CRAT, CRB1, CRBM, CREBBP, CRH, CRHBP, CRS, CRV, CRX, CRYAB, CRYBA1, CRYBB2, CRYGA, CRYGC, CRYGD, CSA, CSE, CSF1R, CSF2RA, CSF2RB, CSF3R, CSF1R, CST3, CSTB, CT, CT7, CT-9/BRD6, CTAA1, CTACK, CTEN, CTH, CTHM, CTLA4, CTM, CTNNB1, CTNS, CTPA, CTSB, CTSC, CTSK, CTSL, CTS1, CUBN, CVD1, CX3CL1, CXCL1, CXCL10, CXCL11, CXCL12, CXCL13, CXCL16, CXCL2, CXCL3, CXCL4, CXCL5, CXCL6, CXCL7, CXCL8, CXCL9, CYB5, CYBA, CYBB, CYBB5, CYFRA 21-1, CYLD, CYLD1, CYMD, CYP11B1, CYP11B2, CYP17, CYP17A1, CYP19, CYP19A1, CYP1A2, CYP1B1, CYP21A2, CYP27A1, CYP27B1, CYP2A6, CYP2C, CYP2C19, CYP2C9, CYP2D, CYP2D6, CYP2D7P1, CYP3A4, CYP7B1, CYPB1, CYP11B1, CYP1A1, CYP1B1, CYRAA, D40, DADI, DAM, DAM-10/MAGE-B1, DAM-6/MAGE-B2, DAX1, DAZ, DBA, DBH, DBI, DBT, DCC, DC-CK1, DCK, DCR, DCX, DDB 1, DDB2, DDIT3, DDU, DECR1, DEK-CAN, DEM, DES, DF, DFN2, DFN4, DFN6, DFNA4, DFNA5, DFNB5, DGCR, DHCR7, DHFR, DHOF, DHS, DIA1, DIAPH2, DIAPH1, DIH1, DIO1, DISCI, DKC1, DLAT, DLD, DLL3, DLX3, DMBT1, DMD, DM1, DMPK, DMWD, DNAI1, DNASE1, DNMT3B, DPEP1, DPYD, DPYS, DRD2, DRD4, DRPLA, DSCR1, DSG1, DSP, DSPP, DSS, DTDP2, DTR, DURS1, DWS, DYS, DYSF, DYT2, DYT3, DYT4, DYT2, DYT1, DYX1, EBAF, EBM, EBNA, EBP, EBR3, EBS1, ECA1, ECB2, ECE1, ECGF1, ECT, ED2, ED4, EDA, EDAR, ECA1, EDN3, EDNRB, EEC1, EEF1A1L14, EEGV1, EFEMP1, EFTUD2/m, EGFR, EGFR/Her1, EGI, EGR2, EIF2AK3, eIF4G, EKV, EI IS, ELA2, ELF2, ELF2M, ELK1, ELN, ELONG, EMD, EML1, EMMPRIN, EMX2, ENA-78, ENAM, END3, ENG, ENO1, ENPP1, ENUR2, ENUR1, EOS, EP300, EPB41, EPB42, EPCAM, EPD, EphA1, EphA2, EphA3, EphrinA2, EphrinA3, EPHX1, EPM2A, EPO, EPOR, EPX, ERBB2, ERCC2 ERCC3, ERCC4, ERCC5, ERCC6, ERVR, ESR1, ETFA, ETFB, ETFDH, ETM1, ETV6-AML1, ETV1, EVC, EVR2, EVR1, EWSR1, EXT2, EXT3, EXT1, EYA1, EYCL2, EYCL3, EYCL1, EZH2, F10, F11, F12, F13A1, F13B, F2, F5, F5F8D, F7, F8, F8C, F9, FABP2, FACL6, FAH, FANCA, FANCB, FANCC, FANCD2, FANCF, FasL, FBN2, FBN1, FBP1, FCG3RA, FCGR2A, FCGR2B, FCGR3A, FCHL, FCMD, FCP1, FDPSL5, FECH, FEO, FEOM1, FES, FGA, FGB, FGD1, FGF2, FGF23, FGF5, FGFR2, FGFR3, FGFR1, FGG, FGS1, FH, FIC1, FIH, F2, FKBP6, FLNA, FLT4, FMO3, FMO4, FMR2, FMR1, FN, FN1/m, FOXC1, FOXE1, FOXL2, FOXO1A, FPDMM, FPF, Fra-1, FRAXF, FRDA, FSHB, FSHMD1A, FSHR, FTH1, FTHL17, FTL, FTZF1, FUCA1, FUT2, FUT6, FUT1, FY, G250, G250/CAIX, G6PC, G6PD, G6PT1, G6PT2, GAA, GABRA3, GAGE-1, GAGE-2, GAGE-3, GAGE-4, GAGE-5, GAGE-6, GAGE-7b, GAGE-8, GALC, GALE, GALK1, GALNS, GALT, GAMT, GAN, GAST, GASTRIN17, GATA3, GATA, GBA, GBE, GC, GCDH, GCGR, GCH1, GCK, GCP-2, GCS1, G-CSF, GCSH, GCSL, GCY, GDEP, GDF5, GDI1, GDNF, GDXY, GFAP, GFND, GGCX, GGT1, GH2, GH1, GHR, GHRHR, GHS, GIF, GINGF, GIP, GJA3, GJA8, GJB2, GJB3, GJB6, GJB1, GK, GLA, GLB, GLB1, GLC3B, GLC1B, GLC1C, GLDC, GLI3, GLP1, GLRA1, GLUD1, GM1 (fuc-GM1), GM2A, GM-CSF, GMPR, GNAI2, GNAS, GNAT1, GNB3, GNE, GNPTA, GNRH, GNRH1, GNRHR, GNS, GnT-V, gp100, GP1BA, GP1BB, GP9, GPC3, GPD2, GPDS1, GPI, GP1BA, GPN1LW, GPNMB/m, GPSC, GPX1, GRHPR, GRK1, GROα, GROβ, GROγ, GRPR, GSE, GSM1, GSN, GSR, GSS, GTD, GTS, GUCA1A, GUCY2D, GULOP, GUSB, GUSM, GUST, GYPA, GYPC, GYS1, GYS2, H0KPP2, H0MG2, HADHA, HADHB, HAGE, HAGH, HAL, HAST-2, HB 1, HBA2, HBA1, HBB, HBBP1, HBD, HBE1, HBG2, HBG1, HBHR, HBP1, HBQ1, HBZ, HBZP, HCA, HCC-1, HCC-4, HCF2, HCG, HCL2, HCL1, HCR, HCVS, HD, HPN, HER2, HER2/NEU, HER3, HERV-K-MEL, HESX1, HEXA, HEXB, HF1, HFE, HF1, HGD, HHC2, HHC3, HHG, HK1 HLA-A, HLA-A*0201-R170I, HLA-A11/m, HLA-A2/m, HLA-DPB1 HLA-DRA, HLCS, HLXB9, HMBS, HMGA2, HMGCL, HMI, HMN2, HMOX1, HMS1 HMW-MAA, HND, HNE, HNF4A, HOAC, HOMEOBOX NKX 3.1, HOM-TES-14/SCP-1, HOM-TES-85, HOXA1 HOXD13, HP, HPC1, HPD, HPE2, HPE1, HPFH, HPFH2, HPRT1, HPS1, HPT, HPV-E6, HPV-E7, HR, HRAS, HRD, HRG, HRPT2, HRPT1, HRX, HSD11B2, HSD17B3, HSD17B4, HSD3B2, HSD3B3, HSN1, HSP70-2M, HSPG2, HST-2, HTC2, HTC1, hTERT, HTN3, HTR2C, HVBS6, HVBS1, HVEC, HV1S, HYAL1, HYR, I-309, IAB, IBGC1, IBM2, ICAM1, ICAM3, iCE, ICHQ, ICR5, ICR1, ICS 1, IDDM2, IDDM1, IDS, IDUA, IF, IFNa/b, IFNGR1, IGAD1, IGER, IGF-1R, IGF2R, IGF1, IGH, IGHC, IGHG2, IGHG1, IGHM, IGHR, IGKC, IHG1, IHH, IKBKG, IL1, IL-1 RA, IL10, IL-11, IL12, IL12RB1, IL13, IL-13Rα2, IL-15, IL-16, IL-17, IL18, IL-1a, IL-1α, IL-1b, IL-1β, IL1RAPL1, IL2, IL24, IL-2R, IL2RA, IL2RG, IL3, IL3RA, IL4, IL4R, IL4R, IL-5, IL6, IL-7, IL7R, IL-8, IL-9, Immature laminin receptor, IMMP2L, INDX, INFGR1, INFGR2, INFα, IFN, INFγ, INS, INSR, INVS, IP-10, IP2, IPF1, IP1, IRF6, IRS1, ISCW, ITGA2, ITGA2B, ITGA6, ITGA7, ITGB2, ITGB3, ITGB4, ITIH1, ITM2B, IV, IVD, JAG1, JAK3, JBS, JBTS1, JMS, JPD, KAL1, KAL2, KALI, KLK2, KLK4, KCNA1, KCNE2, KCNE1, KCNH2, KCNJ1, KCNJ2, KCNJ1, KCNQ2, KCNQ3, KCNQ4, KCNQ1, KCS, KERA, KFM, KFS, KFSD, KHK, ki-67, KIAA0020, KIAA0205, KIAA0205/m, KIF1B, KIT, KK-LC-1, KLK3, KLKB1, KM-HN-1, KMS, KNG, KNO, K-RAS/m, KRAS2, KREV1, KRT1, KRT10, KRT12, KRT13, KRT14, KRT14L1, KRT14L2, KRT14L3, KRT16, KRT16L1, KRT16L2, KRT17, KRT18, KRT2A, KRT3, KRT4, KRT5, KRT6 A, KRT6B, KRT9, KRTHB1, KRTHB6, KRT1, KSA, KSS, KWE, KYNU, L0H19CR1, L1CAM, LAGE, LAGE-1, LALL, LAMA2, LAMA3, LAMB3, LAMB1, LAMC2, LAMP2, LAP, LCA5, LCAT, LCCS, LCCS 1, LCFS2, LCS1, LCT, LDHA, LDHB, LDHC, LDLR, LDLR/FUT, LEP, LEWISY, LGCR, LGGF-PBP, LGI1, LGMD2H, LGMD1A, LGMD1B, LHB, LHCGR, LHON, LHRH, LHX3, LIF, LIG1, LIMM, LIMP2, LIPA, LIPA, LIPB, LIPC, LIVIN, L1CAM, LMAN1, LMNA, LMX1B, LOLR, LOR, LOX, LPA, LPL, LPP, LQT4, LRP5, LRS 1, LSFC, LT-β, LTBP2, LTC4S, LYL1, XCL1, LYZ, M344, MA50, MAA, MADH4, MAFD2, MAFD1, MAGE, MAGE-A1, MAGE-A10, MAGE-A12, MAGE-A2, MAGE-A3, MAGE-A4, MAGE-A6, MAGE-A9, MAGEB1, MAGE-B10, MAGE-B16, MAGE-B17, MAGE-B2, MAGE-B3, MAGE-B4, MAGE-B5, MAGE-B6, MAGE-C1, MAGE-C2, MAGE-C3, MAGE-D1, MAGE-D2, MAGE-D4, MAGE-E1, MAGE-E2, MAGE-F1, MAGE-H1, MAGEL2, MGB1, MGB2, MAN2A1, MAN2B1, MANBA, MANBB, MAOA, MAOB, MAPK8IP1, MAPT, MART-1, MART-2, MART2/m, MAT1A, MBL2, MBP, MBS1, MC1R, MC2R, MC4R, MCC, MCCC2, MCCC1, MCDR1, MCF2, MCKD, MCL1, MC1R, MCOLN1, MCOP, MCOR, MCP-1, MCP-2, MCP-3, MCP-4, MCPH2, MCPH1, MCS, M-CSF, MDB, MDCR, MDM2, MDRV, MDS 1, ME1, ME1/m, ME2, ME20, ME3, MEAX, MEB, MEC CCL-28, MECP2, MEFV, MELANA, MELAS, MEN1 MSLN, MET, MF4, MG50, MG50/PXDN, MGAT2, MGAT5, MGC1 MGCR, MGCT, MGI, MGP, MHC2TA, MHS2, MHS4, MIC2, MIC5, MIDI, MIF, MIP, MIP-5/HCC-2, MITF, MJD, MKI67, MKKS, MKS1, MLH1, MLL, MLLT2, MLLT3, MLLT7, MLLT1, MLS, MLYCD, MMA1a, MMP 11, MMVP1, MN/CA IX-Antigen, MNG1, MN1, MOC31, MOCS2, MOCS1, MOG, MORC, MOS, MOV18, MPD1, MPE, MPFD, MPI, MPIF-1, MPL, MPO, MPS3C, MPZ, MRE11A, MROS, MRP1, MRP2, MRP3, MRSD, MRX14, MRX2, MRX20, MRX3, MRX40, MRXA, MRX1, MS, MS4A2, MSD, MSH2, MSH3, MSH6, MSS, MSSE, MSX2, MSX1, MTATP6, MTC03, MTCO1, MTCYB, MTHFR, MTM1, MTMR2, MTND2, MTND4, MTND5, MTND6, MTND1, MTP, MTR, MTRNR2, MTRNR1, MTRR, MTTE, MTTG, MTTI, MTTK, MTTL2, MTTL1, MTTN, MTTP, MTTS1, MUC1, MUC2, MUC4, MUC5AC, MUM-1, MUM-1/m, MUM-2, MUM-2/m, MUM-3, MUM-3/m, MUT, mutant p21 ras, MUTYH, MVK, MX2, MXI1, MY05A, MYB, MYBPC3, MYC, MYCL2, MYH6, MYH7, MYL2, MYL3, MYMY, MYO15A, MYO1G, MYO5A, MYO7A, MYOC, Myosin/m, MYP2, MYP1, NA88-A, N-acetylglucosaminyl-transferase-V, NAGA, NAGLU, NAMSD, NAPB, NAT2, NAT, NBIA1, NBS1, NCAM, NCF2, NCF1, NDN, NDP, NDUFS4, NDUFS7, NDUFS8, NDUFV1, NDUFV2, NEB, NEFH, NEM1, Neo-PAP, neo-PAP/m, NEU1, NEUROD1, NF2, NF1, NFYC/m, NGEP, NHS, NKS1, NKX2E, NM, NME1, NMP22, NMTC, NODAL, NOG, NOS3, NOTCH3, NOTCH1, NP, NPC2, NPC1, NPHL2, NPHP1, NPHS2, NPHS1, NPM/ALK, NPPA, NQO1, NR2E3, NR3C1, NR3C2, NRAS, NRAS/m, NRL, NROB1, NRTN, NSE, NSX, NTRK1, NUMA1, NXF2, NY-CO1, NY-ESO1, NY-ESO-B, NY-LU-12, ALDOA, NYS2, NYS4, NY-SAR-35, NYS1, NYX, OA3, OA1, OAP, OASD, OAT, OCA1, OCA2, OCD1, OCRL, OCRL1, OCT, ODDD, ODT1, OFC1, OFD1, OGDH, OGT, OGT/m, OPA2, OPA1, OPD1, OPEM, OPG, OPN, OPN1LW, OPN1MW, OPN1SW, OPPG, OPTB1, TTD, ORM1, ORP1, OS-9, OS-9/m, OSM LIF, OTC, OTOF, OTSC1, OXCT1, OYTES1, P15, P190 MINOR BCR-ABL, P2RY12, P3, P16, P40, P4HB, P-501, P53, P53/m, P97, PABPN1, PAFAH1B1, PAFAH1P1, PAGE-4, PAGE-5, PAH, PAI-1, PAI-2, PAK3, PAP, PAPPA, PARK2, PART-1, PATE, PAX2, PAX3, PAX6, PAX7, PAX8, PAX9, PBCA, PBCRA1, PBT, PBX1, PBXP1, PC, PCBD, PCCA, PCCB, PCK2, PCK1, PCLD, PCOS1, PCSK1, PDB1, PDCN, PDE6A, PDE6B, PDEF, PDGFB, PDGFR, PDGFRL, PDHA1, PDR, PDX1, PECAM1, PEE1, PEO1, PEPD, PEX10, PEX12, PEX13, PEX3, PEX5, PEX6, PEX7, PEX1, PF4, PFBI, PFC, PFKFB1, PFKM, PGAM2, PGD, PGK1, PGK1P1, PGL2, PGR, PGS, PHA2A, PHB, PHEX, PHGDH, PHKA2, PHKA1, PHKB, PHKG2, PHP, PHYH, PI, PI3, PIGA, PIM1-KINASE, PIN1, PIP5K1B, PITX2, PITX3, PKD2, PKD3, PKD1, PKDTS, PKHD1, PKLR, PKP1, PKU1, PLA2G2A, PLA2G7, PLAT, PLEC1, PLG, PLI, PLOD, PLP1, PMEL17, PML, PML/RARα, PMM2, PMP22, PMS2, PMS1, PNKD, PNLIP, POF1, POLA, POLH, POMC, PON2, PON1, PORC, POTE, POU1F1, POU3F4, POU4F3, POU1F1, PPAC, PPARG, PPCD, PPGB, PPH1, PPKB, PPMX, PPDX, PPP1R3A, PPP2R2B, PPT1, PRAME, PRB, PRB3, PRCA1, PRCC, PRD, PRDX5/m, PRF1, PRG4, PRKAR1A, PRKCA, PRKDC, PRKWNK4, PRNP, PROC, PRODH, PROM1, PROP1, PROS1, PRST, PRP8, PRPF31, PRPF8, PRPH2, PRPS2, PRPS1, PRS, PRSS7, PRSS1, PRTN3, PRX, PSA, PSAP, PSCA, PSEN2, PSEN1, PSG1, PSGR, PSM, PSMA, PSORS1, PTC, PTCH, PTCH1, PTCH2, PTEN, PTGS1, PTH, PTHR1, PTLAH, PTOS1, PTPN12, PTPNI I, PTPRK, PTPRK/m, PTS, PUJO, PVR, PVRL1, PWCR, PXE, PXMP3, PXR1, PYGL, PYGM, QDPR, RAB27A, RAD54B, RAD54L, RAG2, RAGE, RAGE-1, RAG1, RAP1, RARA, RASA1, RBAF600/m, RB1, RBP4, RBP4, RBS, RCA1, RCAS1, RCCP2, RCD1, RCV1, RDH5, RDPA, RDS, RECQL2, RECQL3, RECQL4, REG1A, REHOBE, REN, RENBP, RENS1, RET, RFX5, RFXANK, RFXAP, RGR, RHAG, RHAMM/CD168, RHD, RHO, Rip-1, RLBP1, RLN2, RLN1, RLS, RMD1, RMRP, ROM1, ROR2, RP, RP1, RP14, RP17, RP2, RP6, RP9, RPD1, RPE65, RPGR, RPGRIP1, RP1, RP10, RPS19, RPS2, RPS4X, RPS4Y, RPS6KA3, RRAS2, RS1, RSN, RSS, RU1, RU2, RUNX2, RUNXI, RWS, RYR1, S-100, SAA1, SACS, SAG, SAGE, SALL1, SARDH, SART1, SART2, SART3, SAS, SAX1, SCA2, SCA4, SCA5, SCA7, SCA8, SCA1, SCC, SCCD, SCF, SCLC1, SCN1A, SCN1B, SCN4A, SCN5A, SCNN1A, SCNN1B, SCNN1G, SCO2, SCP1, SCZD2, SCZD3, SCZD4, SCZD6, SCZD1, SDF-1α/SDHA, SDHD, SDYS, SEDL, SERPENA7, SERPINA3, SERPINA6, SERPINA1, SERPINC1, SERPIND1, SERPINE1, SERPINF2, SERPING1, SERPINI1, SFTPA1, SFTPB, SFTPC, SFTPD, SGCA, SGCB, SGCD, SGCE, SGM1, SGSH, SGY-1, SH2D1A, SHBG, SHFM2, SHFM3, SHFM1, SHH, SHOX, SI, SIAL, SIALYL LEWISX, SIASD, S11, SIM1, SIRT2/m, SIX3, SJS1, SKP2, SLC10A2, SLC12A1, SLC12A3, SLC17A5, SLC19A2, SLC22A1L, SLC22A5, SLC25A13, SLC25A15, SLC25A20, SLC25A4, SLC25A5, SLC25A6, SLC26A2, SLC26A3, SLC26A4, SLC2A1, SLC2A2, SLC2A4, SLC3A1, SLC4A1, SLC4A4, SLC5A1, SLC5A5, SLC6A2, SLC6A3, SLC6A4, SLC7A7, SLC7A9, SLC11A1, SLOS, SMA, SMAD1, SMAL, SMARCB1, SMAX2, SMCR, SMCY, SM1, SMN2, SMN1, SMPD1, SNCA, SNRPN, SOD2, SOD3, SOD1, SOS1, SOST, SOX9, SOX10, Sp17, SPANXC, SPG23, SPG3A, SPG4, SPG5A, SPG5B, SPG6, SPG7, SPINK1, SPINK5, SPPK, SPPM, SPSMA, SPTA1, SPTB, SPTLC1, SRC, SRD5A2, SRPX, SRS, SRY, βhCG, SSTR2, SSX1, SSX2 (HOM-MEL-40/SSX2), SSX4, ST8, STAMP-1, STAR, STARP1, STATH, STEAP, STK2, STK11, STn/KLH, STO, STOM, STS, SUOX, SURF1, SURVIVIN-2B, SYCP1, SYM1, SYN1, SYNS1, SYP, SYT/SSX, SYT-SSX-1, SYT-SSX-2, TA-90, TAAL6, TACSTD1, TACSTD2, TAG72, TAF7L, TAF1, TAGE, TAG-72, TALI, TAM, TAP2, TAP1, TAPVR1, TARC, TARP, TAT, TAZ, TBP, TBX22, TBX3, TBX5, TBXA2R, TBXAS1, TCAP, TCF2, TCF1, TCIRG1, TCL2, TCL4, TCL1A, TCN2, TCOF1, TCR, TCRA, TDD, TDFA, TDRD1, TECK, TECTA, TEK, TEL/AML1, TELAB1, TEX15, TF, TFAP2B, TFE3, TFR2, TG, TGFA, TGF-β, TGFBI, TGFB1, TGFBR2, TGFBRE, TGFβ, TGFβRII, TGIF, TGM-4, TGM1, TH, THAS, THBD, THC, THC2, THM, THPO, THRA, THRB, TIMM8A, TIMP2, TIMP3, TIMP1, TITF1, TKCR, TKT, TLP, TLR1, TLR10, TLR2, TLR3, TLR4, TLR4, TLR5, TLR6, TLR7, TLR8, TLR9, TLX1, TM4SF1, TM4SF2, TMC1, TMD, TMIP, TNDM, TNF, TNFRSF11A, TNFRSF1A, TNFRSF6, TNFSF5, TNFSF6, TNFα, TNFβ, TNNI3, TNNT2, TOC, TOP2A, TOP1, TP53, TP63, TPA, TPBG, TPI, TPI/m, TPI1, TPM3, TPM1, TPMT, TPO, TPS, TPTA, TRA, TRAG3, TRAPPC2, TRC8, TREH, TRG, TRH, TRIM32, TRIM37, TRP1, TRP2, TRP-2/6b, TRP-2/INT2, Trp-p8, TRPS1, TS, TSC2, TSC3, TSC1, TSG101, TSHB, TSHR, TSP-180, TST, TTGA2B, TTN, TTPA, TTR, TU M2-PK, TULP1, TWIST, TYH, TYR, TYROBP, TYROBP, TYRP1, TYS, UBE2A, UBE3A, UBE1, UCHL1, UFS, UGT1A, ULR, UMPK, UMPS, UOX, UPA, UQCRC1, URO5, UROD, UPK1B, UROS, USH2A, USH3A, USH1A, USH1C, USP9Y, UV24, VBCH, VCF, VDI, VDR, VEGF, VEGFR-2, VEGFR-1, VEGFR-2/FLK-1, VHL, VIM, VMD2, VMD1, VMGLOM, VNEZ, VNF, VP, VRNI, VWF, VWS, WAS, WBS2, WFS2, WFS1, WHCR, WHN, WISP3, WMS, WRN, WS2A, WS2B, WSN, WSS, WT2, WT3, WT1, WTS, WWS, XAGE, XDH, XIC, XIST, XK, XM, XPA, XPC, XRCC9, XS, ZAP70, ZFHX1B, ZFX, ZFY, ZIC2, ZIC3, ZNF145, ZNF261, ZNF35, ZNF41, ZNF6, ZNF198, ZWS1, or from fragments or variants thereof. Preferably, such fragments as well as variants exhibit a sequence homology or identity as defined above.

Component (B) may also be selected from protein kinase inhibitors, particularly inhibitors of the protein kinase c-Jun amino terminal kinase, i.e. a JNK inhibitor. Typically, a JNK inhibitor suitable as component (B) of the transporter cargo conjugate molecule may be derived from a human or rat IB1 sequence, preferably from an amino acid sequence as defined or encoded by any of sequences according to SEQ ID NO: 117 (depicts the IB1 cDNA sequence from rat and its predicted amino acid sequence), SEQ ID NO: 118 (depicts the IB1 protein sequence from rat encoded by the exon-intron boundary of the rIB1 gene-splice donor), SEQ ID NO: 119 (depicts the IB1 protein sequence from *Homo sapiens*), or SEQ ID NO: 120 (depicts the IB1 cDNA sequence from *Homo sapiens*), or from any fragments or variants thereof. For a definition of fragments and variants see above.

Preferably, a JNK inhibitor sequence suitable as component (B) comprises preferably a total length of less than 150 amino acid residues, more preferably a range of 5 to 150 amino acid residues, more preferably 10 to 100 amino acid residues, even more preferably 10 to 75 amino acid residues and most preferably a range of 10 to 50 amino acid residues, e.g. 10 to 30, 10 to 20, or 10 to 15 amino acid residues. More preferably, such a JNK inhibitor sequence and the above ranges may be selected from any of the herein mentioned JNK inhibitor sequence, even more preferably from an amino acid sequence as defined according to SEQ ID NO: 119 or as encoded by SEQ ID NO: 120, even more preferably in the region between nucleotides 420 and 980 of SEQ ID NO: 120 or amino acids 105 and 291 of SEQ ID NO: 119, and most preferably in the region between nucleotides 561 and 647 of SEQ ID NO: 120 or amino acids 152 and 180 of SEQ ID NO: 119.

According to a particular embodiment, a JNK inhibitor sequence suitable as component (B) typically binds JNK and/or inhibits the activation of at least one JNK activated transcription factor, e.g. c-Jun or ATF2 (see e.g. SEQ ID NOs: 127 and 128, respectively) or Elk1.

Likewise, a JNK inhibitor sequence suitable as component (B) preferably comprises or consists of at least one amino acid sequence according to any one of SEQ ID NOs: 117 to 200, or a fragment, derivative or variant thereof. More preferably, the JNK inhibitor sequence as used herein may contain 1, 2, 3, 4 or even more copies of an amino acid sequence according to SEQ ID NO:118, SEQ ID NO:119, and one of SEQ ID NO:121 to 200, or a variant, fragment or derivative thereof. If present in more than one copy, these amino acid sequences according to SEQ ID NO:118, SEQ ID NO:119, and one of SEQ ID NO:121 to 200, or variants, fragments, or derivatives thereof as used herein may be directly linked with each other without any linker sequence or via a linker sequence comprising 1 to 10, preferably 1 to 5 amino acids. Amino acids forming the linker sequence are preferably selected from glycine or proline as amino acid residues. More preferably, these amino acid sequences according to SEQ ID NO:118, SEQ ID NO:119, and one of SEQ ID NO:121 to 200, or fragments, variants or derivatives thereof, as used herein, may be separated by each other by a hinge of two, three or more proline residues.

The JNK inhibitor sequence suitable as component (B) may be composed of L-amino acids, D-amino acids, or a combination of both. Preferably, the JNK inhibitor sequences as used herein comprise at least 1 or even 2, preferably at least 3, 4 or 5, more preferably at least 6, 7, 8 or 9 and even more preferably at least 10 or more D- and/or L-amino acids, wherein the D- and/or L-amino acids may be arranged in the JNK inhibitor sequences as used herein in a blockwise, a non-blockwise or in an alternate manner.

According to one preferred embodiment the JNK inhibitor sequence suitable as component (B) may be exclusively composed of L-amino acids. The JNK inhibitor sequences as used herein may then comprise or consist of at least one "native JNK inhibitor sequence" according to SEQ ID NO: 121 or 123. In this context, the term "native" or "native JNK inhibitor sequence(s)" refers to non-altered JNK inhibitor sequences according to any of SEQ ID NOs: 121 or 123, which are entirely composed of L-amino acids.

Accordingly, the JNK inhibitor sequence suitable as component (B) may comprise or consist of at least one (native) amino acid sequence $NH_2$—$X_n^b$—$X_n^a$-RPTTLX-LXXXXXXXQD-$X_n^b$—COOH (L-IB generic (s)) (SEQ ID NO: 123) and/or the JNK binding domain (JBDs) of IB1 XRPTTLXLXXXXXXXQDS/TX (L-IB (generic)) (SEQ ID NO: 131). In this context, each X typically represents an amino acid residue, preferably selected from any (native) amino acid residue. $X_n^a$ typically represents one amino acid residue, preferably selected from any amino acid residue except serine or threonine, wherein n (the number of repetitions of X) is 0 or 1. Furthermore, each $X_n^b$ may be selected from any amino acid residue, wherein n (the number of repetitions of X) is 0-5, 5-10, 10-15, 15-20, 20-30 or more, provided that if n (the number of repetitions of X) is 0 for $X_n^a$, $X_n^b$ does preferably not comprise a serine or threonine at its C-terminus, in order to avoid a serine or threonine at this position. Preferably, $X_n^b$ represents a contiguous stretch of (poly-)peptide residues derived from SEQ ID NOs: 121 or 123. $X_n^a$ and $X_n^b$ may represent either D or L amino acids. Additionally, the JNK inhibitor sequence as used herein may comprise or consist of at least one (native) amino acid sequence selected from the group comprising the JNK binding domain of IB1 DTYRPKRPTTLNLFPQVPR-SQDT (L-IB1) (SEQ ID NO: 129). More preferably, the JNK inhibitor sequence as used herein further may comprise or consist of at least one (native) amino acid sequence $NH_2$—RPKRPTTLNLFPQVPRSQD-COOH (L-IB1(s)) (SEQ ID NO: 121). Furthermore, the JNK inhibitor sequence as used herein may comprise or consist of at least one (native) amino acid sequence selected from the group comprising the JNK binding domain of IB1 L-IB1(s1) ($NH_2$-TLNLFPQVPRSQD-COOH, SEQ ID NO: 133); L-IB1(s2) ($NH_2$-TTLNLFPQVPRSQ-COOH, SEQ ID NO: 134); L-IB1(s3) ($NH_2$-PTTLNLFPQVPRS-COOH, SEQ ID NO: 135); L-IB1(s4) ($NH_2$—RPTTLNLFPQVPR-COOH, SEQ ID NO: 136); L-IB1(s5) ($NH_2$—KRPTTLNLFPQVP-COOH, SEQ ID NO: 137); L-IB1(s6) ($NH_2$—PKRPTTLN-LFPQV-COOH, SEQ ID NO: 138); L-IB1(s7) ($NH_2$—RPKRPTTLNLFPQ-COOH, SEQ ID NO: 139); L-IB1(s8) ($NH_2$-LNLFPQVPRSQD-COOH, SEQ ID NO: 140); L-IB1 (s9) ($NH_2$-TLNLFPQVPRSQ-COOH, SEQ ID NO: 141); L-IB1(s10) ($NH_2$-TTLNLFPQVPRS-COOH, SEQ ID NO: 142); L-IB1(s11) ($NH_2$—PTTLNLFPQVPR-COOH, SEQ ID NO: 143); L-IB1(s12) ($NH_2$—RPTTLNLFPQVP-COOH, SEQ ID NO: 144); L-IB1(s13) ($NH_2$—KRPTTLN-LFPQV-COOH, SEQ ID NO: 145); L-IB1(s14) ($NH_2$—PKRPTTLNLFPQ-COOH, SEQ ID NO: 146); L-IB1(s15) ($NH_2$—RPKRPTTLNLFP-COOH, SEQ ID NO: 147); L-IB1(s16) ($NH_2$—NLFPQVPRSQD-COOH, SEQ ID NO: 148); L-IB1(s17) ($NH_2$-LNLFPQVPRSQ-COOH, SEQ ID NO: 149); L-IB1(s18) ($NH_2$-TLNLFPQVPRS-COOH, SEQ ID NO: 150); L-IB1(s19) ($NH_2$-TTLNLFPQVPR-COOH, SEQ ID NO: 151); L-IB1(s20) ($NH_2$—PTTLNLFPQVP-COOH, SEQ ID NO: 152); L-IB1(s21) ($NH_2$—RPTTLN-LFPQV-COOH, SEQ ID NO: 153); L-IB1(s22) ($NH_2$—KRPTTLNLFPQ-COOH, SEQ ID NO: 154); L-IB1(s23) ($NH_2$—PKRPTTLNLFP-COOH, SEQ ID NO: 155); L-IB1 (s24) ($NH_2$—RPKRPTTLNLF-COOH, SEQ ID NO: 156); L-IB1(s25) ($NH_2$-LFPQVPRSQD-COOH, SEQ ID NO: 157); L-IB1(s26) ($NH_2$—NLFPQVPRSQ-COOH, SEQ ID NO: 158); L-IB1(s27) ($NH_2$-LNLFPQVPRS-COOH, SEQ ID NO: 159); L-IB1(s28) ($NH_2$-TLNLFPQVPR-COOH, SEQ ID NO: 160); L-IB1(s29) ($NH_2$-TTLNLFPQVP-COOH, SEQ ID NO: 161); L-IB1(s30) ($NH_2$—PTTLNLF-PQV-COOH, SEQ ID NO: 162); L-IB1(s31) ($NH_2$—RPT-TLNLFPQ-COOH, SEQ ID NO: 163); L-IB1(s32) ($NH_2$—KRPTTLNLFP-COOH, SEQ ID NO: 164); L-IB1(s33) ($NH_2$—PKRPTTLNLF-COOH, SEQ ID NO: 165); and L-IB1(s34) ($NH_2$—RPKRPTTLNL-COOH, SEQ ID NO: 166).

Additionally, the JNK inhibitor sequence suitable as component (B) may comprise or consist of at least one (native) amino acid sequence selected from the group comprising the (long) JNK binding domain (JBDs) of IB1 PGTGCGDTYR-PKRPTTLNLFPQVPRSQDT (IB1-long) (SEQ ID NO: 125), the (long) JNK binding domain of IB2 IPSPSVEEPH-KHRPTTLRLTTLGAQDS (IB2-long) (SEQ ID NO: 126), the JNK binding domain of c-Jun GAYGYSN-PKILKQSMTLNLADPVGNLKPH (c-Jun) (SEQ ID NO: 127), the JNK binding domain of ATF2 TNEDHLAVHKH-KHEMTLKFGPARNDSVIV (ATF2) (SEQ ID NO: 128). In this context, an alignment revealed a partially conserved 8 amino acid sequence and a further comparison of the JBDs of IB1 and IB2 revealed two blocks of seven and three amino acids that are highly conserved between the two sequences.

The JNK inhibitor sequence suitable as component (B) may be composed partially or exclusively of D-amino acids. More preferably, these JNK inhibitor sequences composed of D-amino acids are non-native D retro-inverso sequences of the above (native) JNK inhibitor sequences.

The term "retro-inverso sequences" refers to an isomer of a linear (poly-)peptide sequence in which the direction of the sequence is reversed and the chirality of each amino acid residue is inverted (see e.g. Jameson et al., Nature, 368,744-746 (1994); Brady et at, Nature, 368, 692-693 (1994)). The advantage of combining D-enantiomers and reverse synthesis is that the positions of carbonyl and amino groups in each amide bond are exchanged, while the position of the side-chain groups at each alpha carbon is preserved. Unless specifically stated otherwise, it is presumed that any given L-amino acid sequence or (poly-)peptide as used according to the present invention may be converted into an D retro-inverso sequence or (poly-)peptide by synthesizing a reverse of the sequence or (poly-)peptide for the corresponding native L-amino acid sequence or (poly-)peptide. In contrast, the term "reverse sequence" refers to a sequence in which the direction of the sequence is reversed (but the chirality of each amino acid residue is not inverted (e.g. D-Arg-L-Arg-L-Arg L-Arg-L-Arg-D-Arg)(SEQ ID NO:307).

Accordingly, the JNK inhibitor sequence suitable as component (B) of the inventive transporter cargo conjugate molecule may comprise or consist of at least one D retro-inverso sequence according to the amino acid sequence $NH_2$—$X_n^b$-DQXXXXXXXLXLTTPR-$X_n^a$—$X_n^b$—COOH (D-IB1 generic (s)) (SEQ ID NO: 124) and/or XS/TDQXXXXXXXLXLTTPRX (D-IB (generic)) (SEQ ID NO: 132). As used in this context, X, $X_n^a$ and $X_n^b$ are as defined above (preferably, representing D amino acids), wherein $X_n^b$ preferably represents a contiguous stretch of residues derived from SEQ ID NO: 122 or 124. Additionally, the JNK inhibitor sequences as used herein may comprise or consist of at least one D retro-inverso sequence according to the amino acid sequence comprising the JNK binding domain (JBDs) of IB1 TDQSRPVQPFLNLTTPRKPRYTD (D-IB1) (SEQ ID NO: 130). More preferably, the JNK inhibitor sequences as used herein may comprise or consist of at least one D retro-inverso sequence according to the amino acid sequence $NH_2$-DQSRPVQPFLNLTTPRKPR-COOH (D-IB1(s)) (SEQ ID NO: 122). Furthermore, the JNK inhibitor sequences as used herein may comprise or consist of at least one D retro-inverso sequence according to the amino acid sequence comprising the JNK binding domain (JBDs) of IB1 D-IB1(s1) ($NH_2$-QPFLNLTTPRKPR-COOH, SEQ ID NO: 167); D-IB1(s2) ($NH_2$—VQPFLNLTTPRKP-COOH, SEQ ID NO: 168); D-IB1(s3) ($NH_2$—PVQPFLNLTTPRK-COOH, SEQ ID NO: 169); D-IB1(s4) ($NH_2$—RPVQPFLNLTTPR-COOH, SEQ ID NO: 170); D-IB1(s5) ($NH_2$—SRPVQPFLNLTTP-COOH, SEQ ID NO: 171); D-IB1(s6) ($NH_2$-QSRPVQPFLNLTT-COOH, SEQ ID NO: 172); D-IB1(s7) ($NH_2$-DQSRPVQPFLNLT-COOH, SEQ ID NO: 173); D-IB1(s8) ($NH_2$—PFLNLTTPRKPR-COOH, SEQ ID NO: 174); D-IB1(s9) ($NH_2$-QPFLNLTTPRKP-COOH, SEQ ID NO: 175); D-IB1 (s10) ($NH_2$-VQPFLNLTTPRK-COOH, SEQ ID NO: 176); D-IB1(s11) ($NH_2$—PVQPFLNLTTPR-COOH, SEQ ID NO: 177); D-IB1(s12) ($NH_2$—RPVQPFLNLTTP-COOH, SEQ ID NO: 178); D-IB1(s13) ($NH_2$—SRPVQPFLNLTT-COOH, SEQ ID NO: 179); D-IB1(s14) ($NH_2$-QSRPVQPFLNLT-COOH, SEQ ID NO: 180); D-IB1(s15) ($NH_2$-DQSRPVQPFLNL-COOH, SEQ ID NO: 181); D-IB1(s16) ($NH_2$—FLNLTTPRKPR-COOH, SEQ ID NO: 182); D-IB1 (s17) ($NH_2$—PFLNLTTPRKP-COOH, SEQ ID NO: 183); D-IB1(s18) ($NH_2$-QPFLNLTTPRK-COOH, SEQ ID NO: 184); D-IB1(s19) ($NH_2$—VQPFLNLTTPR-COOH, SEQ ID NO: 185); D-IB1(s20) ($NH_2$—PVQPFLNLTTP-COOH, SEQ ID NO: 186); D-IB1(s21) ($NH_2$—RPVQPFLNLTT-COOH, SEQ ID NO: 187); D-IB1(s22) ($NH_2$—SRPVQPFLNLT-COOH, SEQ ID NO: 188); D-IB1(s23) ($NH_2$-QSRPVQPFLNL-COOH, SEQ ID NO: 189); D-IB1(s24) ($NH_2$-DQSRPVQPFLN-COOH, SEQ ID NO: 190); D-IB1 (s25) ($NH_2$-DQSRPVQPFL-COOH, SEQ ID NO: 191); D-IB1(s26) ($NH_2$-QSRPVQPFLN-COOH, SEQ ID NO: 192); D-IB1(s27) ($NH_2$—SRPVQPFLNL-COOH, SEQ ID NO: 193); D-IB1(s28) ($NH_2$—RPVQPFLNLT-COOH, SEQ ID NO: 194); D-IB1(s29) ($NH_2$—PVQPFLNLTT-COOH, SEQ ID NO: 195); D-IB1(s30) ($NH_2$—VQPFLNLTTP-COOH, SEQ ID NO: 196); D-IB1(s31) ($NH_2$-QPFLNLTTPR-COOH, SEQ ID NO: 197); D-IB1(s32) ($NH_2$—PFLNLTTPRK-COOH, SEQ ID NO: 198); D-IB1(s33) ($NH_2$—FLNLTTPRKP-COOH, SEQ ID NO: 199); and D-IB1(s34) ($NH_2$-LNLTTPRKPR-COOH, SEQ ID NO: 200).

Exemplary JNK inhibitor sequence suitable as component (B) are presented in Table 3 (SEQ ID NO:s 121 to 200). The table presents the name of the JNK inhibitor sequences as used herein, as well as their sequence identifier number, their length, and amino acid sequence. Furthermore, Table 3 shows IB1 derived sequences as well as their generic formulas, e.g. for SEQ ID NO's: 121 and 122 and SEQ ID NO's: 123 and 124, respectively. Table 3 furthermore discloses L-IB1 sequences according to SEQ ID NOs: 133 to 166 and D-IB1 sequences SEQ ID NOs: 167 to 200.

TABLE 3

| SEQUENCE/PEPTIDE NAME | SEQ ID NO | AA | SEQUENCE |
|---|---|---|---|
| L-IB1(s) | 121 | 19 | RPKRPTTLNLFPQVPRSQD<br>($NH_2$-RPKRPTTLNLFPQVPRSQD-COOH) |
| D-IB1(s) | 122 | 19 | DQSRPVQPFLNLTTPRKPR<br>($NH_2$-DQSRPVQPFLNLTTPRKPR-COOH) |
| L-IB (generic) (s) | 123 | 19 | $NH_2$-$X_n^b$-$X_n^a$-RPTTLXLXXXXXXXQD-$X_n^b$-COOH |
| D-IB (generic) (s) | 124 | 19 | $NH_2$-$X_n^b$-DQXXXXXXXLXLTTPR-$X_n^a$-$X_n^b$-COOH |
| IB1-long | 125 | 29 | PGTGCGDTYRPKRPTTLNLFPQVPRSQDT<br>($NH_2$-PGTGCGDTYRPKRPTTLNLFPQVPRSQDT-COOH) |
| IB2-long | 126 | 27 | IPSPSVEEPHKHRPTTLRLTTLGAQDS<br>($NH_2$-IPSPSVEEPHKHRPTTLRLTTLGAQDS-COOH) |
| c-Jun | 127 | 29 | GAYGYSNPKILKQSMTLNLADPVGNLKPH<br>($NH_2$-GAYGYSNPKILKQSMTLNLADPVGNLKPH-COOH) |

TABLE 3-continued

| SEQUENCE/PEPTIDE NAME | SEQ ID NO | AA | SEQUENCE |
|---|---|---|---|
| ATF2 | 128 | 29 | TNEDHLAVHKHKHEMTLKFGPARNDSVIV ($NH_2$-TNEDHLAVHKHKHEMTLKFGPARNDSVIV-COOH) |
| L-IB1 | 129 | 23 | DTYRPKRPTTLNLFPQVPRSQDT ($NH_2$-DTYRPKRPTTLNLFPQVPRSQDT-COOH) |
| D-IB1 | 130 | 23 | TDQSRPVQPFLNLTTPRKPRYTD ($NH_2$-TDQSRPVQPFLNLTTPRKPRYTD-COOH) |
| L-IB (generic) | 131 | 19 | XRPTTLXLXXXXXXXQDS/TX ($NH_2$-XRPTTLXLXXXXXXXQDS/TX-COOH) |
| D-IB (generic) | 132 | 19 | XS/TDQXXXXXXXLXLTTPRX ($NH_2$-XS/TDQXXXXXXXLXLTTPRX-COOH) |
| L-IB1(s1) | 133 | 13 | TLNLFPQVPRSQD ($NH_2$-TLNLFPQVPRSQD-COOH) |
| L-IB1(s2) | 134 | 13 | TTLNLFPQVPRSQ ($NH_2$-TTLNLFPQVPRSQ-COOH) |
| L-IB1(s3) | 135 | 13 | PTTLNLFPQVPRS ($NH_2$-PTTLNLFPQVPRS-COOH) |
| L-IB1(s4) | 136 | 13 | RPTTLNLFPQVPR ($NH_2$-RPTTLNLFPQVPR-COOH) |
| L-IB1(s5) | 137 | 13 | KRPTTLNLFPQVP ($NH_2$-KRPTTLNLFPQVP-COOH) |
| L-IB1(s6) | 138 | 13 | PKRPTTLNLFPQV ($NH_2$-PKRPTTLNLFPQV-COOH) |
| L-IB1(s7) | 139 | 13 | RPKRPTTLNLFPQ ($NH_2$-RPKRPTTLNLFPQ-COOH) |
| L-IB1(s8) | 140 | 12 | LNLFPQVPRSQD ($NH_2$-LNLFPQVPRSQD-COOH) |
| L-IB1(s9) | 141 | 12 | TLNLFPQVPRSQ ($NH_2$-TLNLFPQVPRSQ-COOH) |
| L-IB1(s10) | 142 | 12 | TTLNLFPQVPRS ($NH_2$-TTLNLFPQVPRS-COOH) |
| L-IB1(s11) | 143 | 12 | PTTLNLFPQVPR ($NH_2$-PTTLNLFPQVPR-COOH) |
| L-IB1(s12) | 144 | 12 | RPTTLNLFPQVP ($NH_2$-RPTTLNLFPQVP-COOH) |
| L-IB1(s13) | 145 | 12 | KRPTTLNLFPQV ($NH_2$-KRPTTLNLFPQV-COOH) |
| L-IB1(s14) | 146 | 12 | PKRPTTLNLFPQ ($NH_2$-PKRPTTLNLFPQ-COOH) |
| L-IB1(s15) | 147 | 12 | RPKRPTTLNLFP ($NH_2$-RPKRPTTLNLFP-COOH) |
| L-IB1(s16) | 148 | 11 | NLFPQVPRSQD ($NH_2$-NLFPQVPRSQD-COOH) |
| L-IB1(s17) | 149 | 11 | LNLFPQVPRSQ ($NH_2$-LNLFPQVPRSQ-COOH) |
| L-IB1(s18) | 150 | 11 | TLNLFPQVPRS ($NH_2$-TLNLFPQVPRS-COOH) |
| L-IB1(s19) | 151 | 11 | TTLNLFPQVPR ($NH_2$-TTLNLFPQVPR-COOH) |
| L-IB1(s20) | 152 | 11 | PTTLNLFPQVP ($NH_2$-PTTLNLFPQVP-COOH) |
| L-IB1(s21) | 153 | 11 | RPTTLNLFPQV ($NH_2$-RPTTLNLFPQV-COOH) |

TABLE 3-continued

| SEQUENCE/PEPTIDE NAME | SEQ ID NO | AA | SEQUENCE |
|---|---|---|---|
| L-IB1(s22) | 154 | 11 | KRPTTLNLFPQ<br>($NH_2$-KRPTTLNLFPQ-COOH) |
| L-IB1(s23) | 155 | 11 | PKRPTTLNLFP<br>($NH_2$-PKRPTTLNLFP-COOH) |
| L-IB1(s24) | 156 | 11 | RPKRPTTLNLF<br>($NH_2$-RPKRPTTLNLF-COOH) |
| L-IB1(s25) | 157 | 10 | LFPQVPRSQD<br>($NH_2$-LFPQVPRSQD-COOH) |
| L-IB1(s26) | 158 | 10 | NLFPQVPRSQ<br>($NH_2$-NLFPQVPRSQ-COOH) |
| L-IB1(s27) | 159 | 10 | LNLFPQVPRS<br>($NH_2$-LNLFPQVPRS-COOH) |
| L-IB1(s28) | 160 | 10 | TLNLFPQVPR<br>($NH_2$-TLNLFPQVPR-COOH) |
| L-IB1(s29) | 161 | 10 | TTLNLFPQVP<br>($NH_2$-TTLNLFPQVP-COOH) |
| L-IB1(s30) | 162 | 10 | PTTLNLFPQV<br>($NH_2$-PTTLNLFPQV-COOH) |
| L-IB1(s31) | 163 | 10 | RPTTLNLFPQ<br>($NH_2$-RPTTLNLFPQ-COOH) |
| L-IB1(s32) | 164 | 10 | KRPTTLNLFP<br>($NH_2$-KRPTTLNLFP-COOH) |
| L-IB1(s33) | 165 | 10 | PKRPTTLNLF<br>($NH_2$-PKRPTTLNLF-COOH) |
| L-IB1(s34) | 166 | 10 | RPKRPTTLNL<br>($NH_2$-RPKRPTTLNL-COOH) |
| D-1B1(s1) | 167 | 13 | QPFLNLTTPRKPR<br>($NH_2$-QPFLNLTTPRKPR-COOH) |
| D-IB1(s2) | 168 | 13 | VQPFLNLTTPRKP<br>($NH_2$-VQPFLNLTTPRKP-COOH) |
| D-IB1(s3) | 169 | 13 | PVQPFLNLTTPRK<br>($NH_2$-PVQPFLNLTTPRK-COOH) |
| D-IB1(s4) | 170 | 13 | RPVQPFLNLTTPR<br>($NH_2$-RPVQPFLNLTTPR-COOH) |
| D-IB1(s5) | 171 | 13 | SRPVQPFLNLTTP<br>($NH_2$-SRPVQPFLNLTTP-COOH) |
| D-IB1(s6) | 172 | 13 | QSRPVQPFLNLTT<br>($NH_2$-QSRPVQPFLNLTT-COOH) |
| D-IB1(s7) | 173 | 13 | DQSRPVQPFLNLT<br>($NH_2$-DQSRPVQPFLNLT-COOH) |
| D-IB1(s8) | 174 | 12 | PFLNLTTPRKPR<br>($NH_2$-PFLNLTTPRKPR-COOH) |
| D-IB1(s9) | 175 | 12 | QPFLNLTTPRKP<br>($NH_2$-QPFLNLTTPRKP-COOH) |
| D-IB1(s10) | 176 | 12 | VQPFLNLTTPRK<br>($NH_2$-VQPFLNLTTPRK-COOH) |
| D-IB1(s11) | 177 | 12 | PVQPFLNLTTPR<br>($NH_2$-PVQPFLNLTTPR-COOH) |
| D-IB1(s12) | 178 | 12 | RPVQPFLNLTTP<br>($NH_2$-RPVQPFLNLTTP-COOH) |

TABLE 3-continued

| SEQUENCE/PEPTIDE NAME | SEQ ID NO | AA | SEQUENCE |
|---|---|---|---|
| D-IB1(s13) | 179 | 12 | SRPVQPFLNLTT ($NH_2$-SRPVQPFLNLTT-COOH) |
| D-IB1(s14) | 180 | 12 | QSRPVQPFLNLT ($NH_2$-QSRPVQPFLNLT-COOH) |
| D-IB1(s15) | 181 | 12 | DQSRPVQPFLNL ($NH_2$-DQSRPVQPFLNL-COOH) |
| D-IB1(s16) | 182 | 11 | FLNLTTPRKPR ($NH_2$-FLNLTTPRKPR-COOH) |
| D-IB1(s17) | 183 | 11 | PFLNLTTPRKP ($NH_2$-PFLNLTTPRKP-COOH) |
| D-IB1(s18) | 184 | 11 | QPFLNLTTPRK ($NH_2$-QPFLNLTTPRK-COOH) |
| D-IB1(s19) | 185 | 11 | VQPFLNLTTPR ($NH_2$-VQPFLNLTTPR-COOH) |
| D-IB1(s20) | 186 | 11 | PVQPFLNLTTP ($NH_2$-PVQPFLNLTTP-COOH) |
| D-IB1(s21) | 187 | 11 | RPVQPFLNLTT ($NH_2$-RPVQPFLNLTT-COOH) |
| D-IB1(s22) | 188 | 11 | SRPVQPFLNLT ($NH_2$-SRPVQPFLNLT-COOH) |
| D-IB1(s23) | 189 | 11 | QSRPVQPFLNL ($NH_2$-QSRPVQPFLNL-COOH) |
| D-IB1(s24) | 190 | 11 | DQSRPVQPFLN ($NH_2$-DQSRPVQPFLN-COOH) |
| D-IB1(s25) | 191 | 10 | DQSRPVQPFL ($NH_2$-DQSRPVQPFL-COOH) |
| D-IB1(s26) | 192 | 10 | QSRPVQPFLN ($NH_2$-QSRPVQPFLN-COOH) |
| D-IB1(s27) | 193 | 10 | SRPVQPFLNL ($NH_2$-SRPVQPFLNL-COOH) |
| D-IB1(s28) | 194 | 10 | RPVQPFLNLT ($NH_2$-RPVQPFLNLT-COOH) |
| D-IB1(s29) | 195 | 10 | PVQPFLNLTT ($NH_2$-PVQPFLNLTT-COOH) |
| D-IB1(s30) | 196 | 10 | VQPFLNLTTP ($NH_2$-VQPFLNLTTP-COOH) |
| D-IB1(s31) | 197 | 10 | QPFLNLTTPR ($NH_2$-QPFLNLTTPR-COOH) |
| D-IB1(s32) | 198 | 10 | PFLNLTTPRK ($NH_2$-PFLNLTTPRK-COOH) |
| D-IB1(s33) | 199 | 10 | FLNLTTPRKP ($NH_2$-FLNLTTPRKP-COOH) |
| D-IB1(s34) | 200 | 10 | LNLTTPRKPR ($NH_2$-LNLTTPRKPR-COOH) |

The JNK inhibitor sequences suitable as component (B) may furthermore comprises or consists of at least one variant, fragment and/or derivative of the above defined native or non-native amino acid sequences according to SEQ ID NOs: 121 to 200. Preferably, these variants, fragments and/or derivatives retain biological functionality/activity of the above disclosed native or non-native JNK inhibitor sequences as used herein, particularly of native or non-native amino acid sequences according to SEQ ID NOs: 121 to 200, i.e. binding JNK and/or inhibiting the activation of at least one JNK activated transcription factor, e.g. c-Jun, ATF2 or Elk1 (for tests on functionality/activity see above).

Effector molecules suitable as component (B) may furthermore be selected from antigens or antigenic fragments, preferably protein and (poly-)peptide antigens, e.g. tumor antigens or antigenic fragments thereof, allergy antigens or antigenic fragments thereof, auto-immune self-antigens or antigenic fragments thereof, pathogenic antigens or antigenic fragments thereof, and antigens or antigenic fragments thereof from viruses, preferably from cytomegalovirus (CMV), orthopox variola virus, orthopox alastrim virus, parapox ovis virus, molluscum contagiosum virus, herpes simplex virus 1, herpes simplex virus 2, herpes B virus, varicella zoster virus, pseudorabies virus, human cytomegaly virus, human herpes virus 6, human herpes virus 7, Epstein-Barr virus, human herpes virus 8, hepatitis B virus, chikungunya virus, O'nyong'nyong virus, rubivirus, hepatitis C virus, GB virus C, West Nile virus, dengue virus, yellow fever virus, louping ill virus, St. Louis encephalitis virus, Japan B encephalitis virus, Powassan virus, FSME virus, SARS, SARS-associated corona virus, human corona virus 229E, human corona virus Oc43, Torovirus, human T cell lymphotropic virus type I, human T cell lymphotropic virus type II, HIV (AIDS), i.e. human immunodeficiency virus type 1 or human immunodeficiency virus type 2, influenza virus, Lassa virus, lymphocytic choriomeningitis virus, Tacaribe virus, Junin virus, Machupo virus, Borna disease virus, Bunyamwera virus, California encephalitis virus, Rift Valley fever virus, sand fly fever virus, Toscana virus, Crimean-Congo haemorrhagic fever virus, Hazara virus, Khasan virus, Hantaan virus, Seoul virus, Prospect Hill virus, Puumala virus, Dobrava Belgrade virus, Tula virus, sin nombre virus, Lake Victoria Marburg virus, Zaire Ebola virus, Sudan Ebola virus, Ivory Coast Ebola virus, influenza virus A, influenza virus B, influenza viruses C, parainfluenza virus, malaria virus, Marburg virus, measles virus, mumps virus, respiratory syncytial virus, human metapneumovirus, vesicular stomatitis Indiana virus, rabies virus, Mokola virus, Duvenhage virus, European bat lyssavirus 1+2, Australian bat lyssavirus, adenoviruses A-F, human papilloma viruses, condyloma virus 6, condyloma virus 11, polyoma viruses, adeno-associated virus 2, rotaviruses, orbiviruses, Varicella including Varizella zoster, etc., or antigens or antigenic fragments from *leishmania*, typanosomes, amibes, bacteria, etc., or may be selected from epitopes or from variants of the above antigens or antigenic fragments. Preferably, fragments as well as variants of antigens as defined above exhibit a sequence homology or identity of about 10%, about 20%, about 30%, about 40%, about 50%, about 60%, about 70%, about 80%, or about 90% with one of the antigens or antigen sequences as shown or described above. In this context, the definition of fragments and variants similarly applies as already defined above. Furthermore, epitopes (also called "antigen determinants") of antigens or antigenic fragments as defined above are encompassed.

Furthermore, effector molecules suitable as component (B) of the transporter cargo conjugate molecule may be selected from antibodies. According to the present invention, such an antibody may be selected from any antibody, e.g. any recombinantly produced or naturally occurring antibodies, known in the art, in particular antibodies suitable for therapeutic, diagnostic or scientific purposes, or antibodies which have been identified in relation to specific cancer diseases. Herein, the term "antibody" is used in its broadest sense and specifically covers monoclonal and polyclonal antibodies (including agonist, antagonist, and blocking or neutralizing antibodies) and antibody species with polyepitopic specificity. According to the invention, "antibody" typically comprises any antibody known in the art (e.g. IgM, IgD, IgG, IgA and IgE antibodies), such as naturally occurring antibodies, antibodies generated by immunization in a host organism, antibodies which were isolated and identified from naturally occurring antibodies or antibodies generated by immunization in a host organism and recombinantly produced by biomolecular methods known in the art, as well as chimeric antibodies, human antibodies, humanized antibodies, bispecific antibodies, intrabodies, i.e. antibodies expressed in cells and optionally localized in specific cell compartments, and fragments and variants of the aforementioned antibodies. In general, an antibody consists of a light chain and a heavy chain both having variable and constant domains. The light chain consists of an N-terminal variable domain, $V_L$, and a C-terminal constant domain, $C_L$. In contrast, the heavy chain of the IgG antibody, for example, is comprised of an N-terminal variable domain, $V_H$, and three constant domains, $C_H1$, $C_H2$ and $C_H3$. Antibodies in this context also comprise fragments and variants of antibodies as described above, e.g. an $F_{ab}$ fragment, an $F_c$ fragment, etc. Preferably, such fragments as well as variants exhibit a sequence homology or identity of about 10%, about 20%, about 30%, about 40%, about 50%, about 60%, about 70%, about 80%, or about 90% with one of the antibodies as described above. In this context, the definition of fragments and variants as defined above similarly applies.

Additionally, component (B) of the inventive transporter cargo conjugate molecule may be selected from apoptotic factors or apoptosis related proteins including AIF, Apaf e.g. Apaf-1, Apaf-2, Apaf-3, oder APO-2 (L), APO-3 (L), Apopain, Bad, Bak, Bax, Bcl-2, Bcl-$x_L$, Bcl-$x_S$, bik, Bok, CAD, Calpain, Caspase e.g. Caspase-1, Caspase-2, Caspase-3, Caspase-4, Caspase-5, Caspase-6, Caspase-7, Caspase-8, Caspase-9, Caspase-10, Caspase-11, ced-3, ced-9, c-Jun, c-Myc, crm A, cytochrom C, CdR1, DcR1, DD, DED, DISC, DNA-$PK_{CS}$, DR3, DR4, DR5, FADD/MORT-1, FAK, Fas (Fas-ligand CD95/fas (receptor)), FLICE/MACH, FLIP, fodrin, fos, G-Actin, Gas-2, gelsolin, granzyme A/B, ICAD, ICE, JNK, lamin A/B, MAP, Max, MCL-1, Mdm-2, MEKK-1, MORT-1, Myd88, NEDD, NF-$_{kappa}$B, NuMa, p38, p53, PAK-2, PARP, perforin, PITSLRE, PKCdelta, pRb, presenilin, prICE, RAIDD, Ras, RIP, sphingomyelinase, thymidinkinase from herpes simplex, TRADD, TRAF2, TRAIL-R1, TRAIL-R2, TRAIL-R3, transglutaminase, etc., or from fragments or variants thereof, or from components of the wnt-signalling pathway, such as β-catenine, or the ICF-family, pololike kinases, CiP2A, PP2A, etc., or from fragments or variants thereof. Preferably, such fragments as well as variants exhibit a sequence homology or identity of about 10%, about 20%, about 30%, about 40%, about 50%, about 60%, about 70%, about 80%, or about 90% with one of the sequences as shown or described above. In this context, the definition of fragments and variants as defined above similarly applies.

Effector molecules suitable as component (B) of the transporter cargo conjugate molecule may furthermore be selected from at least one or more partial or full-length BH3-domain and/or at least one partial or full-length BH3-only protein. In this context, BH3-only proteins are preferably defined as members of the Bcl-2 family representing regulators of apoptosis by interacting with other members of Bcl-2 family. In the context of the present invention component (B) of the transporter cargo conjugate molecule may thus be selected from an amino acid sequence comprising at least one or more partial or full-length BH3-domain sequence(s) of a BH3-only protein or a partial or full-length BH3-only protein (defined as a subclass of the Bcl-2 family proteins), which is (are) capable of inducing apoptosis by either interacting with at least one Bcl-2 family protein or by activating or sensitising at least one pro-apoptotic member of the Bcl-2 family. Their functional activity can be tested by suitable assay methods, e.g. by binding assays or by assaying its pro-apoptotic activity by apoptosis assays. Preferably, an amino acid sequence used as component (B) of the inventive transporter cargo conjugate molecule may comprise or consist of at least one partial or full-length BH3-domain sequence and/or at least one partial or full-length BH3-only protein sequence selected from the group consisting of Bid, Bad, Noxa, Puma, Bim, Bik, Bmf, DP5/Hrk and Bok. Alternatively, an amino acid sequence used as component (B) of the inventive transporter cargo conjugate molecule may comprise or consist of a combination of at least one partial or full-length BH3-domain sequence and/or at least one partial or full-length BH3-only protein sequence, the combinations preferably selected from the group consisting of e.g. Bid and Bad, Bim and Bad, Bik and Bad, Puma and Bad, Noxa and Bad, Bmf and Bad, DP5/Hrk and Bad, Bok and Bad, Bik and Bim, Bik and Bid, Bik and Puma, Bik and Noxa, Bik and Bmf, Bik and DP5/Hrk, Bik and Bok, Bid and Puma, Bid and Noxa, Bid and Bim, Bid and Bmf, Bid and DP5/Hrk, Bid and Bok, Bim and Noxa; Bim and Puma, Bim and Bmf, Bim and DP5/Hrk, Bim and Bok, Puma and Noxa, Puma and Bmf, Puma and DP5/Hrk, Puma and Bok, Noxa and Bmf, Noxa and DP5/Hrk and Noxa and Bok. The (full-length or partial) BH3-sequences or BH3-only protein sequences defined above may be selected from e.g. any mammalian BH3-only protein, in particular from the human isoforms. Accordingly, component (B) of the inventive transporter cargo conjugate molecule may comprise or consist of at least one partial or full-length BH3-domain sequence and/or at least one BH3-only protein sequence as defined by any of SEQ ID NOs: 201 to 217 (see Table BH-3 domain). Preferably, an amino acid sequence used as component (B) of the inventive transporter cargo conjugate molecule may further comprise or consist of at least one fragment or variant of at least one partial or full-length BH3-domain sequence and/or at least one BH3-only protein sequence as defined by any of SEQ ID NOs: 201 to 217. Such fragments as well as variants preferably have a sequence length of less than 50, preferably of less than 40 and even more preferably of less than 30 amino acids, or exhibit a sequence homology or identity of about 10%, about 20%, about 30 about 40%, about 50%, about 60%, about 70%, about 80%, or about 90% with one of the sequences described above or as shown in any of SEQ ID NOs: 201 to 217. In this context the definition of fragments and variants as defined above again applies. Furthermore, fragments or variants of the native sequences typically comprise a BH3-domain sequence or at least partially comprise a BH3-domain sequence (at least 7 amino acids of the BH3-domain sequence).

TABLE BH-3 domain

| SEQUENCE/ PEPTIDE NAME | SEQ ID NO | AA | SEQUENCE |
|---|---|---|---|
| Bid (human) (transcript variant 1) | 201 | 241 | MCSGAGVMMA RWAARGRAGW RSTVRILSPL GHCEPGVSRS CRAAQAMDCE VNNGSSLRDE CITNLLVFGF LQSCSDNSFR RELDALGHEL PVLAPQWEGY DELQTDGNRS SHSRLGRIEA DSESQEDIIR NIARHLAQVG DSMDRSIPPG LVNGLALQLR NTSRSEEDRN RDLATALEQL LQAYPRDMEK EKTMLVLALL LAKKVASHTP SLLRDVFHTT VNFINQNLRT YVRSLARNGM D |
| Bad (human) | 202 | 168 | MFQIPEFEPS EQEDSSSAER GLGPSPAGDG PSGSGKHHRQ APGLLWDASH QQEQPTSSSH HGGAGAVEIR SRHSSYPAGT EDDEGMGEEP SPFRGRSRSA PPNLWAAQRY GRELRRMSDE FVDSFKKGLP RPKSAGTATQ MRQSSSWTRV FQSWWDRNLG RGSSAPSQ |
| Noxa1 (human) | 203 | 483 | MASLGDLVRA WHLGAQAVDR GDWARALHLF SGVPAPPARL CFNAGCVHLL AGDPEAALRA FDQAVTKDTC MAVGFFQRGV ANFQLARFQE ALSDFWLALE QLRGHAAIDY TQLGLRFKLQ AWEVLHNVAS AQCQLGLWTE AASSLREAMS KWPEGSLNGL DSALDQVQRR GSLPPRQVPR GEVFRPHRWH LKHLEPVDFL GKAKVVASAI PDDQGWGVRP QQPQGPGANH DARSLIMDSP RAGTHQGPLD AETEVGADRC TSTAYQEQRP QVEQVGKQAP LSPGLPAMGG PGPGPCEDPA GAGGAGAGGS EPLVTVTVQC AFTVALRARR GADLSSLRAL LGQALPHQAQ LGQLSYLAPG EDGHWVPIPE EESLQRAWQD AAACPRGLQL QCRGAGGRPV LYQVVAQHSY SAQGPEDLGF RQGDTVDVLC EEPDVPLAVD QAWLEGHCDG RIGIFPKCFV VPAGPRMSGA PGRLPR- SQQG DQP |
| Puma (human) | 204 | 193 | MARARQEGSS PEPVEGLARD GPRPFPLGRL VPSAVSCGLC EPGLAAAPAA PTLLPAAYLC APTAPPAVTA ALGGSRWPGG PRSRPRGPRP DGPQPSLSLA EQHLESPVPS APGALAGGPT QAAPGVRGEE EQWAREIGAQ LRRMADDLNA QYERRRQEEQ QRHRPSPWRV LYNLIMGLLP LPRGHRAPEM EPN |
| Bim (human) (transcript variant 1) | 205 | 198 | MAKQPSDVSS ECDREGRQLQ PAERPPQLRP GAPTSLQTEP QGNPEGNHGG EGDSCPHGSP QGPLAPPASP GPFATRSPLF IFMRRSSLLS RSSSGYFSFD TDRSPAPMSC DKSTQTPSPP CQAFNHYLSA MASMRQAEPA DMRPEIWIAQ ELRRIGDEFN AYYARRVFLN NYQAAEDHPR MVILRLLRYI VRLVWRMH |

TABLE BH-3-continued

| domain | | | |
|---|---|---|---|
| SEQUENCE/ PEPTIDE NAME | SEQ ID NO | AA | SEQUENCE |
| Bik (human) | 206 | 160 | MSEVRPLSRD ILMETLLYEQ LLEPPTMEVL GMTDSEEDLD PMEDFDSLEC MEGSDALALR LACIGDEMDV SLRAPRLAQL SEVAMHSLGL AFIYDQTEDI RDVLRSFMDG FTTLKENIMR FWRSPNPGSW VSCEQVLLAL LLLLALLLPL LSGGLHLLLK |
| BH3-domain of Bik (Bik BH3) | 207 | 18 | ALALRLACIG DEMDVSLR |
| BH3-domain of Bad (Bad BH3) | 208 | 18 | RYGRELRRMS DEFVDSFK |
| BH3-domain of Bid (Bid BH3) | 209 | 18 | NIARHLAQVG DSMDRSIP |
| BH3-domain of Bmf (Bmf BH3) | 210 | 18 | QIARKLQCIA DQFHRLHV |
| BH3-domain of DP5/Hrk (DP5Hrk BH3) | 211 | 18 | LTAARLKAIG DELHQRTM |
| BH3-domain of Bim (Bim BH3) | 212 | 18 | WIAQELRRIG DEFNAYYA |
| BH3-domain of Noxa (Noxa BH3) | 213 | 18 | ECATQLRRFG DKLNFRQK |
| BH3-domain of PUMA (PUMA BH3) | 214 | 18 | EIGAQLRRMA DDLNAQYE |
| BH3-domain of Bax (Bax BH3) | 215 | 18 | KLSECLKRIG DELDSNME |
| BH3-domain of Bak (Bak BH3) | 216 | 18 | QVGRQLAIIG DDINRRYD |
| BH3-domain of Bok (Bok BH3) | 217 | 18 | EVCTVLLRLG DELEQIRP |

The proteins or (poly-)peptide sequences as described herein, e.g. of therapeutically active proteins, antigens, antibodies, apoptotic factors, proteases implicated in pathological states, preferably peptidic protease inhibitors, BH3 domains, etc., which can be used as component (B), may be provided as a protein or (poly-)peptide sequence either in the native form composed of L-amino acids or in the retro-inverso D-form (entirely) composed of D amino acids, which means that these sequences have to be inverted by reverting the termini: native C-terminus is the N-terminus of the inverted form and the native N-terminus is the C-Terminus of the inverted form). Alternatively, these proteins or (poly-)peptide sequences as described above, may provide their protein or (poly-)peptide sequence as a mixture of L-amino acids and D-amino acids.

Component (B) may also be selected from nucleic acids, preferably from nucleic acids encoding the above defined proteins or (poly-)peptides, such as therapeutically active proteins and (poly-)peptides, antigens, antibodies, apoptotic factors, proteases implicated in pathological states, preferably peptidic protease inhibitors, BH3-domains or partial or full-length BH3-only proteins or their variants of fragments. In this context, nucleic acids preferably comprise single stranded, double stranded or partially double stranded nucleic acids, preferably selected from genomic DNA, cDNA, RNA, siRNA, antisense DNA, antisense RNA, microRNA, ribozyme, complimentary RNA/DNA sequences with or without expression elements, a mini-gene, gene fragments, regulatory elements, promoters, and combinations thereof.

As a further particular example, component (B) may be selected from siRNAs. In this context, a siRNAs is of interest particularly in connection with the phenomenon of RNA interference. Attention was drawn to the phenomenon of RNA interference in the course of immunological research. In recent years, a RNA-based defense mechanism has been discovered, which occurs both in the kingdom of the fungi and in the plant and animal kingdom and acts as an "immune system of the genome". The system was originally described in various species independently of one another, first in *C. elegans*, before it was possible to identify the underlying mechanisms of the processes as being identical: RNA-mediated virus resistance in plants, PTGS (posttranscriptional gene silencing) in plants, and RNA interference in eukaryotes are accordingly based on a common procedure. The in vitro technique of RNA interference (RNAi) is based on double-stranded RNA molecules (dsRNA), which trigger the sequence-specific suppression of gene expression (Zamore (2001) Nat. Struct. Biol. 9: 746-750; Sharp (2001) Genes Dev. 5:485-490: Hannon (2002) Nature 41: 244-251). In the transfection of mammalian cells with long dsRNA, the activation of protein kinase R and RnaseL brings about unspecific effects, such as, for example, an interferon response (Stark et al. (1998) Annu. Rev. Biochem. 67: 227-264; He and Katze (2002) Viral Immunol. 15: 95-119). These unspecific effects are avoided when shorter, for example 21- to 23-mer, so-called siRNA (small interfering RNA), is used, because unspecific effects are not triggered by siRNA that is shorter than 30 by (Elbashir et al. (2001) Nature 411: 494-498). Recently, dsRNA molecules have also been used in vivo (McCaffrey et al. (2002), Nature 418: 38-39; Xia et al. (2002), Nature Biotech. 20: 1006-1010; Brummelkamp et al. (2002), Cancer Cell 2: 243-247). Thus, an siRNA used as an effector molecule suitable as component (B) of the inventive transporter cargo conjugate molecule typically comprises a (single- or) double stranded, preferably a double-stranded, RNA sequence with about 8 to 30 nucleotides, preferably 17 to 25 nucleotides, even more preferably from 20 to 25 and most preferably from 21 to 23 nucleotides. In principle, all the sections having a length of from 17 to 29, preferably from 19 to 25, most preferably from 21 to 23 base pairs that occur in the coding region of a protein (sequence) as mentioned above, can serve as target sequence for a siRNA. Equally, siRNAs can also be directed against nucleotide sequences of a protein (sequence) described hereinbefore that do not lie in the coding region, in particular in the 5' non-coding region of the RNA, for example, therefore, against non-coding regions of the RNA having a regulatory function. The target sequence of the siRNA can therefore lie in the translated and/or untranslated region of the RNA and/or in the region of the control elements. The target sequence of a siRNA can also lie in the overlapping region of untranslated and translated sequence; in particular, the target sequence can comprise at least one nucleotide upstream of the start triplet of the coding region.

As another particular example, component (B) may be selected from antisense RNA. In this context, an antisense RNA is preferably a (single-stranded) RNA molecule transcribed on the basis of the coding, rather than the template, strand of (genomic) DNA, so that it is complementary to the sense (messenger) RNA. An antisense RNA suitable as component (B) of the inventive transporter cargo conjugate molecule typically forms a duplex between the sense and antisense RNA molecules and is thus capable to block translation of the corresponding mRNA. An antisense RNA as used herein can be directed against any portion of an mRNA sequence, e.g. derived from genomic DNA and/or which may encode any protein, e.g. a protein (poly-)peptide as defined herein such as therapeutically active proteins and (poly-)peptides, antigens, antibodies, apoptotic factors, proteases implicated in pathological states, preferably peptidic protease inhibitors, BH3-domains or partial or full-length BH3-only proteins or their variants of fragments as described hereinbefore, if thereby translation of the encoded protein or (poly-)peptide is reduced/suppressed. Accordingly, the target sequence of the antisense RNA on the targeted mRNA (or the targeted (genomic) DNA) may be located in the translated and/or untranslated region of the mRNA (or the targeted (genomic) DNA), e.g. in the region of the control elements, in particular in the 5' non-coding region of the mRNA (or the targeted (genomic) DNA) exerting a regulatory function. The target sequence of an antisense RNA on the targeted mRNA (or the targeted (genomic) DNA) may also be constructed such that the antisense RNA binds to the mRNA (or the targeted (genomic) DNA) by covering with its sequence a region which is partially complementary to the untranslated and to translated (coding) sequence of the targeted mRNA (or the targeted (genomic) DNA); in particular, the antisense RNA may be complementary to the target mRNA (or the targeted (genomic) DNA) sequence by at least one nucleotide upstream of the start triplet of the coding region of the targeted mRNA. Preferably, the antisense RNA as used herein comprises a length of about 5 to about 5000, of about 500 to about 5000, and, more preferably, of about 1000 to about 5000 or, alternatively, of about 5 to about 1000, about 5 to about 500, about 5 to about 250, of about 5 to about 100, of about 5 to about 50 or of about 5 to about 30 nucleotides, or, alternatively, and even more preferably a length of about 20 to about 100, of about 20 to about 80, or of about 20 to about 60 nucleotides.

As a further particular example, component (B) may also be a pharmaceutical drug, e.g. selected from cytotoxic or anti-tumor drugs which are suitable as a chemotherapy drug. In general, chemotherapy drugs suitable for component (B) can be divided into three main categories based on their mechanism of action. They may (a) stop the synthesis of preDNA molecule building blocks: These agents work in a number of different ways. DNA building blocks are folic acid, heterocyclic bases, and nucleotides, which are made naturally within cells. All of these agents work to block some step in the formation of nucleotides or deoxyribonucleotides (necessary for making DNA). When these steps are blocked, the nucleotides, which are the building blocks of DNA and RNA, cannot be synthesized. Thus the cells cannot replicate because they cannot make DNA without the nucleotides. Examples of drugs in this class include methotrexate (Abitrexate®), fluorouracil (Adrucil®), hydroxyurea (Hydrea®), and mercaptopurine (Purinethol®), thioguanine, tocoferol, or, more generally, also any nucleotide analogue, e.g. 2'-deoxycytidine analogues. Alternatively, chemotherapy drugs may (b) directly damage the DNA in the nucleus of the cell. These agents chemically damage DNA and RNA. They disrupt replication of the DNA and either totally halt replication or cause the manufacture of nonsense DNA or RNA (i.e. the new DNA or RNA does not code for anything useful). Examples of drugs in this class include cisplatin (Platinol®) and antibiotics—daunorubicin (Cerubidine®), doxorubicin (Adriamycin®) belonging to the class of anthracycline antitumor agents (the members of which may be used as component (B) of the inventive transporter cargo conjugate molecule), and etoposide (VePesid®) or any intercalator. Finally, chemotherapy drugs may (c) effect the synthesis or breakdown of the mitotic spindles: Mitotic spindles serve as molecular railroads with "North and South Poles" in the cell when a cell starts to divide itself into two new cells. These spindles are very important because they help to split the newly copied DNA such that a copy goes to each of the two new cells during cell division. These drugs disrupt the formation of these spindles and therefore interrupt cell division. Examples of drugs in this class of mitotic disrupters include: Vinblastine (Velban®), Vincristine (Oncovin®) and Paclitaxel (Taxol®). Component (B) of the inventive transporter cargo conjugate molecule may act according to one of the above modes of action. In other terms, each of the classes of anti-tumor drugs, i.e. alkylating agents, nitrosoureas, antimetabolites, plant alkaloids, antitumor antibiotics, and steroid hormones may be used as component (B) of the inventive transporter cargo conjugate molecule. To describe these drug classes in more detail it is emphasized that each anti cancer drug may also be categorized according to its effect on the cell cycle and cell chemistry as disclosed above. Alkylating agents kill cells by directly attacking DNA. Alkylating agents may be used in the treatment of chronic leukemias, Hodgkin's disease, lymphomas, and certain carcinomas of the lung, breast, prostate and ovary. Cyclophosphamide is an example of a commonly used alkylating agent. Nitrosoureas act similarly to akylating agents and also inhibit changes necessary for DNA repair. These agents cross the blood-brain barrier and are therefore used to treat brain tumors, lymphomas, multiple myeloma, and malignant melanoma. Carmustine and lomustine are the major drugs in this category. Antimetabolites are that drugs block cell growth by interfering with certain activities, usually DNA synthesis. Once ingested into the cell they halt normal development and reproduction. All drugs in this category affect the cell during the "S" phase of the cell cycle. Antimetabolites may be used in the treatment of acute and chronic leukemias, choriocarcinoma, and some tumors of the gastrointestinal tract, breast and ovary. Examples of commonly used antimetabolites are 6-mercaptopurine and 5-fluorouracil (5FU). Antitumor antibiotics are a diverse group of compounds. In general, they act by binding with DNA and preventing RNA synthesis. These agents are widely used in the treatment of a variety of cancers. The most commonly used drugs in this group are doxorubicin (Adriamycin), mitomycin-C, and bleomycin. Plant (vinca)alkaloids are anti-tumor agents derived from plants. These drugs act specifically by blocking cell division during mitosis. They are commonly used in the treatment of acute lymphoblastic leukemia, Hodgkin's and non-Hodgkin's lymphomas, neuroblastomas, Wilms' tumor, and cancers of the lung, breast and testes. Vincristine and vinblastine are commonly used agents in this group. Steroid hormones are useful in treating some types of tumors. This class includes adrenocorticosteroids, estrogens, antiestrogens, progesterones, and androgens. Although their specific mechanism of action is not clear, steroid hormones modify the growth of certain hormone-dependent cancers. Tamoxifen is an example, which is used for estrogen dependent breast cancer. All of the above-mentioned tumor species may be treated by the inventive transporter cargo conjugate molecules comprising as component (B) any of the above antitumor agents.

One group of cytotoxic or anti-tumor drugs, which may be used as effector molecules for component (B) of the inventive transporter cargo conjugate molecule is preferably selected from alkylating drugs, antimetabolica, cytostatics or drugs related to hormone treatment. In this context, it it is preferred to select as cytotoxic or anti-tumor drugs compounds of metal, in particular platin (derivative) and taxol classes. In particular, the drug moiety is selected from the group of drugs consisting of, for example, cisplatin, transplatin, satraplatin, oxaliplatin, carboplatin, nedaplatin, chlorambucil, cyclophosphamide, mephalan, azath ioprin, fluorouracil, (6)-mercaptopurine, methrexate, nandrolone, aminogluthemide, medroxyprogesteron, megestrolacetate, procarbazin, docetaxel, paclitaxel, irinotecan, epipodophyllotoxin, podophyllotoxin, vincristine, vinblastine, docetaxel, daunomycin, daunorubicin, doxorubicin, mitoxantrone, topotecan, bleomycin, gemcitabine, fludarabine, navelbine and 5-FUDR. Particularly preferred is the class of metal containing anticancer drugs, e.g. the class of platinum compounds.

Further cytotoxic or anti-tumor drugs, which may be used as component (B) of the inventive transporter cargo conjugate molecule are (identified by their generic name) Alitretinoin, Altretamine, Azathioprine, Bicalutamide, Busulfan, Capecitabine, Cyclophosphamide, Exemestane, Letrozole, Finasteride, Megestrol Acetate, Triptorelin, Temozolomide, Mifepristone, Tretinoin, Oral, Tamoxifen, Teniposide, Imatinib (Gleevec®), Gefitinib (IRESSA®), Peplomycin sulfate or the class of camptothecins.

Another group of cytotoxic or anti-tumor drugs, which may be used as component (B) are indolocarbazole compounds, e.g. staurosporin (and its analogues) and rebeccamycin. It is to be mentioned that compounds belonging to the class of anilinoquinazolines (e.g. gefitinib) are also particularly preferred as component (B).

A further group of cytotoxic or anti-tumor drugs, which may be used as effector molecules for component (B) of the inventive transporter cargo conjugate molecule, may additionally be selected from inhibitors of topoisomerases, such as irinotecan, or mitotic kinesins or DHFR.

Additionally, cytotoxic or anti-tumor drugs, which may be used as effector molecules for component (B) of the inventive transporter cargo conjugate molecule can be selected from factors inhibiting or stimulating cell proliferation (PDGF), intracellular pathways, e.g the RAS/RAF signaling pathway, such as a member of the RAF/MEK/ERK signaling pathway (e.g. RAF-1) or mitogen-activated protein kinase pathway, CMGC kinase family (containing CDK (cyclin dependent-kinases), MAPK, GSK3, CLK), Ser/Thr kinases that belong to the AGC kinase family containing PKA, PKG, PKC kinase families, receptor tyrosine kinases involved e.g. in neovascularization and tumor progression, including vascular endothelial growth factor receptor (VEGFR)-2, VEGFR-3, platelet-derived growth factor receptor β, Flt-3, the endothelin (ET) system, that includes ET-1, ET-2, ET-3, and the $ET_A$ receptor ($ET_AR$) and $ET_BR$, and c-KIT, which are targeted by e.g. inhibiting their function, and members of the IGF-family, such as IGF-1, IGF-2, IGF-1R, IGF2R, etc.

Another group of cytotoxic or anti-tumor drugs, which may be used as effector molecules for component (B) of the inventive transporter cargo conjugate molecule may be selected from inhibitors that target tumor cell proliferation and tumor angiogenesis. Particularly preferred in this context are small molecule antitumor kinase inhibitors directed toward targets on malignant cells and/or vascular cells have antiangiogenic activity. Kinase inhibitors such as those directed toward EGFR, Her2/neu, BCR-ABL, c-KIT, PKC, Raf and PI3, are antiangiogenic by virtue of blocking secretion of angiogenic factors by affected malignant cells. Kinase inhibitors such as those directed toward VEGFR2, VEGFR1, PDGFR, PKC, Raf and PI3, are antiangiogenic by effects on vascular cells. Examples of synthetic inhibitors of cyclin dependent kinases (CDKIs) are e.g. olomoucine, flavopiridol, butyrolactone and their derivatives and thus constrain tumor cell proliferation. On the other hand, antitumor compounds suitable as component (B) of the inventive transporter cargo conjugate molecule may be selected from activators of apoptosis programs in cancer cells (e.g. staurosporine) or by downregulating antiapoptotic proteins, e.g. Bcl-2.

It is common to all of the above compounds that they have to cross the cell membrane in order to act as anticancer drugs. By coupling compounds belonging to each of these classes (compounds directly damaging the DNA in the nucleus of the cell, effecting the synthesis or breakdown of the mitotic spindles or stopping the synthesis of pre-DNA molecule building blocks) as component (B) to component (A) to form the inventive transporter cargo conjugate molecule, the entry of the anticancer compounds into the cell is enhanced and/or their solubility is enhanced, thereby increasing the efficacy of these therapeutic compounds. In turn, increased cell take-up and, preferably, better solubility of these compounds in the aqueous environment (e.g. the cytosol) allows to lower the dosage of the therapeutic anti-cancer compound.

Additionally, component (B) of the inventive transporter cargo conjugate molecule may also comprise small organic comounds or drug molecules, such as protease inhibitors which inhibit proteases, in particular proteases which are involved in the infection cycle of infectious agents, e.g. viral, bacterial or protozoological proteases. In a preferred embodiment, these protease inhibitors (organic comounds or drug molecules) as part of an inventive conjugate molecule may serve to treat viral, bacterial infections or protozoological infections, e.g. malaria. In particular, virus infections may be treated by protease inhibitors, e.g. retroviral diseases. The use of conjugate molecules comprising protease inhibitors are strongly preferred for the treatment of HIV infections. The protease inhibitors to be used for coupling to carrier sequence as disclosed herein may be selected from a group containing the 640385, abacavir sulfate, AG1776, amprenavir (141W94 or VX-478), atazanavir (BMS-232632), Cathepsin S protease inhibitor, D1927, D9120, efavirenz, emtricitabine, enfuvirtide (T-20), fosamprenavir (GW-433908 or VX-175), GS 9005, GW640385 (VX-385), HCV protease inhibitor, indinavir (MK-639), L-756, 423, levoprin-ZG, lopinavir (ABT-378), lopinavir/ritonavir (LPV ABT-378/r), MK-944A, mozenavir (DMP450), nelfinavir (AG-1343), nevirapine, P-1946, PL-100, prinomastat, ritonavir (ABT-538), RO033-4649, TMC114, saquinavir (Ro-31-8959), tenofovir disoproxil fumarate, tipranavir (PNU-140690), TLK 19781, TMC-114, Vertex 385, VX-950.

Finally, effector molecules suitable as component (B) of the inventive transporter cargo conjugate molecule may additionally be selected as a separate component from a label as defined above for the inventive transporter cargo conjugate molecule. Such an inventive transporter cargo conjugate molecule is particularly suitable for in vitro or in vivo assays. In this context, labels may comprise radioactive labels, i.e. radioactive phosphorylation or a radioactive label with sulphur, hydrogen, carbon, nitrogen, etc.; colored dyes (e.g. digoxygenin, etc.); fluorescent groups (e.g. fluorescein, rhodamine, flourochrome proteins as defined below, etc.); chemoluminescent groups; or combination of these labels. Preferably, flourochrome proteins comprise any fluorochrome protein, which can be activated such as to emit a fluorescence signal. More preferably, the fluorochrome protein is selected from any fluorescent protein, e.g. from a group comprising the Green Fluorescent Protein (GFP), derivatives of the Green Fluorescent Protein (GFP), e.g. EGFP, AcGFP, TurboGFP, Emerald, Azami Green, the photo activatable-GFP (PA-GFP), or Blue Fluorescent Protein (BFP) including EBFP, Sapphire, T-Sapphire, or Cyan Fluorescent Proteins (CFP) including the enhanced cyan fluorescent protein (ECFP), mCFP, Cerulan, CyPet, or Yellow Fluorescent Proteins (YFP), including Topaz, Venus, mCitrine, Ypet, PhiYFP, mBanana, the yellow shifted green fluorescent protein (Yellow GFP), the enhanced yellow fluorescent protein (EYFP), or Orange and Red Flourescent Proteins (RFP) including Kusibara Orange, mOrange, dTomato-Tandem, DsRed-Monomer, mTangerine, mStrawberry, monomeric red fluorescent protein (mRFP1) (also designated herein as mRFP), mCherry, mRaspberry, HcRed-Tandem, mPlum, as well as optical highlighters selected from PA-GFP, CoralHue Dronpa (G), PS-CFP (C), PS-CFP (G), mEosFP (G), mEosFP (G), or other monomeric fluorescent proteins such as or the kindling fluorescent protein (KFP1), aequorin, the autofluorescent proteins (AFPs), or the fluorescent proteins JRed, TurboGFP, PhiYFP and PhiYFP-m, tHc-Red (HcRed-Tandem), PS-CFP2 and KFP-Red (as available from EVRQGEN, see also www.evrogen.com), or other suitable fluorescent proteins.

The inventive transporter cargo conjugate molecule comprising components (A) and (B) may furthermore comprise at least one optional additional component, etc., preferably different to component (B). This at least one optional additional portion may award additional functions to the inventive fusion protein. The at least one optional additional component can be a portion (e.g, HA, HSV-Tag, His6-Tag, FLAG-Tag), which may render the inventive transporter cargo conjugate molecule amenable to purification and/or isolation. If desired, the component needed for purification can then be removed from the other components of the inventive transporter cargo conjugate molecule (e.g., by proteolytic cleavage or other methods known in the art) at the end of the production process.

Furthermore, the optional at least one additional component of the inventive transporter cargo conjugate molecule may for example be a signal sequence or localisation sequence, which efficiently directs the inventive transporter cargo conjugate molecule to a particular intracellular target localization or to a particular cell type, preferably without loss of the enhanced cell permeability properties of the inventive transporter cargo conjugate molecule. Typically, such a signal sequence or localisation sequence directs the inventive transporter cargo conjugate molecule to specific cell compartments, e.g., endoplasmic reticulum, mitochondrion, gloom apparatus, lysosomal vesicles, etc. Exemplary signal sequences or localisation sequences include, without being limited thereto, localisation sequences for the endoplasmic reticulum, such as KDEL (SEQ ID NO: 218), DDEL (SEQ ID NO: 219), DEEL (SEQ ID NO: 220), QEDL (SEQ ID NO: 221), RDEL (SEQ ID NO: 222), sequences for the localisation into the nucleus, such as PKKKRKV (SEQ ID NO: 223), PQKKIKS (SEQ ID NO: 224), QPKKP (SEQ ID NO: 225), RKKR (SEQ ID NO: 226), sequences for the localisation for the nuclear region, such as RKKRRQRRRAHQ (SEQ ID NO: 227), RQARRNRRRRWRERQR (SEQ ID NO: 228), MPLTRRRPAASQALAPPTP (SEQ ID NO: 229), sequences for the localisation into the endodomal compartiment, such as MDDQRDLISNNEQLP (SEQ ID NO: 230), etc.

The inventive transporter cargo conjugate molecule may furthermore comprise at least one modification, preferably at its termini, either at the C- or the N-terminus or both. The C-terminus may preferably be modified by an amide modification, whereas the N-terminus may be modified by any suitable $NH_2$-protection group, such as e.g. acylation, or any further modification as already indicated above for L-amino acids.

The components (A), (B) of the inventive transporter cargo conjugate molecule and, if present, further optional components (C), (D) and/or (E), etc. are typically coupled with each other, via covalent bonds or via electrostatic bonding (e.g. poly-lysine), preferably via covalent bonds. In this context the term “covalent bond” relates to a stable chemical link between two atoms produced by sharing one or more pairs of electrons. Preferably, all components (A) and (B) of the inventive transporter cargo conjugate molecule and, if present, further optional components (C), (D) and/or (E), etc. may be coupled as to form a linear molecule or a non-linear (branched) molecule, preferably a linear molecule. In a linear molecule, all the above components (A) and (B) and, if present, optional components (C), (D) and/or (E), etc. are linked to each other via their terminal ends of in a linear form without leading to branched transporter cargo conjugate molecule. In a non-linear (branched) molecule all the above components (A) and (B) and, if present, optional components (C), (D) and/or (E), etc. are linked to each other via their terminal ends of in a form which leads to a branched transporter cargo conjugate molecule, e.g. having an Y-shaped form, etc.

As component (A) of the inventive transporter cargo conjugate molecule is per definition a (poly-)peptide sequence, the (covalent) attachment of further components (B) and, if present, of optional components (C), (D) and/or (E), may, of course, depend on the type and nature of the components to be attached, i.e. as to whether the single components are proteins or (poly-)peptides, nucleic acids, (small) organic compounds, etc.

The order, in which component (B) of the inventive transporter cargo conjugate molecule and, if present, further optional components (C), (D) and/or (E), are linked with component (A) and each other to form a preferably linear molecule, typically may comprise any order. Accordingly, any of components (A), (B), and if present, (C), (D), (E) etc., may be attached with each other. However, component (A) is preferably attached at the terminal ends of the inventive transporter cargo conjugate molecule. If any of components (B), and if present, components (C), (D), (E) etc., is a protein or a (poly-)peptide sequence, component (A) is preferably contained at the C-terminal end of the inventive transporter cargo conjugate molecule, e.g., at the C-terminal end of component (B) as defined above or, if present, of components (C), (D), (E) etc., when occurring as a (poly-)peptide or a protein. Such a position of component (A) in the inventive transporter cargo conjugate molecule prevents the cargo (poly-)peptide or protein sequence of components (B), (C), (D), (E) etc. to be degraded prior to its/their transport to the desired target site, e.g. the cell, the nucleus, etc., by a peptidase, particularly a carboxy peptidase such as carboxy-terminal peptidase N. Alternatively, if there are aminoterminal peptidases in the cell systems used, the component (A) may be located at the aminoterminal end of the inventive transporter cargo conjugate molecule.

If component (B) and/or, if present, any further optional component, is a (poly-)peptide or protein sequence, the link between protein or (poly-)peptide components (A) and (B), and/or any further (poly-)petide component of the inventive transporter cargo conjugate molecule is preferably a (poly-) peptide bond. Such a (poly-)peptide bond may be formed using a chemical synthesis involving both components (an N-terminal end of one component and the C-terminal end of the other component) to be linked, or may be formed directly via a protein synthesis of the entire (poly-)peptide sequence of both components, wherein both (protein or (poly-)peptide) components are preferably synthesized in one step. Such protein synthesis methods include e.g., without being limited thereto, liquid phase (poly-)peptide synthesis methods or solid (poly-)peptide synthesis methods, e.g. solid (poly-)peptide synthesis methods according to Merrifield, t-Boc solid-phase (poly-)peptide synthesis, Fmoc solid-phase (poly-)peptide synthesis, BOP (Benzotriazole-1-yl-oxy-tris-(dimethylamino)-phosphonium hexafluorophosphate) based solid-phase (poly-)peptide synthesis, etc.

Furthermore, the components (A) and component (B) of the inventive transporter cargo conjugate molecule can be coupled via a linker or directly (without linker) by e.g. an amide bridge, if the components to be linked have reactive amino or carboxy groups. Alternatively, ester or ether linkages are preferred.

If present, further components (C), (D) and/or (E), etc., as mentioned above, can be coupled in an analogous manner to component (A) and/or component (B) or, optionally, with each other to then be linked as one single moiety to either component (A) or component (B). Linker sequences can also be used to fuse the components of inventive transporter cargo conjugate molecule with at least one other component (see below). The mode of coupling further component(s) to the either component (A) or component (B) of the inventive transporter cargo conjugate molecule will depend on its chemical character. If additional components (C), (D), (E), etc., belong to the class of peptidic sequences, they will preferably linked to the inventive transporter cargo conjugate molecule to either terminus of component (A) or, alternatively, be linked via component (A)'s L- or D amino acid side chains, e.g. by a disulfide bridge. Further components of other chemical nature may be likewise attached to component (A) (terminal groups or chemically active side chain groups) or component (B). The linkage via a side chain will preferably be based on side chain amino, thiol or hydroxyl groups, e.g. via an amide or ester or ether linkage. It has to be noted that, according to the invention, all amino acids (of any of component (A), and, if built of amino acids, components (C), (D), (E) etc.,) are preferably D-enantiomeric amino acids, which reflect its eventually naturally occurring analogue by being linked in retro-inverso order. Nevertheless, components (C), (D), (E) etc., if composed of amino acids, may also be composed of L-amino acids (in their naturally occurring sequence order) or built of a combination of D and L amino acids.

If peptidic linker sequences are used, the linker sequences preferably form a flexible sequence of 2 to 10 residues, more preferably 1 to 5 residues. In a preferred embodiment the linker sequence contains at least 20%, more preferably at least 40% and even more preferably at least 50% Gly or β-alanine residues, e.g. GlyGlyGlyGlyGly (SEQ ID NO:308), GlyGlyGlyGly(SEQ ID NO:309), GlyGlyGly (SEQ ID NO:310), CysGlyGly (SEQ ID NO:311) or GlyGlyCys(SEQ ID NO:312), etc. Appropriate linker sequences can be easily selected and prepared by a person skilled in the art. They may be composed of D and/or L amino acids.

Peptide linker sequences may also be introduced between a component (A) and a component (B), and/or further optional component(s), i.e. (C), (D), (E) etc., of the inventive transporter cargo conjugate molecule, wherein an aminoterminal methionine is added to component (A) and/or prior to a protein or (poly-)peptide sequence component (B), (C), (D), (E) etc.

Preferably, component (A) and component (B) are linked by chemical coupling in any suitable manner known in the art, such as cross-linking methods. However, attention is drawn to the fact that many known chemical cross-linking methods are non-specific, i.e., they do not direct the point of coupling to any particular site on the carrier moiety or cargo moiety. Thus, the use of non-specific cross-linking agents may attack functional sites or sterically block active sites, rendering the fused components of the inventive transporter cargo conjugate molecule biologically inactive. It is referred to the knowledge of the skilled artisan to block potentially reactice groups by using appropriate protecting groups. Alternatively, the use of the powerful and versatile oxime and hydrazone ligation techniques, which are chemo-selective entities that can be applied for the cross-linking of component (A) to component (B), may be employed. This linking technology is described e.g. by Rose et al. (1994), JACS 116, 30. If present, further components (C), (D), (E) etc., as mentioned above, can be chemically coupled in an analogous manner to one another or to component (A) and/or (B).

Coupling specificity can be increased by direct chemical coupling to a functional group found only once or a few times in component (A), which functional group is to be cross-linked to the organic molecule of component (B). As an example, the cystein thiol group may be used, if just one cystein residue is present on component (A) of the inventive transporter cargo conjugate molecule. Also, for example, if a conjugate molecule component (A) contains no lysine residues, a cross-linking reagent specific for primary amines will be selective for the amino terminus of component (A). Alternatively, cross-linking may also be carried out via the side chain of a glutamic acid residue placed at the N-terminus of the (poly-)peptide such that a amide bond can be generated through its side-chain. Therefore, it may be advantageous to link a glutamic acid residue to the N-terminus of component (A) of the inventive transporter cargo conjugate molecule. However, if a cysteine residue is to be introduced into component (A), introduction at or near its N- or C-terminus is preferred. Conventional methods are available for such amino acid sequence alterations based on modifications of component (A) by either adding one or more additional amino acids, e.g. inter alia an cystein residue, to the translocation sequence or by substituting at least one residue of the translocation sequence(s) being comprised in component (A). In case a cystein side chain is used for coupling purposes, component (A) of the inventive transporter cargo conjugate molecule has preferably one cystein residue. Any second cystein residue should preferably be avoided and can, eventually, be replaced when they occur in component (A) of the inventive transporter cargo conjugate molecule. When a cysteine residue is replaced in the original translocation sequence to be used as or as part of component (A), it is typically desirable to minimize resulting changes in component (A) (poly-)peptide folding. Changes in component (A) folding are minimized when the replacement is chemically and sterically similar to cysteine. Therefore, serine is preferred as a replacement for cystein.

Coupling of the two components of the inventive transporter cargo conjugate molecule can be accomplished via a coupling or conjugating agent including standard (poly-)peptide synthesis coupling reagents such as HOBt, HBTU, DICI, TBTU. There are several intermolecular cross-linking reagents which can be utilized, see for example, Means and Feeney, Chemical Modification of Proteins, Holden-Day, 1974, pp. 39-43. Among these reagents are, for example, N-succinimidyl 3-(2-pyridyldithio)propionate (SPDP) or N,N'-(1,3-phenylene)bismaleimide; N,N'-ethylene-bis-(iodoacetamide) or other such reagent having 6 to 11 carbon methylene bridges; and 1,5-difluoro-2,4-dinitrobenzene. Other cross-linking reagents useful for this purpose include: p,p'-difluoro-m,m'-dinitrodiphenylsulfone; dimethyl adipimidate; phenol-1,4-disulfonylchloride; hexamethylenediisocyanate or diisothiocyanate, or azophenyl-p-diisocyanate; glutaraldehyde and disdiazobenzidine. Cross-linking reagents may be homobifunctional, i.e., having two functional groups that undergo the same reaction. A preferred homobifunctional cross-linking reagent is bismaleimidohexane (BMH). BMH contains two maleimide functional groups, which react specifically with sulfhydryl-containing compounds under mild conditions (pH 6.5-7.7). The two maleimide groups are connected by a hydrocarbon chain. Therefore, BMH is useful for irreversible cross-linking of proteins (or polypeptides) that contain cysteine residues. Cross-linking reagents may also be heterobifunctional. Heterobifunctional cross-linking agents have two different functional groups, for example an amine-reactive group and a thiol-reactive group, that will cross-link two proteins having free amines and thiols, respectively. Examples of heterobifunctional cross-linking agents are Succinimidyl-4-(N-maleimidomethyl)-cyclohexane-1-carboxylate (SMCC), m-maleimidobenzoyl-N-hydroxysuccinimide ester (MBS), and succinimide 4-(p-maleimidophenyl)butyrate (SMPB), an extended chain analog of MBS. The succinimidyl group of these cross-linkers reacts with a primary amine, and the thiol-reactive maleimide forms a covalent bond with the thiol of a cysteine residue. Because cross-linking reagents often have low solubility in water, a hydrophilic moiety, such as a sulfonate group, may be added to the cross-linking reagent to improve its water solubility. Sulfo-MBS and sulfo-SMCC are examples of cross-linking reagents modified for water solubility. Many cross-linking reagents yield a conjugate that is essentially non-cleavable under cellular conditions. Therefore, some cross-linking reagents contain a covalent bond, such as a disulfide, that is cleavable under cellular conditions. For example, Traut's reagent, dithiobis (succinimidylpropionate) (DSP), and N-succinimidyl 3-(2-pyridyldithio)propionate (SPDP) are well-known cleavable cross-linkers. The use of a cleavable cross-linking reagent permits the cargo moiety component (B), (C), (D), (E) etc. to separate from the novel transporter construct component (A) after delivery into the target cell. For this purpose, direct disulfide linkage may also be useful. Chemical cross-linking may also include the use of spacer arms. Spacer arms provide intramolecular flexibility or adjust intramolecular distances between conjugated moieties and thereby may help preserve biological activity. A spacer arm may be in the form of a protein (or polypeptide) moiety that includes spacer amino acids, e.g. proline. Alternatively, a spacer arm may be part of the cross-linking reagent, such as in "long-chain SPDP" (Pierce Chem. Co., Rockford, Ill., cat. No. 21651 H). Numerous cross-linking reagents, including the ones discussed above, are commercially available. Detailed instructions for their use are readily available from the commercial suppliers. A general reference on protein cross-linking and conjugate preparation is: Wong, Chemistry of Protein Conjugation and Cross-Linking, CRC Press (1991).

A person skilled in the art will readily understand that the different components of the transporter cargo conjugate molecule should be coupled in a manner so that the different components can still convey at least part of their individual special activity and/or properties to the entire transporter cargo conjugate molecule. For example, coupling of the components shall preferably not lead to a total loss in white blood cell targeting etc.

According to a further aspect, the present invention furthermore provides a pharmaceutical composition, the pharmaceutical composition preferably comprising the inventive transporter cargo conjugate molecule as defined above, and optionally a pharmaceutically acceptable carrier and/or vehicle, or any excipient, buffer, stabilizer or other materials well known to those skilled in the art.

The inventive pharmaceutical composition comprises an inventive transporter cargo conjugate molecule as defined herein. Preferably, said pharmaceutical composition comprisies as component (A) at least one WBC targeting (poly-)peptide according to the present invention, and as a component (B) a further substance (cargo). The component (B) may be any pharamceutically active substance. Particular examples for such a pharmaceutically active substances are disclosed above. In particular component (B) may be an therapeutically active effector molecule, selected from proteins or (poly-)peptides, protein kinase inhibitors, particularly inhibitors of the protein kinase c-Jun amino terminal kinase, antigens, antibodies, apoptotic factors, proteases implicated in pathological states, preferably peptidic protease inhibitors, BH3-domains BH3-only proteins, or selected from nucleic acids, siRNAs, or from cytotoxic agents, small organic compounds, etc. As mentioned above, the inventive transporter cargo conjugate molecule may contain optional additional components (C), (D), and/or (E), etc.

As a further ingredient, the inventive pharmaceutical composition may or may not comprise a pharmaceutically acceptable carrier and/or vehicle. In the context of the present invention, a pharmaceutically acceptable carrier typically includes the liquid or non-liquid basis of the inventive inventive pharmaceutical composition. If the inventive pharmaceutical composition is provided in liquid form, the carrier will typically be pyrogen-free water; isotonic saline or buffered (aqueous) solutions, e.g phosphate, citrate etc. buffered solutions. Particularly for injection of the inventive inventive pharmaceutical composition, water or preferably a buffer, more preferably an aqueous buffer, may be used, containing a sodium salt, preferably at least 50 mM of a sodium salt, a calcium salt, preferably at least 0.01 mM of a calcium salt, and optionally a potassium salt, preferably at least 3 mM of a potassium salt. According to a preferred embodiment, the sodium, calcium and, optionally, potassium salts may occur in the form of their halogenides, e.g. chlorides, iodides, or bromides, in the form of their hydroxides, carbonates, hydrogen carbonates, or sulfates, etc. Without being limited thereto, examples of sodium salts include e.g. NaCl, NaI, NaBr, $Na_2CO_3$, $NaHCO_3$, $Na_2SO_4$, examples of the optional potassium salts include e.g. KCl, KI, KBr, $K_2CO_3$, $KHCO_3$, $K_2SO_4$, and examples of calcium salts include e.g. $CaCl_2$, $CaI_2$, $CaBr_2$, $CaCO_3$, $CaSO_4$, $Ca(OH)_2$. Furthermore, organic anions of the aforementioned cations may be contained in the buffer. According to a more preferred embodiment, the buffer suitable for injection purposes as defined above, may contain salts selected from sodium chloride (NaCl), calcium chloride ($CaCl_2$) and optionally potassium chloride (KCl), wherein further anions may be present additional to the chlorides. $CaCl_2$ can also be replaced by another salt like KCl. Typically, the salts in the injection buffer are present in a concentration of at least 50 mM sodium chloride (NaCl), at least 3 mM potassium chloride (KCl) and at least 0.01 mM calcium chloride ($CaCl_2$). The injection buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

However, one or more compatible solid or liquid fillers or diluents or encapsulating compounds may be used as well for the inventive pharmaceutical composition, which are suitable for administration to a patient to be treated. The term "compatible" as used here means that these constituents of the inventive pharmaceutical composition are capable of being mixed with the inventive transporter cargo conjugate molecule as defined above in such a manner that no interaction occurs which would substantially reduce the pharmaceutical effectiveness of the inventive pharmaceutical composition under typical use conditions. Pharmaceutically acceptable carriers, fillers and diluents must, of course, have sufficiently high purity and sufficiently low toxicity to make them suitable for administration to a person to be treated. Some examples of compounds which can be used as pharmaceutically acceptable carriers, fillers or constituents thereof are sugars, such as, for example, lactose, glucose and sucrose; starches, such as, for example, corn starch or potato starch; cellulose and its derivatives, such as, for example, sodium carboxymethylcellulose, ethylcellulose, cellulose acetate; powdered tragacanth; malt; gelatin; tallow; solid glidants, such as, for example, stearic acid, magnesium stearate; calcium sulfate; vegetable oils, such as, for example, groundnut oil, cottonseed oil, sesame oil, olive oil, corn oil and oil from theobroma; polyols, such as, for example, polypropylene glycol, glycerol, sorbitol, mannitol and polyethylene glycol; alginic acid.

The inventive pharmaceutical composition may be administered orally, parenterally, by inhalation spray, topically, rectally, nasally, buccally, vaginally or via an implanted reservoir or any other suitable administration route known to the skilled artisan. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques.

Preferably, the inventive pharmaceutical composition may be administered by parenteral injection, more preferably by subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or via infusion techniques. Sterile injectable forms of the inventive pharmaceutical compositions may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1.3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation of the inventive pharmaceutical composition.

For intravenous, cutaneous or subcutaneous injection, or injection at the site of affliction, the active ingredient will preferably be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives may be included, as required.

The inventive pharmaceutical composition as defined above may also be administered orally in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient, i.e. the inventive transporter cargo conjugate molecule as defined above, is combined with emulsifying and suspending agents. If desired, certain sweetening, flavoring or coloring agents may also be added.

The inventive pharmaceutical composition may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the inventive pharmaceutical composition may be formulated in a suitable ointment, containing the inventive immunostimulatory composition, particularly its components as defined above, suspended or dissolved in one or more carriers. Carriers for topical administration include, but are not limited to, mineral oil, liquid petrolatum, white petrolatum, propylene glycol, polyoxyethylene, polyoxypropylene compound, emulsifying wax and water. Alternatively, the inventive pharmaceutical composition can be formulated in a suitable lotion or cream. In the context of the present invention, suitable carriers include, but are not limited to, mineral oil, sorbitan monostearate, polysorbate 60, cetyl esters wax, cetearyl alcohol, 2-octyldodecanol, benzyl alcohol and water.

Whether it is a (poly-)peptide, a nucleic acid molecule, or any other pharmaceutically useful compound according to the present invention that is to be given as component (B) to an individual, administration is preferably in a "prophylactically effective amount" or a "therapeutically effective amount" (as the case may be), this being sufficient to show benefit to the individual. The actual amount administered, and rate and time-course of administration, will depend on the nature and severity of what is being treated.

Due to the remarkable uptake of the WBC targeting (poly-)peptides employed in the present invention into cells, into WBCs in particular, the amount of a transporter cargo conjugate molecule (active ingredient) in the pharmaceutical composition to be administered to a subject may—without being limited thereto—have a very low dose. Thus, the dose may be much lower than for peptide drugs known in the art, such as DTS-108 (Florence Meyer-Losic et al., Clin Cancer Res., 2008, 2145-53). This brings about several positive aspects, for example a reduction of potential side reactions and a reduction in costs.

Preferably, the dose (per kg bodyweight) is in the range of up to 10 mmol/kg, preferably up to 1 mmol/kg, more preferably up to 100 μmol/kg, even more preferably up to 10 μmol/kg, even more preferably up to 1 μmol/kg, even more preferably up to 100 nmol/kg, most preferably up to 50 nmol/kg.

Thus, the dose range may preferably be from about 1 pmol/kg to about 1 mmol/kg, from about 10 pmol/kg to about 0.1 mmol/kg, from about 10 pmol/kg to about 0.01 mmol/kg, from about 50 pmol/kg to about 1 μmol/kg, from about 100 pmol/kg to about 500 nmol/kg, from about 200 pmol/kg to about 300 nmol/kg, from about 300 pmol/kg to about 100 nmol/kg, from about 500 pmol/kg to about 50 nmol/kg, from about 750 pmol/kg to about 30 nmol/kg, from about 250 pmol/kg to about 5 nmol/kg, from about 1 nmol/kg to about 10 nmol/kg, or a combination of any two of said values.

A person skilled in the art will understand that the effective amount of a transporter cargo conjugate molecule according to the present invention is positively affected by the advantageous properties of the WBC targeting (poly-) peptide according to the present invention, but also depends on the efficacy of component (B), i.e. the drug or effector molecule conjugated to the WBC targeting (poly-)peptide. Therefore, the actually preferred dose may vary from one transporter cargo conjugate molecule to another.

In this context, prescription of treatment, e.g. decisions on dosage etc. when using the above pharmaceutical composition is typically within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in REMINGTON'S PHARMACEUTICAL SCIENCES, 16th edition, Osol, A. (ed), 1980. Accordingly, the inventive pharmaceutical composition typically comprises a "safe and effective amount" of the components of the inventive pharmaceutical composition, particularly of the inventive transporter cargo conjugate molecule as defined above. As used herein, a "safe and effective amount" means an amount of the inventive transporter cargo conjugate molecule as defined above that is sufficient to significantly induce a positive modification of a disease or disorder as defined herein. At the same time, however, a "safe and effective amount" is small enough to avoid serious side-effects, that is to say to permit a sensible relationship between advantage and risk. The determination of these limits typically lies within the scope of sensible medical judgment. A "safe and effective amount" of the components of the inventive pharmaceutical composition, particularly of the inventive transporter cargo conjugate molecule as defined above, will furthermore vary in connection with the particular condition to be treated and also with the age and physical condition of the patient to be treated, the body weight, general health, sex, diet, time of administration, rate of excretion, drug combination, the activity of the specific components (A), (B), (C), (D) and/or (E), etc. of the inventive transporter cargo conjugate molecule as defined above, the severity of the condition, the duration of the treatment, the nature of the accompanying therapy, of the particular pharmaceutically acceptable carrier used, and similar factors, within the knowledge and experience of the accompanying doctor. The inventive pharmaceutical composition may be used for human and also for veterinary medical purposes, preferably for human medical purposes, as a pharmaceutical composition in general or as a vaccine.

According to a specific embodiment, the inventive pharmaceutical composition may be provided as a vaccine, e.g. if component (B) of the inventive transporter cargo conjugate molecule is a therapeutically active protein such as a(n) (protein or (poly-)peptide) antigen or antigenic fragment or any molecule as described above, which is suitable to elicit an immune response. Such an inventive vaccine is typically composed like the inventive pharmaceutical composition and preferably supports an innate and/or an adaptive immune response of the immune system of a patient to be treated, depending on the nature of the components (B), (C), (D) and/or (E) etc., of the inventive transporter cargo conjugate molecule as defined above. As an example, if any of these components provides or encodes a ((poly-)peptide) antigen or antigenic fragment, the vaccine typically will lead to an adaptive immune response in the patient to be treated. Similarly, any of the further components (B), (C), (D) and/or (E) etc. of the inventive transporter cargo conjugate molecule as defined herein may lead to an innate and/or adaptive immune response.

The inventive vaccine may also comprise a pharmaceutically acceptable carrier, adjuvant, and/or vehicle as defined above for the inventive pharmaceutical composition. In the specific context of the inventive vaccine, the choice of a pharmaceutically acceptable carrier is determined in principle by the manner in which the inventive vaccine is administered. The inventive vaccine can be administered, for example, systemically or locally. Routes for systemic administration in general include, for example, transdermal, oral, parenteral routes, including subcutaneous, intravenous, intramuscular, intraarterial, intradermal and intraperitoneal injections and/or intranasal administration routes. Routes for local administration in general include, for example, topical administration routes but also intradermal, transdermal, subcutaneous, or intramuscular injections or intralesional, intracranial, intrapulmonal, intracardial, and sublingual injections. More preferably, vaccines may be administered by an intradermal, subcutaneous, or intramuscular route. Inventive vaccines are therefore preferably formulated in liquid (or sometimes in solid) form. The suitable amount of the inventive vaccine to be administered can be determined by routine experiments with animal models. Such models include, without implying any limitation, rabbit, sheep, mouse, rat, dog and non-human primate models. Preferred unit dose forms for injection include sterile solutions of water, physiological saline or mixtures thereof. The pH of such solutions should be adjusted to about 7.4. Suitable carriers for injection include hydrogels, devices for controlled or delayed release, polylactic acid and collagen matrices. Suitable pharmaceutically acceptable carriers for topical application include those which are suitable for use in lotions, creams, gels and the like. If the inventive vaccine is to be administered orally, tablets, capsules and the like are the preferred unit dose form. The pharmaceutically acceptable carriers for the preparation of unit dose forms which can be used for oral administration are well known in the prior art. The choice thereof will depend on secondary considerations such as taste, costs and storability, which are not critical for the purposes of the present invention, and can be made without difficulty by a person skilled in the art.

The inventive vaccine can additionally contain one or more auxiliary substances in order to further increase its immunogenicity. A synergistic action of the inventive transporter cargo conjugate molecule as defined above and of an auxiliary substance, which may be optionally contained in the inventive vaccine as described above, is preferably achieved thereby. Depending on the various types of auxiliary substances, various mechanisms can come into consideration in this respect. For example, compounds that permit the maturation of dendritic cells (DCs), for example lipopolysaccharides, TNF-alpha or CD40 ligand, form a first class of suitable auxiliary substances. In general, it is possible to use as auxiliary substance any agent that influences the immune system in the manner of a "danger signal" (LPS, GP96, etc.) or cytokines, such as GM-CFS, which allow an immune response produced by the immune-stimulating adjuvant according to the invention to be enhanced and/or influenced in a targeted manner. Particularly preferred auxiliary substances are cytokines, such as monokines, lymphokines, interleukins or chemokines, that further promote the innate immune response, such as IL-1, IL-2, IL-3, IL-4, IL-5, IL-6, IL-7, IL-8, IL-9, IL-10, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, INF-alpha, IFN-beta, INF-gamma, GM-CSF, G-CSF, M-CSF, LT-beta or TNF-alpha, growth factors, such as hGH.

Further additives which may be included in the pharmaceutical composition or inventive vaccine are emulsifiers, such as, for example, Tween®; wetting agents, such as, for example, sodium lauryl sulfate; colouring agents; taste-imparting agents, pharmaceutical carriers; tablet-forming agents; stabilizers; antioxidants; preservatives.

The inventive vaccine can also additionally contain any further compound, which is known to be immune-stimulating due to its binding affinity (as ligands) to human Toll-like receptors TLR1, TLR2, TLR3, TLR4, TLR5, TLR6, TLR7, TLR8, TLR9, TLR10, or due to its binding affinity (as ligands) to murine Toll-like receptors TLR1, TLR2, TLR3, TLR4, TLR5, TLR6, TLR7, TLR8, TLR9, TLR10, TLR11, TLR12 or TLR13.

Another class of compounds, which may be added to an inventive vaccine in this context, may be CpG nucleic acids, in particular CpG-RNA or CpG-DNA. A CpG-RNA or CpG-DNA can be a single-stranded CpG-DNA (ss CpG-DNA), a double-stranded CpG-DNA (dsDNA), a single-stranded CpG-RNA (ss CpG-RNA) or a double-stranded CpG-RNA (ds CpG-RNA). The CpG nucleic acid is preferably in the form of CpG-RNA, more preferably in the form of single-stranded CpG-RNA (ss CpG-RNA). The CpG nucleic acid preferably contains at least one or more (mitogenic) cytosine/guanine dinucleotide sequence(s) (CpG motif(s)). According to a first preferred alternative, at least one CpG motif contained in these sequences, that is to say the C (cytosine) and the G (guanine) of the CpG motif, is unmethylated. All further cytosines or guanines optionally contained in these sequences can be either methylated or unmethylated. According to a further preferred alternative, however, the C (cytosine) and the G (guanine) of the CpG motif can also be present in methylated form.

According to a further aspect of the present invention, the inventive transporter cargo conjugate molecule, the inventive pharmaceutical composition or the inventive vaccine as defined above may be used (for the preparation of a pharmaceutical composition or a vaccine, preferably both as defined herein,) for the prophylaxis, treatment, attenuation and/or amelioration of any of the diseases and disorders as defined herein.

In particular, the transporter cargo conjugate molecules, the inventive pharmaceutical composition or the inventive vaccine as mentioned herein may be used to efficiently target a substance of interest (cargo molecule), such as drugs and effector molecules, into white blood cells. Therefore, the transport into white blood cells may occur according to the present invention for example in vivo, in vitro and/or ex vivo.

Consequently, the transporter cargo conjugate molecules, the inventive pharmaceutical composition or the inventive vaccine as defined herein can be used for the treatment, prophylaxis, attenuation and/or amelioration of a disease and/or disorder involving white blood cells.

The term "diseases and/or disorders involving white blood cells", as used herein, refers to:

a) Diseases and/or disorders which are caused by a defect in white blood cells themselves (defect in WBCs are the primary cause of disease), b) Diseases and/or disorders in which defects in WBCs are not the primary cause of the disease but in which WBCs contribute to the disease state and symptoms thereof (WBCs are a secondary cause of disease), and/or c) Diseases and/or disorders (and symptoms) thereof, which are neither primarily nor secondarily caused or or negatively influenced by WBCs, but which may be treated, prevented, attenuated or ameliorated by action of white blood cells (potentially stimulated via the transporter cargo conjugate molecule of the present invention).

Non-exhaustive, merely illustrative examples for a) are genetic defects in white blood cells and cancer of WBCs such as leukemias and lymphomas. A non-exhaustive, merely illustrative example for b) are many types of inflammatory diseases. A non-exhaustive, merely illustrative classic example for c) are most infections diseases.

"White blood cells" (WBC, also termed leucocytes), as used herein, refers to any kind of white blood cell. The white blood cells may be primary cells, immortalized cells and/or transgenic cells. They may be selected for example from granulocytes, lymphocytes, monocytes, macrophages, dendritic cells, mast cells and/or microglial cells. Granulocytes can be selected from the group consisting of neutrophils, eosinophils and basophils. Lymphocytes can for example be selected from NK cells, Helper T cells, cytotoxic T cells, γδ T cells, and B cells. The term may also comprises precursor cells and/or different developmental stages of white blood cells.

There are several possibilities to employ the transporter cargo conjugate molecule, the inventive pharmaceutical composition or the inventive vaccine as defined above of the present invention in a method of treatment. For instance, the transporter cargo conjugate molecule of the present invention may be used for the treatment, prophylaxis, attenuation and/or amelioration of a disease and/or disorder involving white blood cells which are selected from viral infections, in particular from viral infections of white blood cells.

Examples for such viral infections, in particular for viral infections of white blood cells, and examples for treatment (some of which may function as component (B) of the represent invention) are given in Table 4.

TABLE 4

| Virus | Disease (s) | WBC Target | Examples for Treatment |
|---|---|---|---|
| HIV | AIDS | CD4 | |
| Epstein Barr Virus | Mononucleosis | B cells | Prednisone, Acyclovir, Intravenous immunoglobulin (Gammagard S/D, Gammar-P, Polygam) |
| Morbillivirus (measles) | Measles | Monocytes | |
| Paramyxovirus | Mumps | Current Topics in Virology, 2002; Flodstro, 2003; Samarkos, 2005. | |
| Rubivirus | Rubella | Flodstro, 2003; Samarkos, 2005. | |
| Herpes Virus Type 6 | Roseola Infantum | CD4 | Emergency treatment is supportive |
| Herpes Virus | Cytomegalovirus | Reduces surface expression of class I MHC molecules-preventing antigen presentation to CD8+ T cells | |
| Dengue Virus | Dengue Fever | Turuel-Leupez, 1991; Kyle, 2007; Liu, 2002; Kubelka, 2001; Kurane, 1991 | |
| Herpes Simplex Virus 1 | Oral Herpes | Reduces surface expression of class I MHC molecules-preventing antigen presentation to CD8+ T cells | Oral: Acyclovir (Zovirax), valacyclovir (Valtrex), and famciclovir (Famvir) Topical-Penciclovir (Denavir), Acyclovir Cream, Docosanol cream (Abreva) |
| Herpes Simplex Virus 2 | Genital Herpes | Reduces surface expression of class I MHC molecules-preventing antigen presentation to CD8+ T cells | Acyclovir (Zovirax), valacyclovir (Valtrex), and famciclovir (Famvir) |
| Parvovirus | Parvovirus B19 | Occasionally the virus infects neutrophils | IVIG (intravenous immunoglobulin) |
| Respiratory Syncytial Virus | Bronchiolitis, RSV | Moore, 2006; McNamara, 2002; Zhang, 2006 | |
| Variola Virus | Smallpox | Stanford, 2007 | |
| Varicella | Chicken Pox, Shingles | Arvin, 2006; Quinlivan, 2006 | Acyclovir (Zovirax), valacyclovir (Valtrex), and famciclovir (Famvir) |

TABLE 4-continued

| Virus | Disease (s) | WBC Target | Examples for Treatment |
|---|---|---|---|
| Flavivirus | Yellow Fever | Tomori, 2004; ter Meulen, 2004 | |
| Human T-lymphotropic virus Type 1 | Adult T cell Leukemia virus, HTLV-associated uveitis, HTLV associated infective dermatitis, HTLV-1-associated myelopathy | Albrecht, 2002; Bangham, 2003 | |
| Human T-lymphotropic virus Type 2 | | | |
| Human T-lymphotropic virus Type 3 | Asssociated with AIDS | | |
| Human T-lymphotropic virus Type 4 | Similar to HIV | | |
| Hepatitis A Virus | Hepatitis A | Vallbracht, 1992; Hashimoti, 1996 | |
| Hepatitis B Virus | Hepatitis B | Reduces surface expression of class I MHC molecules-preventing antigen presentation to CD8+ T cells | Interferon, lamivudine, adefovir dipivoxil |
| Hepatitis C Virus | Hepatitis C | Hashimoti, 1996 | Combination Therapy: Pegylated Interferon & Ribavirin (see link for overview) |
| Hepatitis D Virus | Hepatitis D | Casey, 1998; Nisini, 1997 | Acute care: Supportive; Chronic care: Interferon alpha |
| Hepatitis E Virus | Hepatitis E | Zhao, 2001; Srivastava, 2007 | Supportive only |
| Lassa Virus | Lassa Fever | Sbrana, 2006 | Ribavirin |
| Influenza A (incl. Subtypes H1N1 and H3N2) | Flu | Sloadkovoa, 2006; Trushinskaia, 1988 | Oseltamivir, Zanamivir |
| Influenza B | Flu | Schultz-Cherry, 1998; Zambon, 2001 | Oseltamivir, Zanamivir |
| Influenza C | Flu | Matsuzaki, 1997 | Oseltamivir, Zanamivir |

Further examples for a disease and/or disorder involving white blood cells are given in Table 5.

TABLE 5

| Name of disease | Brief description | Target | Cause |
|---|---|---|---|
| Neutrophilia | Increase in number of neutrophils | Neutrophils | Stress; labor; infection; inflammation; tissue necrosis; drugs/chemicals; metabolic changes |
| Neutropenia | Decrease in number of neutrophils | Neutrophils | Cancer; certain medicines; radiation; hereditary disorders |
| Leukopenia | Decrease in number of leukocytes | Leukocytes | Chemotherapy; radiation treatment; leukemia; myelofibrosis; aplastic anemia; infections |
| Basopenia | Decrease in the number of basophils | Basophils | Response to thyrotoxicosis; acute hypersenstivity reaction; infections |
| Basophilia | Increase in the number of basophiles | Basophils | Hypothroidism; myeloproliferative disorders (eg: polycythemia vera; myelofibrosis); Hypersensitivity reactions |
| Eosinopenia | Decrease in the number of eosinophils | Eosinophils | Cushing's syndrome; Stress reactions; Steriods |

TABLE 5-continued

| Name of disease | Brief description | Target | Cause |
|---|---|---|---|
| Eosinophilia | Increased number of eosinophils | Eosinophils | Allergic reactions; Neoplasia; Addison's disease; collagen vascular disease; parasites |
| Idiopathic hypereosinophilic syndrome | Increased number of eosinophils (1,500 cells/ ul of blood) | Eosinophils | Cause of eosinophilia is unknown |
| Lymphocytic Leukocytosis; Lymphocytosis | Abnormally high number of lymphocytes | Lymphocytes | Viral diseases; bacterial infections such as tuberculosis; cancer such as lymphoma, acute or chronic lymphocytic leukema; Grave's disease; Crohn's disease; Drug senstivity |
| Lymphocytopenia | Abnormally low number of lymphocytes | Lymphocytes | AIDS; Cancer such as leukemia, lymphoma, Hodgkin's disease; Chronic infections such as miliary tuberculosis; Hereditary disorders such as certain agammaglobulinemias; DiGeorge anomal, Wiskott-Aldrich syndrome, severe combined immunodeficiency syndrome and ataxia-telangiectasia; Rheumatoid arthritis; systemic lupus erythematosus; some viral infections |
| Monocytosis | Increased number of monocytes | Monocyte | Chronic infections; autoimmune disease; blood disorders; cancer; gastrointestinal disorders |
| Monocytopenia | Decreased number of monocytes | Monocyte | Release of toxins in blood by bacteria; chemotherapy; corticosteroids |
| May Hegglin Anomaly | Presence of Dohle bodies in leukocytes | Leukocytes | Association with human gene, MYH9 is suspected |
| Pelger-Huet Anomaly | Neutrophils cannot segment; <75% of neutrophils | Neutrophils | Inherited defect, secondary to the mutations in the lamin B receptor (LBR); Drug therapy; cancer and certain infections |
| Alder-Reilly Anomaly | Accumulation of partially degraded mucopoly-saccharide within lysosomes | Leukocytes | Mucopolysaccaridosis such as Hurler's syndrome, Hunter's syndrome |
| Chedial-Higashi Syndrome | Giant lysosomal inclusions resulting from fusion of lysozymes | Granulocytes; leukocytes; monocytes | Inherited Functional Disorders |
| Job's Syndrome; hyper-IgE | Directionaly motility impaired; recurrent boils and abscesses | Granulocytes | Inherited Functional Disorders |
| Lazy Leukocyte Syndrome | Random and directed movement are defective, cells fails to respond to inflammatory stimuli | Granulocytes | Inherited Functional Disorders |
| Congenital C3 deficiency | Inability to ingest microorganisms, repeated severe infections | Granulocytes | Inherited Functional Disorders |
| Chronic Granulomatous Disease | Deficient ability of neutrophils to undergo oxidative burst; cannot kill bacteria | Granulocytes | Associated with muscular dystrophy |
| Leukocyte Glucose-6-Phosphate Dehydrogenase | Inability to kill bacteria; recurrent pyogenic | Granulocytes | Inherited Functional Disorders |

TABLE 5-continued

| Name of disease | Brief description | Target | Cause |
|---|---|---|---|
| Deficiency | infection | | |
| Myeloperoxidase Deficiency-benign | Slow bacterial killing, but complete | Granulocytes | Inherited Functional Disorders |
| Severe Combined Immunodeficiency Disease | Failure in humoral and cellular immunity | Lymphocyte | Inherited Functional Disorders |
| DiGeorge's syndrome | Partial or complete failure of development of the thymus and parathyroids | Lymphocyte-T cells | Inherited Functional Disorders |
| Nezelof's Syndrome | Defective thymus function | Lymphocyte-T cells | Inherited Functional Disorders |
| Infantile sex-linked agammaglobulinemia | Recurrent bacterial infections | Lymphocyte-B cells | Inherited Functional Disorders |
| Common Variable Hypogammaglobulinemia | One or a combination of immunoglobulins is missing; inability og Bcells to mature/function as plasma cells | Lymphocyte-B cells | Inherited Functional Disorders |
| Mucopolysaccharidosis | Deficiency in specific enzymens to degrade mucopolysaccharides | Monocyte-Macrophage | Inherited Functional Disorders |
| Lipodoses | Lipid storage disease-macrophages become overloaded with lipids | Monocyte-Macrophage | Inherited Functional Disorders |
| Gaucher disease | Deficiency of enzyme glucocerebrosidase | | |
| Niemann-pick disease | Acumulation of fat and cholesterol in cells of liver, spleen, bone marrow, lungs and brain | | |
| Fabry disease | α-galactosidase-A deficiency; accumulation of fatty material in the autonomic nervous system, eyes, kidneys, and cardiovascular system | | |
| Farber's disease | Ceramidase deficiency; accumulation of fatty material in the joints, tissues, and central nervous system | | |
| Gangliosidoses; Tay Sachs; Sandhoff disease | Accumulation of gangliosides | | |
| Krabbe disease | Galactosyl-ceramidase deficiency | | |
| Metachromatic leukodystrophy | Build-up in the white matter of the central nervous system and in the peripheral nerves | | |

TABLE 5-continued

| Name of disease | Brief description | Target | Cause |
|---|---|---|---|
| Wolman's disease | Lipase deficiency | | |
| Leukemia | Cancer | Leukocytes | Abnormal and uncontrolled cell growth |
| Acute Lymphocytic Leukemia (L1, L2. L3) | Proliferation of lymphoblasts | B-cells or T-cells | Radiation; Drugs and chemicals; viruses; genetic factors |
| Chronic Lymphocytic Leukemia | Proliferation of small mature B-lymphocytes | B-cells | Radiation; Drugs and chemicals; viruses; genetic factors |
| Acute Myelogenous Leukemia (AML) | Proliferation of myeloblasts | Bone marrow blast cells | Radiation; Drugs and chemicals; viruses; genetic factors |
| Undifferentiated AML (M0) | Bone marrow cells show no significant signs of differentiation | Bone marrow blast cells | Radiation; Drugs and chemicals; viruses; genetic factors |
| Myeloblastic Leukemia (M1) | Bone marrow cells show signs of granulocytic differentiation. | Bone marrow blast cells | Radiation; Drugs and chemicals; viruses; genetic factors |
| Myeloblastic Leukemia (M2) | Maturation of bone marrow cells is at or beyond the promyelocyte (early granulocyte) stage | Bone marrow blast cells | Radiation; Drugs and chemicals; viruses; genetic factors |
| Promyelocytic Leukemia (M3) | Most cells are abnormal early granulocytes that are between myeloblasts and myelocytes in their stage of development | Early granulocytes | Radiation; Drugs and chemicals; viruses; genetic factors |
| Myelomonocytic Leukemia (M4) | Marrow and circulating blood have variable amounts of differentiated granulocytes and monocytes; May also contain a number of abnormal eosinophils | Granulocyte; Monocytes | Radiation; Drugs and chemicals; viruses; genetic factors |
| Monocytic Leukemia (M5) | Poorly differentiated monoblasts; large population of monoblasts, promonocytes, and monocytes | Monoblasts; Promonocytes; Monocytes | Radiation; Drugs and chemicals; viruses; genetic factors |
| Erytholeukemia (M6) | Abnormal red blood cell-forming cells | Red blood cells | Radiation; Drugs and chemicals; viruses; genetic factors |
| Megakaryoblastic Leukemia (M7) | Extensive fibrous tissue deposits (fibrosis) in the bone marrow. | Bone marrow blast cells | Radiation; Drugs and chemicals; viruses; genetic factors |
| Chronic Myelogenous Leukemia | Proliferation of more mature granulocytes | Bone marrow cells | Radiation; Drugs and chemicals; viruses; genetic factors |
| Lymphoma | Malignant proliferation of lymphoid cells-Hodgkin's, Non Hogkin's disease | B-cells; T-cells | Infections; HIV; Autoimmune disease; chemicals; genetics; age |

Preferably, the transporter cargo conjugate molecules, the inventive pharmaceutical composition or the inventive vaccine as defined above are used for the treatment, prophylaxis, attenuation and/or amelioration of a disease and/or disorder selected from cancer or tumor diseases, including diseases caused by defective apoptosis, inflammatory diseases, infectious diseases including bacterial and viral (infectious) diseases, diseases strongly related to JNK signalling, autoimmune disorders or diseases, cardiovascular diseases, neuronal or neurodegenerative diseases, diseases of the liver, diseases of the spine, diseases of the uterus, major depressive disorders, non-chronic or chronic inflammatory digestive diseases, diabetes, hair loss, hearing loss or diseases of the inner ear. The inventive transporter cargo conjugate molecule may also be used (for the preparation of a pharmaceutical composition) for use in tissue transplantation either by treating the organs/tissue/cells to be transplanted or by treating the recipient of the organ/tissue/cells, e.g. with the aim of preventing white blood cells from initiating graft rejection.

Prophylaxis, treatment, attenuation and/or amelioration of a disease as defined herein typically include administration of a pharmaceutical composition as defined above. The term “prophylaxis” is typically directed to the prevention of a disease as defined herein in a patient, preferably prior to manifestation of the disease in the patient. The term “treatment” generally refers to any treatment of a disease as defined herein in a patient, wherein the disease may have already been diagnosed or shall be prevented, i.e. prior, parallel and subsequent to manifestation of the disease in the patient. The term “treatment”, used for example in the term “treating a condition”, furthermore preferably means at least the administration of a therapeutically effective amount of a therapeutic compound to elicit a therapeutic effect. It does not necessarily imply “curing”, but rather having preferably at least some minimal physiological effect upon a condition upon administration to a living body having such a condition. For example, treatment could encompass administering an agent and the presence of that agent resulting in a change in the physiology of a recipient animal. “Attenuation”, as used herein, refers to the effect that progression of an otherwise progressive disease is slowed down or halted, e.g. at a specific stage. Finally, the term “amelioration” preferably includes any modification of a disease as defined herein, preferably a positive modification of the disease as defined herein. The specific modification may be dependent on the disease to be treated.

An inventive pharmaceutical composition, a vaccine or an inventive transporter cargo conjugate molecule as defined above may be administered directly to a patient using the administration routes as described above for pharmaceutical compositions. Alternatively, a pharmaceutical composition, a vaccine or an inventive transporter cargo conjugate molecule as defined above may be administered to a patient using an ex vivo approach, e.g. by introducing the pharmaceutical composition, the vaccine or the inventive transporter cargo conjugate molecule as defined above into cells, preferably autologous cells, i.e. cells derived from the patient to be treated, and transplanting these cells into the site of the patient to be treated, optionally subsequent to storing and/or culturing these cells prior to treatment.

According to one preferred embodiment, the inventive transporter cargo conjugate molecule, the inventive pharmaceutical composition or the inventive vaccine as defined above, may be used for (the preparation of a medicament for) the prophylaxis, treatment and/or amelioration of e.g. cancer or tumor diseases, including diseases caused by defective apoptosis, preferably selected from acusticus neurinoma, anal carcinoma, astrocytoma, basalioma, Behcet’s syndrome, bladder cancer, blastomas, bone cancer, brain metastases, brain tumors, brain cancer (glioblastomas), breast cancer (mamma carcinoma), Burkitt’s lymphoma, carcinoids, cervical cancer, colon carcinoma, colorectal cancer, corpus carcinoma, craniopharyngeomas, CUP syndrome, endometrial carcinoma, gall bladder cancer, genital tumors, including cancers of the genitourinary tract, glioblastoma, gliomas, head/neck tumors, hepatomas, histocytic lymphoma, Hodgkin’s syndromes or lymphomas and non-Hodgkin’s lymphomas, hypophysis tumor, intestinal cancer, including tumors of the small intestine, and gastrointestinal tumors, Kaposi’s sarcoma, kidney cancer, kidney carcinomas, laryngeal cancer or larynx cancer, leukemia, including acute myeloid leukaemia (AML), erythroleukemia, acute lymphoid leukaemia (ALL), chronic myeloid leukaemia (CML), and chronic lymphocytic leukaemia (CLL), lid tumor, liver cancer, liver metastases, lung carcinomas (=lung cancer=bronchial carcinoma), small cell lung carcinomas and non-small cell lung carcinomas, and lung adenocarcinoma, lymphomas, lymphatic cancer, malignant melanomas, mammary carcinomas (=breast cancer), medulloblastomas, melanomas, meningiomas, Mycosis fungoides, neoplastic diseases neurinoma, oesophageal cancer, oesophageal carcinoma (=oesophageal cancer), oligodendroglioma, ovarian cancer (=ovarian carcinoma), ovarian carcinoma, pancreatic carcinoma (=pancreatic cancer), penile cancer, penis cancer, pharyngeal cancer, pituitary tumour, plasmocytoma, prostate cancer (=prostate tumors), rectal carcinoma, rectal tumors, renal cancer, renal carcinomas, retinoblastoma, sarcomas, Schneeberger’s disease, skin cancer, e.g. melanoma or non-melanoma skin cancer, including basal cell and squamous cell carcinomas as well as psoriasis, pemphigus vulgaris, soft tissue tumours, spinalioma, stomach cancer, testicular cancer, throat cancer, thymoma, thyroid carcinoma, tongue cancer, urethral cancer, uterine cancer, vaginal cancer, various virus-induced tumors such as, for example, papilloma virus-induced carcinomas (e.g. cervical carcinoma=cervical cancer), adenocarcinomas, herpes virus-induced tumors (e.g. Burkitt’s lymphoma, EBV-induced B-cell lymphoma, cervix carcinoma), heptatitis B-induced tumors (hepatocell carcinomas), HTLV-1- and HTLV-2-induced lymphomas, vulval cancer, wart conditions or involvement, etc. In the present context, the terms “therapy” and “therapeutic” preferably mean to have at least some minimal physiological effect upon being administered to a living body. For example, a physiological effect upon administering a “therapeutic” anti-tumor compound may be the inhibition of tumor growth, or decrease in tumor size, or prevention reoccurrence of the tumor. Preferably, in the treatment of cancer or neoplastic disease, a compound which inhibits the growth of a tumor or decreased the size of the tumor or prevents the reoccurrence of the tumor would be considered therapeutically effective. The term “anti-tumor drug” therefore preferably means any therapeutic agent having therapeutic effect against a tumor, neoplastic disease or cancer.

According to an alternative preferred embodiment, the inventive transporter cargo conjugate molecule, the inventive pharmaceutical composition or the inventive vaccine as defined above, may be used for (the preparation of a medicament for) the prophylaxis, treatment, and/or amelioration of inflammatory diseases, such as inflammatory diseases of the lung or lung diseases, including Acute Respiratory Distress Syndrome (ARDS), or pulmonary fibrosis, inflammations of the tissue, including, without being limited thereto, formation of fibrous tissue, including cystic fibrosis, meningitis, and graft rejection or transplant rejection reactions, chronic illness involving the respiratory system, including Asthma, chronic obstructive pulmonary disease (COPD), pneumonia, and pulmonary fibrosis.

According to an alternative preferred embodiment, the inventive transporter cargo conjugate molecule, the inventive pharmaceutical composition or the inventive vaccine as defined above, may be used for (the preparation of a medicament for) the prophylaxis, treatment, and/or amelioration of e.g. infectious diseases, preferably viral, retroviral, bacterial or protozoological infectious diseases. Such infectious diseases are typically selected from AIDS, anthrax, Japanese encephalitis, bacterial infectious diseases such as miscarriage (prostate inflammation), anthrax, appendicitis, borreliosis, botulism, Camphylobacter, Chlamydia trachomatis (inflammation of the urethra, conjunctivitis), cholera, diphtheria, donavanosis, epiglottitis, typhus fever, gas gangrene, gonorrhoea, rabbit fever, *Heliobacter pylori*, whooping cough, climatic bubo, osteomyelitis, Legionnaire's disease, chicken-pox, condyloma acuminata, cytomegalic virus (CMV), dengue fever, early summer meningoencephalitis (ESME), Ebola virus, colds, fifth disease, foot-and-mouth disease, herpes simplex type I, herpes simplex type II, herpes zoster, HSV, infectious diseases caused by parasites, protozoa or fungi, such as amoebiasis, bilharziosis, Chagas disease, *Echinococcus*, fish tapeworm, fish poisoning (Ciguatera), fox tapeworm, athlete's foot, canine tapeworm, candidosis, yeast fungus spots, scabies, cutaneous Leishmaniosis, lambliasis (giardiasis), lice, malaria, microscopy, onchocercosis (river blindness), fungal diseases, bovine tapeworm, schistosomiasis, porcine tapeworm, toxoplasmosis, trichomoniasis, trypanosomiasis (sleeping sickness), visceral Leishmaniosis, nappy/diaper dermatitis or miniature tapeworm, infectious erythema, influenza, Kaposi's sarcoma, Lassa fever, Leishmaniasis, leprosy, listeriosis, Lyme borreliosis, malaria, Marburg virus infection, measles, meningitis, including bacterial meningitis, molluscum contagiosum, mononucleosis, mumps, *Mycoplasma hominis*, neonatal sepsis (Chorioamnionitis), noma, Norwalk virus infection, otitis media, paratyphus, Pfeiffer's glandular fever, plague, pneumonia, polio (poliomyelitis, childhood lameness), pseudo-croup, rabies, Reiter's syndrome, Rocky Mountain spotted fever, *Salmonella paratyphus, Salmonella typhus*, SARS, scarlet fever, shingles, hepatitis, smallpox, soft chancre, syphilis, tetanus,three-day fever, tripper, tsutsugamushi disease, tuberculosis, typhus, vaginitis (colpitis), viral diseases caused by cytomegalovirus (CMV), orthopox variola virus, orthopox alastrim virus, parapox ovis virus, molluscum contagiosum virus, herpes simplex virus 1, herpes simplex virus 2, herpes B virus, varicella zoster virus, pseudorabies virus, human cytomegaly virus, human herpes virus 6, human herpes virus 7, Epstein-Barr virus, human herpes virus 8, hepatitis B virus, chikungunya virus, O'nyong'nyong virus, rubivirus, hepatitis C virus, GB virus C, West Nile virus, dengue virus, yellow fever virus, louping ill virus, St. Louis encephalitis virus, Japan B encephalitis virus, Powassan virus, FSME virus, SARS, SARS-associated corona virus, human corona virus 229E, human corona virus Oc43, Torovirus, human T cell lymphotropic virus type I, human T cell lymphotropic virus type II, HIV (AIDS), i.e. human immunodeficiency virus type 1 or human immunodeficiency virus type 2, influenza virus, Lassa virus, lymphocytic choriomeningitis virus, Tacaribe virus, Junin virus, Machupo virus, Borna disease virus, Bunyamwera virus, California encephalitis virus, Rift Valley fever virus, sand fly fever virus, Toscana virus, Crimean-Congo haemorrhagic fever virus, Hazara virus, Khasan virus, Hantaan virus, Seoul virus, Prospect Hill virus, Puumala virus, Dobrava Belgrade virus, Tula virus, sin nombre virus, Lake Victoria Marburg virus, Zaire Ebola virus, Sudan Ebola virus, Ivory Coast Ebola virus, influenza virus A, influenza virus B, influenza viruses C, parainfluenza virus, measles virus, mumps virus, respiratory syncytial virus, human metapneumovirus, vesicular stomatitis Indiana virus, rabies virus, Mokola virus, Duvenhage virus, European bat lyssavirus 1+2, Australian bat lyssavirus, adenoviruses A-F, human papilloma viruses, condyloma virus 6, condyloma virus 11, polyoma viruses, adeno-associated virus 2, rotaviruses, or orbiviruses, Varicella including Varizella zoster, and malaria virus, viral infectious diseases such as AIDS, infectious diseases caused by Condyloma acuminata, hollow warts, Dengue fever, three-day fever, Ebola virus, cold, early summer meningoencephalitis (FSME), flu, shingles, hepatitis, herpes simplex type I, herpes simplex type II, Herpes zoster, influenza, Japanese encephalitis, Lassa fever, Marburg virus, warts, West Nile fever, yellow fever, etc.

According to another preferred embodiment, the inventive transporter cargo conjugate molecule, the inventive pharmaceutical composition or the inventive vaccine, may be used for (the preparation of a medicament for) the prophylaxis, treatment, and/or amelioration of diseases strongly related to JNK signaling in a subject. Such diseases or disorders strongly related to JNK signaling in a subject, without being limited thereto, are preferably selected from autoimmune disorders, cardiovascular diseases, cancer or tumor diseases as defined above, diabetes, including diabetes type 1 or type 2, inflammatory diseases as defined above, hair loss, including Alopecia areata, diseases of the lung, neuronal or neurodegenerative diseases, diseases of the liver, diseases of the spine, diseases of the uterus, (viral) infectious diseases and depressive disorders. In the case of diseases or disorders strongly related to JNK signaling the term "amelioration" may include the suppression of expression of JNK when it is over-expressed, and/or the suppression of phosphorylation of c-jun, ATF2 or NFAT4 in any of the above diseases, for example, by using at least one JNK inhibitor sequence as defined herein coupled to the inventive novel transporter molecule within the above definitions, as a competitive inhibitor of the natural c-jun, ATF2 and NFAT4 binding site in a cell. In this specific context, the term "modulate" also includes suppression of hetero- and homomeric complexes of transcription factors made up of, without being limited thereto, c-jun, ATF2, or NFAT4 and their related partners, such as for example the AP-1 complex that is made up of c-jun, AFT2 and c-fos. When a disease or disorder strongly related to JNK signaling as defined above is associated with JNK overexpression, such suppressive JNK inhibitor sequences can be introduced to a cell. In some instances, "modulate" in the context of diseases or disorders strongly related to JNK signaling may also include the increase of JNK expression, for example by use of an IB (poly-)peptide-specific antibody that blocks the binding of an IB-peptide to JNK, thus preventing JNK inhibition by the IB-related (poly-)peptide. Prevention and/or treatment of a subject with the pharmaceutical composition as disclosed above may be typically accomplished by administering (in vivo) an ("therapeutically effective") amount of said pharmaceutical composition to a subject, wherein the subject may be e.g. any mammal, e.g. a human, a primate, mouse, rat, dog, cat, cow, horse or pig. The term "therapeutically effective" means that the active component of the pharmaceutical composition is of sufficient quantity to ameliorate the disease or disorder strongly related to JNK signaling as defined above. Further example may be found for the other diseases mentioned herein.

Accordingly, the inventive transporter cargo conjugate molecule, the inventive pharmaceutical composition or the inventive vaccine, may be used for (the preparation of a medicament for) the prophylaxis, treatment, and/or amelioration of autoimmune disorders or diseases. Autoimmune disorders or diseases can be broadly divided into systemic and organ-specific or localised autoimmune disorders, depending on the principal clinico-pathologic features of each disease. Autoimmune diseases may be divided into the categories of systemic syndromes, including systemic lupus erythematosus (SLE), Sjögren's syndrome, Scleroderma, Rheumatoid Arthritis and polymyositis or local syndromes which may be endocrinologic (type I diabetes (Diabetes mellitus Type 1), Hashimoto's thyroiditis, Addison's disease etc.), dermatologic (pemphigus vulgaris), haematologic (autoimmune haemolytic anaemia), neural (multiple sclerosis) or can involve virtually any circumscribed mass of body tissue. The autoimmune diseases to be treated may be selected from the group consisting of type I autoimmune diseases or type II autoimmune diseases or type III autoimmune diseases or type IV autoimmune diseases, such as, for example, multiple sclerosis (MS), rheumatoid arthritis, diabetes, type I diabetes (Diabetes mellitus Type 1), chronic polyarthritis, Basedow's disease, autoimmune forms of chronic hepatitis, colitis ulcerosa, type I allergy diseases, type II allergy diseases, type III allergy diseases, type IV allergy diseases, fibromyalgia, hair loss, Bechterew's disease, Crohn's disease, Myasthenia gravis, neurodermitis, Polymyalgia rheumatica, progressive systemic sclerosis (PSS), Reiter's syndrome, rheumatic arthritis, psoriasis, vasculitis, etc, or type II diabetes. While the exact mode as to why the immune system induces an immune reaction against autoantigens has not been elucidated so far, there are several findings with regard to the etiology. Accordingly, the autoreaction may be due to a T-Cell bypass. A normal immune system requires the activation of B-cells by T-cells before the former can produce antibodies in large quantities. This requirement of a T-cell can be by-passed in rare instances, such as infection by organisms producing super-antigens, which are capable of initiating polyclonal activation of B-cells, or even of T-cells, by directly binding to the g-subunit of T-cell receptors in a non-specific fashion. Another explanation deduces autoimmune diseases from a Molecular Mimicry. An exogenous antigen may share structural similarities with certain host antigens; thus, any antibody produced against this antigen (which mimics the self-antigens) can also, in theory, bind to the host antigens and amplify the immune response. The most striking form of molecular mimicry is observed in Group A beta-haemolytic streptococci, which shares antigens with human myocardium, and is responsible for the cardiac manifestations of rheumatic fever.

The inventive transporter cargo conjugate molecule, the inventive pharmaceutical composition or the inventive vaccine, may also be used for (the preparation of a medicament for) the prophylaxis, treatment, and/or amelioration of cardiovascular diseases, preferably selected from heart diseases and coronary heart diseases, arteriosclerosis, apoplexy, dilatation of the abdominal aorta, such as infrarenal aneurism hypertension, and myocardial infarction.

Additionally, the inventive transporter cargo conjugate molecule, the inventive pharmaceutical composition or the inventive vaccine, may be used for (the preparation of a medicament for) the prophylaxis, treatment, and/or amelioration of neuronal or neurodegenerative diseases selected from, without being limited thereto, Alzheimer's disease, Parkinson's disease, amyotrophic lateral sclerosis (ALS), dystonia, epilepsy, optic nerve disease, including glaucoma, eye infection, multiple sclerosis, meningitis, neuronal diseases caused by or disorders or diseases or disorders of the nervous system, including the "cutting" or disruption of axons, such as axotomy, pain, particularly neuropathic pain, stroke, including ischemic stroke, and viral encephalopathy.

The inventive transporter cargo conjugate molecule, the inventive pharmaceutical composition or the inventive vaccine, may also be used for (the preparation of a medicament for) the prophylaxis, treatment, and/or amelioration of diseases of the liver selected from, without being limited thereto, Hepatitis, and hepatotoxicity.

Additionally, the inventive transporter cargo conjugate molecule, the inventive pharmaceutical composition or the inventive vaccine, may be used for (the preparation of a medicament for) the prophylaxis, treatment, and/or amelioration of diseases of the spine, selected from, without being limited thereto, disc herniation.

According to one preferred embodiment, the inventive transporter cargo conjugate molecule, the inventive pharmaceutical composition or the inventive vaccine, may be used for (the preparation of a medicament for) the prophylaxis, treatment, and/or amelioration of diseases of the uterus selected from, without being limited thereto, endometriosis.

According to another preferred embodiment, the inventive transporter cargo conjugate molecule, the inventive pharmaceutical composition or the inventive vaccine, may be used for (the preparation of a medicament for) the prophylaxis, treatment, and/or amelioration of depressive disorders selected from, without being limited thereto, major depressive disorders, also known as major depression, unipolar depression, clinical depression, or simply depression, bipolar disorders, mania and maniac depression.

According to a further preferred embodiment, the inventive transporter cargo conjugate molecule, the inventive pharmaceutical composition or the inventive vaccine, may be used for (the preparation of a medicament for) the prophylaxis, treatment, and/or amelioration of non-chronic or chronic inflammatory digestive diseases in a subject. The term "non-chronic or chronic inflammatory digestive disease" as used herein typically denotes non-chronic or chronic inflammatory diseases that pertain to the gastrointestinal tract. This includes diseases of the esophagus, stomach, first, second, third and fourth part of the duodenum, jejunum, ileum, the ileo-cecal complex, large intestine, (ascending, transverse and descending colon) sigmoid colon and rectum. Preferably included in this respect are chronic inflammatory digestive diseases, which are characterized by an inflammation of the colon, such as colitis, including e.g. Colitis ulcerosa (ulcerative colitis), Morbus Crohn (Crohn's disease), diversion colitis, ischemic colitis, infectious colitis, fulminant colitis, chemical colitis, microscopic colitis, lymphocytic colitis, collageneous colitis, indeterminate colitis and atypical colitis, etc.

In the context of the above, the invention relates also to the use of the inventive transporter cargo conjugate molecule the inventive pharmaceutical composition or the inventive vaccine, for the prophylaxis, treatment, and/or amelioration of diseases or disorders as mentioned herein. It also includes in particular the use of the inventive transporter cargo conjugate molecule, the inventive pharmaceutical composition or the inventive vaccine, for inoculation or the use of these components as an inoculant. According to one particularly preferred embodiment of the present invention, such a method for prophylaxis, treatment, and/or amelioration of the above-mentioned diseases or disorders, or an inoculation method for preventing the above-mentioned diseases, typically comprises administering the described inventive transporter cargo conjugate molecule, pharmaceutical composition or vaccine to a patient in need thereof (e.g. suffering from any of the above diseases or showing symptoms thereof), in particular to a human being, preferably in a “safe and effective amount” and in one of the above formulations as described above. The administration mode also may be as described above for inventive pharmaceutical compositions or vaccines.

According to a fifth aspect of the present invention, the inventive pharmaceutical composition, the inventive vaccine, the inventive transporter cargo conjugate molecule as defined above, the WBC targeting (poly-)peptide as defined herein, or variants or fragments thereof within the above definitions, may be utilized as a medicament. Such a medicament may be a pharmaceutical composition or a vaccine as shown above. It may be utilized in medical applications in general, preferably for any of the prophylaxis, treatment, and/or amelioration of diseases or disorders as mentioned herein.

According to a further aspect of the present invention, the inventive transporter cargo conjugate molecule may be utilized for the transport of any cargo molecule (preferably as defined herein) into white blood cells of a patient to be treated. In this context, the cargo molecule may be suitable for a therapy as mentioned herein, particularly for the prophylaxis, treatment, attenuation and/or amelioration of diseases or disorders as mentioned herein and may be selected from any cargo molecule suitable therefore, more preferably from any cargo molecule as described above for any of components (B), (C), (D) and/or (E) etc. of the inventive transporter cargo conjugate molecule.

In one embodiment of the present invention the the transporter cargo conjugate molecule, the inventive pharmaceutical composition or the inventive vaccine as defined herein are not used for the treatment, prophylaxis, attenuation and/or amelioration of one, two or more diseases and/or disorders selected from: cancer or tumor diseases, including diseases caused by defective apoptosis; inflammatory diseases, viral (infectious) diseases, diseases strongly related to JNK signalling, autoimmune disorders or diseases, cardiovascular diseases, neuronal or neurodegenerative diseases, diseases of the liver, diseases of the spine, diseases of the uterus, major depressive disorders, non-chronic or chronic inflammatory digestive diseases, diabetes and/or hair loss. Rather they are selected from the remaining diseases and/or disorders disclosed herein. Similarly, in one embodiment of the present invention the transporter cargo conjugate molecule as described herein does not comprise a JNK inhibitor but an other alternative disclosed herein. In a further embodiment of the present invention the transporter cargo molecule as described herein does not comprise SEQ ID NO: 1 as component (A) but an alternative component (A), e.g. one of the examples disclosed herein.

According to a further aspect of the present invention, the WBC targeting (poly-)peptide, the inventive transporter cargo conjugate molecule as defined above or variants or fragments of these within the above definitions, the inventive pharmaceutical composition or the inventive vaccine may be utilized in diagnosis as a diagnostic tool, e.g. in (in vivo or in vitro) assays, e.g. in immunoassays, to detect, prognose, diagnose, or monitor various conditions and disease states of disorders or diseases mentioned.

As an example, immunoassay may be performed by a method comprising contacting a sample derived from a patient with an inventive transporter cargo conjugate molecule as defined above, wherein component (B) and/or any of components (C), (D) and/or (E) etc. of the inventive transporter cargo conjugate molecule may be directed against a component or compound, e.g. a (cell) specific component or compound, contained in the sample. Such a component (B) or any of components (C), (D) and/or (E) of the inventive transporter cargo conjugate molecule may be e.g. an antibody directed to a (cell) specific component or compound of the sample, wherein such (cell) specific component or compound of the sample may be e.g. a compound or component as described above for any of components (B), (C), (D) and/or (E) etc. as defined herein. Contacting of the sample is typically carried out under conditions that immunospecific-binding may occur, and subsequently detecting or measuring the amount of any immunospecific-binding by the antibody. In a specific embodiment, an antibody specific for a (cell) specific component or compound of the sample, e.g. component (B), (C), (D) and/or (E) etc. as defined herein, may be used to analyze a tissue or serum sample from a patient for the presence of such a component (B), (C), (D) and/or (E) as defined above or a disease associated therewith. Such diseases may include diseases or disorders as described herein. The immunoassays that may be utilized include, but are not limited to, competitive and non-competitive assay systems using techniques such as Western Blots, radioimmunoassays (RIA), enzyme linked immunosorbent assay (ELISA), “sandwich” immunoassays, immunoprecipitation assays, precipitin reactions, gel diffusion precipitin reactions, immunodiffusion assays, agglutination assays, fluorescent immunoassays, complement-fixation assays, immunoradiometric assays, and protein-A immunoassays, etc.

Alternatively, (in vitro) assays may be performed by delivering the inventive pharmaceutical composition, a vaccine or the inventive transporter cargo conjugate molecule as defined above or variants or fragments thereof within the above definitions to target cells typically selected from e.g. cultured animal cells, human cells or micro-organisms, and to monitor the cell response by biophysical methods typically known to a skilled person. The target cells typically used therein may be cultured cells (in vitro) or in vivo cells, i.e. cells composing the organs or tissues of living animals or humans, or microorganisms found in living animals or humans. Particularly preferable in this context are so called markes or labels, which may be contained as a component (B) or any of components (C), (D) and/or (E) etc. of the inventive transporter cargo conjugate molecule, wherein such labels may be as defined in general above for the inventive transporter cargo conjugate molecule.

In a further aspect the present invention relates to the use of WBC targeting (poly-)peptide according to the present invention for the manufacture of a transporter cargo conjugate molecule for the transport of a substance of interest (cargo molecule) into white blood cells.

In a further embodiment the present invention also relates to a method for the transport of a substance of interest (cargo molecule) into white blood cells, the method comprising the following step:

i) Contacting a transporter cargo conjugate molecule comprising:
   a) as component (A): a (poly-)peptide comprising an amino acid sequence fragment, variant, or variant of such fragment of HIV TAT protein (SEQ ID NO: 1), b) as component (B): a cargo molecule, and c) optionally one or more further components, and a white blood cell.

Said method may be a method of treatment, i.e. the contacting occurs in the subject to be treated. Alternatively, said method may be an ex vivo or in vitro method. Consequently, the present invention relates in a further embodiment also to a (isolated) white blood cell comprising a transporter cargo conjugate molecule, the transporter cargo conjugate molecule comprising:

a) as component (A): a (poly-)peptide comprising an amino acid sequence fragment, variant, or variant of such fragment of HIV TAT protein (SEQ ID NO: 1), b) as component (B): a cargo molecule, and c) optionally one or more further components.

The present invention also relates to a white blood cell comprising just the remaining fragments of the transporter cargo conjugate molecule. This may be the case when the transporter cargo conjugate molecule comprises, for example an protease cleavage site which leads to a break down of the original transporter cargo conjugate molecule.

According to a final aspect of the present invention, the present invention also provides kits, particularly kits of parts, comprising as components alone or in combination, the WBC targeting (poly-)peptide or fragments or variants thereof, the inventive transporter cargo conjugate molecule, the inventive pharmaceutical composition and/or the inventive vaccine, and optionally technical instructions with information on the administration and dosage of these components. Such kits, preferably kits of parts, may be applied, e.g., for or in any of the above mentioned applications or uses. The present invention additionally particularly provides the use of kits for diagnostic or therapeutic purposes, particular for the treatment, prevention or monitoring of diseases or disorders as disclosed.

The present invention is not to be limited in scope by the specific embodiments described herein. Indeed, various modifications of the invention in addition to those described herein will become apparent to those skilled in the art from the foregoing description and accompanying figures. Such modifications fall within the scope of the appended claims.

Various publications are cited herein, the disclosures of which are incorporated by reference in their entirety.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting. Other features and advantages of the invention will be apparent from the following detailed description and claims.

The construct used was FITC-labeled D-TAT (SEQ ID NO: 4). The FITC-labeled D-TAT was stronger internalized in WBC-line 077 macrophage cells) than in non WBC-lines (HepG2; A549).

Figure 1:
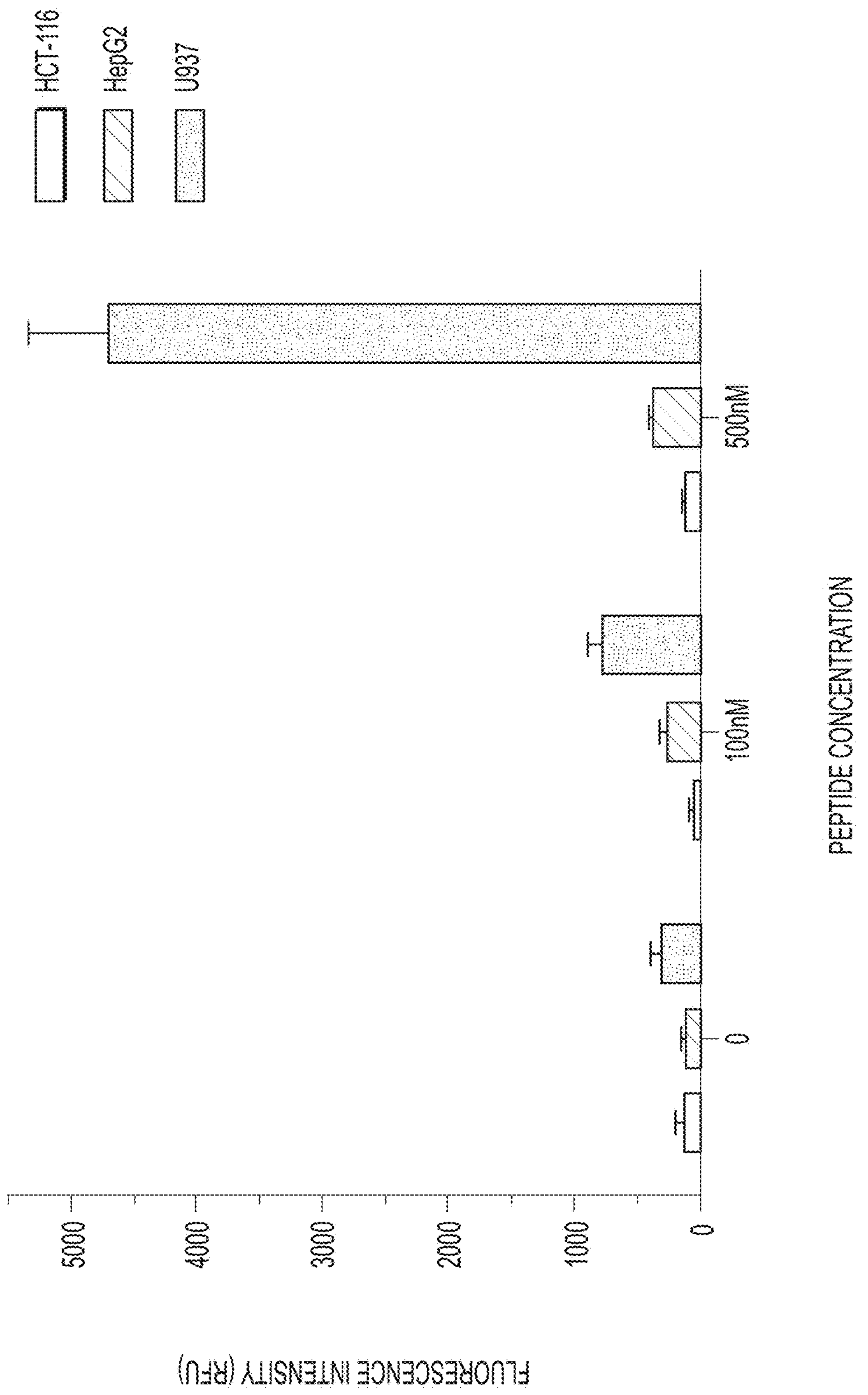
FIG. 1: illustrates the uptake (internalization) of FITC-labeled TAT derived transporter constructs in vitro (0; 100 nM or 500 nM) in HepG2 hepatocarcinoma cells, in HCT-116 tumoral colon cells and in U937 lymphoma cells. The construct used was FITC-labeled D-TAT (SEQ ID NO: 4). The FITC-labeled D-TAT was higher internalized in WBC-line (U937; lymphoma) than in non WBC-lines (HepG2: hepatocarcinoma cells; HCT-116: tumoral colon cells).
Figure 2:
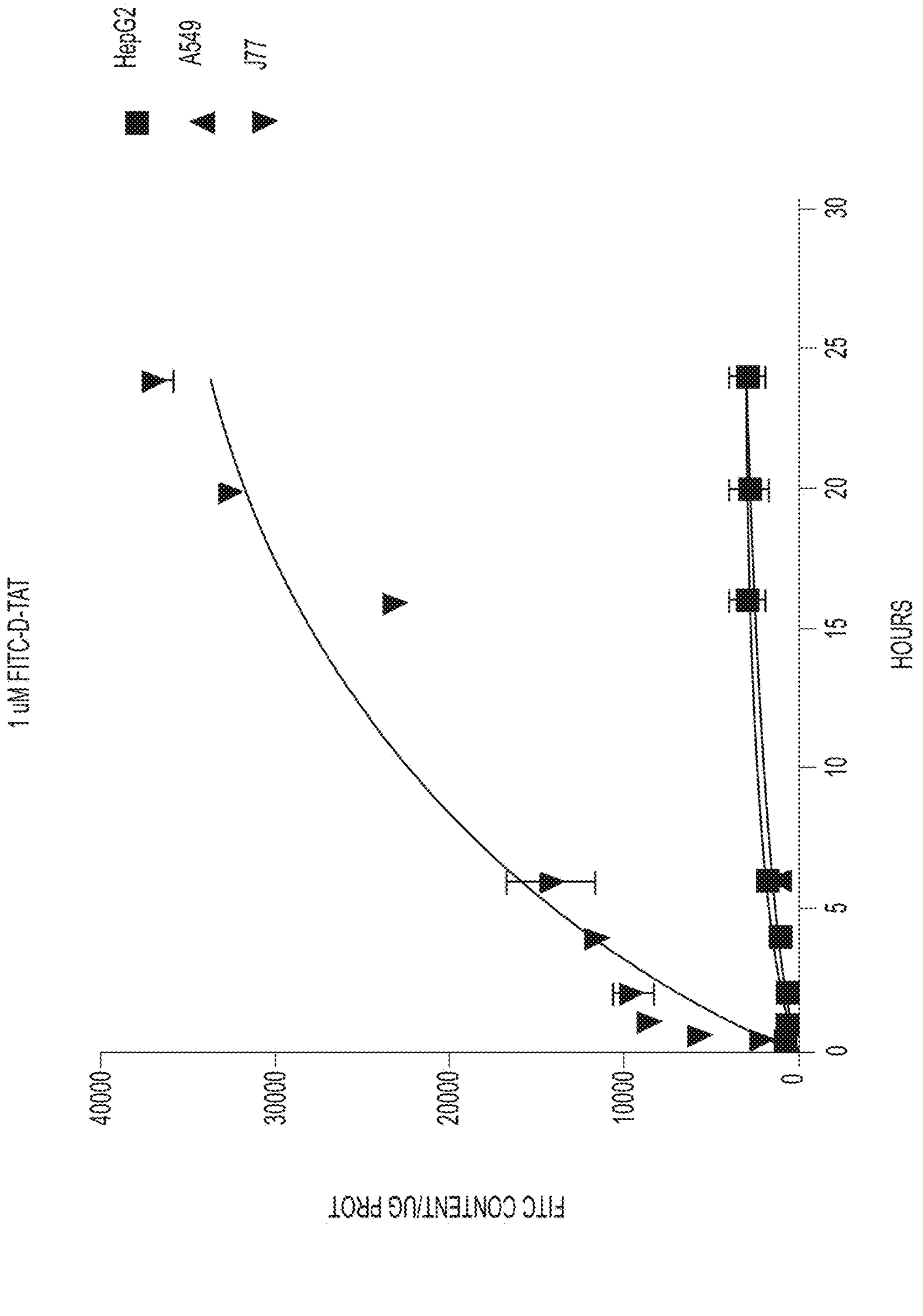
FIG. 2: illustrates the uptake (internalization) of a FITC-labeled TAT derived transporter construct (1 μM) in vitro over time. Three different cell lines were used (HepG2 hepatocarcinoma cells, A549 lung carcinoma cells and J77 macrophage cells).
Figure 3:
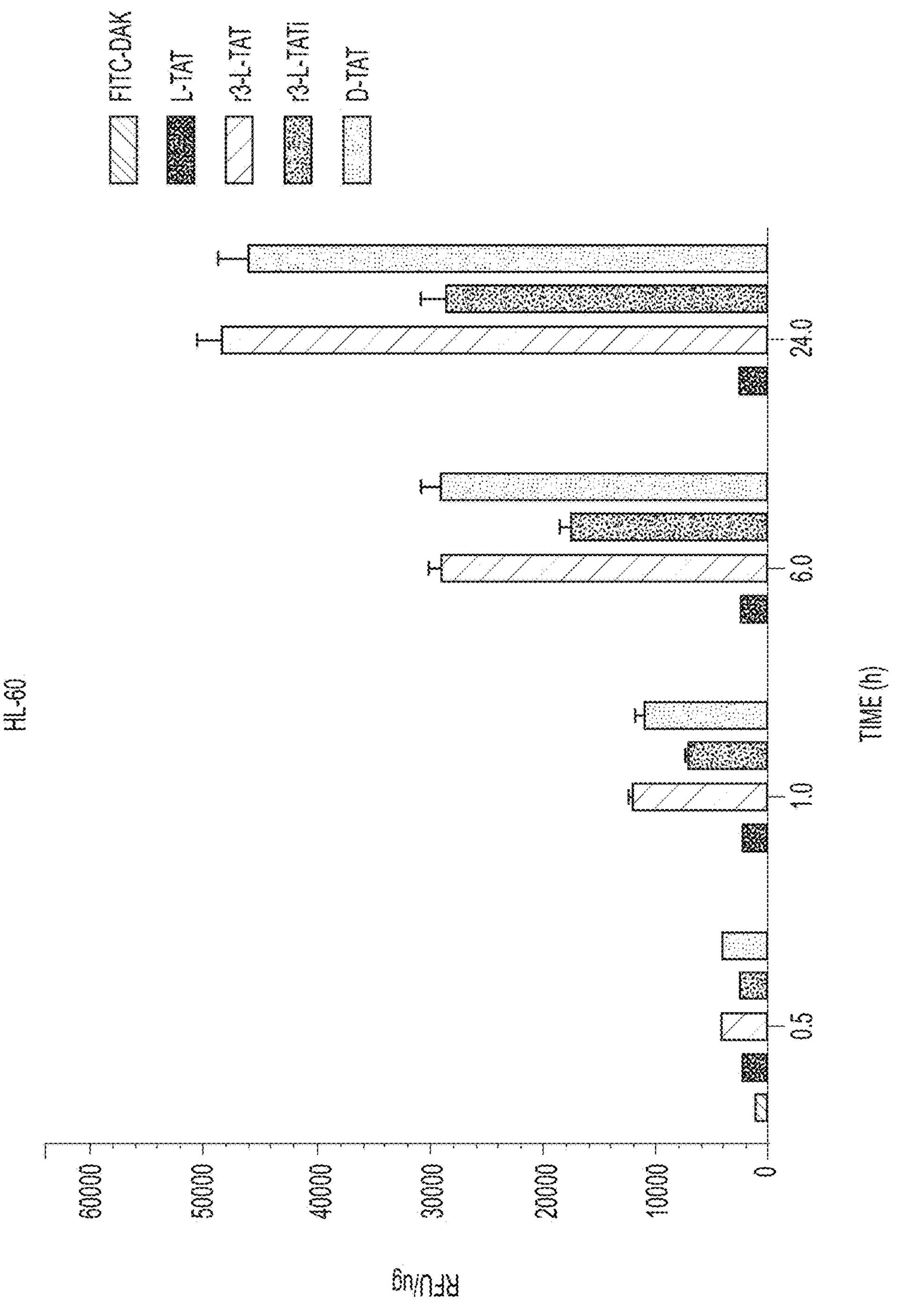

FIG. 3: depicts the results of the time dependant internalization (uptake) of FITC-labeled TAT derived transporter constructs into cells of the HL-60 cell line. The transporter cargo conjugate molecule used were FITC labeled DAK (SEQ ID NO: 232), FITC labeled L-TAT (SEQ ID NO: 2), FITC labeled r3-L-TAT (SEQ ID NO: 15), FITC labeled r3-L-TATi (SEQ ID NO: 16), and FITC labeled D-TAT (SEQ ID NO: 4). HL-60 cells were incubated 30 min, 1, 6 or 24 hours with 10 M of the TAT-derivative transporters. The cells were then washed twice with an acidic buffer (0.2 M Glycin, 0.15 M NaCl, pH 3.0) and twice with PBS. Cells were broken by the addition of RIPA lysis buffer. The relative amount of internalized peptide was then determined by reading the fluorescence intensity (Fusion Alpha plate reader; PerkinElmer) of each extract followed by background substraction and protein content normalization. The r3-L-TAT transporter construct showed an internalization capability as effective as the D-TAT transporter construct.

Figure 4:
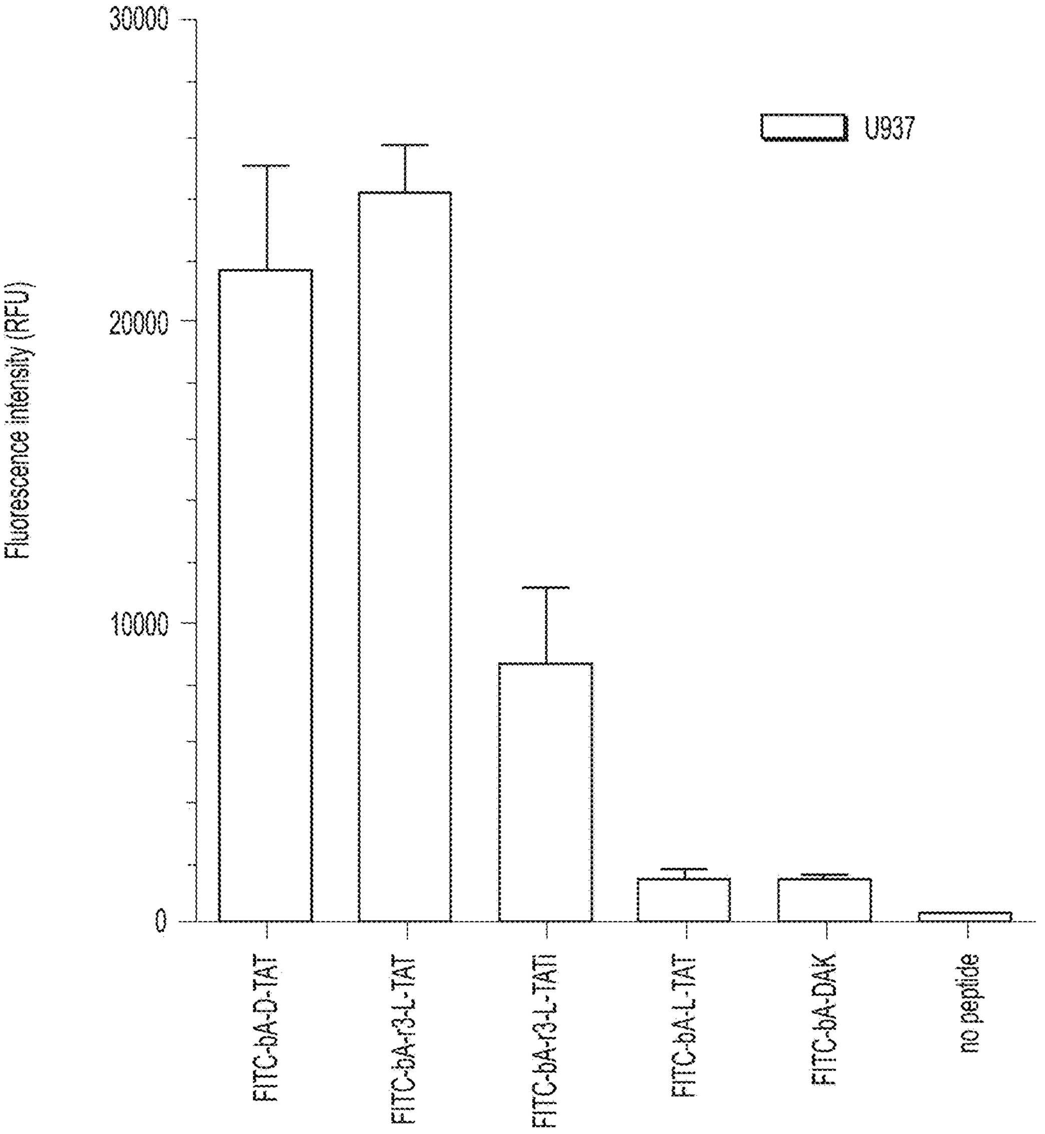

FIG. 4: shows the uptake (internalization) of FITC-labeled TAT derived transporter constructs in vitro (10 μM, U937, Lymphoma, 24 h). The constructs used were four different TAT derived transporter constructs (termed L-TAT (SEQ ID NO:2), r3-TAT (also termed r3-L-Tat) (SEQ ID NO:15), r3-TATi (also termed r3-L-TATi) (SEQ ID NO:16), and D-TAT) (SEQ ID NO:4), each having a length of 9 amino acids but a different D-/L-pattern. Additionally, the construct DAK (SEQ ID NO: 232) was used for comparison and a control sample, containing only the amino acids D, A and K. As can be seen, the uptake of r3-TAT (SEQ ID NO: 15), r3-TATi(SEQ ID NO: 16) and D-TAT (SEQ ID NO: 4) transporter constructs into the cells was most efficient, wherein L-TAT (SEQ ID NO: 2) showed a lower uptake into the cells.

Figure 5:
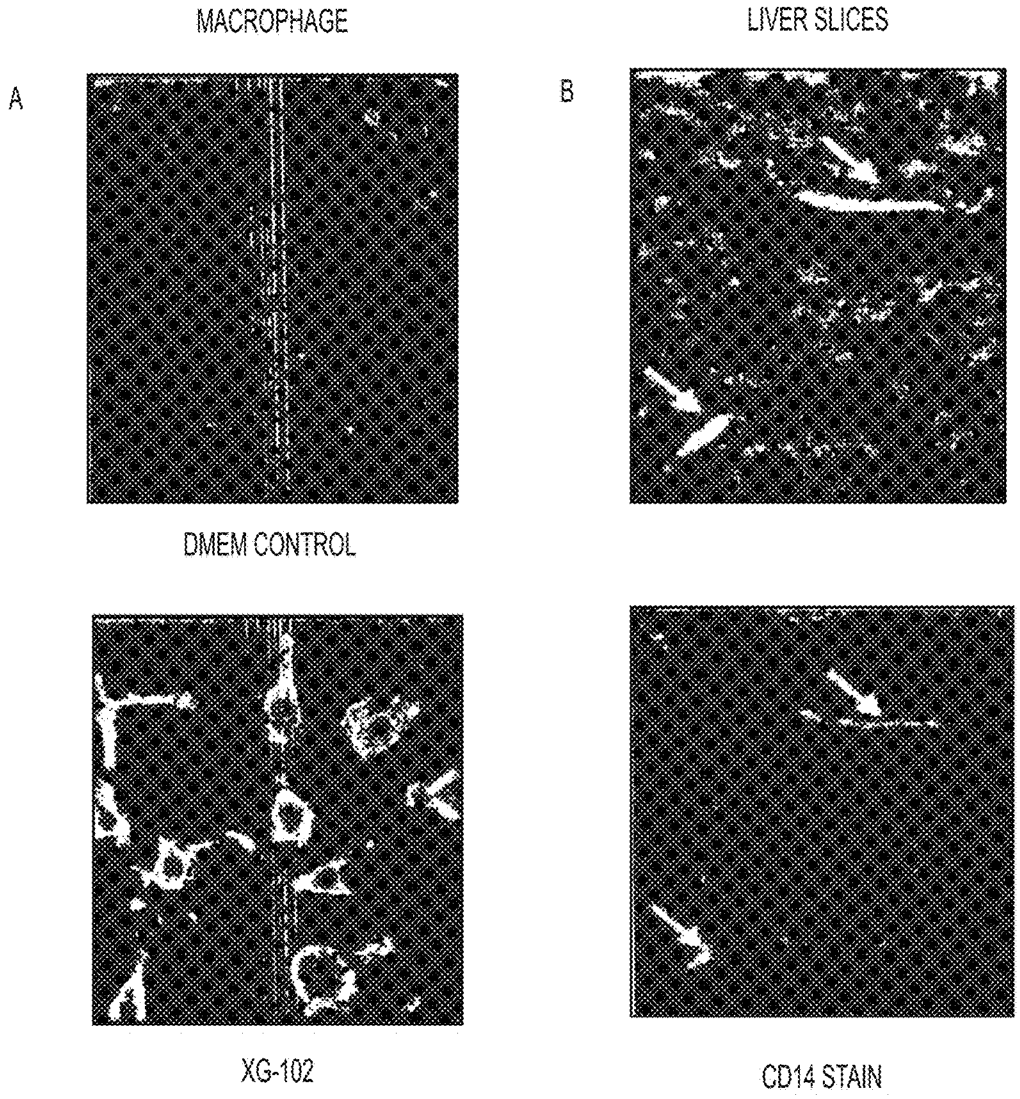

FIG. 5: (A): Primary cultured macrophages were incubated with XG-102 (SEQ ID NO: 233) and extensively washed. Presence of XG-102 (SEQ ID NO: 233) was revealed using a specific antibody against XG-102. XG-102 is strongly incorporated into primary macrophages. (B): Mice were injected i.v. with 0.1 mg/kg FITC-D-TAT (SEQ ID NO: 4 plus FITC) and were sacrificed 24 hours later with PAF perfusion through the heart. Slices were obtained after cryoprotection using cryostat. Immunostaining against CD-14 receptor (present at the cell surface of macrophages and granulocytes) showed colocalization between FITC-D-TAT labelled-cells and CD-14 positive cells (resident macrophages of the liver are called Kupffer cells)

Figure 6:
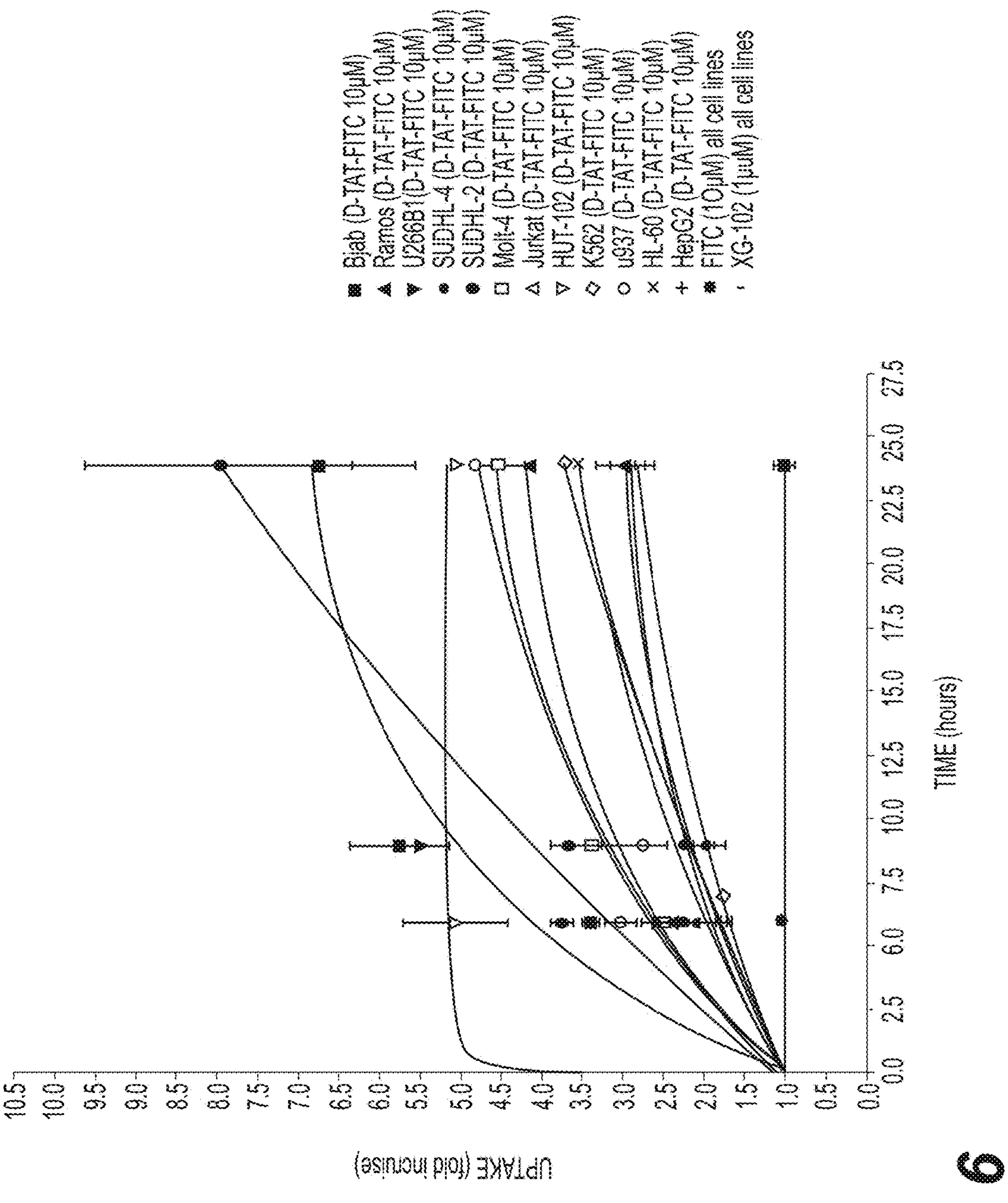

FIG. 6: shows the uptake (internalization) of FITC-labeled TAT derived transporter construct (SEQ ID NO:4) in 11 different WBC-lines (10 uM). All WBC lines tested internalized the D-TAT-FITC, in a time dependant manner.

Figure 7:
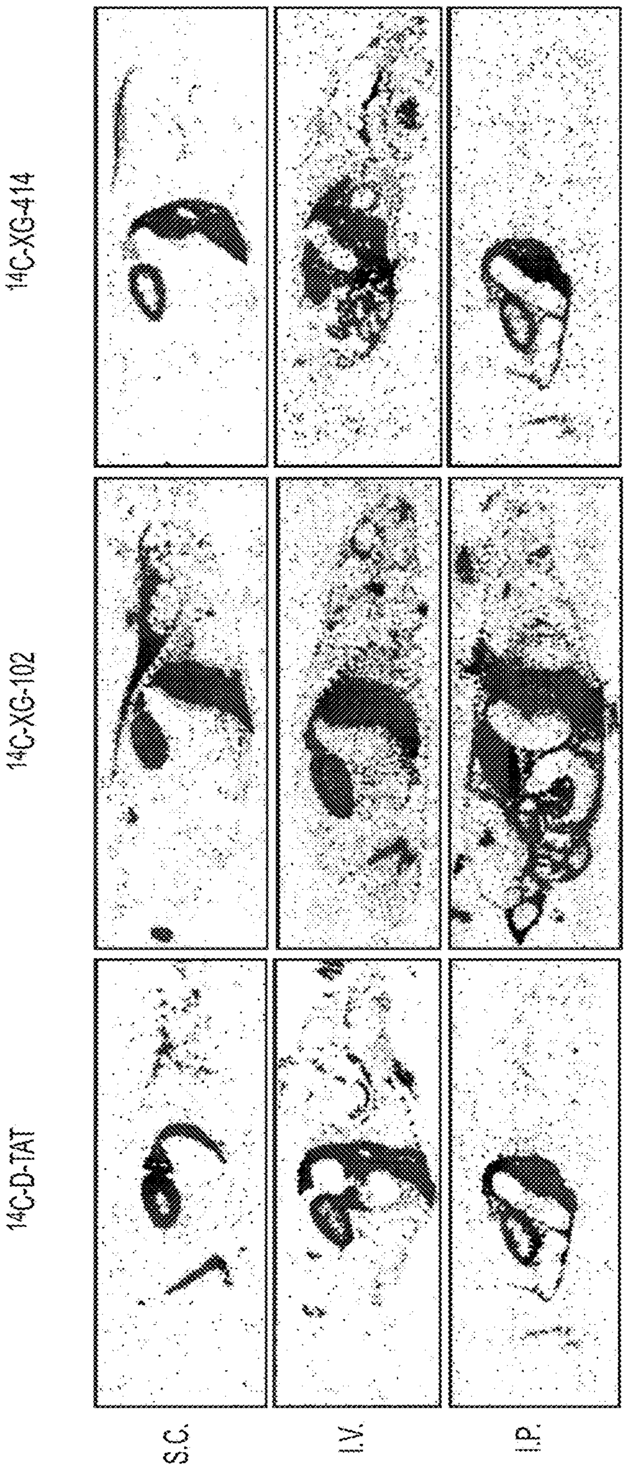

FIG. 7: shows the impact of TAT on the tissue distribution. Mice were treated via three different routes of administration (s.c., i.v., i.p.) with radiolabeled peptides with $C^{14}$ (1 mg/kg). Animals were sacrificed 72 hours after injection and processed for immunoradiography. Sagital sections were exposed and revealed the accumulation of three different D-TAT-tagged peptides in the liver, spleen, and bone marrow predominantly (D-TAT: SEQ ID NO: 4; XG-102: SEQ ID NO: 233; XG-414: D-TAT coupled to d BH3 domain of Bok). This illustrates that the transporter D-TAT is responsible for the tissue distribution.

Figure 8:
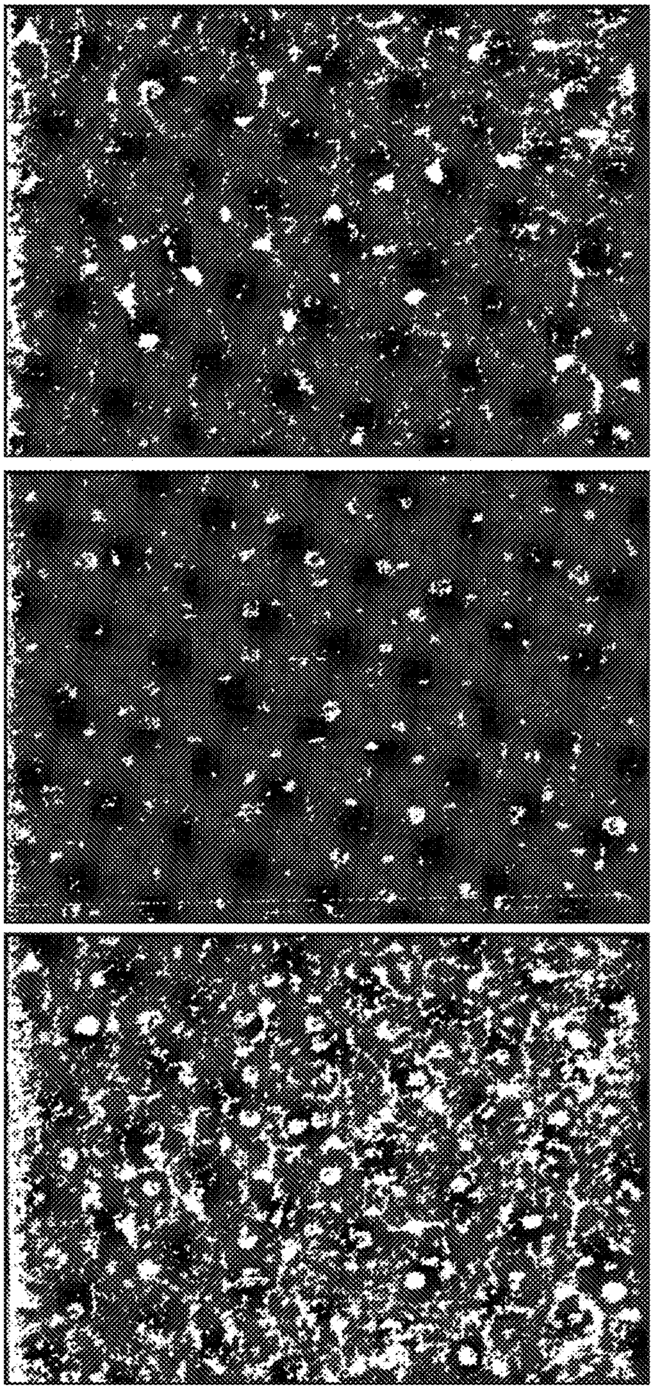

FIG. 8: FITC-D-TAT (SEQ ID NO: 4) exhibits pronounced uptake in Kupffer's cells. Mice were injected i.v. with 0.1 mg/kg of FITC-D-TAT (SEQ ID NO: 4) and were sacrificed by perfusion 24 h later. Liver was removed, cryoprotected and cut into slices with a cryostat. D-TAT was directly visualized via FITC fluorescence and cell nuclei were labeled with Hoechst dye. Hepatocytes are big cells (89% of liver cells) that display a large nucleus, whereas Kupffer cells (resident macrophages of the liver) represent approximately 10% of the cells and are small and thin, elongated cells with small nucleus. Based on the morphology, it can be concluded that FITC-D-TAT (SEQ ID NO: 4) accumulates predominantly in Kupffer cells.

Figure 9:
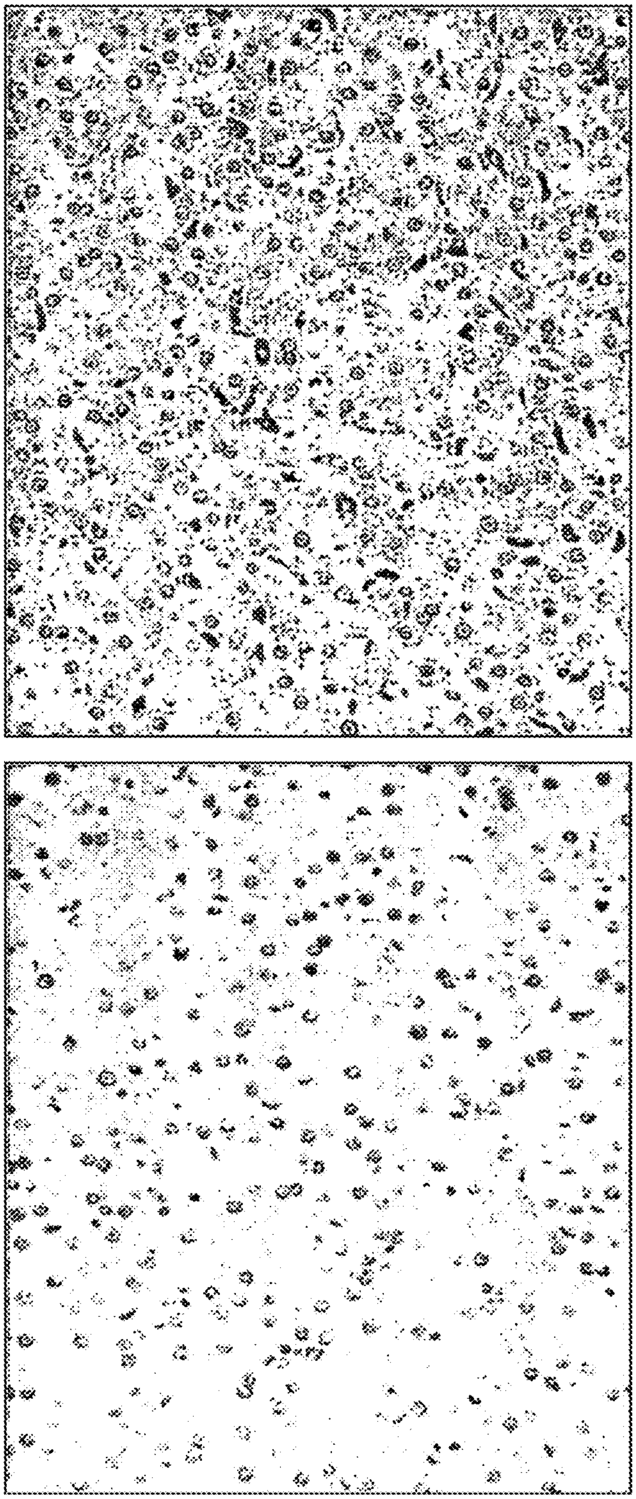

FIG. 9: shows an immunostaining against XG-102 (SEQ ID NO: 233) in the liver of rats injected with 1 mg/kg of XG-102 i.v. Animals were sacrificed 24 hours after injection. Revelation was done using DAB substrate. This figure shows again the pronounced accumulation of XG-102 in the liver, and especially, in the Kupffer cells.

Figure 10:
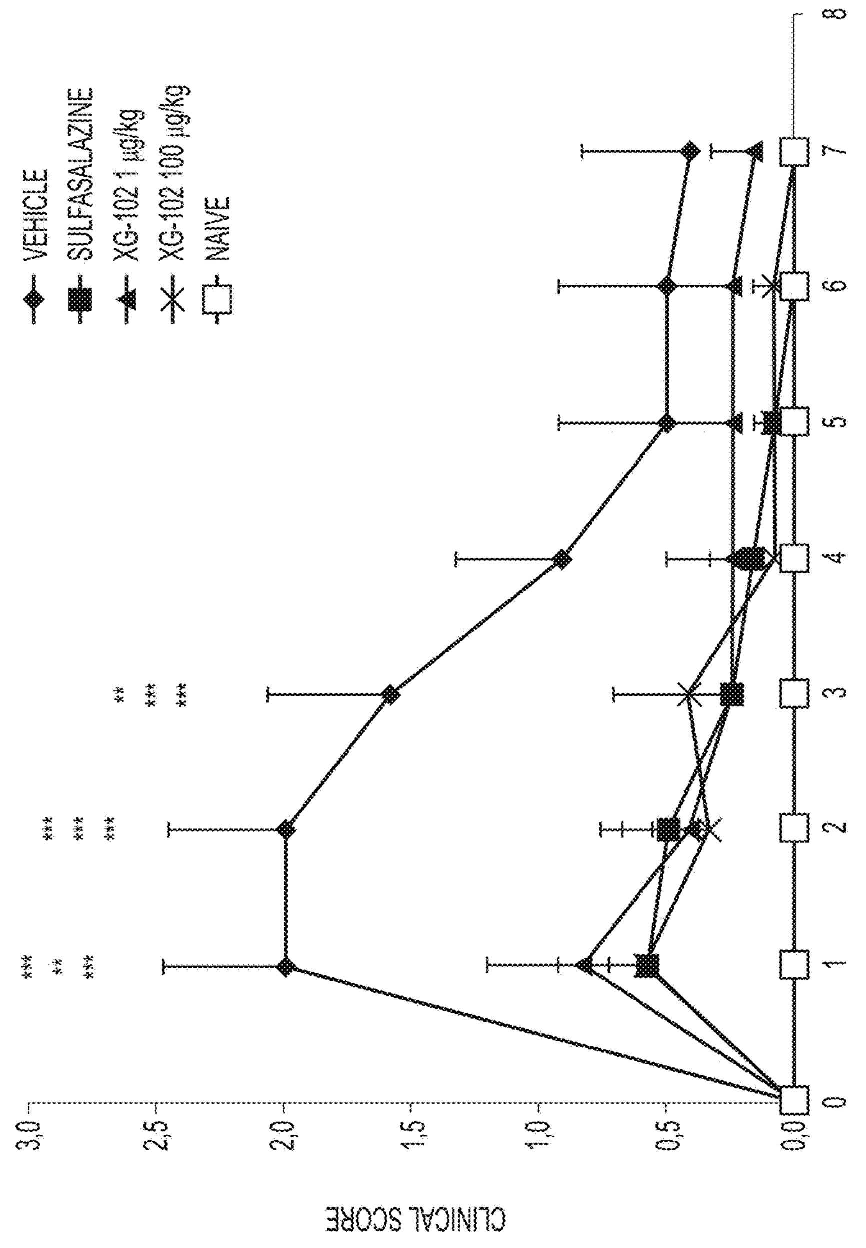

FIG. 10: shows the clinical scores upon treatment with XG-102 (SEQ ID NO: 233) in an IBD study (IBD: inflammatory bowel disease) with a treatment using XG-102 in a concentration of 1 and 100 μg/kg SC daily.

Figure 11:
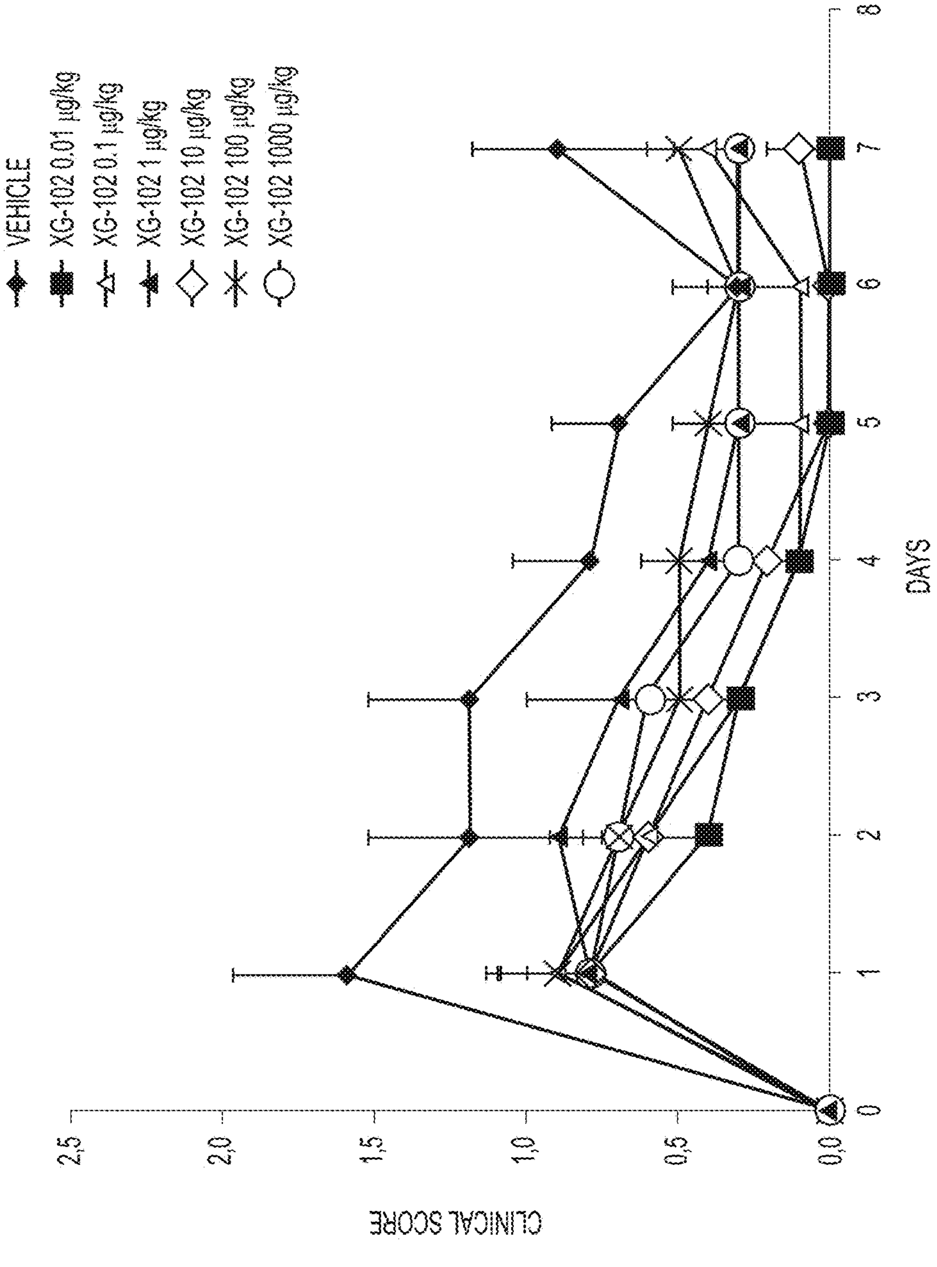

FIG. 11: shows a dose response curve upon treatment with XG-102 (SEQ ID NO: 233) in an IBD study with a treatment using XG-102, in a concentration of 0.01, 0.1, 1, 10, 100 and 1000 μg/kg SC daily.

Figure 12:
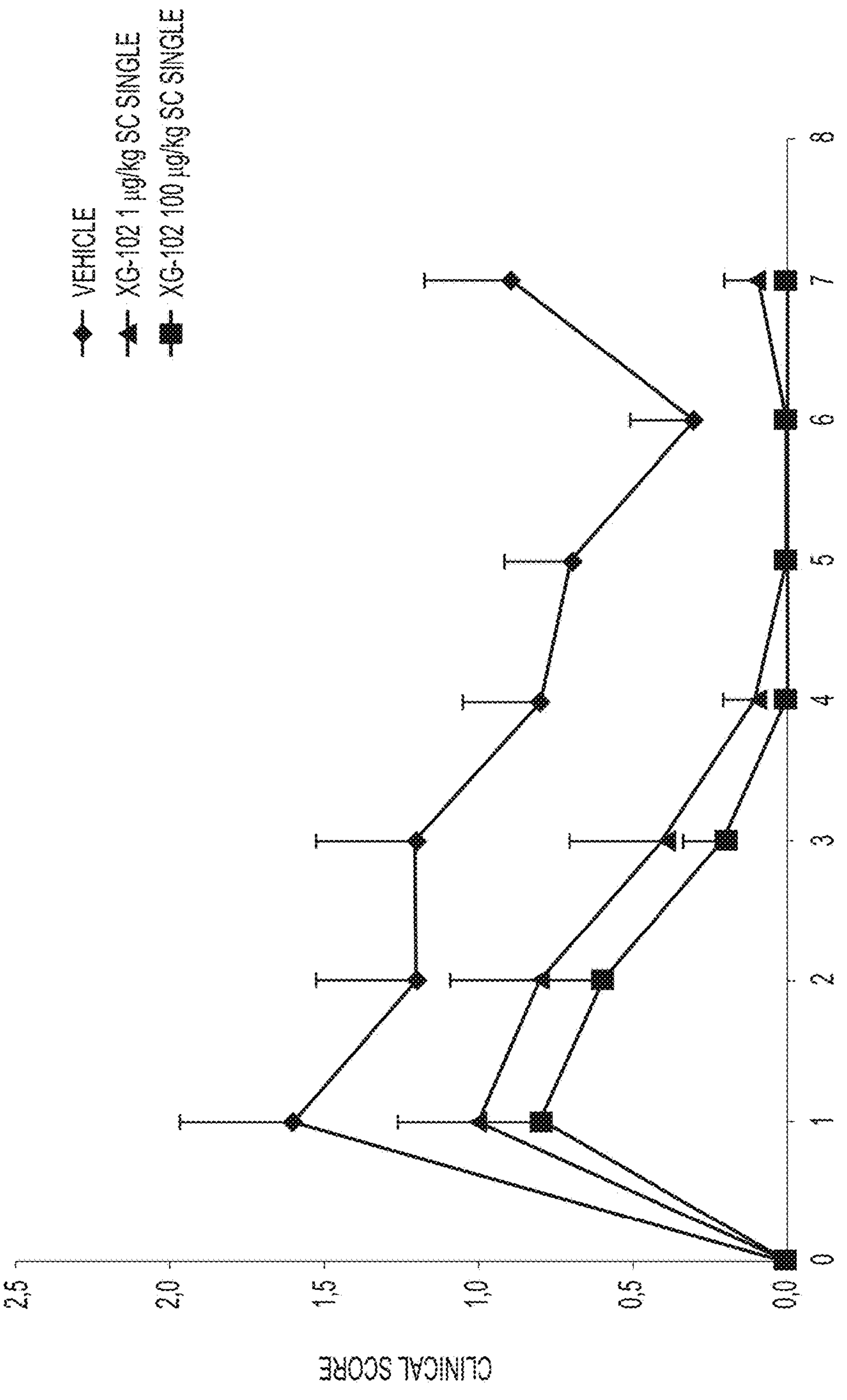

FIG. 12: shows the clinical scores upon treatment with XG-102 (SEQ ID NO: 233) in an IBD study with a treatment using XG-102 (single dose SC) in a concentration of 1 and 100 μg/kg SC as a single dose on day 0.

Figure 13:
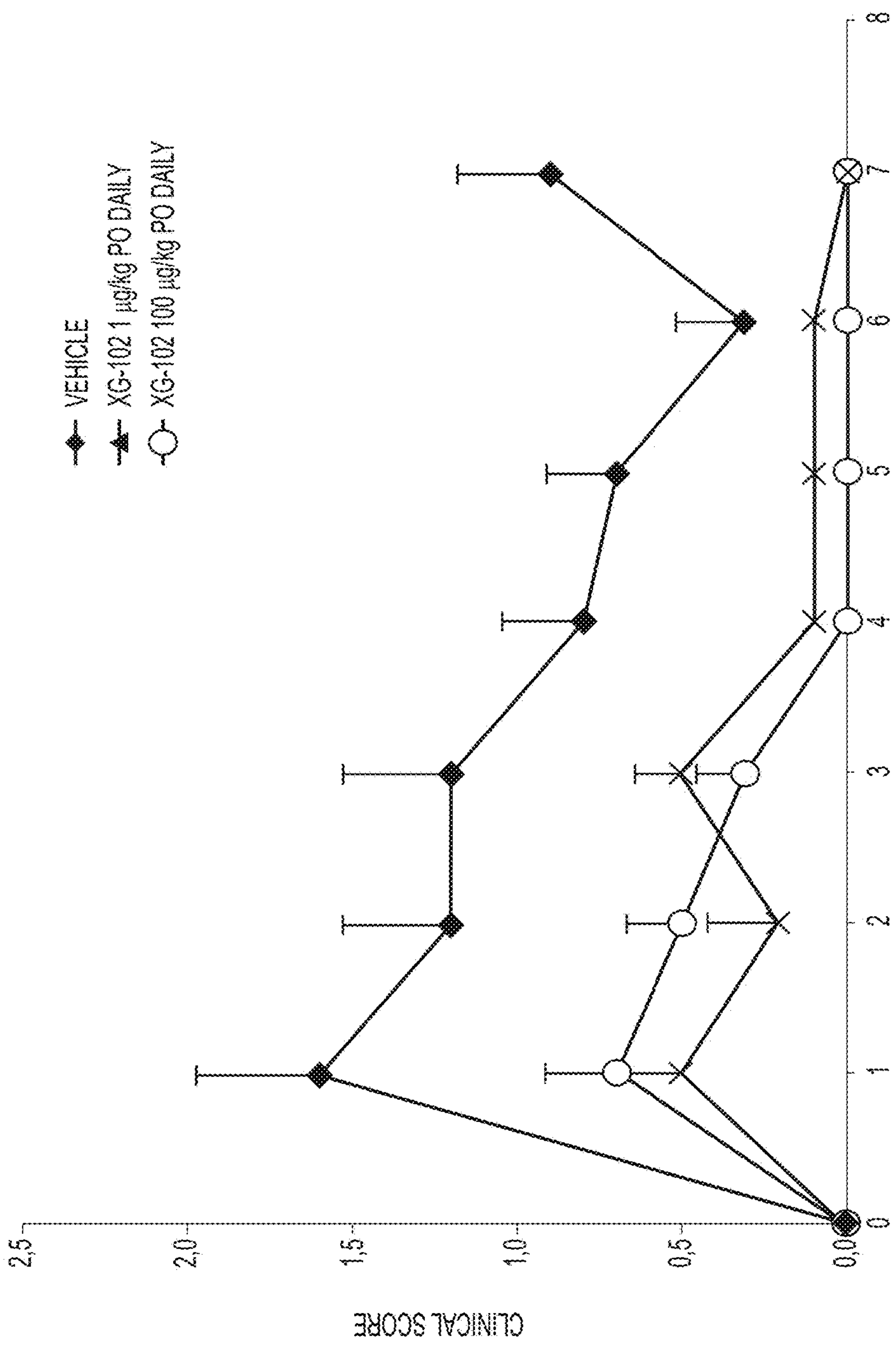

FIG. 13: shows the clinical scores upon treatment with XG-102 (SEQ ID NO: 233) in an IBD study with a treatment using XG-102 (daily, PO) in a concentration of 1 and 100 μg/kg PO as a repeated dose.

Figure 14:
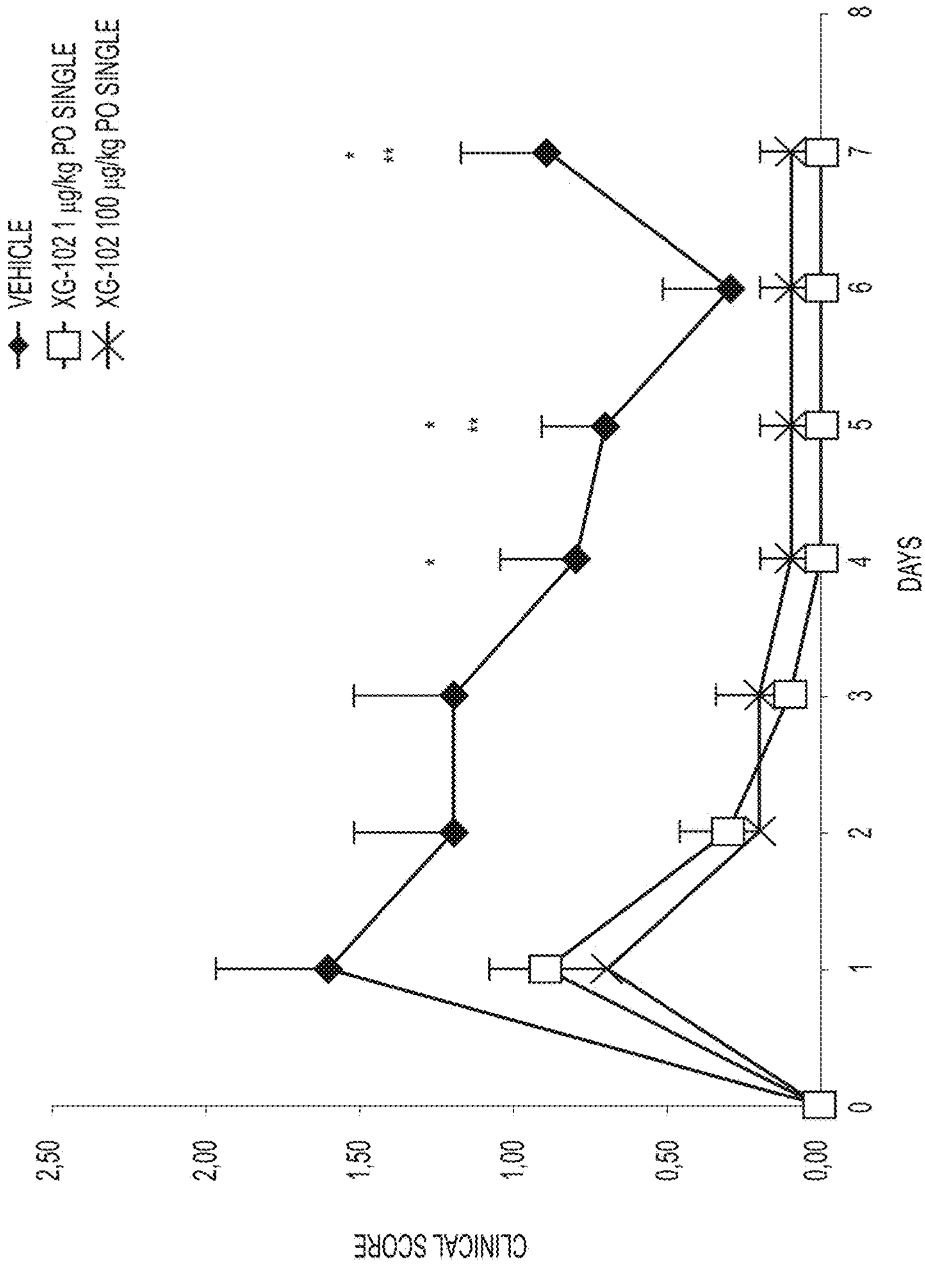

FIG. 14: shows the clinical scores upon treatment with XG-102 (SEQ ID NO: 233) in an IBD study with a treatment using XG-102 (single dose PO) in a concentration of 1 and 100 μg/kg PO as a single dose on day 0.

Figure 15A:
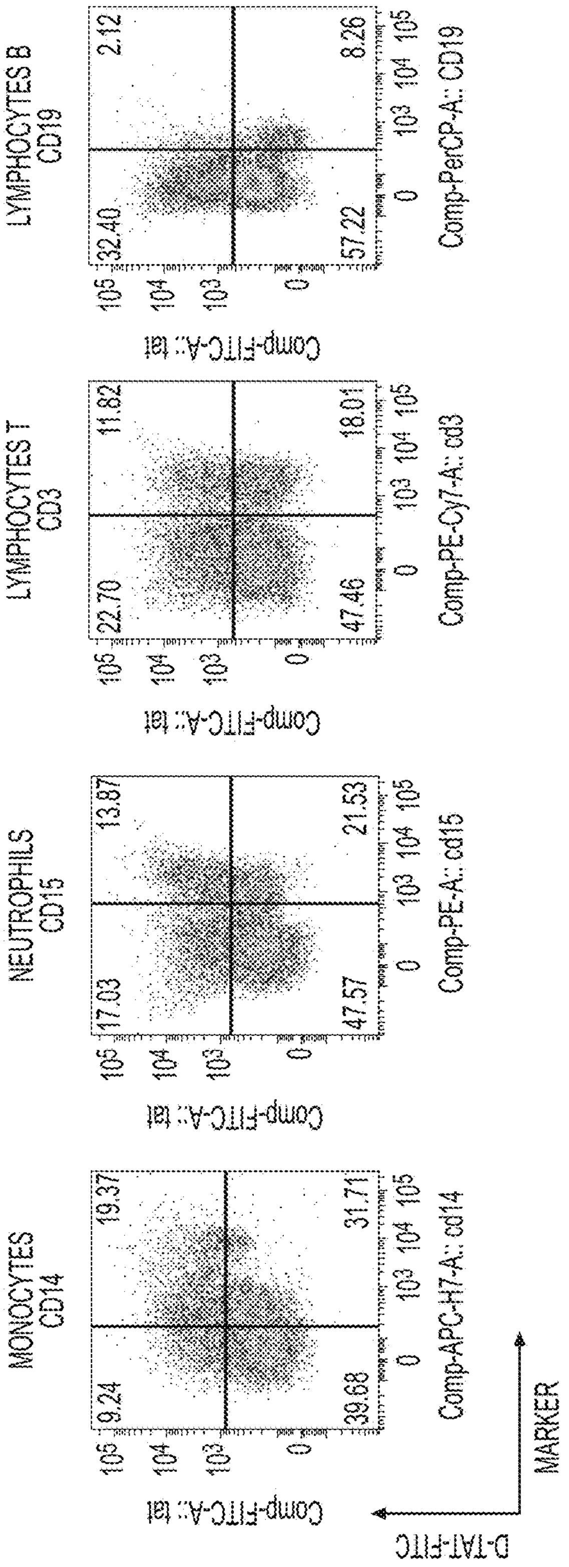
Figure 15B:
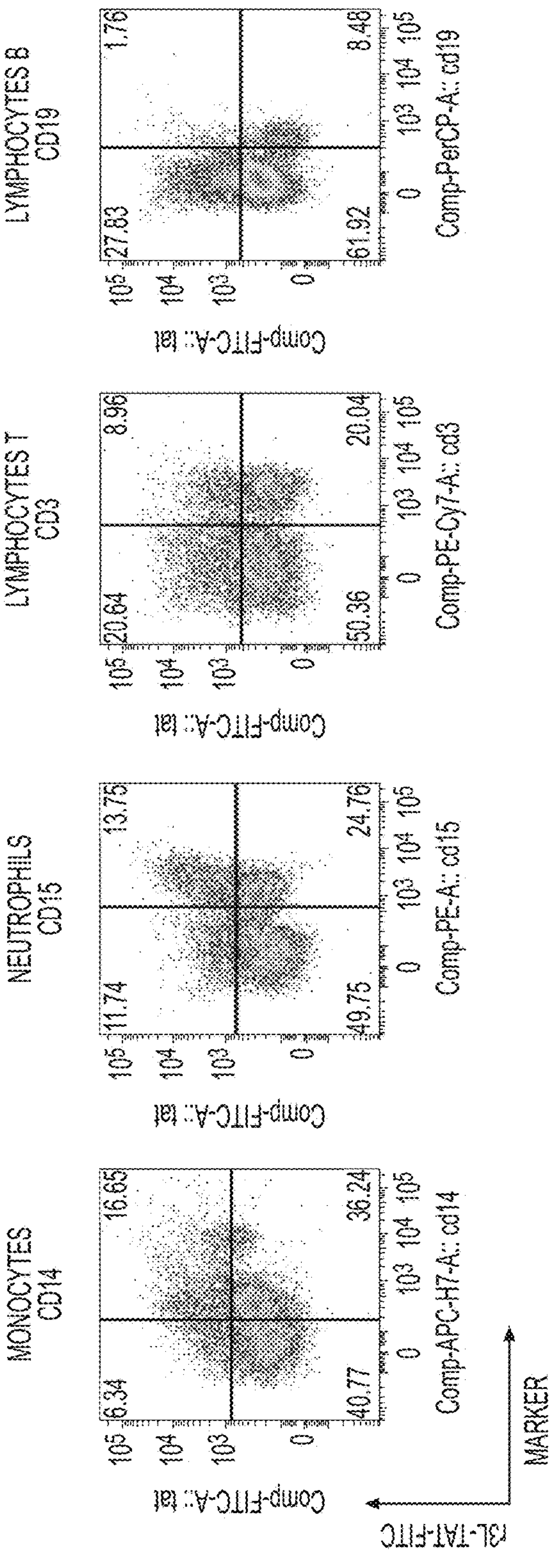

FIG. 15A and FIG. 15B: Fluorescent TAT derivative transporters D-TAT (SEQ ID NO: 4)-FITC or r3-L-TAT (SEQ ID NO: 15)-FITC target different human leukocyte populations.

FIG. 15A: D-TAT (SEQ ID NO: 4)-FITC. The percentage of cells gated in the respective quadrants is as follows (given clockwise beginning with upper left quadrant):

| | |
|---|---|
| Monocytes (CD14) | 9.24; 19.37; 31.71; 39.68; |
| Neutrophils (CD15) | 17.03; 13.87; 21.53; 47.57; |
| Lymphocytes T (CD3) | 22.7; 11.82; 18.01; 47.46; |
| Lymphocytes B (CD19) | 32.40; 2.12; 8.26; 57.22. |

FIG. 15B: r3-L-TAT (SEQ ID NO: 15)-FITC. The percentage of cells gated in the respective quadrants is as follows (given clockwise beginning with upper left quadrant):

| | |
|---|---|
| Monocytes (CD14) | 6.34; 16.65; 36.24; 40.77; |
| Neutrophils (CD15) | 11.74; 13.75; 24.76; 49.75; |

-continued

| | |
|---|---|
| Lymphocytes T (CD3) | 20.64; 8.96; 20.04; 50.36; |
| Lymphocytes B (CD19) | 27.83; 1.76; 8.48; 61.92. |

FIG. 16: The table indicates the mean fluorescence values for fluorescent TAT derivative transporters D-TAT (SEQ ID NO: 4)-FITC or r3-L-TAT (SEQ ID NO: 15)-FITC in each cell type as shown in FIG. 15 (FITC channel).

FIG. 17: Uptake of selected transporter constructs according to the present invention by different cell types. Uptake is normalized versus D-TAT (SEQ ID NO: 4). Raw: Macrophage cells (mouse; leucocyte cell line); J77: Macrophage cells (mouse; leucocyte cell line); BMDM: Bone Marrow-Derived Macrophages (mouse; purified primary leucocytes). *n=2 independent experiments (in duplicate) (except for peptide #64 n=1 in duplicate); n=2 experiment (in duplicate) (except for peptide #64 n=2 in duplicate); *n=1 experiment (in duplicate).

FIG. 18: Uptake of selected transporter constructs according to the present invention by different cell types. Uptake is normalized versus $r_3$-L-TAT (SEQ ID NO: 15). Raw: Macrophage cells (mouse; leucocyte cell line); J77: Macrophage cells (mouse; leucocyte cell line); BMDM: Bone Marrow-Derived Macrophages (mouse; purified primary leucocytes). *n=2 independent experiments (in duplicate) (except for peptide #64 n=1 in duplicate); n=2 experiment (in duplicate) (except for peptide #64 n=2 in duplicate); *n=1 experiment (in duplicate).

Figure 19A:
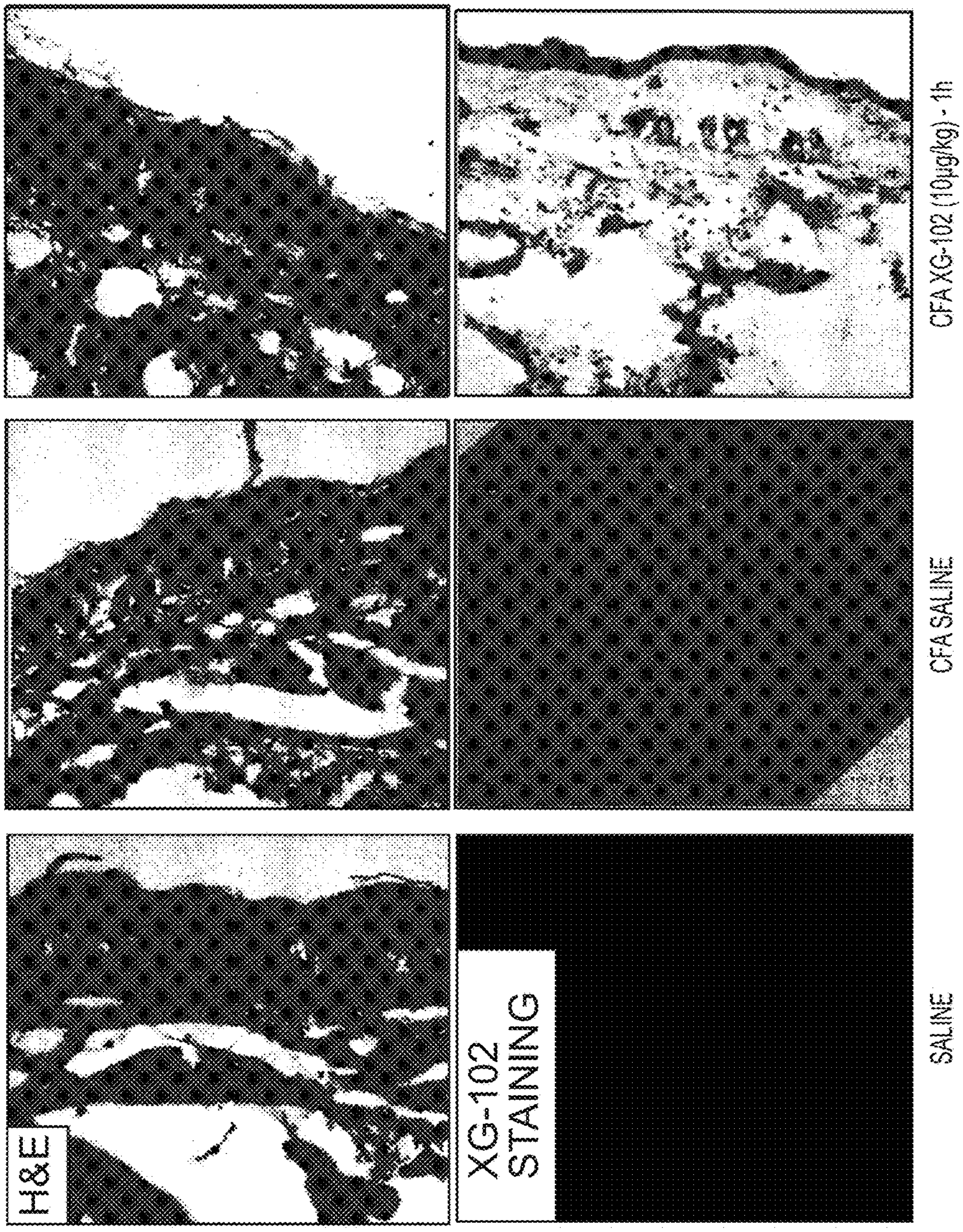
Figure 19B:
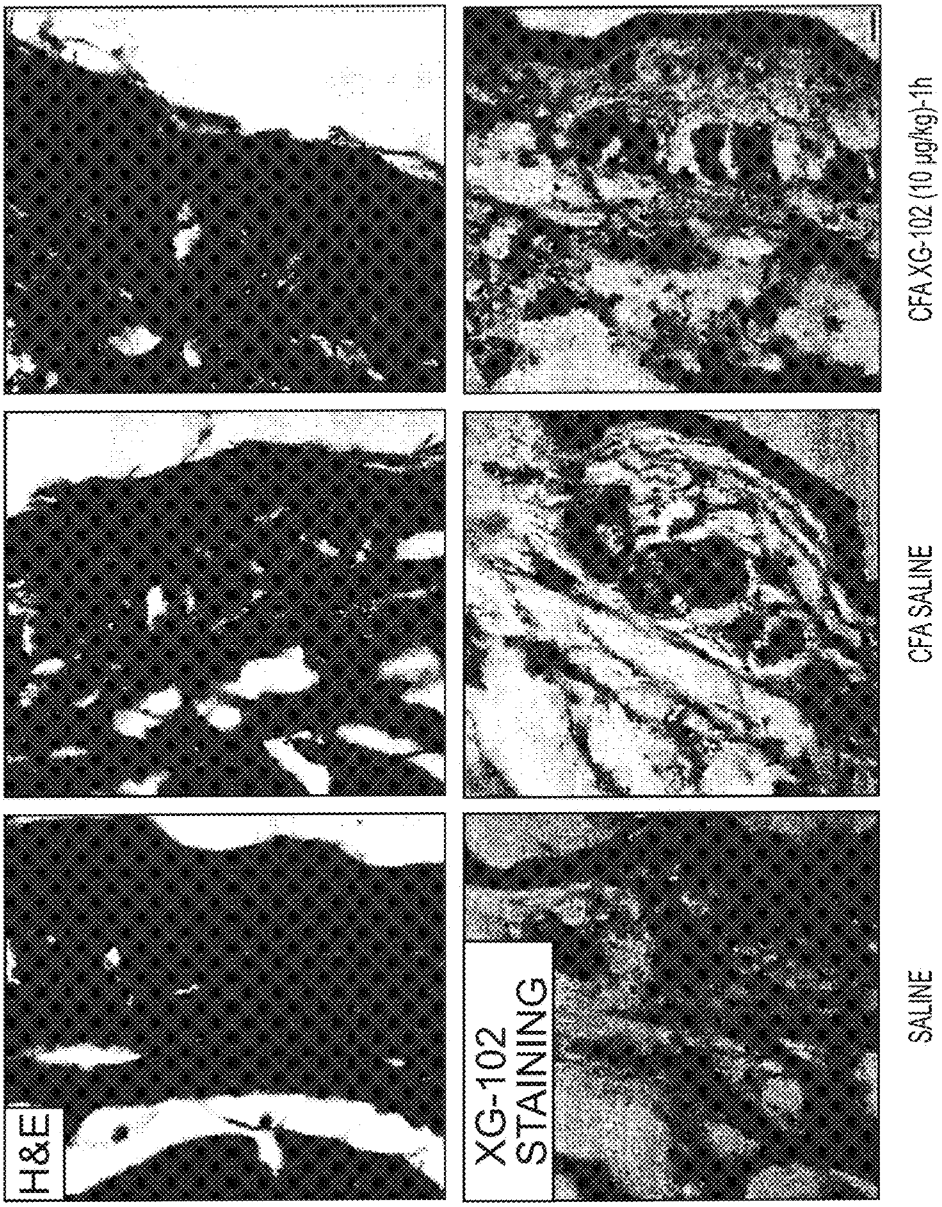
Figure 19C:

FIG. 19A, FIG. 19B, and FIG. 19C: Immunohistochemistry staining on paw from CFA-induced inflammation (4 h). Upper panels represent the Hematoxylin and Eosin (H&E) staining of hindpays. From left to right: a saline-treated animal which was not treated with CFA (Complete Freund's Adjuvant), a saline-treated animal which received CFA and a XG-102-(SEQ ID NO: 233) treated animal which also received a CFA injection. After CFA treatment, muscular and epithelial layers appear to be less organized due to edema. The presence of XG-102 (SEQ ID NO:233) positive cells was detected only in animal treated with XG-102 (upper right panel). HRP (horse radish peroxidise) staining (lower panels) revealed the presence of XG-102 in leucocytes as evidenced by the brown staining of the cells only visible in the CFA-XG-102 treated animals (lower right panel). 19A: Magnification ×20; 19B: Magnification ×40; 19C: Magnification ×100.

Figure 20A:
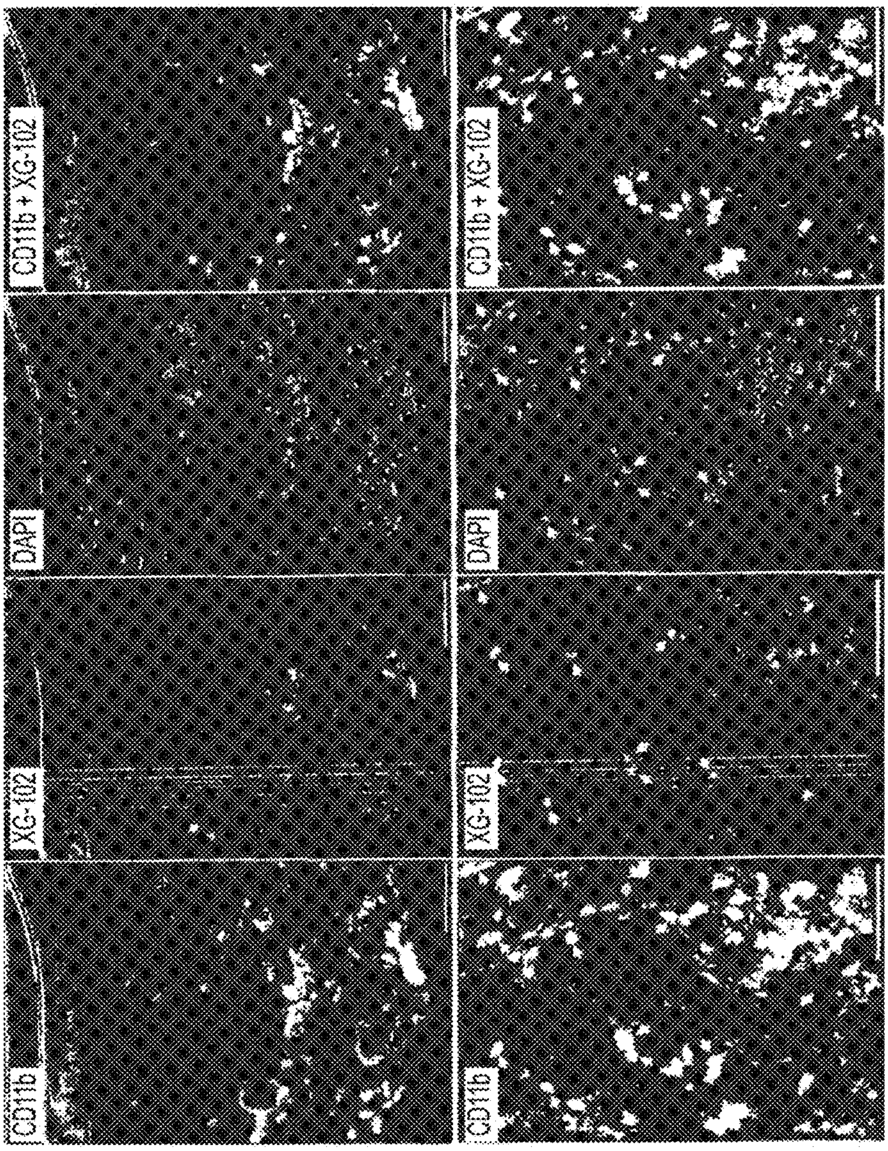
Figure 20B:
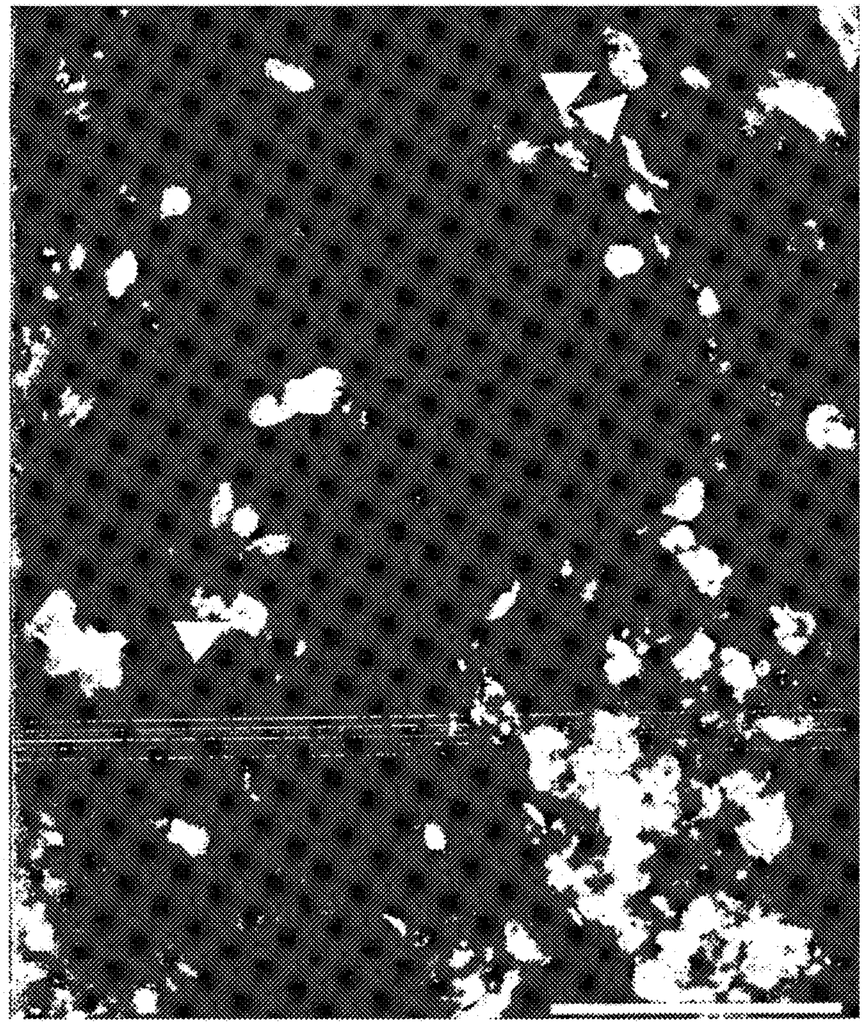
Figure 21A:
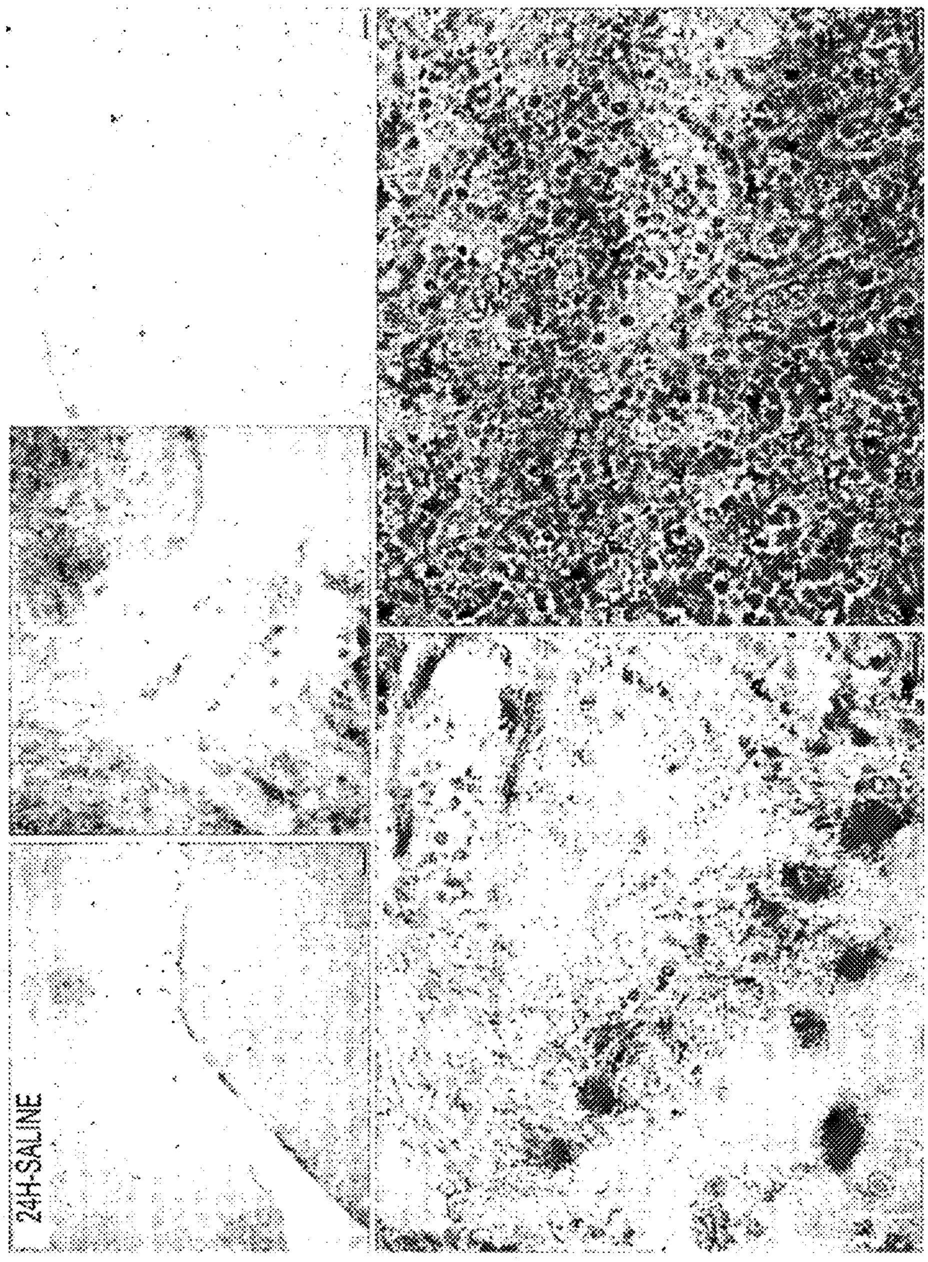
Figure 21B:
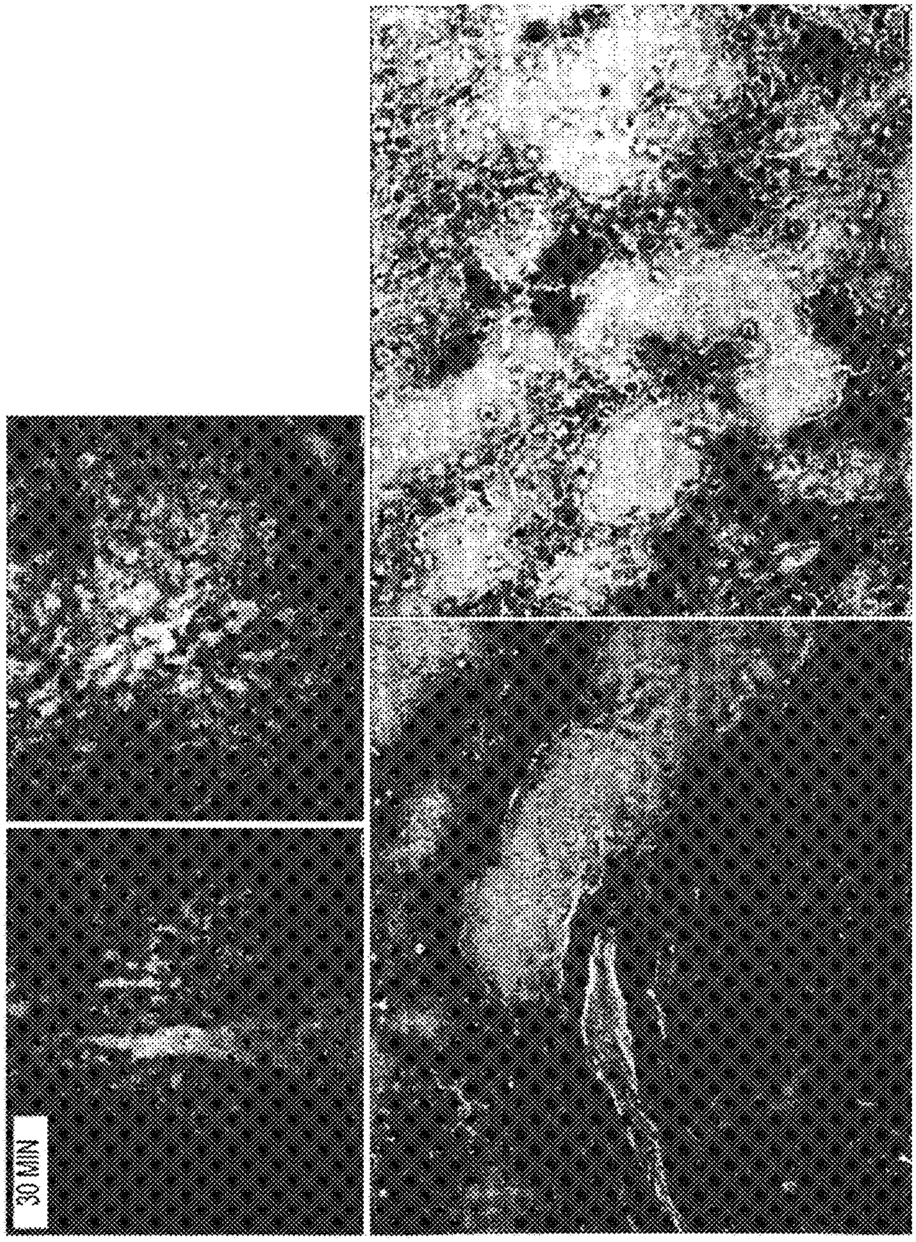
Figure 21C:
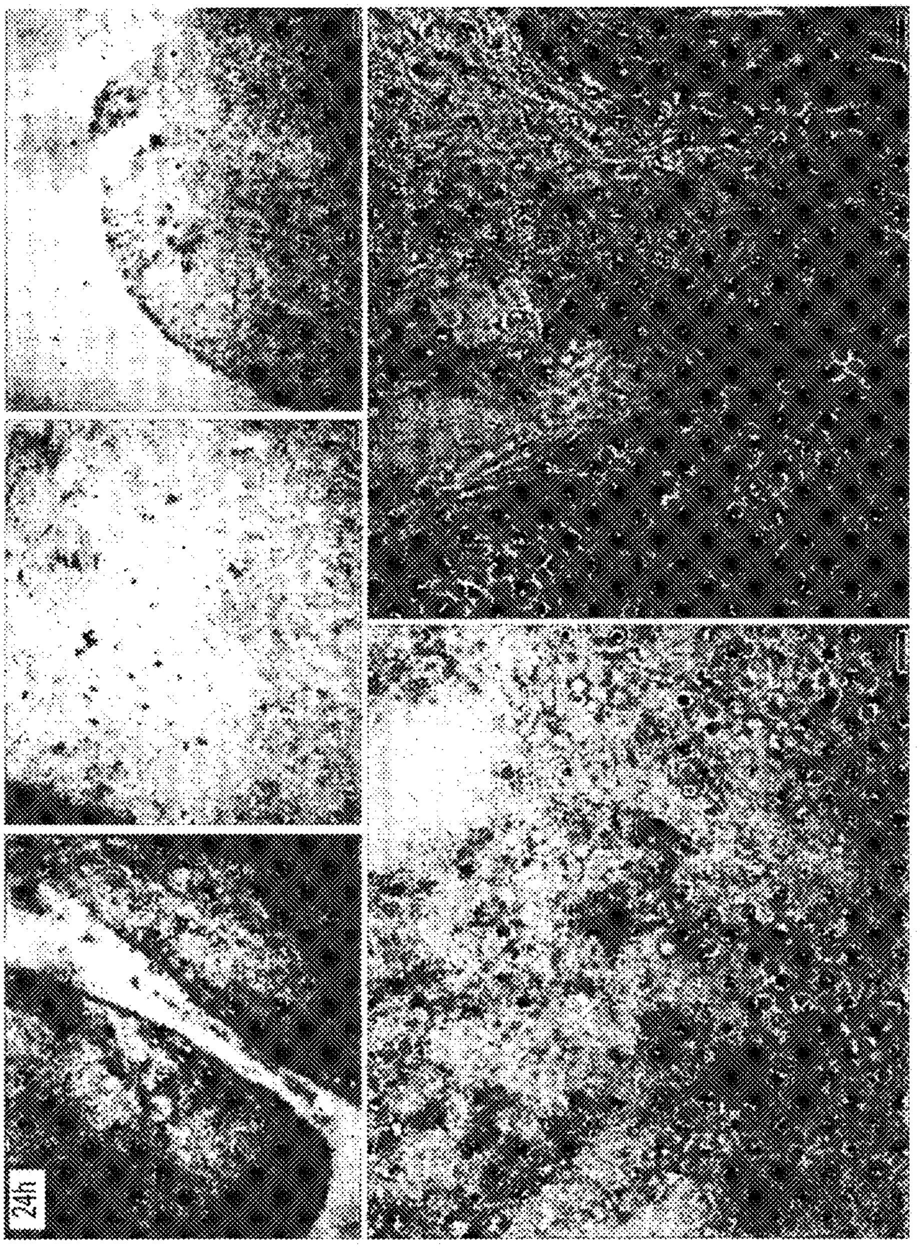
Figure 21D:
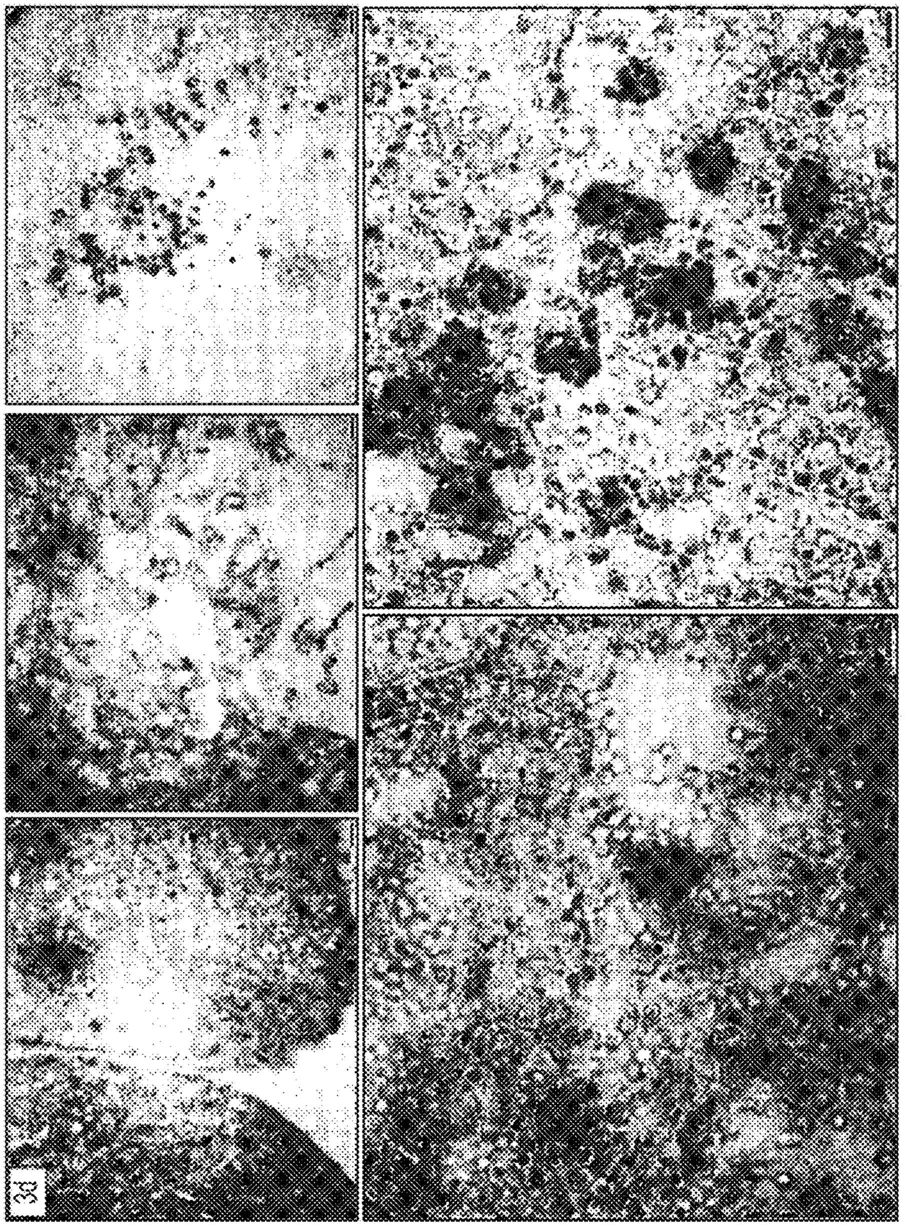
Figure 21E:
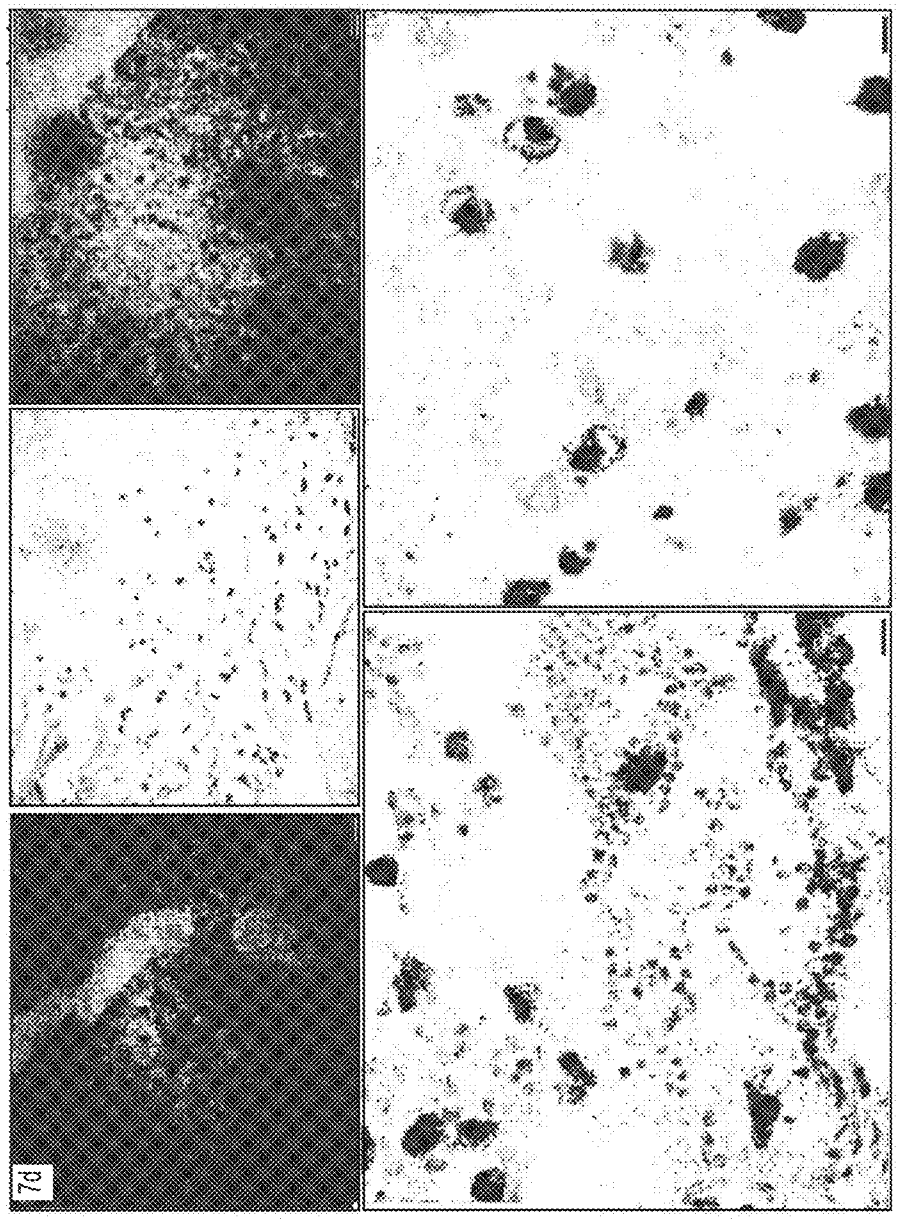
Figure 21F:
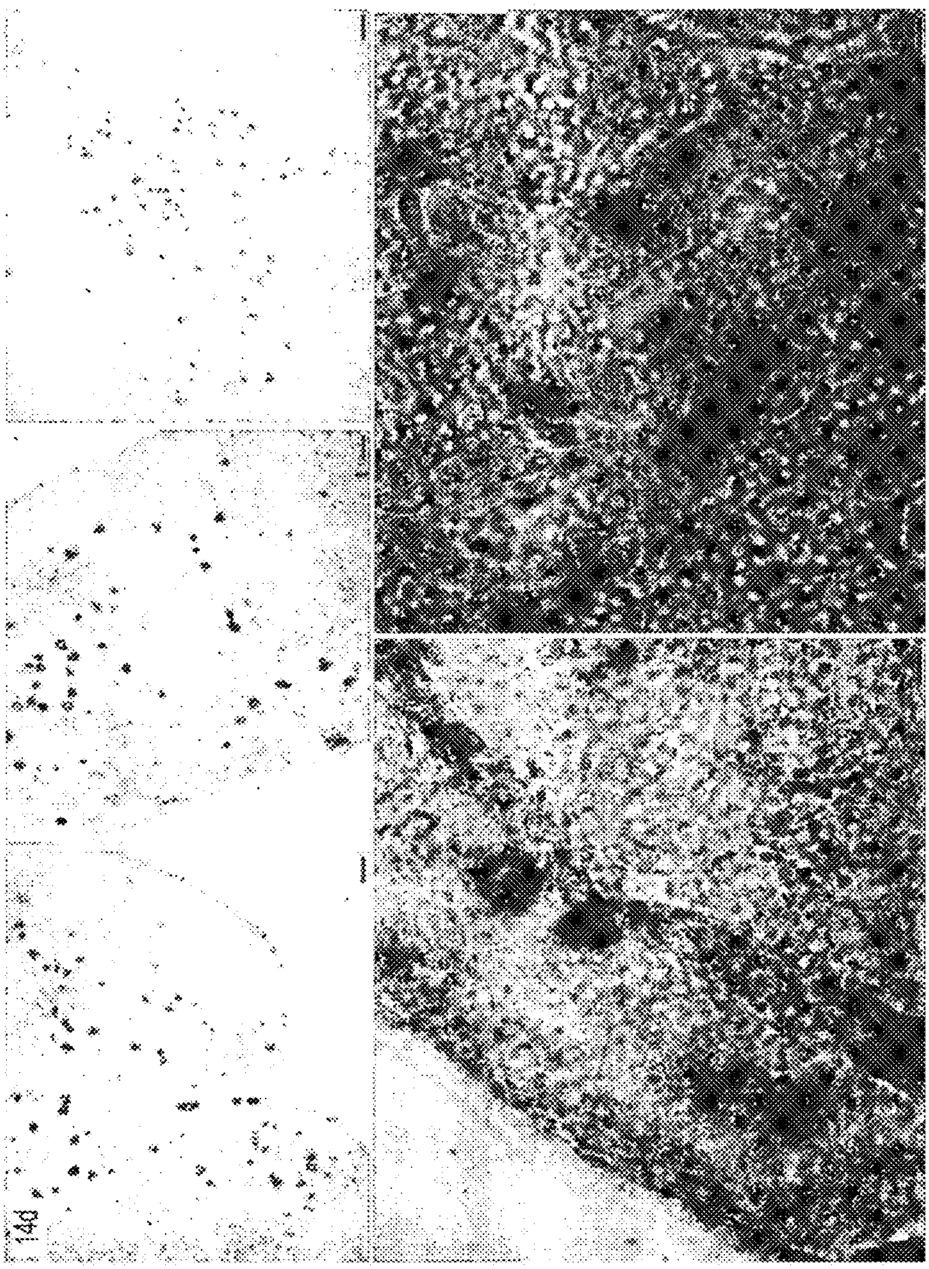
Figure 21G:
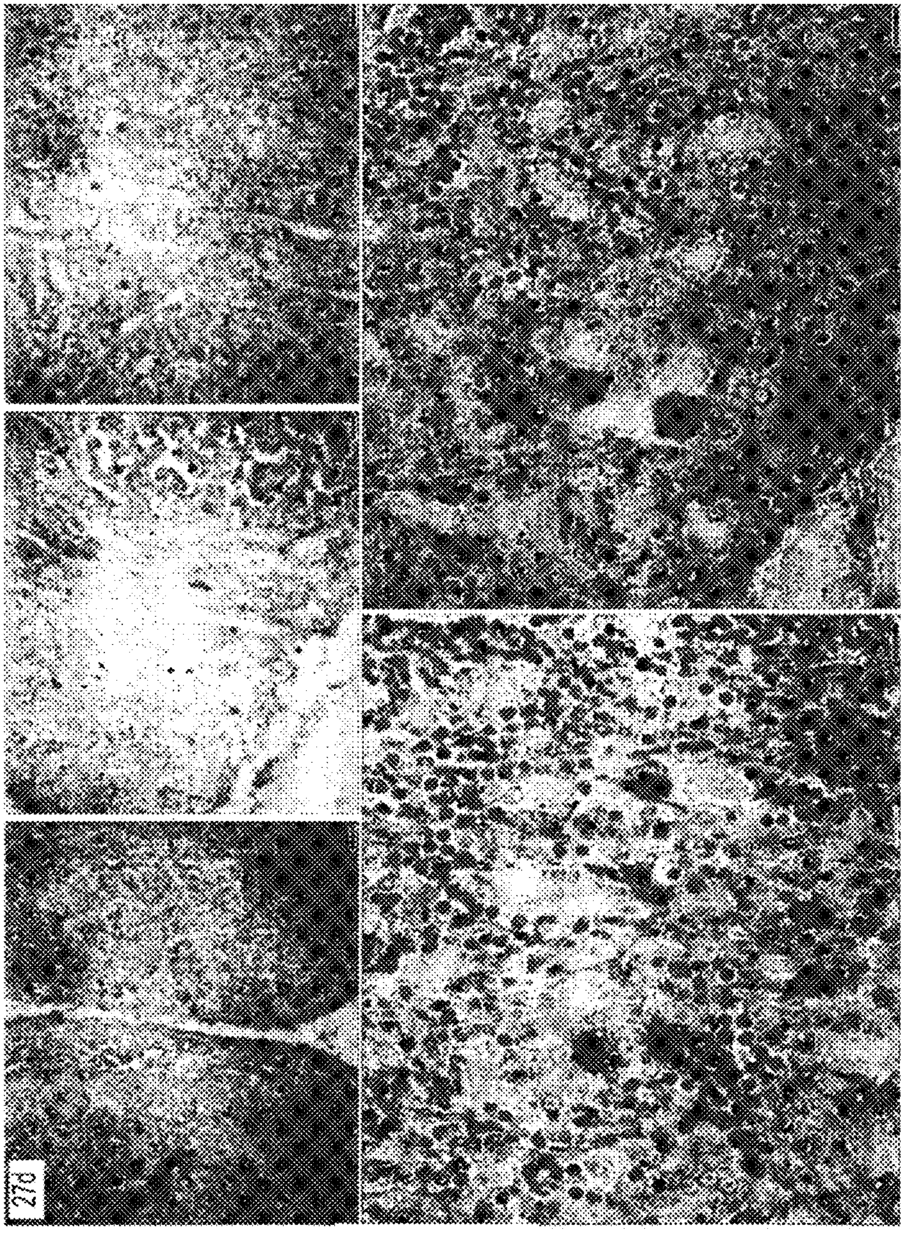

FIG. 20A and FIG. 20B: XG-102 (SEQ ID NO: 233) co-localizes with a certain leucocyte population in CFA (Complete Freund's Adjuvant) treated animal during inflammation. FIG. 20A represents the hind paw section of a CFA treated animal stained with three different dyes. The four upper panels represent the same portion at high magnification of a distal region. Distribution of the leucocyte marker (mainly granulocytes, macrophages and monocytes) cd11b (first from left) and XG-102 (SEQ ID NO: 233, second from left) as well as the Dapi nuclear stain (3rd from left) are indicated. The upper right panel represents the merge image of cd11b and XG-102 positive stain. Lower panels (higher magnification) represent another region of hind paw with edema and focuses on some selected inflammatory cells (arrows) in which leucocyte infiltration (cd11b positive cells) is clearly visible (see left lower panel). The lower right panel represents the merge image of cd11b and XG-102 positive stain. FIG. 20B is a magnification of the lower right panel of FIG. 20A.

FIG. 21A, FIG. 21B, FIG. 21C, FIG. 21D, FIG. 21E, FIG. 21F, and FIG. 21G: Study on lymph nodes—XG-102 (SEQ ID NO: 233) detection using peroxidase revelation. Composite image of several Lymph node regions (upper figures ×10 objective) which describe different structures and cell types. From left to right, the lymphatic efferent hilus, the medulla cord and the cortex. The two lower panels are representative of the medullary cord (left) and the cortex (right) (obj ×40, bar, 20 μm). 24 h saline injected animals section was used to detect the background in the presence of the anti-XG-102 (SEQ ID NO: 233) antibody. Immunostaining of lymph nodes originating from rat injected previously with XG-102 (SEQ ID NO: 233) revealed the presence of XG-102 (SEQ ID NO: 233) in leucocytes (resident and circulating macrophages mostly as indicated by XG-102 containing vacuoles) from 30 min after injection up to 28 days. 21A: 24 h saline injected animals, upper panel: ×10; bar 50 μm; lower panel: ×40; bar 20 μm; 21 B: 30 min XG-102 injected animals, upper panel: ×10; bar 50 μm; lower panel: ×40; bar 20 μm; 21C: 24 h XG-102 injected animals, upper panel: ×10; bar 50 μm; lower panel: ×40; bar 20 μm; 21D: 3 d XG-102 injected animals, upper panel: ×10; bar 50 μm; lower panel: ×40; bar 20 μm; 21E: 7 d XG-102 injected animals, upper panel: ×10; bar 50 μm; lower panel: ×40; bar 20 μm; 21F: 14 d XG-102 injected animals, upper panel: ×10; bar 50 μm; lower panel: ×40; bar 20 μm; 21G: 27 d XG-102 injected animals, upper panel: ×10; bar 50 μm; lower panel: ×40; bar 20 μm.

Figure 22A:
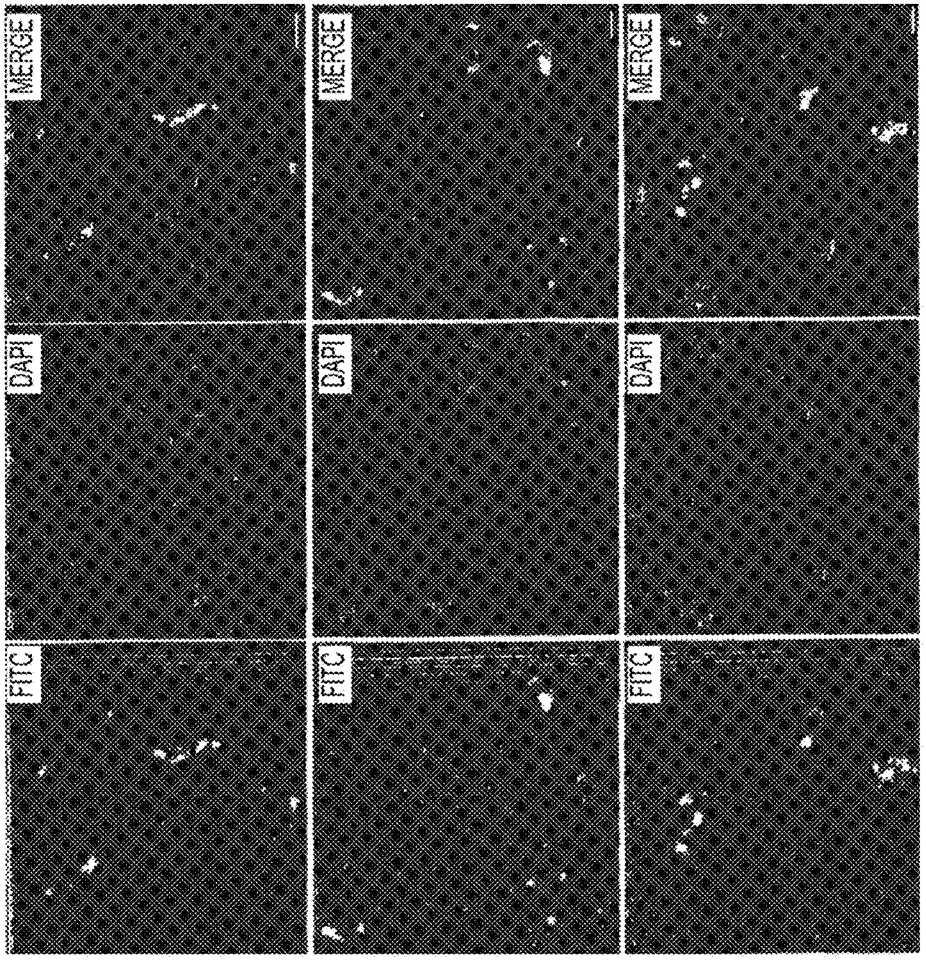
Figure 22B:
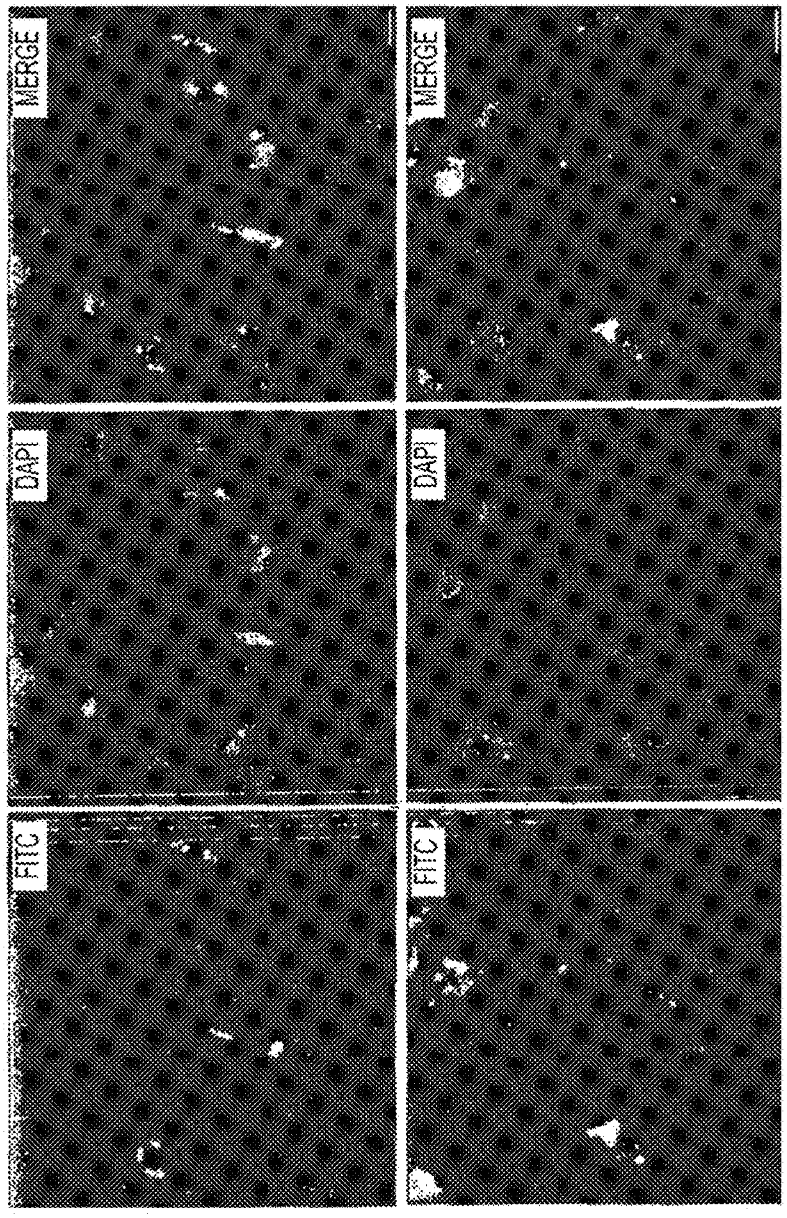

FIG. 22A and FIG. 22B: 22A: FITC-XG-102 (SEQ ID NO: 233) localization in the liver. Three cellular fields of FITC-XG-102-labelled cells isolated from liver. From left to right, FITC-labelled XG-102, corresponding DAPI nuclear stain and merge of both images. FITC staining and cellular distribution efficiently decorates Kupfer cells in contrast to hepatocytes which only show a background staining level. Typicall Kupfer cell shape and nucleus can be differentiated from hepatocytes by their shape. Small and triangle in Kupfer cells in contrast to big exagonal, well organized hepatocytes. Obj 63; bar, 20 μm. 22B: FITC-D-TAT (SEQ ID NO: 4) localization in the liver. Two cellular fields of FITC-D-TAT-labelled cells isolated from liver. From left to right, FITC-labelled XG-102, corresponding DAPI nuclear stain and merge of both images. FITC staining and cellular distribution efficiently decorates Kupfer cells in contrast to hepatocytes which only show a background staining level. Typicall Kupfer cell shape and nucleus can be differentiated from hepatocytes by their shape. Small and triangle in Kupfer cells in contrast to big exagonal, well organized hepatocytes. Obj 63; bar, 20 μm.

Figure 23A:
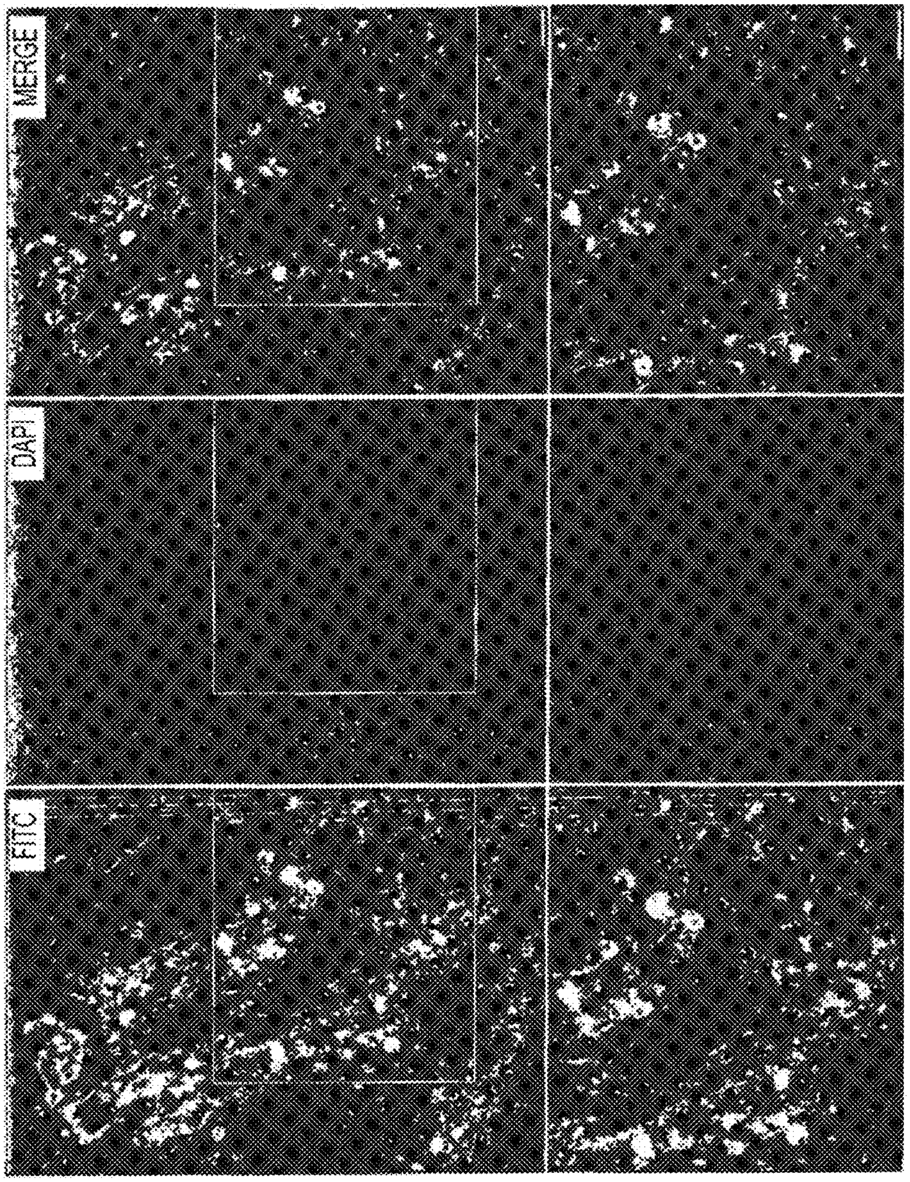
Figure 23B:
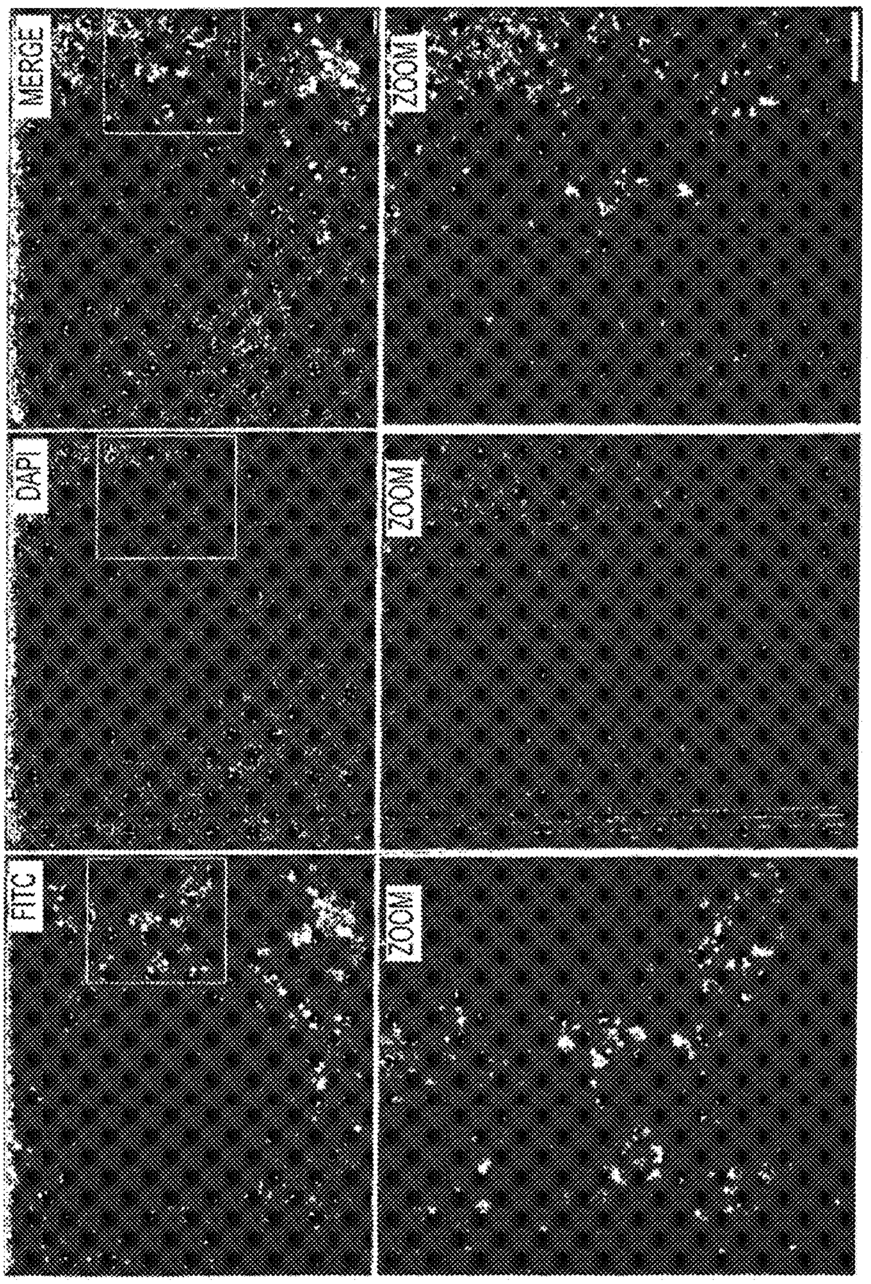

FIG. 23A and FIG. 23B: 23A: FITC-XG-102 (SEQ ID NO: 233) localization in lymph nodes. Cellular field of FITC-XG-102-labelled cells isolated from lymph nodes. Upper panels from left to right: the composite image is organized with one cellular field stained with FITC-XG-102 (left), Dapi for nuclear stain (middle) and the corresponding merged image (right). In the lower panels, a zoomed cell cluster of each image is illustrated. FITC fluorescence generously decorates the cytoplasm of FITC-positive cells which anatomically decorates subcapsular sinus macrophages and constitutive migrating alveolar macrophages. The absence of FITC staining in the lymphoid follicles allows distinguishing from the medullary corde and cortex area. Medullary zone seems to have incorporated the FITC-XG-102, composed in majority by macrophages. Obj 10; bar, 50 μm.

23B: FITC-D-TAT (SEQ ID NO: 4) localization in lymph nodes. Cellular field of FITC-D-TAT-labelled cells isolated from lymph nodes. Upper panels from left to right: the composite image is organized with one cellular field stained with FITC-D-TAT (left), Dapi for nuclear stain (middle) and the corresponding merged image (right). In the lower panels, a zoomed cell cluster of each image is illustrated. FITC fluorescence generously decorates the cytoplasm of FITC-positive cells which anatomically decorates subcapsular sinus macrophages and constitutive migrating alveolar macrophages. The absence of FITC staining in the lymphoid follicles allows distinguishing from the medullary corde and cortex area. Medullary zone seems to have incorporated the FITC-D-TAT, composed in majority by macrophages. Obj 10; bar, 50 μm.

DETAILED DESCRIPTION OF THE EMBODIMENTS

Examples

Example 1

Preparation of INK Inhibitor Fusion Proteins

JNK inhibitor fusion proteins according to SEQ ID NO: 234 (L-TAT-IB1(s) were synthesized by covalently linking the C-terminal end of SEQ ID NO: 121 to a N-terminal 10 amino acid long carrier peptide derived from the HIV-TAT4 g 57 (Vives et al, J Biol. Chem. 272: 16010 (1997)) according to SEQ ID NO: 3 via a linker consisting of two proline residues. This linker was used to allow for maximal flexibility and prevent unwanted secondary structural changes. The basic constructs were also prepared and designated L-IB1(s) (SEQ ID NO: 121) and L-TAT (SEQ ID NO: 3), respectively.

All-D retro-inverso peptides according to SEQ ID NO: 233 were synthesized accordingly. The basic constructs were also prepared and designated D-IB1(s) (SEQ ID NO: 122) and D-TAT (SEQ ID NO: 5), respectively.

All D and L fusion peptides according were produced by classical Fmock synthesis and further analysed by Mass Spectrometry. They were finally purified by HPLC. To determine the effects of the proline linker, two types of TAT peptide were produced one with and one without two prolines. The addition of the two prolines did not appear to modify the entry or the localization of the TAT peptide inside cells.

Example 2

Synthesis of All-D Retro-Inverso IB(s) Peptides and Variants Thereof

Peptides of the invention may be all-D amino acid peptides synthesized in reverse to prevent natural proteolysis (i.e. all-D retro-inverso peptides). An all-D retro-inverso peptide of the invention would provide a peptide with functional properties similar to the native peptide, wherein the side groups of the component amino acids would correspond to the native peptide alignment, but would retain a protease resistant backbone.

Retro-inverso peptides of the invention are analogs synthesized using D-amino acids by attaching the amino acids in a peptide chain such that the sequence of amino acids in the retro-inverso peptide analog is exactly opposite of that in the selected peptide which serves as the model. To illustrate, if the naturally occurring TAT protein (formed of L-amino acids) has the sequence GRKKRRQRRR (SEQ ID NO: 3), the retro-inverso peptide analog of this peptide (formed of D-amino acids) would have the sequence RRRQRRKKRG (SEQ ID NO: 5). The procedures for synthesizing a chain of D-amino acids to form the retro-inverso peptides are known in the art (see e.g. Jameson et al., Nature, 368,744-746 (1994); Brady et al., Nature, 368,692-693 (1994); Guichard et al., J. Med. Chem. 39,2030-2039 (1996)). Specifically, the retro-peptides were produced by classical F-mock synthesis and further analyzed by Mass Spectrometry. They were finally purified by HPLC.

Since an inherent problem with native peptides is degradation by natural proteases and inherent immunogenicity, the heterobivalent or heteromultivalent compounds of this invention will be prepared to include the "retro-inverso isomer" of the desired peptide. Protecting the peptide from natural proteolysis should therefore increase the effectiveness of the specific heterobivalent or heteromultivalent compound, both by prolonging half-life and decreasing the extent of the immune response aimed at actively destroying the peptides.

Example3

Long Term Biological Activity of All-D Retro-Inverso IB(s) Peptides and Variants Thereof Long term biological activity is predicted for the D-TAT-IB1(s) (XG-102; dqsrpvqpflnlttprkprpprrrqrrkkrg; SEQ ID NO: 233) retro-inverso containing peptide heteroconjugate (see chimeric sequences above) when compared to the native L-amino acid analog owing to protection of the D-TAT-IB(s) peptide from degradation by native proteases.

Inhibition of IL-1 induced pancreatic beta-cell death by the D-TAT-IB1(s) peptide was analyzed. TC-3 cells were incubated for 30 minutes with one single addition of the indicated peptides (1, μM), then IL-1 (10 ng/ml) was added.

Apoptotic cells were then counted after two days of incubation with IL-1 by use of Propidium Iodide and Hoechst 33342 nuclear staining. A minimum of 1,000 cells were counted for each experiment. The D-TAT-IB1 peptide decreased IL-1 induced apoptosis to a similar extent as L-TAT-IB peptides.

Long term inhibition of IL-1P induced cell-death by the D-TAT-IB1 peptide was also analyzed. TC-3 cells were incubated for 30 minutes with one single addition of the indicated peptides (1 μM), then IL-1 (10 ng/ml) was added, followed by addition of the cytokine every two days. Apoptotic cells were then counted after 15 days of incubation with IL-1 by use of propidium iodide and Hoechst 33342 nuclear staining. Note that one single addition of the TAT-IB1 peptide does not confer long-term protection. A minimum of 1.000 cells were counted for each experiment. As a result, D-TAT-IB1(s), but not L-TAT-IB1(s), was able to confer long term (15 day) protection.

Example 4

Evaluation of the Therapeutical Activity of D- and L-TAT-IB1(s) Peptides as Used According to the Present Invention a) Test System:

i) Species/Strain: Mouse/BALB/c ii) Source: Harlan Israel, Ltd.

iii) Gender: Female iv) Total No. of Animals: n=150 v) Age: Young adults, 7 weeks of age at study initiation vi) Body Weight: Weight variation of animals at the time of treatment initiation does not exceed ±20% of the mean weight.

vii) Animals Health: The health status of the animals used in this study is examined on arrival; only animals in good health are acclimatized to laboratory conditions (at least seven days) and are used in the study.

viii) Randomization: Animals are randomly assigned to experimental groups according to a Table of Random Numbers.

ix) Termination: At the end of the study surviving animals are euthanized by cercical dislocation.

b) Constitution of Test Groups and Dose Levels

The table below lists the experimental groups comprising the study.

| Group # | Group size | Test Item | Route | Dose | Volume (ml/kg) | Regime |
|---|---|---|---|---|---|---|
| 1F | N = 10 | Vehicle | PO | 0 | 5 | Once daily for 7 days |
| 2F | N = 10 | Sulfasalazine | PO | 10 mg/kg | 5 | Once daily for 7 days |
| 3F | N = 10 | Remicade | IP | 5 mg/kg | 5 | Once daily for 7 days |
| 4F | N = 10 | XG-102 | SC | 0.01 μg/kg | 5 | Once daily for 7 days |
| 5F | N = 10 | XG-102 | SC | 0.1 μg/kg | 5 | Once daily for 7 days |
| 6F | N = 10 | XG-102 | SC | 1 μg/kg | 5 | Once daily for 7 days |
| 7F | N = 10 | XG-102 | SC | 10 μg/kg | 5 | Once daily for 7 days |
| 8F | N = 10 | XG-102 | SC | 100 μg/kg | 5 | Once daily for 7 days |
| 9F | N = 10 | XG-102 | SC | 1000 μg/kg | 5 | Once daily for 7 days |
| 10F | N = 10 | XG-102 | SC | 1 μg/kg | 5 | Single dose |
| 11F | N = 10 | XG-102 | SC | 100 μg/kg | 5 | Single dose |
| 12F | N = 10 | XG-102 | PO | 1 μg/kg | 5 | Once daily for 7 days |
| 13F | N = 10 | XG-102 | PO | 100 μg/kg | 5 | Once daily for 7 days |
| 14F | N = 10 | XG-102 | PO | 1 μg/kg | 5 | Single dose |
| 15F | N = 10 | XG-102 | PO | 100 μg/kg | 5 | Single dose |

XG-102 = SEQ ID NO: 233

IP = intraperitoneal administration

PO = peroral administration

SC = subcutaneous administration c) Test Procedures

Colitis was induced by administration of TNBS dissolved in 50% Ethanol

All animals were then treated with doses of XG-102 in the range of 0.1 to 1000 μg/kg, either intraperitoneally or subcutaneously, as a single or repeated daily doses (see above).

d) Observations and Examinations i) Clinical Signs

Throughout the duration of the above experiment, careful clinical examinations were carried out and recorded. Observations included changes external appearance, e.g. of the skin, fur, eyes, mucous membranes, occurrence of secretions and excretions (e.g. diarrhea), and autonomic activity. Changes in gait, posture and response to handling, as well as the presence of bizarre behavior, tremors, convulsions, sleep and coma were also noted.

ii) Body Weights

Determination of individual body weight of animals was made on a daily basis.

iii) Clinical Assessment of Colitis

Body weight, stool consistency and bleeding per rectum were all recorded daily and served as the parameters of disease severity score:

| Score | Weight loss (%) | Stool consistency | Presence of blood per rectum |
|---|---|---|---|
| 0 | None | Normal | Negative |
| 1 | 1-5 | Redness, swelling of the anus | Negative |
| 2 | 5-10 | Loose stool | Negative |
| 3 | 10-15 | Diarrhea | Negative |
| 4 | >15 | Diarrhea | Bleeding |
| 5 | | Death | |

iv) Gross Pathology of the Colon

On the last day of the experiment, animals were euthanized and the colon was removed for gross pathology evaluation according to the following score:

| Grade | Signs |
|---|---|
| 0 | No abnormalities detected |
| 1 | Edema and redness on one location |
| 2 | Edema and redness on more than one location, or a very massive endema and redness capture more than 50% of the colon |
| 3 | One ulcer |
| 4 | More than one ulcer or a very long severe ulcer |

e) Results i) Clinical Signs

No abnormalities were observed during clinical examinations following the treatment with XG-102 (SEQ ID NO: 233).

ii) Mortality Rate

No mortality was recorded.

iii) Body Weights

TNBS induced a significant weight loss on day 1. XG-102 (SEQ ID NO: 233) administration either prevented the weight loss or ameliorated the symptoms and supported recovery.

iv) Clinical Score

TNBS injected vehicle treated animals reached a maximum score on study day 1 and recovered fully only on or after study day 5. Sulfasalazine treatment resulted in reduction in the clinical score. XG-102 (SEQ ID NO: 233), administered using any dose, route or time schedule as defined above (single dose or daily dose) resulted in an effect equivalent to or better than the one observed with the commonly used reference drug sulfasalazine.

v) Cross Pathology Score

Gross analysis at the end of the study revealed that the TNBS injected vehicle treated animals were injured with edema and ulcers along the colon. Sulfasalazine was effective in reducing the gross pathology completely.

vi) Colon Length

No effect of disease induction or treatment was observed on colon length.

vii) Colon Weight

No effect of disease induction or treatment was observed on colon weight.

f) Conclusions

In view of the above findings obtained under the conditions of the above experiment and confined to the in-life data, the exemplary sequence XG-102 according to SEQ ID NO: 233 administered either SC or PO was active in enhancing diseases recovery.

Example 5

Determining the Activity of All-D Retro-Inverso IB(s) Peptides and Variants Thereof in the Treatment of Chronic Obstructive Pulmonary Disease (COPD)

In order to determine the activity of the exemplary all-D retro-inverso IB(s) peptide XG-102 (SEQ ID NO: 233) in the treatment of Chronic Obstructive Pulmonary Disease (COPD) XG-102 (SEQ ID NO: 233) is used in an animal model of Bleomycin induced acute lung inflammation and fibrosis. The protocol of bleomycin induced inflammation and fibrosis has been described before in the literature. The aim of the Experiment was to investigate the effect of XG-102 (SEQ ID NO: 233) by subcutaneous (s.c.) route on neutrophil recruitment in broncho alveolar lavage (BAL) and lung in bleomycin induced inflammation and fibrosis:

at 1 day after a single bleomycin administration (10 mg/kg)

and at day 10 with the development of fibrosis

1) Method and Experimental Approach

The test compound XG-102 (SEQ ID NO: 233) at two doses and vehicle control were given s.c. with a single intranasal administration of bleomycin and mice were analyzed after 1 and 10 days. The animals used in the model were 10 C57BL/6 mice (8 weeks old) per group. The experimental groups included vehicle, 0.001 mg/kg XG-102 (SEQ ID NO: 233) and 0.1 mg/kg XG-102 (SEQ ID NO: 233), and the treatment consisted of repeated sub-cutaneous administration of XG-102 (SEQ ID NO: 233), prior to bleomycin administration then every 3 days. Acute lung inflammation at 24 h was monitored by BAL lavage, cytology, cell counts, and lung myeloperoxidase activity. The effect of the compound was compared with vehicle controls. Lung fibrosis was assessed histologically using hematoxylin and eosin staining at day 10 after the single dose of bleomycin.

1.1) Bleomycin Administration

Bleomycin sulfate in saline (10 mg/kg body weight) from Bellon Laboratories (Montrouge, France) or saline were given through the airways by nasal instillation in a volume of 40 μL under light ketamine-xylasine anesthesia. The groups for Bleomycin administration for both bleomycin induced inflammation and fibrosis included: Vehicle, 0.001 mg/kg XG-102 (SEQ ID NO: 233) and 0.1 mg/kg XG-102 (SEQ ID NO: 233). The route for bleomycin induced inflammation was subcutaneous (s.c.) route, and administration occurred as a single dose. The route for bleomycin induced fibrosis was subcutaneous (s.c.) route, and administration occurred 3 times in 10 days.

1.2) Bronchoalveolar Lavage Fluid (BALE)

After incision of the trachea, a plastic cannula was inserted and airspaces were washed using 0.3 ml of PBS solution, heated to 37° C. The samples collected were dispatched in 2 fractions: the first one (1 ml corresponding to the 2 first lavages) was used for mediator measurement and the second one for the cell determination (4 ml). The first fraction was centrifuged (600 g for 10 min) and supernatant was fractionated and kept at −80° C. until mediator determination. The cell pellet was then resuspended in 0.4 ml sterile NaCl, 0,9%, and pooled with the second fraction and was used for cell counts.

1.3) Lung Homogenization

After BAL the whole lung was removed and placed inside a microtube (Lysing matrix D, Q Bio Gene, Illkrich, France) with 1 ml of PBS, total lung tissue extract was prepared using a Fastprep® system (FP120, Q Bio Gene, Illkrich, France), the extract was then centrifuged and the supernatant stored at −80° C. before mediator measurement and collagen assay with Sircol Collagen Assay (France Biochem Division, France).

1.4) Cell Count and Determination

Total cell count was determined in BAL fluid using a Malassez hemocytometer. Differential cell counts were performed on cytospin preparations (Cytospin 3, Thermo Shandon) after staining with MGG Diff-quick (Dade Behring AG). Differential cell counts were made on 200 cells using standard morphological criteria.

1.5) TNF Measurement

TNF level in BALF was determined using ELISA assay kits (Mouse DuoSet, R&D system, Minneapolis, USA) according to manufacturer's instructions. Results are reported as pg/ml.

1.6) MPO-Measurement

MPO-levels were measured upon administration of XG-102. MPO was not significantly induced after bleomycin in this experiment. Furthermore, XG-102 had no effect on MPO levels in the lung.

1.7) Histology

After BAL and lung perfusion, the large lobe was fixed in 4% buffered formaldehyde for standard microscopic analysis. 3-m sections were stained with hematoxylin and eosin (H&E).

2.) Results

A) First Study: Bleomycin (BLM) Induced Acute Lung Inflammation

Groups: Vehicle, XG-102 (SEQ ID NO: 233) 0.001 mg/kg and XG-102 (SEQ ID NO: 233) 0.1 mg/kg Route: s.c. route, single dose a) Cell Recruitment in Bronchoalveolar Lavage Space At 0.1 mg/kg, XG-102 (SEQ ID NO: 233) reduces significantly the neutrophil recruitment and the number of total cells recruited during the inflammatory stage. At 0.001 mg/kg, XG-102 (SEQ ID NO: 233) has no effect on neutrophil recruitment or other cell types into the bronchoalveolar space (one representative experiment with n=5 mice per group; *, $p<0.05$; **, $p<0.001$).

b) Cell Recruitment in Lung Using MPO in Lung Homogenization

Myeloperoxidase (MPO) plays an important role in host defense systems. This 140 kDa protein, composed of two heavy chains of 53 kDa and two light chains of 15 kDa, was first discovered in the 1960s. The release of MPO from the granules of neutrophils and monocytes in response to the activation of leukocytes allows the conversion of hydrogen peroxide and chloride ions into hypochlorous acid (HOCl), a strong oxidizing agent. Although MPO serves an important purpose in the defense system, various studies show that MPO also plays a role in several inflammatory conditions, wherein an elevated MPO level e.g. has been linked to coronary artery diseases. Furthermore, tissue MPO levels reflect the state of activation of neutrophils and gives an indication on neutrophil tissue infiltration.

In the present experiment, MPO was not significantly induced after bleomycin administration. XG-102 (SEQ ID NO: 233) had thus no effect on the MPO levels in the lung.

c) TNF Measurement

When measuring TNF levels, a trend to reduction of the TNF level in BALF after administration of XG-102 (SEQ ID NO: 233) was observed, although TNF levels were very low after BLM administration.

d) Conclusion

It could be observed that at 0.1 mg/kg, XG-102 (SEQ ID NO: 233) decreases the neutrophil and total cell recruitment into the bronchoalveolar space and induces a trend to decrease the TNF level. Moreover, the study of the histological slides showed a decrease of the inflammatory cell accumulation in the peribronchial space. It can thus be concluded that XG-102 (SEQ ID NO: 233) reduces the Bleomycin-induced inflammation.

According to the acquired results, the experiment was additionally performed in a fibrosis model.

B) Second Study: Bleomycin (BLM) Induced Lung Fibrosis

Groups: Vehicle, XG-102 (SEQ ID NO: 233) 0.001 mg/kg and XG-102 (SEQ ID NO: 233) 0.1 mg/kg Route: s.c. route, 3 times in 10 days a) Cell Recruitment in Bronchoalveolar Lavage Space At 0.001 mg/kg, XG-102 (SEQ ID NO: 233) reduced significantly the lymphocyte recruitment and the number of total cells recruited during the inflammatory stage characterised at this point by the lymphocytes recruitment. At 0.1 mg/kg, XG-102 (SEQ ID NO: 233) had no effect (n=5 mice per group; *, $p<0.05$; **, $p<0.001$).

a) Histology

3 μm sections of lungs were stained with haematoxylin and eosin. Inflammatory cells accumulation, fibrotic areas, loss of lung architecture were observed 10 days after BLM administration. A decrease of these parameters was observed after administration of XG-102 at the low dose (0.001 mg/kg) but not with the high dose (0.1 mg/kg).

b) Conclusion:

It can be concluded that XG-102 (SEQ ID NO: 233) administered 3 times at the low dose of 0,001 mg/kg decreases the Bleomycin-induced later inflammation, in particular the lymphocytes recruitment observed at this time. Moreover, the test substance administered 3 times at this dose attenuates the Bleomycin-induced fibrosis. Less extended fibrotic areas with a more conserved lung structure could be observed.

Example 6

Determining the Activity of All-D Retro-Inverso IB(s) Peptides and Variants Thereof in the Treatment of Alzheimer's Disease In order to determine the activity of the exemplary all-D retro-inverso IB(s) peptide XG-102 (SEQ ID NO: 233) in Alzheimer's disease, XG-102 (SEQ ID NO: 233) was evaluated in the hAPP-transgenic mice model overexpressing APP751 with London and Swedish mutations using the behavioral Morris Water Maze test as well as immunohistological tests measuring plaque load and ELISA tests measuring β-amyloid$_{1-40}$ and β-amyloid$_{1-42}$ levels in the brain of mice.

a) METHODS i) Introduction

The study was designed to evaluate the efficacy of the test substance (XG-102, SEQ ID NO: 233) on behavioral, biochemical and histological markers using 5 months (±2 weeks) old female hAPP Tg mice. Therefore, mice were treated every two or three weeks up to 4 months and in the end of the treatment period behavior was evaluated in the Morris Water Maze. At sacrifice brain, CSF and blood were collected. Aβ40 and Aβ42 levels were determined in four different brain homogenate fractions as well as in CSF of Tg mice. Plaque load was quantified in the cortex and the hippocampus of 8 Tg animals per treatment group.

ii) Animals

Female Tg mice with a C57BU6xDBA background and an age of 5 months (±2 week) were randomly assigned to treatment groups 1 to 3 (n=12). Animals were subjected to administration of vehicle or XG-102 (SEQ ID NO: 233) in two different concentrations beginning at 5 months of age and continued for up to 4 months with subcutaneous (s.c.) applications every second or third week. All animals which were used for the present study had dark eyes and were likely to perceive the landmarks outside the MWM pool. However, it had to be excluded that seeing abilities of an animal were poor, which was controlled in the visible platform training, the so called pretest, before treatment start for all animals including reserves enclosed to the study. In case a seeing handicap for a specific animal would have been affirmed, the mouse would have been excluded from the study.

iii) Animal Identification and Housing

Mice were individually identified by ear markings. They were housed in individual ventilated cages (IVCs) on standardized rodent bedding supplied by Rettenmaier®. Each cage contained a maximum of five mice. Mice were kept according to the JSW Standard Operating Procedures (SOP GEN011) written on the basis of international standards. Each cage was identified by a colored card indicating the study number, sex, the individual registration numbers (IRN) of the animals, date of birth, as well as the screening date and the treatment group allocation. The temperature during the study was maintained at approximately 24° C. and the relative humidity was maintained at approximately 40-70%. Animals were housed under a constant light-cycle (12 hours light/dark). Normal tap water was available to the animals ad libitum.

iv) Treatment

Forty female hAPP transgenic mice were treated with either 0.1 mg/kg b.w./every two weeks or 10 mg/kg b.w./every three weeks of the test substance XG-102 (SEQ ID NO: 233) in two different dosages (n=12/group) or treated with the vehicle (n=12) s.c. once every three weeks over four months.

v) Morris Water Maze (MWM)

The Morris Water Maze (MWM) task was conducted in a black circular pool of a diameter of 100 cm. Tap water was filled in with a temperature of 22±1° C. and the pool was virtually divided into four sectors. A transparent platform (8 cm diameter) was placed about 0.5 cm beneath the water surface. During the whole test session, except the pretest, the platform was located in the southwest quadrant of the pool. One day before the 4 days lasting training session animals had to perform a so called "pre-test" (two 60 sec lasting trials) to ensure that the seeing abilities of each animal were normal. Only animals that fulfilled this task were enclosed to the MWM testing. In the MWM task each mouse had to perform three trials on four consecutive days. A single trial lasted for a maximum of maximum one minute. During this time, the mouse had the chance to find the hidden, diaphanous target. If the animal could not find a "way" out of the water, the investigator guided to or placed the mouse on the platform. After each trial mice were allowed to rest on the platform for 10-15 sec. During this time, the mice had the possibility to orientate in the surrounding. Investigations took place under dimmed light conditions, to prevent the tracking system from negative influences (Kaminski; PCS, Biomedical Research Systems). On the walls surrounding the pool, posters with black, bold geometric symbols (e.g. a circle and a square) were fixed which the mice could use the symbols as landmarks for their orientation. One swimming group per trial consisted of five to six mice, so that an intertrial time of about five to ten minutes was ensured. For the quantification of escape latency (the time [second]—the mouse needed to find the hidden platform and therefore to escape from the water), of pathway (the length of the trajectory [meter] to reach the target) and of the abidance in the goal quadrant a computerized tracking system was used. The computer was connected to a camera placed above the centre of the pool. The camera detected the signal of the light emitting diode (LED), which was fixed with a little hairgrip on the mouse's tail. One hour after the last trial on day 4 the mice had to fulfill a so-called probe trial. At this time, the platform was removed from the pool and during the one-minute probe trial; the experimenter counted the number of crossings over the former target position. Additionally the abidance in this quadrant as well as the three other quadrants was calculated. Through out this trial a mouse could not get any, howsoever-natured, clue from the platform.

vi) Tissue Sampling

At the end of the treatment period, and following all behavioral testing, all remaining mice (n=28) were sacrificed. Therefore, all mice were sedated by standard inhalation anesthesia (Isofluran, Baxter) as described in SOP MET030. Cerebrospinal fluid (CSF) was obtained by blunt dissection and exposure of the foramen magnum. Upon exposure, a Pasteur pipette was inserted to the approximate depth of 0.3-1 mm into the foramen magnum. CSF was collected by suctioning and capillary action until flow fully ceases. Two aliquots of each sample were immediately frozen and kept at −80° C. until ready for further analysis with ELISA technique. After CSF sampling, each mouse was placed in dorsal recumbence, thorax was opened and a 26-gauge needle attached to a 1 cc syringe was inserted into the right cardiac ventricular chamber. Light suction was applied to the needle and blood was collected into EDTA and consequently used to obtain plasma. To get plasma, blood samples from each mouse were spun at 1,750 rpm (700 g) for 10 minutes in a centrifuge (GS-6R Beckman) using a rotor with swing buckets (GH-3.8 Beckman). Plasma was frozen and stored at −20° C. until further analysis. After blood sampling transgenic mice were intracardially perfused with 0.9% sodium chloride. Brains were rapidly removed the cerebellum was cut off. The right hemispheres of all mice were immersion fixed in freshly produced 4% Paraformaldehyde/PBS (pH 7.4) for one hour at room temperature. Thereafter brains were transferred to a 15% sucrose PBS solution for 24 hours to ensure cryoprotection. On the next day brains were frozen in isopentane and stored at −80° C. until used for histological investigations (SOP MET042). The left hemispheres were weighed and frozen in liquid nitrogen and stored at −80° C. for biochemical analysis.

vii) Determination of $A\beta_{1-40}$ and $A\beta_{1-42}$

In four different brain homogenate fractions of each Tg mouse as well as in CSF samples the $A\beta_{1-40}$ and $A\beta_{1-42}$ levels were evaluated with ELISA technique. Highly sensitive $A\beta_{1-40}$ and $A\beta_{1-42}$, ELISA test kits were purchased from *The Genetics Company*™, Switzerland (SOP MET058). CSF was prepared as described above. For the brain homogenates frozen hemispheres were homogenized in TRIS buffered saline (TBS)—buffer (5 ml) containing protease inhibitor cocktail. 1.25 ml of this initial brain TBS homogenate was stored at −80° C., 1.25 ml have been further investigatated. The remaining brain homogenate (2.5 ml) was centrifuged and the resulting supernatant (=TBS fraction) was aliquoted and kept at −20° C. until ELISA determination. The pellet was suspended in Triton X-100 (2.5 ml), centrifuged and the supernatant (=Triton X-100 fraction) was aliquoted and kept at −20° C. These steps were repeated with SDS (2.5 ml). The pellet out of the SDS fraction was suspended in 70% formic acid (0.5 ml) prior to subsequent centrifugation. The obtained supernatant was neutralized with 1 M TRIS (9.5 ml) aliquoted and kept at −20° C. (=FA fraction). Samples of the four brain homogenate fraction (TBS, Triton X-100, SDS, and FA) were used for $A\beta_{1-40}$ and $A\beta_{1-42}$ determination with ELISA technique. ELISA test kits were purchased from *The Genetics Company*™, Switzerland (SOP MET062). It could be assumed that TBS and Triton X-100 solubilize monomeric to oligomeric structures. Polymers like protofibrils and water insoluble fibrils could be dissolved in SDS and FA. In this regard the investigation of all four fractions also provides insight in A polymerization status.

viii) Evaluation of Brain Morphology

Brain tissues of all Tg animals investigated were handled in exactly the same way to avoid bias due to variation of this procedure. From brain halves of 24 Tg mice (8 of each group) 20 cryo-sections per layer (altogether 5 layers), each 10 μm thick (Leica CM 3050S) were sagittally cut and 5 (one from each layer) were processed and evaluated for quantification of plaque load. The five sagittal layers corresponded with the FIGS. 104 to 105, 107 to 108, 111 to 112, 115 to 116 and 118 to 119 according to the morphology atlas "The Mouse Brain" from Paxinos and Franklin (2nd edition). The first layer was specified by the requirement to include the whole hippocampus with it's regions CA1, CA2, CA3, GDlb and GDmb. Immunoreactivity was quantitatively evaluated in the hippocampus and in the cortex using the monoclonal human Aβ-specific antibody 6E10 (Signet) as well as ThioflavinS staining. Remaining brain hemispheres or tissue not used were saved and stored at JSW CNS until the end of the project.

b) Evaluation i) Behavior

In the Morris Water Maze trials length of swimming path, escape latencies, swimming speed and in the probe trial crossings over the former platform position and the time spent in each quadrant of the pool were measured for each Tg animal with a special computer software.

ii) Biochemical Evaluation

From all Tg mice CSF samples as well as samples from the brain preparations were analyzed with commercially available $A\beta_{1-40}$ and $A\beta_{1-42}$ ELISAs. Measurements of adequate standards were performed concurrently. Samples from brain preparations were analyzed in duplicates. Due to the small sample amount CSF samples were analyzed in a single measurement only.

iii) Histology i1) Measurement of Amyloid Depositions and Plaque Load

For 6E10 immunohistochemistry the following evaluation procedure was used:

aa) Contrasting the image for visualization of slice borders without applying the contrast on the image.

bb) Interactive drawing of the cortical outlines and the following measurement of the cortical area (=region area).

cc) Interactive drawing of the area of interest (AOI), in which stained objects are detected over a certain intensity based threshold level (the same for each image) and above a size of 8 $\mu m^2$.

dd) Measurement of the area of each object, the sum of stained area in the A01 as well as the number of objects after a smooth contrasting to enhance signal/noise ratio (the same for each image).

ee) Repetition of aa)-dd) for the hippocampus.

ff) Calculation of the mean plaque size (="sum area of plaques/number of plaques"), the relative plaque number and area (="number of plaques/region area" and "sum area of plaques/region area*100").

gg) Automated data export into an Excel spread sheet, including the parameters "image title, region area, number of plaques, sum of plaque area, relative plaque number, relative plaque area and mean plaque size. A field for remarks was used to record image quality and exclusion criteria, respectively. Exclusion criteria were missing parts of the slice, many wrinkles, dominant flaws or staining inconsistencies (e.g. due to bulges, which can impede the full reaction of the blocking reagent).

hh) Closing the image without saving (to keep raw data raw).

c) Results i) General Observations

In total 40 female hAPP Tg mice were enclosed to study. From these mice 12 animals died due to unknown reason before the treatment period was finished.

ii) Behavioral Results

Spatial learning in the MWM remained widely uninfluenced by XG-102 (SEQ ID NO: 233) treatment. 0.1 mg/kg treated mice showed a tendency to have worse learning performance between day 1 and day 4. A two-way ANOVA of the mean performance on day 1 and 4 revealed highly significant learning for all groups ($p<0.001$), but also a significant influence of factor treatment ($p=0.045$). However, Bonferroni's post tests did not reach significance.

iii) Biochemical Results aa) Aβ Levels in the Brain Homogenate Fractions

A treatment with the test compound XG-102 (SEQ ID NO: 233) did not affect brain homogenate $A\beta_{1-40}$ levels. Group differences in $A\beta_{1-42}$ levels appeared in Triton X-100 fraction, only. There, animals treated with the low dose of the test compound XG-102 (SEQ ID NO: 233) (0.1 mg/kg) featured a significant reduction compared to the vehicle group ($p<0.05$) as well as compared to the high dose group ($p<0.01$).

bb) CSF AR Levels

After treatment with the test substance XG-102 (SEQ ID NO: 233) $A\beta_{1-40}$ and $A\beta_{1-42}$ levels were significantly decreased in CSF compared to vehicle group. For both, $A\beta_{1-40}$ and $A\beta_{1-42}$ p-values were $p<0.01$ for the high dosage (10 mg/kg) and <0.05 for the lose dosage of XG-102 (SEQ ID NO: 233).

iv) Results of Brain Histology and Immunohistochemistry aa) Amyloid Depositions and Plaque Load Plaque load was quantified with two different methods. On the one hand an IHC staining with 6E10 primary directed against AA1-17 of the human amyloid peptide was performed, on the other hand a ThioflavinS staining marking beta-sheet structures and cores of mature, neuritic plaques was carried out. First of all, measured region areas, cortex and hippocampus, were highly constant throughout all groups, indicating that problems in the cutting and IHC procedures can be excluded and to a certain degree also a treatment induced atrophy (changes of >5% would be detectable with this method). 6E10 and ThioflavinS quantifications revealed a selective reduction of beta-sheet structures in the center of the plaques after XG-102 (SEQ ID NO: 233) treatment, whereas human amyloid remained uninfluenced from treatment or slightly increased. In detail cortical 6E10 IR plaque load was increased versus vehicle in the 10 mg/kg XG-102 (SEQ ID NO: 233) treated mice, however, significance level was reached for the number of hippocampal plaques. In contrast to 6E10 IHC, XG-102 (SEQ ID NO: 233) treatment led to a negatively dose dependent reduction of the number of hippocampal ThioflavinS positive plaques, as well as area percentage (number of plaques: $p<0.05$ for 10 mg/kg, $p<0.01$ for 0.1 mg/kg XG-102 (SEQ ID NO: 233)). 0.1 mg/kg XG-102 (SEQ ID NO: 233) treatment also reduced mean plaque size, however this effect did not reach significance level in the ANOVA (unpaired, two-tailed T-test: $p=0.074$) These effects were not given for cortical plaques, a circumstance which is most probably due to the later onset of plaque pathology in the hippocampus than in the cortex. Treatment start at five months of age exactly hits the time point of plaque deposition in the hippocampus, whereas cortical plaques start to become visible at the used magnification for quantification at the age of three months. Qualitatively the proportion of 6E10 to ThioflavinS stained plaques increase and the beta-sheet plaque cores, as seen in doubly labeled slices, become smaller in size. Summarized, these data support that XG-102 (SEQ ID NO: 233) treatment acts against beta-sheet formation in the early phase of plaque deposition and beta sheet formation in plaque cores, respectively.

d) Summary of Effects and Conclusions

Spatial navigation measured in the Morris water maze remained widely uninfluenced from treatment. 0.1 mg/kg XG-102 (SEQ ID NO: 233) treatment resulted in a slightly poorer learning performance between the first and the last training day.

Except a decrease in the Triton X-100 fraction in the 0.1 mg/kg XG-102 (SEQ ID NO: 233) group $A\beta_{1-40}$ and $A\beta_{1-42}$ brain levels stayed stable.

A decrease of Aβ levels was detectable in CSF for both dosages and fragments.

XG-102 (SEQ ID NO: 233) treatment led to a tendentious increase of human amyloid beta in the higher dosed group in the 6E10 quantifications, which is in compliance with data obtained in Aβ ELISA.

In contrast to that hippocampal beta-sheet load detected by ThioflavinS staining was dose dependently reduced after XG-102 (SEQ ID NO: 233) treatment, to a higher degree at lower dose 0.1 mg/kg XG-102 (SEQ ID NO: 233), whereas cortical plaque load remained unchanged. In accordance with the age-dependent onset of plaque deposition in the hippocampus at treatment start this hints at an early action on beta-sheet formation in the early phase of plaque deposition.

Example 7

Determining the Activity of All-D Retro-Inverso IB(s) Peptides and Variants Thereof in the Treatment of Diabetes Type 2

The aim was to determine the activity of IB(s) peptides and all-D retro-inverso IB(s) peptides and variants thereof in the treatment of Diabetes Type 2, particularly to determine the effect of chronic treatment with XG-102 (SEQ ID NO: 233) in the db/db mice model of type 2 diabetes by evaluating fasting blood glucose levels every third day (28 days)

a) Materials and Methods i) Animals

A total of twenty (20) male db/db mice (8 weeks old) were obtained from Charles River (Germany). Upon arrival, animals were group housed (n=6-7/group) and offered regular rodent chow (Altromin standard #1324 chow; C. Petersen, Ringsted, Denmark) and water ad libitum unless otherwise stated.

The mice were housed under a 12:12 L/D cycle (lights on at 4:00 and lights off at 16:00) and in temperature and humidity controlled rooms.

ii) Groups and Randomization

On day −4, mice were randomized according to blood glucose level (fasted; blood glucose measured on Biosen S line analyzer (EKF diagnostic, Germany) to participate in one of the following drug treatment groups (n=6):

1) Vehicle control, S.C. (physiological saline)
2) XG-102 (SEQ ID NO: 233); 1 mg/kg; s.c.
3) XG-102 (SEQ ID NO: 233); 10 mg/kg; s.c All doses listed were calculated for the free-base. Drug purity: 95.28%, peptide content: 78.0%. All compounds were administered sub-cutaneously (s.c.) in a volume of 3 ml/kg. The formulation instructions for vehicle control and XG-102 (SEQ ID NO: 233) were as follows:

First, XG-102 (SEQ ID NO: 233) was dissolved in the vehicle. The formulations (concentrations of 0.33 and 3.3 mg/ml, corresponding to the doses of 1 and 10 mg/kg, respectively) were prepared according to the procedure detailed below. Concentrations were calculated and expressed taking into account test items purity and peptide content (multiplier coefficient was 1.346).

Preparation of a stock solution: the freeze-dried test compound XG-102 (SEQ ID NO: 233) is thawed for one hour minimum and prepared as a stock solution in the vehicle at 1 mM (corresponding to 3.823 mg/mL). Aliquots are prepared for each treatment day and stored at approximately −80° C. Dilutions of this stock solution to the required concentrations are performed on each treatment day;

Storage of the stock solution: at approximately −80° C.;

Storage of the diluted preparations: at room temperature for 24 hours maximum.

Prior to solubilisation, the powder was stored at −20° C. The stability of the stock solution is 3 months at approximately −80° C.; the stability of the diluted formulations for animal dosing is 24 hours at room temperature. Unused diluted material could be stored for up to 7 days if kept at 4-8° C.

c) Experimental Procedure

Following 8 days of acclimatization the mice were treated daily at 08.00 AM for 21 days by SC dosing 8 hours prior to lights out at 04.00 PM according to the outline groups. Then, on study day 21 dosing of the highest concentration of XG-102 (SEQ ID NO: 233 (10 mg/kg) was stopped, whereas daily dosing of vehicle control and XG-102 (SEQ ID NO: 233 (1 mg/kg) were continued until day study 28. From day 28 until termination at day 111 the vehicle and XG-102 (SEQ ID NO: 233 (10 mg/kg) treated mice were observed in a wash-out period (no dosing), whereas the mice treated with XG-102 (SEQ ID NO: 233 (1 mg/kg) was terminated after 28 days of treatment i) Blood Glucose Blood glucose was measured from 7 hour fasted animals 6 hours post dosing by collection of 10 μl blood samples from the tail-vein in hematocrite tubes and subsequent analysis on a Biosen s-line analyzer (EKF-diagnostic; Germany).

ii) Metabolic Cages

Groups 1+3: Mice were placed in metabolic cages for the recording of 24-hour food and water intake as well as 24-hour urine and faeces production. Mice were stratified into two sub-teams of n=6-7 and subsequently the metabolic characterisation were performed on study days 71-72.

iii) Adipokine Panel

Groups 1+3: On three occasions (study days 57, 66 and 108) blood was collected from the tail vein using EDTA coated hematocrite tubes (100 μl). Following centrifugation of blood the plasma was collected and stored at −20° C. until measurement. Then, the following panel of adipokines/cytokines was determined using Luminex based 7-plex: leptin, resistin, MCP-1, PAI-1, TNF, insulin and interleukin-6 (IL-6).

iv) Termination

Groups 1+3 (day 111): The following organs were excised and weighed:

inguinal subcutaneous fat, epididymal fat, retroperitoneal fat, brain, liver, kidney, spleen and heart. All organs described above were samples in 4% PFA for possible future histo-pathological examination. Also, pancreas (en bloc) was sampled for possible stereological and imunohistochemical analysis, and eyes were sampled for possible later analysis of retinopathy. Group 2 (day 28): No tissues or plasma were collected.

c) Results i) General Observations

During the acute dosing period animals showed normal levels of alertness and activity and there were no signs of sedation in the drug treated animals. Food and water intake were within normal ranges among vehicle treated animals. However, after approximately two weeks dosing, nodular fibrosis was observed in the subcutaneous tissue as a reaction to the XG-102 (SEQ ID NO: 233)compound in the high dose, these progressed into open wounds all of the mice from group C. In group B mild nodular fibrosis was observed. As a consequence an alternation of injection sites were used. Following the end of dosing of the animals the animals healed and the nodular fibrosis was gradually disappearing. We observed no clinical effects in the vehicle treated animals.

ii) Blood Glucose

Fasting blood glucose (absolute and relativelevels) was measured every third day until day 68 and on a regular basis until termination at day 111 in groups A and C. We observed a clear and significant ($p<0.001$) decrease in the level of fasting blood glucose of the diabetic db/db mice treated with XG-102 (SEQ ID NO: 233) (10 mg/kg) as compared to vehicle control. The fasting blood glucose levels of the mice treated with XG-102 (SEQ ID NO: 233) (10 mg/kg) reached a low plateau of approximately 5 mmol/L. This effect was evident after 14 days of dosing and persisted throughout the study, thus during the entire wash-out period from day 21 to day 111. In contrast, we observed no effect of low dose of XG-102 (SEQ ID NO: 233) (1 mg/kg) during 28 days of dosing.

iii) Body Weight

We observed a clear and significant ($p<0.001$) prevention of body weight increase in mice treated with XG-102 (SEQ ID NO: 233) (10 mg/kg) as compared to vehicle control. This effect was evident from day 28 of dosing and remained until the day of termination day 111. In contrast, we observed no effect of low dose of XG-102 (SEQ ID NO: 233) (1 mg/kg) on body weight during 28 days of dosing.

iv) Metabolic Cages

The effect of vehicle or XG-102 (SEQ ID NO: 233) (10 mg/kg) on 24 hour food and water intake, and urine and faeces production as measured in metabolic cages on study day 68 (normalized to g of body weight) was studied. We observed no significant effects of XG-102 (SEQ ID NO: 233) (10 mg/kg) on any of the measured parameters as compared to vehicle control though a trend towards a decrease in food intake and urine production was observed.

v) Adipokines

The effect of vehicle or XG-102 (SEQ ID NO: 233) (10 mg/kg) as measured on day 57, 77 and 108 on plasma levels of insulin, MCP-1, IL-6; on plasma levels of tPAI-1, TNF and resistin was analyzed; We observed no significant effects of XG-102 (SEQ ID NO: 233) (10 mg/kg) on any of the measured parameters as compared to vehicle control except the levels of plasma resistin, which was significantly higher in XG-102 (SEQ ID NO: 233) treated animals at day 77 and 108.

vi) Tissue Weight at Termination

The effect of vehicle or XG-102 (SEQ ID NO: 233) (10 mg/kg) on tissue weight of epididymal, inguinal subcutaneous, and retroperitoneal fat pads was analyzed. We observed a significant decrease of epididymal ($p<0.05$) and retroperitoneal ($p<0.01$) fat mass in the mice treated with XG-102 as compared to vehicle control. The effect of vehicle or XG-102 (SEQ ID NO: 233) (10 mg/kg) on tissue weight of brain, spleen and heart was analyzed. We observed no significant effects of XG-102 (SEQ ID NO: 233) (10 mg/kg) on these parameters as compared to vehicle control. Finally, the effect of vehicle or XG-102 (SEQ ID NO: 233) (10 mg/kg) on tissue weight of kidney and liver was analyzed. We observed a significant decrease of kidney ($p<0.05$) and liver ($p<0.01$) mass in the mice treated with XG-102 (SEQ ID NO: 233) as compared to vehicle control.

Summarizing the results, administration of XG-102 (SEQ ID NO: 233), 10 mg/kg, appears to lead to a significant decrease in blood glucose levels and therefore, XG-102 (SEQ ID NO: 233) appears to be a promising new tool for treating diabetes and elevated blood glucose levels.

8. Uptake (Internalization) of Peptides into Cells and Measurement of Peptide Internalization into Cells In this experiment, the internalization (uptake) capacity of FITC-labeled TAT derived transporter constructs in vitro was evaluated with a fluorescence plate reader in cell lines HL-60 (Leukemia).

8.1. Test Samples Used in the Experiments

The constructs used in this experiment were four different TAT derived transporter constructs (termed L-TAT, r3-TAT (also termed r3-L-Tat), r3-TATi (also termed r3-L-TATi), and D-TAT), each prepared as described above. These constructs have a length of 9 amino acids but a different D-/L-pattern. Furthermore, the construct DAK was used as a control, which comprised no transporter sequence. The constructs were N-terminally protected with beta-Alanine (βA) and labeled with FITC.

| | |
|---|---|
| FITC-βA-L-TAT | FITC-βA-RKKRQRRR (SEQ ID NO: 313) |
| FITC-βA-D-TAT | FITC-βA-rrrqrrkkr (SEQ ID NO: 314) |
| FITC-βA-$r_3$-L-TAT | FITC-βA-rKKRrQRRr (SEQ ID NO: 315) |
| FITC-βA-$r_3$-L-TATi | FITC-βA-rRRQrRKKr (SEQ ID NO: 314) |
| FITC-βA-DAK (ctl) | FITC-βA-DAK (SEQ ID NO: 316) (no transporter sequence) |

The constructs were prepared as described above, purified, stored as 10 mM solution in sterile water, and used as purified without any further treatment.

8.2. Further Transporter Contructs TAT(s2-1)-TAT(s2-96)

Further transporter contructs TAT(s2-1)-TAT(s2-96) were prepared as described above in general for inventive transporter constructs. Following sequences and protecting groups were used therefore during synthesis (bound to resin):

```
TATs2-1:
                                        (SEQ ID NO: 317)
D-Arg(Pmc)-Ala-Lys(Boc)-Arg(Pmc)-D-Arg(Pmc)-

Gln(Trt)-Arg(Pmc)-Arg(Pmc)-D-Arg(Pmc)-RESIN

TATs2-2:
                                        (SEQ ID NO: 318)
D-Arg(Pmc)-Lys(Boc)-Ala-Arg(Pmc)-D-Arg(Pmc)-

Gln(Trt)-Arg(Pmc)-Arg(Pmc)-D-Arg(Pmc)-RESIN

TATs2-3:
                                        (SEQ ID NO: 319)
D-Arg(Pmc)-Lys(Boc)-Lys(Boc)-Ala-D-Arg(Pmc)-

Gln(Trt)-Arg(Pmc)-Arg(Pmc)-D-Arg(Pmc)-RESIN

TATs2-4:
                                        (SEQ ID NO: 320)
D-Arg(Pmc)-Lys(Boc)-Lys(Boc)-Arg(Pmc)-D-Arg(Pmc)-

Ala-Arg(Pmc)-Arg(Pmc)-D-Arg(Pmc)-RESIN

TATs2-5:
                                        (SEQ ID NO: 321)
D-Arg(Pmc)-Lys(Boc)-Lys(Boc)-Arg(Pmc)-D-Arg(Pmc)-

Gln(Trt)-Ala-Arg(Pmc)-D-Arg(Pmc)-RESIN

TATs2-6:
                                        (SEQ ID NO: 322)
D-Arg(Pmc)-Lys(Boc)-Lys(Boc)-Arg(Pmc)-D-Arg(Pmc)-

Gln(Trt)-Arg(Pmc)-Ala-D-Arg(Pmc)-RESIN

TATs2-7:
                                        (SEQ ID NO: 323)
D-Arg(Pmc)-Asp(OBut)-Lys(Boc)-Arg(Pmc)-D-Arg(Pmc)-

Gln(Trt)-Arg(Pmc)-Arg(Pmc)-D-Arg(Pmc)-RESIN

TATs2-8:
                                        (SEQ ID NO: 324)
D-Arg(Pmc)-Lys(Boc)-Asp(OBut)-Arg(Pmc)-D-Arg(Pmc)-

Gln(Trt)-Arg(Pmc)-Arg(Pmc)-D-Arg(Pmc)-RESIN

TATs2-9:
                                        (SEQ ID NO: 325)
D-Arg(Pmc)-Lys(Boc)-Lys(Boc)-Asp(OBut)-D-Arg(Pmc)-

Gln(Trt)-Arg(Pmc)-Arg(Pmc)-D-Arg(Pmc)-RESIN
```

-continued

TATs2-10:
(SEQ ID NO: 326)
D-Arg(Pmc)-Lys(Boc)-Lys(Boc)-Arg(Pmc)-D-Arg(Pmc)-Asp(OBut)-Arg(Pmc)-Arg(Pmc)-D-Arg(Pmc)-RESIN

TATs2-11:
(SEQ ID NO: 327)
D-Arg(Pmc)-Lys(Boc)-Lys(Boc)-Arg(Pmc)-D-Arg(Pmc)-Gln(Trt)-Asp(OBut)-Arg(Pmc)-D-Arg(Pmc)-TATs2-RESIN

TATs2-12:
(SEQ ID NO: 328)
D-Arg(Pmc)-Lys(Boc)-Lys(Boc)-Arg(Pmc)-D-Arg(Pmc)-Gln(Trt)-Arg(Pmc)-Asp(OBut)-D-Arg(Pmc)-TATs2-RESIN

TATs2-13:
(SEQ ID NO: 329)
D-Arg(Pmc)-Glu(OBut)-Lys(Boc)-Arg(Pmc)-D-Arg(Pmc)-Gln(Trt)-Arg(Pmc)-Arg(Pmc)-D-Arg(Pmc)-RESIN

TATs2-14:
(SEQ ID NO: 330)
D-Arg(Pmc)-Lys(Boc)-Glu(OBut)-Arg(Pmc)-D-Arg(Pmc)-Gln(Trt)-Arg(Pmc)-Arg(Pmc)-D-Arg(Pmc)-RESIN

TATs2-15:
(SEQ ID NO: 331)
D-Arg(Pmc)-Lys(Boc)-Lys(Boc)-Glu(OBut)-D-Arg(Pmc)-Gln(Trt)-Arg(Pmc)-Arg(Pmc)-D-Arg(Pmc)-RESIN

TATs2-16:
(SEQ ID NO: 332)
D-Arg(Pmc)-Lys(Boc)-Lys(Boc)-Arg(Pmc)-D-Arg(Pmc)-Glu(OBut)-Arg(Pmc)-Arg(Pmc)-D-Arg(Pmc)-RESIN

TATs2-17:
(SEQ ID NO: 333)
D-Arg(Pmc)-Lys(Boc)-Lys(Boc)-Arg(Pmc)-D-Arg(Pmc)-Gln(Trt)-Glu(OBut)-Arg(Pmc)-D-Arg(Pmc)-RESIN

TATs2-18:
(SEQ ID NO: 334)
D-Arg(Pmc)-Lys(Boc)-Lys(Boc)-Arg(Pmc)-D-Arg(Pmc)-Gln(Trt)-Arg(Pmc)-Glu(OBut)-D-Arg(Pmc)-RESIN

TATs2-19:
(SEQ ID NO: 335)
D-Arg(Pmc)-Phe-Lys(Boc)-Arg(Pmc)-D-Arg(Pmc)-Gln(Trt)-Arg(Pmc)-Arg(Pmc)-D-Arg(Pmc)-RESIN

TATs2-20:
(SEQ ID NO: 336)
D-Arg(Pmc)-Lys(Boc)-Phe-Arg(Pmc)-D-Arg(Pmc)-Gln(Trt)-Arg(Pmc)-Arg(Pmc)-D-Arg(Pmc)-RESIN

TATs2-21:
(SEQ ID NO: 337)
D-Arg(Pmc)-Lys(Boc)-Lys(Boc)-Phe-D-Arg(Pmc)-Gln(Trt)-Arg(Pmc)-Arg(Pmc)-D-Arg(Pmc)-RESIN

TATs2-22:
(SEQ ID NO: 338)
D-Arg(Pmc)-Lys(Boc)-Lys(Boc)-Arg(Pmc)-D-Arg(Pmc)-Phe-Arg(Pmc)-Arg(Pmc)-D-Arg(Pmc)-RESIN

-continued

TATs2-23:
(SEQ ID NO: 339)
D-Arg(Pmc)-Lys(Boc)-Lys(Boc)-Arg(Pmc)-D-Arg(Pmc)-Gln(Trt)-Phe-Arg(Pmc)-D-Arg(Pmc)-RESIN

TATs2-24:
(SEQ ID NO: 340)
D-Arg(Pmc)-Lys(Boc)-Lys(Boc)-Arg(Pmc)-D-Arg(Pmc)-Gln(Trt)-Arg(Pmc)-Phe-D-Arg(Pmc)-RESIN

TATs2-25:
(SEQ ID NO: 341)
D-Arg(Pmc)-Arg(Pmc)-Lys(Boc)-Arg(Pmc)-D-Arg(Pmc)-Gln(Trt)-Arg(Pmc)-Arg(Pmc)-D-Arg(Pmc)-RESIN

TATs2-26:
(SEQ ID NO: 342)
D-Arg(Pmc)-Lys(Boc)-Arg(Pmc)-Arg(Pmc)-D-Arg(Pmc)-Gln(Trt)-Arg(Pmc)-Arg(Pmc)-D-Arg(Pmc)-RESIN

TATs2-27:
(SEQ ID NO: 343)
D-Arg(Pmc)-Lys(Boc)-Lys(Boc)-Lys(Boc)-D-Arg(Pmc)-Gln(Trt)-Arg(Pmc)-Arg(Pmc)-D-Arg(Pmc)-RESIN

TATs2-28:
(SEQ ID NO: 344)
D-Arg(Pmc)-Lys(Boc)-Lys(Boc)-Arg(Pmc)-D-Arg(Pmc)-Arg(Pmc)-Arg(Pmc)-Arg(Pmc)-D-Arg(Pmc)-RESIN

TATs2-29:
(SEQ ID NO: 345)
D-Arg(Pmc)-Lys(Boc)-Lys(Boc)-Arg(Pmc)-D-Arg(Pmc)-Gln(Trt)-Lys(Boc)-Arg(Pmc)-D-Arg(Pmc)-RESIN

TATs2-30:
(SEQ ID NO: 346)
D-Arg(Pmc)-Lys(Boc)-Lys(Boc)-Arg(Pmc)-D-Arg(Pmc)-Gln(Trt)-Arg(Pmc)-Lys(Boc)-D-Arg(Pmc)-RESIN

TATs2-31:
(SEQ ID NO: 347)
D-Arg(Pmc)-His(Trt)-Lys(Boc)-Arg(Pmc)-D-Arg(Pmc)-Gln(Trt)-Arg(Pmc)-Arg(Pmc)-D-Arg(Pmc)-RESIN

TATs2-32:
(SEQ ID NO: 348)
D-Arg(Pmc)-Lys(Boc)-His(Trt)-Arg(Pmc)-D-Arg(Pmc)-Gln(Trt)-Arg(Pmc)-Arg(Pmc)-D-Arg(Pmc)-RESIN

TATs2-33:
(SEQ ID NO: 349)
D-Arg(Pmc)-Lys(Boc)-Lys(Boc)-His(Trt)-D-Arg(Pmc)-Gln(Trt)-Arg(Pmc)-Arg(Pmc)-D-Arg(Pmc)-RESIN

TATs2-34:
(SEQ ID NO: 350)
D-Arg(Pmc)-Lys(Boc)-Lys(Boc)-Arg(Pmc)-D-Arg(Pmc)His(Trt)-Arg(Pmc)-Arg(Pmc)-D-Arg(Pmc)-RESIN

TATs2-35:
(SEQ ID NO: 351)
D-Arg(Pmc)-Lys(Boc)-Lys(Boc)-Arg(Pmc)-D-Arg(Pmc)-Gln(Trt)-His(Trt)-Arg(Pmc)-D-Arg(Pmc)-RESIN

-continued

TATs2-36:

(SEQ ID NO: 352)

D-Arg(Pmc)-Lys(Boc)-Lys(Boc)-Arg(Pmc)-D-Arg(Pmc)-Gln(Trt)-Arg(Pmc)-His(Trt)-D-Arg(Pmc)-RESIN

TATs2-37:

(SEQ ID NO: 353)

D-Arg(Pmc)-Ile-Lys(Boc)-Arg(Pmc)-D-Arg(Pmc)-Gln(Trt)-Arg(Pmc)-Arg(Pmc)-D-Arg(Pmc)-RESIN

TATs2-38:

(SEQ ID NO: 354)

D-Arg(Pmc)-Lys(Boc)-Ile-Arg(Pmc)-D-Arg(Pmc)-Gln(Trt)-Arg(Pmc)-Arg(Pmc)-D-Arg(Pmc)-RESIN

TATs2-39:

(SEQ ID NO: 355)

D-Arg(Pmc)-Lys(Boc)-Lys(Boc)-Ile-D-Arg(Pmc)-Gln(Trt)-Arg(Pmc)-Arg(Pmc)-D-Arg(Pmc)-RESIN

TATs2-40:

(SEQ ID NO: 356)

D-Arg(Pmc)-Lys(Boc)-Lys(Boc)-Arg(Pmc)-D-Arg(Pmc)-Ile-Arg(Pmc)-Arg(Pmc)-D-Arg(Pmc)-RESIN

TATs2-41:

(SEQ ID NO: 357)

D-Arg(Pmc)-Lys(Boc)-Lys(Boc)-Arg(Pmc)-D-Arg(Pmc)-Gln(Trt)-Ile-Arg(Pmc)-D-Arg(Pmc)-RESIN

TATs2-42:

(SEQ ID NO: 358)

D-Arg(Pmc)-Lys(Boc)-Lys(Boc)-Arg(Pmc)-D-Arg(Pmc)-Gln(Trt)-Arg(Pmc)-Ile-D-Arg(Pmc)-RESIN

TATs2-43:

(SEQ ID NO: 359)

D-Arg(Pmc)-Leu-Lys(Boc)-Arg(Pmc)-D-Arg(Pmc)-Gln(Trt)-Arg(Pmc)-Arg(Pmc)-D-Arg(Pmc)-RESIN

TATs2-44:

(SEQ ID NO: 360)

D-Arg(Pmc)-Lys(Boc)-Leu-Arg(Pmc)-D-Arg(Pmc)-Gln(Trt)-Arg(Pmc)-Arg(Pmc)-D-Arg(Pmc)-RESIN

TATs2-45:

(SEQ ID NO: 361)

D-Arg(Pmc)-Lys(Boc)-Lys(Boc)-Leu-D-Arg(Pmc)-Gln(Trt)-Arg(Pmc)-Arg(Pmc)-D-Arg(Pmc)-RESIN

TATs2-46:

(SEQ ID NO: 362)

D-Arg(Pmc)-Lys(Boc)-Lys(Boc)-Arg(Pmc)-D-Arg(Pmc)-Leu-Arg(Pmc)-Arg(Pmc)-D-Arg(Pmc)-RESIN

TATs2-47:

(SEQ ID NO: 363)

D-Arg(Pmc)-Lys(Boc)-Lys(Boc)-Arg(Pmc)-D-Arg(Pmc)-Gln(Trt)-Leu-Arg(Pmc)-D-Arg(Pmc)-RESIN

TATs2-48:

(SEQ ID NO: 364)

D-Arg(Pmc)-Lys(Boc)-Lys(Boc)-Arg(Pmc)-D-Arg(Pmc)-Gln(Trt)-Arg(Pmc)-Leu-D-Arg(Pmc)-RESIN

-continued

TATs2-49:

(SEQ ID NO: 365)

D-Arg(Pmc)-Met-Lys(Boc)-Arg(Pmc)-D-Arg(Pmc)-Gln(Trt)-Arg(Pmc)-Arg(Pmc)-D-Arg(Pmc)-RESIN

TATs2-50:

(SEQ ID NO: 366)

D-Arg(Pmc)-Lys(Boc)-Met-Arg(Pmc)-D-Arg(Pmc)-Gln(Trt)-Arg(Pmc)-Arg(Pmc)-D-Arg(Pmc)-RESIN

TATs2-51:

(SEQ ID NO: 367)

D-Arg(Pmc)-Lys(Boc)-Lys(Boc)-Met-D-Arg(Pmc)-Gln(Trt)-Arg(Pmc)-Arg(Pmc)-D-Arg(Pmc)-RESIN

TATs2-52:

(SEQ ID NO: 368)

D-Arg(Pmc)-Lys(Boc)-Lys(Boc)-Arg(Pmc)-D-Arg(Pmc)-Met-Arg(Pmc)-Arg(Pmc)-D-Arg(Pmc)-RESIN

TATs2-53:

(SEQ ID NO: 369)

D-Arg(Pmc)-Lys(Boc)-Lys(Boc)-Arg(Pmc)-D-Arg(Pmc)-Gln(Trt)-Met-Arg(Pmc)-D-Arg(Pmc)-RESIN

TATs2-54:

(SEQ ID NO: 370)

D-Arg(Pmc)-Lys(Boc)-Lys(Boc)-Arg(Pmc)-D-Arg(Pmc)-Gln(Trt)-Arg(Pmc)-Met-D-Arg(Pmc)-RESIN

TATs2-55:

(SEQ ID NO: 371)

D-Arg(Pmc)-Asn(Trt)-Lys(Boc)-Arg(Pmc)-D-Arg(Pmc)-Gln(Trt)-Arg(Pmc)-Arg(Pmc)-D-Arg(Pmc)-RESIN

TATs2-56:

(SEQ ID NO: 372)

D-Arg(Pmc)-Lys(Boc)-Asn(Trt)-Arg(Pmc)-D-Arg(Pmc)-Gln(Trt)-Arg(Pmc)-Arg(Pmc)-D-Arg(Pmc)-RESIN

TATs2-57:

(SEQ ID NO: 373)

D-Arg(Pmc)-Lys(Boc)-Lys(Boc)-Asn(Trt)-D-Arg(Pmc)-Gln(Trt)-Arg(Pmc)-Arg(Pmc)-D-Arg(Pmc)-RESIN

TATs2-58:

(SEQ ID NO: 374)

D-Arg(Pmc)-Lys(Boc)-Lys(Boc)-Arg(Pmc)-D-Arg(Pmc)-Asn(Trt)-Arg(Pmc)-Arg(Pmc)-D-Arg(Pmc)-RESIN

TATs2-59:

(SEQ ID NO: 375)

D-Arg(Pmc)-Lys(Boc)-Lys(Boc)-Arg(Pmc)-D-Arg(Pmc)-Gln(Trt)-Asn(Trt)-Arg(Pmc)-D-Arg(Pmc)-RESIN

TATs2-60:

(SEQ ID NO: 376)

D-Arg(Pmc)-Lys(Boc)-Lys(Boc)-Arg(Pmc)-D-Arg(Pmc)-Gln(Trt)-Arg(Pmc)-Asn(Trt)-D-Arg,(Pmc)-RESIN

TATs2-61:

(SEQ ID NO: 377)

D-Arg(Pmc)-Gln(Trt)-Lys(Boc)-Arg(Pmc)-D-Arg(Pmc)-Gln(Trt)-Arg(Pmc)-Arg(Pmc)-D-Arg(Pmc)-RESIN

-continued

TATs2-62:
(SEQ ID NO: 378)
D-Arg(Pmc)-Lys(Boc)-Gln(Trt)-Arg(Pmc)-D-Arg(Pmc)-Gln(Trt)-Arg(Pmc)-Arg(Pmc)-D-Arg(Pmc)-RESIN

TATs2-63:
(SEQ ID NO: 379)
D-Arg(Pmc)-Lys(Boc)-Lys(Boc)-Gln(Trt)-D-Arg(Pmc)-Gln(Trt)-Arg(Pmc)-Arg(Pmc)-D-Arg(Pmc)-RESIN

TATs2-64:
(SEQ ID NO: 380)
D-Arg(Pmc)-Lys(Boc)-Lys(Boc)-Arg(Pmc)-D-Arg(Pmc)Lys(Boc)-Arg(Pmc)-Arg(Pmc)-D-Arg(Pmc)-RESIN

TATs2-65:
(SEQ ID NO: 381)
D-Arg(Pmc)-Lys(Boc)-Lys(Boc)-Arg(Pmc)-D-Arg(Pmc)-Gln(Trt)-Gln(Trt)-Arg(Pmc)-D-Arg(Pmc)-RESIN

TATs2-66:
(SEQ ID NO: 382)
D-Arg(Pmc)-Lys(Boc)-Lys(Boc)-Arg(Pmc)-D-Arg(Pmc)-Gln(Trt)-Arg(Pmc)-Gln(Trt)-D-Arg(Pmc)-RESIN

TATs2-67:
(SEQ ID NO: 383)
D-Arg(Pmc)-Ser(But)-Lys(Boc)-Arg(Pmc)-D-Arg(Pmc)-Gln(Trt)-Arg(Pmc)-Arg(Pmc)-D-Arg(Pmc)-RESIN

TATs2-68:
(SEQ ID NO: 384)
D-Arg(Pmc)-Lys(Boc)-Ser(But)-Arg(Pmc)-D-Arg(Pmc)-Gln(Trt)-Arg(Pmc)-Arg(Pmc)-D-Arg(Pmc)-RESIN

TATs2-69:
(SEQ ID NO: 385)
D-Arg(Pmc)-Lys(Boc)-Lys(Boc)-Ser(But)-D-Arg(Pmc)-Gln(Trt)-Arg(Pmc)-Arg(Pmc)-D-Arg(Pmc)-RESIN

TATs2-70:
(SEQ ID NO: 386)
D-Arg(Pmc)-Lys(Boc)-Lys(Boc)-Arg(Pmc)-D-Arg(Pmc)Ser(But)-Arg(Pmc)-Arg(Pmc)-D-Arg(Pmc)-RESIN

TATs2-71:
(SEQ ID NO: 387)
D-Arg(Pmc)-Lys(Boc)-Lys(Boc)-Arg(Pmc)-D-Arg(Pmc)-Gln(Trt)-Ser(But)-Arg(Pmc)-D-Arg(Pmc)-RESIN

TATs2-72:
(SEQ ID NO: 388)
D-Arg(Pmc)-Lys(Boc)-Lys(Boc)-Arg(Pmc)-D-Arg(Pmc)-Gln(Trt)-Arg(Pmc)-Ser(But)-D-Arg(Pmc)-RESIN

TATs2-73:
(SEQ ID NO: 389)
D-Arg(Pmc)-Thr(But)-Lys(Boc)-Arg(Pmc)-D-Arg(Pmc)-Gln(Trt)-Arg(Pmc)-Arg(Pmc)-D-Arg(Pmc)-RESIN

TATs2-74:
(SEQ ID NO: 390)
D-Arg(Pmc)-Lys(Boc)-Thr(But)-Arg(Pmc)-D-Arg(Pmc)-Gln(Trt)-Arg(Pmc)-Arg(Pmc)-D-Arg(Pmc)-RESIN

-continued

TATs2-75:
(SEQ ID NO: 391)
D-Arg(Pmc)-Lys(Boc)-Lys(Boc)-Thr(But)-D-Arg(Pmc)-Gln(Trt)-Arg(Pmc)-Arg(Pmc)-D-Arg(Pmc)-RESIN

TATs2-76:
(SEQ ID NO: 392)
D-Arg(Pmc)-Lys(Boc)-Lys(Boc)-Arg(Pmc)-D-Arg(Pmc)Thr(But)-Arg(Pmc)-Arg(Pmc)-D-Arg(Pmc)-RESIN

TATs2-77:
(SEQ ID NO: 393)
D-Arg(Pmc)-Lys(Boc)-Lys(Boc)-Arg(Pmc)-D-Arg(Pmc)-Gln(Trt)-Thr(But)-Arg(Pmc)-D-Arg(Pmc)-RESIN

TATs2-78:
(SEQ ID NO: 394)
D-Arg(Pmc)-Lys(Boc)-Lys(Boc)-Arg(Pmc)-D-Arg(Pmc)-Gln(Trt)-Arg(Pmc)-Thr(But)-D-Arg(Pmc)-RESIN

TATs2-79:
(SEQ ID NO: 395)
D-Arg(Pmc)-Val-Lys(Boc)-Arg(Pmc)-D-Arg(Pmc)-Gln(Trt)-Arg(Pmc)-Arg(Pmc)-D-Arg(Pmc)-RESIN

TATs2-80:
(SEQ ID NO: 396)
D-Arg(Pmc)-Lys(Boc)-Val-Arg(Pmc)-D-Arg(Pmc)-Gln(Trt)-Arg(Pmc)-Arg(Pmc)-D-Arg(Pmc)-RESIN

TATs2-81:
(SEQ ID NO: 397)
D-Arg(Pmc)-Lys(Boc)-Lys(Boc)-Val-D-Arg(Pmc)-Gln(Trt)-Arg(Pmc)-Arg(Pmc)-D-Arg(Pmc)-RESIN

TATs2-82:
(SEQ ID NO: 398)
D-Arg(Pmc)-Lys(Boc)-Lys(Boc)-Arg(Pmc)-D-Arg(Pmc)-Val-Arg(Pmc)-Arg(Pmc)-D-Arg(Pmc)-RESIN

TATs2-83:
(SEQ ID NO: 399)
D-Arg(Pmc)-Lys(Boc)-Lys(Boc)-Arg(Pmc)-D-Arg(Pmc)-Gln(Trt)-Val-Arg(Pmc)-D-Arg(Pmc)-RESIN

TATs2-84:
(SEQ ID NO: 400)
D-Arg(Pmc)-Lys(Boc)-Lys(Boc)-Arg(Pmc)-D-Arg(Pmc)-Gln(Trt)-Arg(Pmc)-Val-D-Arg(Pmc)-RESIN

TATs2-85:
(SEQ ID NO: 401)
D-Arg(Pmc)-Trp(Boc)-Lys(Boc)-Arg(Pmc)-D-Arg(Pmc)-Gln(Trt)-Arg(Pmc)-Arg(Pmc)-D-Arg(Pmc)-RESIN

TATs2-86:
(SEQ ID NO: 402)
D-Arg(Pmc)-Lys(Boc)-Trp(Boc)-Arg(Pmc)-D-Arg(Pmc)-Gln(Trt)-Arg(Pmc)-Arg(Pmc)-D-Arg(Pmc)-RESIN

TATs2-87:
(SEQ ID NO: 403)
D-Arg(Pmc)-Lys(Boc)-Lys(Boc)-Trp(Boc)-D-Arg(Pmc)-Gln(Trt)-Arg(Pmc)-Arg(Pmc)-D-Arg(Pmc)-RESIN

-continued

TATs2-88:

(SEQ ID NO: 404)

D-Arg(Pmc)-Lys(Boc)-Lys(Boc)-Arg(Pmc)-D-Arg(Pmc)Trp(Boc)-Arg(Pmc)-Arg(Pmc)-D-Arg(Pmc)-RESIN

TATs2-89:

(SEQ ID NO: 405)

D-Arg(Pmc)-Lys(Boc)-Lys(Boc)-Arg(Pmc)-D-Arg(Pmc)-Gln(Trt)-Trp(Boc)-Arg(Pmc)-D-Arg(Pmc)-RESIN

TATs2-90:

(SEQ ID NO: 406)

D-Arg(Pmc)-Lys(Boc)-Lys(Boc)-Arg(Pmc)-D-Arg(Pmc)-Gln(Trt)-Arg(Pmc)-Trp(Boc)-D-Arg(Pmc)-RESIN

TATs2-91:

(SEQ ID NO: 407)

D-Arg(Pmc)-Tyr(But)-Lys(Boc)-Arg(Pmc)-D-Arg(Pmc)-Gln(Trt)-Arg(Pmc)-Arg(Pmc)-D-Arg(Pmc)-RESIN

TATs2-92:

(SEQ ID NO: 408)

D-Arg(Pmc)-Lys(Boc)-Tyr(But)-Arg(Pmc)-D-Arg(Pmc)-Gln(Trt)-Arg(Pmc)-Arg(Pmc)-D-Arg(Pmc)-RESIN

TATs2-93:

(SEQ ID NO: 409)

D-Arg(Pmc)-Lys(Boc)-Lys(Boc)-Tyr(But)-D-Arg(Pmc)-Gln(Trt)-Arg(Pmc)-Arg(Pmc)-D-Arg(Pmc)-RESIN

TATs2-94:

(SEQ ID NO: 410)

D-Arg(Pmc)-Lys(Boc)-Lys(Boc)-Arg(Pmc)-D-Arg(Pmc)Tyr(But)-Arg(Pmc)-Arg(Pmc)-D-Arg(Pmc)-RESIN

TATs2-95:

(SEQ ID NO: 411)

D-Arg(Pmc)-Lys(Boc)-Lys(Boc)-Arg(Pmc)-D-Arg(Pmc)-Gln(Trt)-Tyr(But)-Arg(Pmc)-D-Arg(Pmc)-RESIN

TATs2-96:

(SEQ ID NO: 412)

D-Arg(Pmc)-Lys(Boc)-Lys(Boc)-Arg(Pmc)-D-Arg(Pmc)-Gln(Trt)-Arg(Pmc)-Tyr(But)-D-Arg(Pmc)-RESIN 8.3 Materials and Methods for Uptake Experiments a) Cell Line:

The cell line used for this experiment was HL-60 (Ref CCL-240, ATCC, Lot 116523)

b) Culture Medium and Plates

RPMI (Ref 21875-091, Invitrogen, Lot 8296) or DMEM (Ref 41965, Invitrogen, Lot 13481) complemented on 05.05.2008 with:

10% FBS (Ref A64906-0098, PAA, Lot A15-151): decomplemented at 56° C., 30 min, on 04.04.2008.

1 mM Sodium Pyruvate (Ref S8636, Sigma, Lot 56K2386)

Penicillin (100 unit/ml)/Streptomycin (100 μg/ml) (Ref P4333, Sigma, Lot 106K2321)

PBS 10× (Ref 70011, Invitrogen, Lot 8277): diluted to 1× with sterile $H_2O$

Trypsine-0.05% EDTA (Ref L-11660, PAA, Lot L66007-1194)

6 well culture plates (Ref 140675, Nunc, Lot 102613)

24 well culture plates (Ref 142475, Nunc, Lot 095849)

96 well culture plates (Ref 167008, Nunc, Lot 083310)

96 well plates for protein dosing (Ref 82.1581, Sarstedt)

96 well plates for fluorescence measurement (Ref 6005279, Perkin Elmer)

c) Solutions

Poly-D-lysine coating solution (Sigma P9011 Lot 095K5104): 25 μg/ml final diluted in PBS 1×

Acidic wash buffer: 0.2M Glycin, 0.15M NaCl, pH 3.0

Ripa lysis buffer: 10 mM $NaH_2PO_4$ pH 7.2, 150 mM NaCl, 1% Triton X-100, 1 mM EDTA pH 8.0, 200 μM $Na_3VO_2$, 0.1% SDS, 1× protease inhibitor cocktail (Ref 11873580001, Roche, Lot 13732700)

d) Microscopy and Fluorescence Plate Reader

Cells were observed and counted using an inverted microscope (Axiovert 40 CFL; Zeiss; 20×).

The fluorescence was read with the Fusion Alpha Plate reader (Perkin Elmer).

e) Method

FITC marked peptide internalization was studied on suspension cells. Cells were plated into poly-DL-lysine coated dishes at a concentration of $1\times10^6$ cells/ml. Plates were then incubated for 24 h at 37° C., 5% CO, and 100% relative humidity prior to the addition of a known concentration of peptide. After peptide addition, the cells were incubated 30 min, 1, 6 or 24 h at 37° C., 5% CO, and 100% relative humidity. Cells were then washed twice with an acidic buffer (Glycin 0.2 M, NaCl 0.15 M, pH 3.0) in order to remove the cell-surface adsorbed peptide (see Kameyama et al., (2007), *Biopolymers,* 88, 98-107). The acidic buffer was used as peptides rich in basic amino acids adsorb strongly on the cell surfaces, which often results in ovestimation of internalized peptide. The cell wash using an acidic buffer was thus employed to remove the cell-surface adsorbed peptides. The acid wash was carried out in determining cellular uptake of Fab/cell-permeating peptide conjugates, followed by two PBS washes. Cells were broken by the addition of the RIPA lysis buffer. The relative amount of internalized peptide was then determined by fluorescence after background substraction and protein content normalization.

The steps are thus: 1. Cell culture

2. Acidic wash and cellular extracts

3. Analysis of peptide internalization with a fluorescence plate reader f) Cell Culture and Peptide Treatment (1) The 6 well culture plates are coated with 3 ml of Poly-D-Lys (Sigma P9011; 25 μg/ml in PBS), the 24 well plates with 600 μl and the 96 well plates with 125 μl and incubated for 4 h at 37° C., $CO_2$ 5% and 100% relative humidity.

(2) After 4 hours the dishes were washed twice with 3.5 ml PBS, 700 μl or 150 μl PBS for the 6, 24 or 96 well plates, respectively.

(3) The cells were plated into the dishes in 2.4 ml medium (RPMI) at plating densities of 1'000'000 cells/ml for suspension cells. After inoculation, the plates were incubated at 37° C., 5% $CO_2$ and 100% relative humidity for 24 hours prior to the addition of the peptide. Adherent cells should be at a density of 90-95% the day of treatment and were plated in DMEM :

| well | Surface of culture ($cm^2$) | Medium | Nb adherent cells | Nb suspension cells |
|---|---|---|---|---|
| 96 well | 0.3 | 100-200 µl | 8'000-30'000 | 100'000 |
| 24 well | 2 | 500-1000 µl | 100'000-200'000 | 500'000-1'000'000 |
| 35 mm (P35)/ 6 well | 10 | 2.4 ml | 250'000-2'100'000 | 2'400'000 |
| 60 mm (P60) | 20 | 3.5 ml | 15 * $10^5$ | 1'000'000/ml |
| 10 cm (P100) | 60 | 10 ml | 15-60 * $10^5$ | |

(4) The cells were treated with the desired concentration of FITC labeled peptide (stock solution at a concentration of 10 mM in $H_2O$).

(5) Following peptide addition, the cells were incubated 0 to 24 hours (e.g. 30 min, 1, 6 or 24 hours) at 37° C., $CO_2$ 5% and 100% relative humidity.

Acidic Wash and Cellular Extracts:

(6) The extracts were cooled on ice.

Suspension cells (or cells, which don attach well to the dish):

Transfer the cells in « Falcon 15 ml ». To recover the maximum of cells, wash the dish with 1 ml of PBS.

Harvest the cells 2 min at 2400 rpm max.

Suspend the cells in 1 ml cold PBS.

Transfer the cells into a coated “Eppendorf tube” (coated with 1 ml of poly D-Lys for 4 hours and washed twice with 1 ml PBS).

Wash three times with 1 ml of cold acidic wash buffer and centrifuge 2 min at 2400 rpm max. Beware of the spreading of the cells in the “eppendorf”.

Wash twice with 1 ml cold PBS to neutralize.

Add 50 µl of lysis RIPA Buffer.

Incubate 30 min-1 h on ice with agitation.

Adherent Cells:

Wash three times with 3 ml, 1 ml or 200 µl (for 6, 24 or 96 well plates, respectively) of cold acidic wash buffer. Beware of the cells who detach from the dish.

Wash twice with 1 ml cold PBS (for 6, 24 or 96 well plates, respectively) to neutralize.

Add 50 µl of lysis RIPA buffer.

Incubate 30 min-1 h on ice with agitation.

Scrap the cells with a cold scrapper. The 24 and 96 well plates were directly centrifuged at 4000 rpm at 4° for 15 min to remove the cellular debris. Then the supernatants (100 or 50 ml respectively for the 24 or 96 well plates) were directly transferred in a dark 96 well plated. The plates were read by a fluorescence plate reader (Fusion Alpha, Perkin Elmer).

Transfer the lysate in a coated “eppendorf” (coated with 1 ml of poly D-Lys for 4 hours and wash twice with 1 ml PBS).

The lysed cells were then centrifuged 30 min at 10000 g at 4° C. to remove the cellular debris.

Remove the supernatant and store it at −80° C. in a coated “Eppendorf tube” (coated with 1 ml of poly D-Lys for 4 hours and washed twice with 1 ml PBS).

Analysis of Peptide Internalization with a Fluorescence Plate Reader:

(7) The content of each protein extract was determined by a standard BCA assay (Kit N° 23225, Pierce), following the instructions of the manufacturer.

(8) The relative fluorescence of each sample is determined after reading 10 µl of each sample in a fluorescence plate reader (Fusion Alpha, Perkin Elmer), background subtraction and normalization by protein concentration.

8.4 Internalization Experiments and Analysis

The time dependant internalization (uptake) of FITC-labeled TAT derived transporter constructs into cells of the HL-60 cell line was carried out with materials and methods as described above.

Briefly, HL-60 cells were incubated 30 min, 1, 6 or 24 hours with 10 µM of the TAT-derivative transporters. The cells were then washed twice with an acidic buffer (0.2 M Glycin, 0.15 M NaCl, pH 3.0) and twice with PBS. Cells were broken by the addition of RIPA lysis buffer. The relative amount of internalized peptide was then determined by reading the fluorescence intensity (Fusion Alpha plate reader; PerkinElmer) of each extract followed by background substraction and protein content normalization. The r3-L-TAT transporter construct showed an internalization capability as effective as the D-TAT transporter construct. The r3-L-TATi transporter construct, which internalized in a time dependent manner, as both previous transporters, seems to be less efficient but still suitable, whereas L-TAT doesn’t accumulate over a period of 24 hours.

Furthermore, a confocal microscopy was carried out with cells treated with fluorescently labeled TAT derived transporter constructs as described above. The dissociated cortical primary neurons from P2 Sprague Dawley rats were cultured 12 days in neurobasal medium before exposure 24 hours to 500 nM of the FITC-labeled TAT derivative transporters. The cells were washed five times with PBS on ice and then mounted in fluorsave mounting medium without prior fixation. Acquisitions were performed on LSM510 metaconfocal microscope (Zeiss). Images were processed with LSM510 software and mounted using Adobe photoshop. Visualization by confocal microscopy of labeling with 500 nM FITC-transporters (A: green). Nuclei were stained by Hoechst (B: blue). The r3-L-TAT as well as the D-TAT and the r3-L-TATi transporter constructs were internalized into the cytoplasm of the non stressed neurons (C: Merge panel). However, after 24 hours incubation, the L-TAT transporter was not present anymore.

8.5 Further Internalization Experiments and Analysis

The time dependant internalization (uptake) of FITC-labeled TAT derived transporter constructs into cells of the HL-60 cell line was furthermore carried out with materials and methods as described above using sequences of the 96-FITC-labeled D-TAT derivative transporters. These sequences are listed below.

| SEQ ID NO: | peptide No: abbreviation | | | | | | | | | | | |
|---|---|---|---|---|---|---|---|---|---|---|---|---|
| 15 | r3-L-TAT | H2N | dR | K | K | R | dR | Q | R | R | dR | CONH2 |
| 21 | 1 | H2N | dR | A | K | R | dR | Q | R | R | dR | CONH2 |
| 22 | 2 | H2N | dR | K | A | R | dR | Q | R | R | dR | CONH2 |
| 23 | 3 | H2N | dR | K | K | A | dR | Q | R | R | dR | CONH2 |
| 24 | 4 | H2N | dR | K | K | R | dR | A | R | R | dR | CONH2 |
| 25 | 5 | H2N | dR | K | K | R | dR | Q | A | R | dR | CONH2 |
| 26 | 6 | H2N | dR | K | K | R | dR | Q | R | A | dR | CONH2 |
| 27 | 7 | H2N | dR | D | K | R | dR | Q | R | R | dR | CONH2 |
| 28 | 8 | H2N | dR | K | D | R | dR | Q | R | R | dR | CONH2 |
| 29 | 9 | H2N | dR | K | K | D | dR | Q | R | R | dR | CONH2 |
| 30 | 10 | H2N | dR | K | K | R | dR | D | R | R | dR | CONH2 |
| 31 | 11 | H2N | dR | K | K | R | dR | Q | D | R | dR | CONH2 |
| 32 | 12 | H2N | dR | K | K | R | dR | Q | R | D | dR | CONH2 |
| 33 | 13 | H2N | dR | E | K | R | dR | Q | R | R | dR | CONH2 |
| 34 | 14 | H2N | dR | K | E | R | dR | Q | R | R | dR | CONH2 |
| 35 | 15 | H2N | dR | K | K | E | dR | Q | R | R | dR | CONH2 |
| 36 | 16 | H2N | dR | K | K | R | dR | E | R | R | dR | CONH2 |
| 37 | 17 | H2N | dR | K | K | R | dR | Q | E | R | dR | CONH2 |
| 38 | 18 | H2N | dR | K | K | R | dR | Q | R | E | dR | CONH2 |
| 39 | 19 | H2N | dR | F | K | R | dR | Q | R | R | dR | CONH2 |
| 40 | 20 | H2N | dR | K | F | R | dR | Q | R | R | dR | CONH2 |
| 41 | 21 | H2N | dR | K | K | F | dR | Q | R | R | dR | CONH2 |
| 42 | 22 | H2N | dR | K | K | R | dR | F | R | R | dR | CONH2 |
| 43 | 23 | H2N | dR | K | K | R | dR | Q | F | R | dR | CONH2 |
| 44 | 24 | H2N | dR | K | K | R | dR | Q | R | F | dR | CONH2 |
| 45 | 25 | H2N | dR | R | K | R | dR | Q | R | R | dR | CONH2 |
| 46 | 26 | H2N | dR | K | R | R | dR | Q | R | R | dR | CONH2 |
| 47 | 27 | H2N | dR | K | K | K | dR | Q | R | R | dR | CONH2 |
| 48 | 28 | H2N | dR | K | K | R | dR | R | R | R | dR | CONH2 |
| 49 | 29 | H2N | dR | K | K | R | dR | Q | K | R | dR | CONH2 |
| 50 | 30 | H2N | dR | K | K | R | dR | Q | R | K | dR | CONH2 |
| 51 | 31 | H2N | dR | H | K | R | dR | Q | R | R | dR | CONH2 |
| 52 | 32 | H2N | dR | K | H | R | dR | Q | R | R | dR | CONH2 |
| 53 | 33 | H2N | dR | K | K | H | dR | Q | R | R | dR | CONH2 |
| 54 | 34 | H2N | dR | K | K | R | dR | H | R | R | dR | CONH2 |
| 55 | 35 | H2N | dR | K | K | R | dR | Q | H | R | dR | CONH2 |
| 56 | 36 | H2N | dR | K | K | R | dR | Q | R | H | dR | CONH2 |
| 57 | 37 | H2N | dR | I | K | R | dR | Q | R | R | dR | CONH2 |
| 58 | 38 | H2N | dR | K | I | R | dR | Q | R | R | dR | CONH2 |
| 59 | 39 | H2N | dR | K | K | I | dR | Q | R | R | dR | CONH2 |
| 60 | 40 | H2N | dR | K | K | R | dR | I | R | R | dR | CONH2 |
| 61 | 41 | H2N | dR | K | K | R | dR | Q | I | R | dR | CONH2 |
| 62 | 42 | H2N | dR | K | K | R | dR | Q | R | I | dR | CONH2 |
| 63 | 43 | H2N | dR | L | K | R | dR | Q | R | R | dR | CONH2 |
| 4 | 44 (D-TAT) | H2N | dR | dR | dR | dQ | dR | dR | dK | dK | dR | CONH2 |
| 16 | 45 (r3-L-TATi) | H2N | dR | R | R | Q | dR | R | K | K | dR | CONH2 |
| 15 | 46 (r3-L-TAT) | H2N | dR | K | K | R | dR | Q | R | R | dR | CONH2 |
| 14 | 47 (L-TAT) | H2N | R | K | K | R | R | Q | R | R | R | CONH2 |
| 68 | 48 | H2N | dR | K | K | R | dR | Q | R | L | dR | CONH2 |
| 69 | 49 | H2N | dR | M | K | R | dR | Q | R | R | dR | CONH2 |
| 70 | 50 | H2N | dR | K | M | R | dR | Q | R | R | dR | CONH2 |
| 71 | 51 | H2N | dR | K | K | M | dR | Q | R | R | dR | CONH2 |
| 72 | 52 | H2N | dR | K | K | R | dR | M | R | R | dR | CONH2 |
| 73 | 53 | H2N | dR | K | K | R | dR | Q | M | R | dR | CONH2 |
| 74 | 54 | H2N | dR | K | K | R | dR | Q | R | M | dR | CONH2 |
| 75 | 55 | H2N | dR | N | K | R | dR | Q | R | R | dR | CONH2 |
| 76 | 56 | H2N | dR | K | N | R | dR | Q | R | R | dR | CONH2 |
| 77 | 57 | H2N | dR | K | K | N | dR | Q | R | R | dR | CONH2 |
| 78 | 58 | H2N | dR | K | K | R | dR | N | R | R | dR | CONH2 |
| 79 | 59 | H2N | dR | K | K | R | dR | Q | N | R | dR | CONH2 |
| 80 | 60 | H2N | dR | K | K | R | dR | Q | R | N | dR | CONH2 |
| 81 | 61 | H2N | dR | Q | K | R | dR | Q | R | R | dR | CONH2 |
| 82 | 62 | H2N | dR | K | Q | R | dR | Q | R | R | dR | CONH2 |
| 83 | 63 | H2N | dR | K | K | Q | dR | Q | R | R | dR | CONH2 |
| 84 | 64 | H2N | dR | K | K | R | dR | K | R | R | dR | CONH2 |
| 85 | 65 | H2N | dR | K | K | R | dR | Q | Q | R | dR | CONH2 |
| 86 | 66 | H2N | dR | K | K | R | dR | Q | R | Q | dR | CONH2 |
| 87 | 67 | H2N | dR | S | K | R | dR | Q | R | R | dR | CONH2 |
| 88 | 68 | H2N | dR | K | S | R | dR | Q | R | R | dR | CONH2 |
| 89 | 69 | H2N | dR | K | K | S | dR | Q | R | R | dR | CONH2 |
| 90 | 70 | H2N | dR | K | K | R | dR | S | R | R | dR | CONH2 |
| 91 | 71 | H2N | dR | K | K | R | dR | Q | S | R | dR | CONH2 |
| 92 | 72 | H2N | dR | K | K | R | dR | Q | R | S | dR | CONH2 |
| 93 | 73 | H2N | dR | T | K | R | dR | Q | R | R | dR | CONH2 |
| 94 | 74 | H2N | dR | K | T | R | dR | Q | R | R | dR | CONH2 |
| 95 | 75 | H2N | dR | K | K | T | dR | Q | R | R | dR | CONH2 |
| 96 | 76 | H2N | dR | K | K | R | dR | T | R | R | dR | CONH2 |
| 97 | 77 | H2N | dR | K | K | R | dR | Q | T | R | dR | CONH2 |

-continued

| SEQ ID NO: | peptide No: abbreviation | | | | | | | | | | |
|---|---|---|---|---|---|---|---|---|---|---|---|
| 98 | 78 | H2N | dR | K | K | R | dR | Q | R | T | dR | CONH2 |
| 99 | 79 | H2N | dR | V | K | R | dR | Q | R | R | dR | CONH2 |
| 100 | 80 | H2N | dR | K | V | R | dR | Q | R | R | dR | CONH2 |
| 101 | 81 | H2N | dR | K | K | V | dR | Q | R | R | dR | CONH2 |
| 102 | 82 | H2N | dR | K | K | R | dR | V | R | R | dR | CONH2 |
| 103 | 83 | H2N | dR | K | K | R | dR | Q | V | R | dR | CONH2 |
| 104 | 84 | H2N | dR | K | K | R | dR | Q | R | V | dR | CONH2 |
| 105 | 85 | H2N | dR | W | K | R | dR | Q | R | R | dR | CONH2 |
| 106 | 86 | H2N | dR | K | W | R | dR | Q | R | R | dR | CONH2 |
| 107 | 87 | H2N | dR | K | K | W | dR | Q | R | R | dR | CONH2 |
| 108 | 88 | H2N | dR | K | K | R | dR | W | R | R | dR | CONH2 |
| 109 | 89 | H2N | dR | K | K | R | dR | Q | W | R | dR | CONH2 |
| 110 | 90 | H2N | dR | K | K | R | dR | Q | R | W | dR | CONH2 |
| 111 | 91 | H2N | dR | Y | K | R | dR | Q | R | R | dR | CONH2 |
| 112 | 92 | H2N | dR | K | Y | R | dR | Q | R | R | dR | CONH2 |
| 113 | 93 | H2N | dR | K | K | Y | dR | Q | R | R | dR | CONH2 |
| 114 | 94 | H2N | dR | K | K | R | dR | Y | R | R | dR | CONH2 |
| 115 | 95 | H2N | dR | K | K | R | dR | Q | Y | R | dR | CONH2 |
| 116 | 96 | H2N | dR | K | K | R | dR | Q | R | Y | dR | CONH2 |

In the above table D amino acids are indicated by a small "d" prior to the respective amino acid residue (e.g. dR=D-Arg).

For a few sequences synthesis failed in the first approach unfortunately due to technical reasons. However, the remaining sequences were used in the internalization experiments.

All transporters with the consensus sequence rXXXrXXXr (see above for a selection of possible sequences) showed a higher internalization capability than the L-TAT transporter. Hela cells were incubated 24 hours in 96 well plate with 10 mM of the r3-L-TAT-derived transporters. Alternatively, human lymphoma cells are used. The cells were then washed twice with an acidic buffer (0.2M Glycin, 0.15M NaCl, pH 3.0) and twice with PBS. Cells were broken by the addition of RIPA lysis buffer. The relative amount of internalized peptide was then determined by reading the fluorescence intensity (Fusion Alpha plate reader; PerkinElmer) of each extract followed by background subtraction One position appears to be critical for highest transporter activity and for improved kinetics of transport activity: Y in position 2 (peptide N° 91 corresponding to SEQ ID NO: 111). Briefly, Hela cells were incubated 2, 6 or 24 hours in 24 well plate with increasing dose of the r3-L-TAT-derivative transporters (0, 500 nM, 1 mM or 10 mM). The cells were then washed twice with an acidic buffer (0.2M Glycin, 0.15M NaCl, pH 3.0) and twice with PBS. Cells were broken by the addition of RIPA lysis buffer. The relative amount of internalized peptide was then determined by reading the fluorescence intensity (Fusion Alpha plate reader; PerkinElmer) of each extract followed by background substraction.

The conclusion of this experiment is as follows:

After 24 hours incubation, all transporters with the consensus sequence rXXXrXXXr (SEQ ID NO: 413) (see Table 1 for a selection of possible sequences) showed a higher internalization capability than the L-TAT transporter. Those results fully validate the consensus sequence rXXXrXXXr (SEQ ID NO: 413).

One position has impact on transporter activity: Y in position 2 (sequence 91 corresponding to SEQ ID NO: 111).

One position has impact on improved kinetics of transport activity: Y in position 2 (sequence 91 corresponding to SEQ ID NO: 111).

Accordingly, such TAT derived sequences as shown in Table 1 are preferred, which exhibit an Y in position 2, particularly when the sequence according to generic formula (I) exhibits 9 aa.

9. Determination of Intracellular Concentration of Specific Transporter Constructs Subsequent to Uptake (Internalization) of these Peptides into U937 Cells According to a further experiment, the concentration of specific transporter constructs subsequent to uptake (internalization) of these peptides into U937 cells were determined. The experiments were carried out using the sequences RKKRRQRRR (L-TAT) (SEQ ID NO: 2), rrrqrrkkr (D-TAT) (SEQ ID NO: 4), rKKRrQRRr (r3-L-TAT) (SEQ ID NO: 15) and rYKRrQRRr (XG-91) (SEQ ID NO: 111), each in a concentration of 10 μM each.

| 10 μM | 2 h | 4 h | 6 h | 24 h |
|---|---|---|---|---|
| RKKRRQRRR (L-TAT) | 1.20 | 1.38 | 1.07 | 0.5 |
| rrrqrrkkr (D-TAT) | 2.00 | 2.24 | 3.55 | 17.3 |
| rKKRrQRRr (r3-L-TAT) | 2.34 | 3.16 | 3.56 | 11.2 |
| rYKRrQRRr (XG-91, sequence 91 corresponding to SEQ ID NO: 111) | 3.16 | 4.27 | 4.68 | 50 |

Surprisingly, the accumulation of rYKRrQRRr (XG-91, sequence 91 corresponding to SEQ ID NO: 111), shows an extremely accumulation in the cell, which is even significantly higher than the concentration of the transporter construct in the medium or the average concentration of about 20 μM which was expected for D-TAT construct. This underlines the importance of transporter constructs according to generic formula (I), particular of transporter constructs which comprise a TAT derived sequence as shown in Table 1, which exhibits an Y in position 2, and preferably has 9 aa and the consensus sequence rXXXrXXXr (SEQ ID NO: 413).

10. Uptake (Internalization) of Peptides into Cells and Measurement of Peptide Internalization in Cell Lines HepG2 (Hepatocarcinoma), HCT-116 (Tumoral Colon), U937 (Lymphoma), in WBC Cell Lines (White Blood Cell Lines) and non-WBC Cell Lines In these experiments, the internalization (uptake) capacity of of FITC-labeled TAT derived transporter constructs in vitro was evaluated with a fluorescence plate reader in further cell lines HepG2 (hepatocarcinoma), HCT-116 (tumoral colon), U937 (Lymphoma), in WBC cell lines (white blood cell lines) and non-WBC cell lines.

Test samples and conditions used in the experiments

The constructs and conditions used in this experiment were as described above for experiment 3 with following amendments and cell lines:

a) Uptake (internalization) of FITC-labeled TAT derived transporter constructs in vitro (10 μM, HepG2 hepatocarcinoma, HCT-116 tumoral colon, 24 h)

The constructs used were different TAT derived transporter constructs termed D-TAT and r3-TATi (also termed r3-L-TATi), D-TAT, each having a length of 9 amino acids but a different r3-/L-pattern, and the constructs $r_6R_3$ (rrrRRRrrr) and DAK, wherein the constructs additionally have been labeled with beta-Alanine at their N-terminus. The uptake was most efficient for constructs D-TAT and $r_6R_3$, followed by $r_3$-L-TATi.

b) Uptake (internalization) of FITC-labeled TAT derived transporter constructs in vitro (10 μM, U937, Lymphoma, 24 h).

The constructs used were four different TAT derived transporter constructs (termed L-TAT, r3-TAT (also termed r3-L-Tat), r3-TATi (also termed r3-L-TATi), and D-TAT), each having a length of 9 amino acids but a different D-/L-pattern. Additionally, the construct DAK was used for comparison and a control sample, ontaining no peptide. The uptake of r3-TAT, r3-TATi and D-TAT transporter constructs into the cells was most efficient, wherein L-TAT showed a significantly lower uptake into the cells.

c) HSPG dependency of uptake (internalization) of the D-TAT transporter construct An experiment was carried out to see, whether the uptake (internalization) of the D-TAT transporter construct is HSPG-dependent. As found, the uptake (internalization) of the D-TAT transporter construct is HSPG-dependent at a concentration of 500 nm over 24 hours in U937 cells, Lymphoma. The construct used for the experiment was D-TAT (SEQ ID NO:4), having a length of 9 amino acids and being labeled with FITC and at its N-terminus with beta-Alanine.

d) Exit of the FITC-labeled TAT derived transporter constructs in U937 cells (lymphoma)

A further experiment was carried out to see, whether the FITC-labeled TAT derived transporter constructs exit U937 cells. As a result, an exit is not observed in U937 cells at 500 nM FITC-D-TAT. The construct used for the experiment was D-TAT, having a length of 9 amino acids and being labeled with FITC and at its N-terminus with beta-Alanine.

Furthermore, it could be seen, that an exit of the FITC-labeled TAT derived transporter constructs is observed at 10 μM FITC-D-TAT, and is HSPG-dependent in U937 cells (lymphoma). The construct used for the experiment was again D-TAT as above.

e) Uptake (internalization) and an exit of the FITC-labeled TAT derived transporter constructs at 10 μM FITC-D-TAT in non WBC-lines (white blood cells lines)

In a further experiment an uptake (internalization) and an exit of the FITC-labeled TAT derived transporter constructs are observed at 10 μM FITC-D-TAT in non WBC-lines (white blood cells lines). The construct used for the experiment was D-TAT, having a length of 9 amino acids and being labeled with FITC and at its N-terminus with beta-Alanine.

f) Conclusions

As a conclusion of the above uptake (internalization) experiments, uptake (internalization) of FITC-labeled TAT derived transporter constructs containing or exclusively composed of D-amino acids is linear over several hrs in vitro. Furthermore, at 24 hrs, the uptake (internalization) of these FITC-labeled TAT derived transporter constructs in vitro reaches 50-100 fold higher intracellular concentrations than L-TAT. Additionally, the uptake (internalization) of FITC-labeled TAT derived transporter constructs containing or exclusively composed of D-amino acids by WBC-lines (white blood cells lines) is 10-50 fold more efficient than by non-WBC-lines in vitro. For all these experiments, an exit was shown to be efficient at high intracellular concentration, but is not observed at low concentrations in WBCs 11. Synthesis of Cytotoxic Transporter Cargo Conjugate Molecule D-Tat-cisplatin, r3-L-TAT-Cisplatin and r3-L-TATi-Cisplatin 11.1 Peptide Synthesis The peptide sequence of D-TAT (rrrqrrkkr) (SEQ ID NO: 4), r3-L-TAT (rKKRrQRRr) (SEQ ID NO: 5) and r3-L-TATi (rRRQrRKKr) (SEQ ID NO: 16) including an additional methionine is synthesized manually on 0.4 mmol Fmoc-Amide-AM resin by using Fmoc chemistry. The peptide is then cleaved from the resin with TFA, filtered under a reduced pressure, precipitated with cold ether, and dried. The crude peptide is purified by Semi-preparative HPLC and characterized by ESI-MS.

11.2 Alkylation of Peptide to Cisplatin 5.0 μmol of Cisplatin (1.5 mg in 3.0 ml Sodium Chloride buffer, pH 5.0) are dissolved in 2.0 ml of 10 mM $Na_2HPO_4$ buffer (pH 7.4), and pH value of the solution is 7.0. 5.0 μmol of D-TAT-Methionine peptide (or of r3-L-TAT-Methionine peptide or of r3-L-TATi-Methionine peptide) is prepared in 10 mM $Na_2HPO_4$ buffer (pH 7.4) and pH value of the solution is 6.0. Then the alkylation is started by mixing two solutions at room temperature in dark (pH value of the mixture is 7.0). After 0 h, 1 h, 3 h and 24 h, the product is analysed by analytic RP-HPLC, and characterized by ESI-MS. The expected peak solution is finally purified by Semi-preparative RP-HPLC and lyophilized.

12. Synthesis of Cytotoxic Transporter Cargo Conjugate Molecule D-Tat-Oxaliplatin, r3-L-TAT-Oxaliplatin and r3-L-TATi-Oxaliplatin

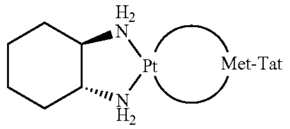

12.1. Peptide (D-Tat-Methionine, r3-L-TAT-Methionine and r3-L-TATi-Methionine) Synthesis The peptide sequence of D-TAT (rrrqrrkkr), r3-L-TAT (rKKRrQRRr) and r3-L-TATi (rRRQrRKKr) is synthesized manually on 0.23 mmol Fmoc-Rink Amide resin by using Fmoc chemistry. Thus, each amino acid from C-terminal Gly to N-terminal I-Met (L-Form) is sequentially attached to the resin with with a cycle of Fmoc-deprotection (20% piperidine in DMF) and amino acid coupling (HBTU/HOBt/DIEA in DMF activation). The peptide is cleaved from the resin with TFA (2 h in the presence of 2.5% $dH_2O$, 0.5% EDT and 2.0% TIS), filtred at atmospheric pressure, volume reduced by $N_2$ bubbling, precipitated with cold ether and air-dried. The crude peptide is purified by semi-preparative RP-HPLC and characterized by ESI-MS.

12.2. Alkylation of Peptide to Oxaliplatin

10 μmol Oxaliplatin, formulated as Eloxatin® (Oxaliplatinum 4.0 mg, lactosum monohydricum 36.0 mg) in 5.0 ml 10 mM $Na_2HPO_4$ buffer (pH 7.4). 10 μmol of D-Tat-Methionine peptide (or of r3-L-TAT-Methionine peptide or of r3-L-TATi-Methionine peptide) is prepared in $dH_2O$ 5.0 ml. Alkylation is started by mixing the two solutions at room temperature. Reaction is then left at 37° C. and monitored by analytical RP-HPLC at 214 and 280 nm over 24 h, target peak is characterized by ESI-MS and purified by semi-preparative RP-HPLC followed by lyophilization.

12.3. Test Conditions

Effects of a treatment with increasing concentrations of a conjugate molecule of the invention (D-Tat-oxaliplatin, r3-L-TAT-oxaliplatin, or r3-L-TATi-oxaliplatin) on the survival of MCF-7 (human breast adenocarcinoma cell line) and SiHa (human cervix squamous carcinoma cell line) are determined. The effects of D-Tat-oxaliplatin, r3-L-TAT-oxaliplatin, or r3-L-TATi-oxaliplatin is compared to the conjugate L-Tat-oxaliplatin and to two unconjugated anti-cancer drugs (Oxaliplatin and Cisplatin). Cells of each cell line (10'000 cells per well) are plated into 96 well plates (200 μl total volume of MEM supplemented with 10% FBS, 1% L-glutamine, 1% Na-pyruvate, 1% non-essential amino acids for MCF-7 and of MEM/Earle's supplemented with 10% FBS, 1% Na-pyruvate, 1% non-essential amino acids for SiHa cells). 6 to 10 different concentrations for each test substance are tested. The control cells are non-treated. Cells are incubated at 37° C. for 24 h before treatment with the test substance. Each experiment is carried in triplicate. Cell incubation after treatment is performed for 96 hours at 37° C. The effects of the test molecules on the survival of these cell lines (in vitro cytotoxic activity) is measured by the MTT assay. 20 μl of a 5 mg/ml 0.22 μm filtered Thiazolyl Blue Tetrazolium Bromide solution (MTT, Sigma, Ref. No. 88415) in Phosphate Buffered saline (PBS, CHUV) are added to each well and the plate is incubated for 4 hours at 37° C. The supernatant is removed and formazan crystals are dissolved with DMSO (200 μl per well). Absorbancy (OD) is measured in a microplate reader at 595 nm (Expert Plus Reader, Asys Hitech). The $IC_{50}$ (concentration of the drug inhibiting 50% of the cell growth) for the test substances is calculated using Prism software.

13. Synthesis of Cytotoxic Transporter Cargo Conjugate Molecule D-Tat-Chlorambucil, r3-L-TAT-Chlorambucil and r3-L-TATi-Chlorambucil

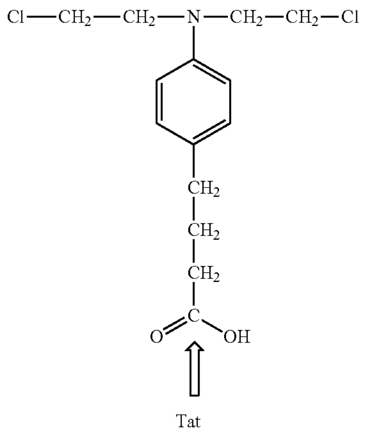 [SMILES: O=C(O)CCCc1ccc(N(CCCl)CCCl)cc1]

13.1 Conjugate Molecule (D-Tat-Chlorambucil, r3-L-TAT-Chlorambucil and r3-L-TATi-Chlorambucil) Synthesis The D-TAT (rrrqrrkkr), r3-L-TAT (rKKRrQRRr) or r3-L-TATi (rRRQrRKKr) peptide sequence is synthesized manually on 0.23 mmol Fmoc-Rink Amide resin by using Fmoc chemistry. Thus, each amino acid from C-terminal Gly to N-terminal I-A (L-form) is sequentially attached to the resin with with a cycle of Fmoc-deprotection (20% piperidine in DMF) and amino acid coupling (HBTU/HOBt/DIEA in DMF activation).

Following Fmoc-deprotection (20% piperidine in DMF) of N-terminal I-A, coupling of chlorambucil is achieved using standard amino acid coupling conditions (HBTU/HOBt/DIEA in DMF activation). The conjugate molecule is cleaved from the resin with TFA (70 min in the presence of 3% $dH_2O$ and 3% TIS), filtred at atmospheric pressure, volume reduced by $N_2$ bubbling, precipitated with cold ether and air-dried. The crude conjugate molecule is purified by semi-preparative RP-HPLC, characterized by ESI-MS followed by lyophilization.

13.2 Comparative Studies

Effects of a treatment with increasing concentrations of D-Tat-chlorambucil, r3-L-TAT-chlorambucil, or r3-L-TATi-chlorambucil on the survival of MCF-7 (human breast adenocarcinoma cell line) and SiHa (human cervix squamous carcinoma cell line) is determined. The effects of D-Tat-chlorambucil, r3-L-TAT-chlorambucil, or r3-L-TATi-chlorambucil is furthermore compared to the conjugate L-Tat-chlorambucil and to two u chlorambucil nconjugated anti-cancer drugs (Chlorambucil and Cisplatin). Cells of each cell line (10'000 cells per well) are plated into 96 well plates (200 μl total volume of MEM supplemented with 10% FBS, 1% L-glutamine, 1% Na-pyruvate, 1% non-essential amino acids for MCF-7 and of MEM/Earle's supplemented with 10% FBS, 1% Na-pyruvate, 1% non-essential amino acids for SiHa cells). 6 to 10 different concentrations for each test substance are tested. The control cells are non-treated. Cells are incubated at 37° C. for 24 h before treatment with the test substance. Each experiment is carried in triplicate. Cell incubation after treatment is performed for 96 hours at 37° C. The effects of the test molecules on the survival of these cell lines (in vitro cytotoxic activity) is measured by the MTT assay. 20 μl of a 5 mg/ml 0.22 μm filtered Thiazolyl Blue Tetrazolium Bromide solution (MTT, Sigma, Ref. No. 88415) in Phosphate Buffered saline (PBS, CHUV) are added to each well and the plate is incubated for 4 hours at 37° C. The supernatant is removed and formazan crystals are dissolved with DMSO (200 μl per well). Absorbancy (OD) is measured in a microplate reader at 595 nm (Expert Plus Reader, Asys Hitech). The $IC_{50}$ (concentration of the drug inhibiting 50% of the cell growth) for the test substances is calculated using Prism software.

14. Synthesis of Cytotoxic Transporter Cargo Conjugate Molecule D-Tat-Doxorubicine, r3-L-TAT-Doxorubicine and r3-L-TATi-Doxorubicine

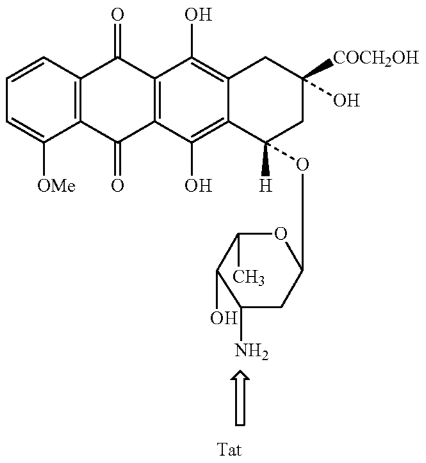

14.1. Conjugate Molecule (D-Tat-doxorubicine, r3-L-TAT-Doxorubicine and r3-L-TATi-Doxorubicine) Synthesis The D-TAT (rrrqrrkkr) (SEQ ID NO: 4), r3-L-TAT (rKKRrQRRr) (SEQ ID NO: 15) and r3-L-TATi (rRRQrRKKr) (SEQ ID NO: 16) peptide sequence is synthesized manually on 0.23 mmol Fmoc-Rink Amide resin by using Fmoc chemistry. Thus, each amino acid from C-terminal Gly to N-terminal I-E (L-form) is sequentially attached to the resin with with a cycle of Fmoc-deprotection (20% piperidine in DMF) and amino acid coupling (HBTU/HOBt/DIEA in DMF activation).

Following Fmoc-deprotection (20% piperidine in DMF) of N-terminal I-E, acetylation (acetic anhydride, DIEA in DMF activation) is done. Removal of the Odmab side-chain protecting group is performed using 2% hydrazine monohydrate in DMF. Coupling of chlorambucil formulated as Adriblastin® (Doxorubicinie.HCl 18%, NaCl 82% lyophilized) is achieved via OBt ester (DIPCDI/HOBt/DIEA in DCM/DMF activation).

The conjugate molecule is cleaved from the resin with TFA (2 h in the presence of 1.7% $dH_2O$ and 1.7% TIS), filtred at atmospheric pressure, volume reduced by $N_2$ bubbling, precipitated with cold ether and air-dried. The crude conjugate molecule is purified by semi-preparative RP-HPLC, characterized by ESI-MS followed by lyophilization.

15. Synthesis of Cytotoxic Transporter Cargo Conjugate Molecule D-Tat-Saquinavir, r3-L-TAT-Saquinavir and r3-L-TATi-Saquinavir

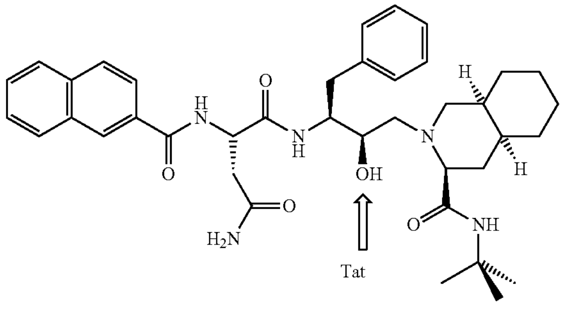

15.1. Peptide (D-TAT-D-Cysteine r3-L-TAT-D-Cysteine and r3-L-TATi-D-Cysteine) Synthesis The D-TAT (rrrqrrkkr) (SEQ ID NO: 4), r3-L-TAT (rKKRrQRRr) (SEQ ID NO: 15) and r3-L-TATi (rRRQrRKKr) (SEQ ID NO: 16) peptide sequence is synthesized manually on 0.40 mmol Fmoc-Rink Amide resin by using Fmoc chemistry. Thus, each amino acid from C-terminal D-Arg to N-terminal D-Cys is sequentially attached to the resin with with a cycle of Fmoc-deprotection (20% piperidine in DMF) and amino acid coupling (TBTU/HOBt/DIEA in DMF activation). The peptide is cleaved from the resin with TFA, pre-incubated on ice (5 h in the presence of 2.5% $dH_2O$, 2.5% EDT and 1.0% TIS), filtred at reduced pressure, precipitated with cold ether and vacuum dried. The crude peptide is purified by semi-preparative RP-HPLC and characterized by ESI-MS.

15.2. Preparation of Saquinavir Active Ester

375 μmol Boc-Gly-OH is dissolved in anhydrous DCM at room temperature, and to this is added 265 μmol DMAP, 375 μmol DIPCI and 110 μmol Saquinavir, formulated as Invirase® (lactose, excipiens pro compresso obducto) at 0° C. The reaction mixture is allowed to warm to room temperature and stirred overnight. The product is ished with 0.1 N HCl, dried over $MgSO_4$, and evaporated under reduced pressure to yield the solid product SQV-Gly(Boc). The Boc protecting group is removed by incubating SQV-Gly(Boc) ester for 3 h in a mixture of $CH_2Cl_2$ and TFA (50:50). The product is recristallized from cold ether and dried under vacuum overnight. 47 μmol SQV-Gly ester is dissolved in 3 ml anhydrous DMSO at room temperature, and to this is added 94 μmol SPDP. The reaction mixture pH is adjusted to 8.0 under constant stirring at room temperature. The reaction is left for 3 h under constant stirring. The crude product SQV-Gly-COCH2CH2-SS-pyridyl is purified by semi-preparative RP-HPLC and characterized by ESI-MS.

15.3. Conjugation of Peptide D-TAT (rrrqrrkkr) (SEQ ID NO: 4), r3-L-TAT (rKKRrQRRr) (SEQ ID NO: 15) or r3-L-TATi (rRRQrRKKr)(SEQ ID NO: 16)-D-Cysteine to Saquinavir 27 μmol SQV-Gly-COCH2CH2-SS-pyridyl is dissolved in 0.5 ml PBS buffer pH 7.5 at room temperature, and to this is added 54 μmol D-TAT (rrrqrrkkr) (SEQ ID NO: 4), r3-L-TAT (rKKRrQRRr) (SEQ ID NO: 15) or r3-L-TATi (rRRQrRKKr)(SEQ ID NO: 16)-D-Cysteine in 0.5 ml PBS buffer pH 7.5. The reaction is left at room temperature for 3 h under constant stirring. The crude conjugate D-TAT (rrrqrrkkr)(SEQ ID NO: 4)-Saquinavir, r3-L-TAT (rKKRrQRRr)(SEQ ID NO: 15)-Saquinavir and r3-L-TATi (rRRQrRKKr)(SEQ ID NO: 16)-Saquinavir is purified by semi-preparative RP-HPLC and characterized by ESI-MS.

16. Cellular Import of Inventive Transporter Cargo Conjugate Molecules Comprising TAT Derived Transporter Constructs According to SEQ ID NOs: 1 to 116 and INK1 or IB1 Derived Cargo Peptides According to any of SEQ ID NO:118, SEQ ID NO:119, and one of SEQ ID NO:121 to 200

The ability of the transporter cargo conjugate molecules comprising TAT derived transporter constructs according to any of SEQ ID NOs: 1 to 116 and JNK1 or IB1 derived cargo peptides according to any of SEQ ID NO:118, SEQ ID NO:119, and one of SEQ ID NO:121 to 200 to enter cells is evaluated. Inventive transporter constructs and inventive transporter cargo conjugate molecules are labeled by N-terminal addition of a glycine residue conjugated to fluorescein. These labeled peptides (1 μM) are added to TC-3 cell cultures. At predetermined times cells are fished with PBS and fixed for five minutes in ice-cold methanol-acetone (1:1) before being examined under a fluorescence microscope. Fluorescein-labeled BSA (1 μM, 12 moles/mole BSA) is used as a control.

Fluorescent Signals from these Transporter Constructs and Inventive Transporter Cargo 17. Inhibition of Irradiation Induced Pancreatic β-Cell Death by Inventive Transporter Cargo Conjugate Molecules Comprising TAT Derived Transporter Constructs According to any of SEQ ID NOs: 1 to 116 and INK1 or IB1 Derived Cargo Peptides According to any of SEQ ID NO:118, SEQ ID NO:119, and one of SEQ ID NO:121 to 200

JNK is also activated by ionizing radiation. To determine whether inventive transporter cargo conjugate molecules comprising TAT derived transporter constructs according to any of SEQ ID NOs: 1 to 116 and JNK1 or IB1 derived cargo peptides according to any of SEQ ID NO:118, SEQ ID NO:119, and one of SEQ ID NO:121 to 200 would provide protection against radiation-induced JNK damage, "WiDr" cells are irradiated (30 Gy) in presence or absence of D-TAT, L-TAT and inventive transporter cargo conjugate molecules comprising TAT derived transporter constructs according to any of SEQ ID NOs: 1 to 116 and JNK1 or IB1 derived cargo peptides according to any of SEQ ID NO:118, SEQ ID NO:119, and one of SEQ ID NO:121 to 200 (1 μM added 30 minutes before irradiation). Control cells (CTRL) are not irradiated. Cells are analyzed 48 hours later by means of PI and Hoechst 3342 staining, as described above. N=3, SEM are indicated.

18. Radioprotection to Ionizing Radiation by Inventive Transporter Cargo Conjugate Molecules Comprising TAT Derived Transporter Constructs According to Any of SEQ ID NOs: 1 to 116 and JNK1 or IB1 Derived Cargo Peptides According to any of SEQ SEQ ID NO:119, and one of SEQ ID NO:121 to 200

To determine the radioprotective effects of the inventive transporter cargo conjugate molecules comprising TAT derived transporter constructs according to any of SEQ ID NOs: 1 to 116 and JNK1 or IB1 derived cargo peptides according to any of SEQ SEQ ID NO:119, and one of SEQ ID NO:121 to 200, C57B1/6 mice (2 to 3 months old) are irradiated with a Phillips RT 250R-ray at a dose rate of 0.74 Gy/min (17 mA, 0.5 mm Cu filter). Thirty minutes prior to irradiation, the animals are injected i.p. with inventive transporter cargo conjugate molecules comprising TAT derived transporter constructs according to any of SEQ ID NOs: 1 to 116 and JNK1 or IB1 derived cargo peptides according to any of SEQ ID NO:118, SEQ ID NO:119, and one of SEQ ID NO:121 to 200. Briefly, mice are irradiated as follows: mice are placed in small plastic boxes with the head lying outside the box. The animals are placed on their back under the irradiator, and their neck fixed in a small plastic tunnel to maintain their head in a correct position. The body is protected with lead. Prior to irradiation mice are maintained on standard pellet mouse chow, however post irradiation mice are fed with a semi-liquid food that is renewed each day. The reaction of the lip mucosa is then scored by 2 independent observers according to the scoring system developed by Parkins et al. (Parkins et al, Radiotherapy & Oncology, 1: 165-173, 1983), in which the erythema status as well as the presence of edema, desquamation and exudation is quoted. Additionally, animals are weighed before each recording of their erythema/edema status.

19. Treatment of Noise Trauma

Inventive transporter cargo conjugate molecules comprising TAT derived transporter constructs according to any of SEQ ID NOs: 1 to 116 and JNK1 or IB1 derived cargo peptides according to any of SEQ ID NO:118, SEQ ID NO:119, and one of SEQ ID NO:121 to 200, particularly inventive transporter cargo conjugate molecules comprising peptidic inhibitors L-TAT-IB1(s1-34) or D-TAT-IB1(s1-34), are applied onto the round window membrane of the cochlea of 3 groups of guinea pigs (each group with 6 animals) in 2 microliters of a gel formulation of 2.6% buffered hyaluronic acid (Hylumed, Genzyme Corp.) at a concentration of 100 μM either 30 minutes before noise trauma (120 dB at 6 kHz during 30 minutes) or 30 minutes or 4 hours thereafter. Untreated ears served as control. Hearing threshold shifts are evaluated by auditory brainstem response measurements 20 minutes after noise trauma (temporary threshold shift, TTS) and 15 days following the trauma (permanent threshold shift, PTS). Administration of D-TAT-IB1(s) protected against permanent hearing loss even if applied after exposure to excessive noise compared to non-treated ears.

20. Evaluation of the Therapeutical Activity of Inventive Transporter Cargo Conjugate Molecules Comprising TAT Derived Transporter Constructs According to any of SEQ ID NOs: 1 to 116 and INK1 or IB1 Derived Cargo Peptides According to any of SEQ ID NO:118, SEQ ID NO:119, and one of SEQ ID NO:121 to 200 in the Treatment of Colitis a) Test system:

i) Species/Strain: Mouse/BALB/c ii) Source: Harlan Israel, Ltd.

iii) Gender: Female iv) Total No. of Animals: n=150 v) Age: Young adults, 7 weeks of age at study initiation vi) Body Weight: Weight variation of animals at the time of treatment initiation does not exceed ±20% of the mean weight.

vii) Animals Health: The health status of the animals used in this study is examined on arrival, only animals in good health are acclimatized to laboratory conditions (at least seven days) and are used in the study.

viii) Randomization: Animals are randomly assigned to experimental groups according to a Table of Random Numbers.

ix) Termination: At the end of the study surviving animals are euthanized by cercical dislocation.

b) Test Procedures

Colitis is induced by administration of TNBS dissolved in 50% Ethanol

All animals are then treated with doses of inventive transporter cargo conjugate molecules comprising TAT derived transporter constructs according to any of SEQ ID NOs: 1 to 116 and JNK1 or IB1 derived cargo peptides according to any of SEQ ID NO:118, SEQ ID NO:119, and one of SEQ ID NO:121 to 200 in the range of 0.1 to 1000 μg/kg, either intraperitoneally or subcutaneously, as a single or repeated daily doses (see above).

c) Observations and Examinations i) Clinical Signs

Throughout the duration of the above experiment, careful clinical examinations are carried out and recorded. Observations included changes external appearance, e.g. of the skin, fur, eyes, mucous membranes, occurrence of secretions and excretions (e.g. diarrhea), and autonomic activity. Changes in gait, posture and response to handling, as well as the presence of bizarre behavior, tremors, convulsions, sleep and coma are also noted.

ii) Body Weights

Determination of individual body weight of animals is made on a daily basis.

iii) Clinical Assessment of Colitis

Body weight, stool consistency and bleeding per rectum are all recorded daily and served as the parameters of disease severity score:

| Score | Weight loss (%) | Stool consistency | Presence of blood per rectum |
|---|---|---|---|
| 0 | None | Normal | Negative |
| 1 | 1-5 | Redness, swelling of the anus | Negative |
| 2 | 5-10 | Loose stool | Negative |
| 3 | 10-15 | Diarrhea | Negative |
| 4 | >15 | Diarrhea | Bleeding |
| 5 | | Death | |

iv) Gross Pathology of the Colon

On the last day of the experiment, animals are euthanized and the colon is removed for gross pathology evaluation according to the following score:

| Grade | Signs |
|---|---|
| 0 | No abnormalities detected |
| 1 | Edema and redness on one location |
| 2 | Edema and redness on more than one location, or a very massive endema and redness capture more than 50% of the colon |
| 3 | One ulcer |
| 4 | More than one ulcer or a very long severe ulcer |

21. Determining the Activity of Inventive Transporter Cargo Conjugate Molecules Comprising TAT Derived Transporter Constructs According to any of SEQ ID NOs: 1 to 116 and INK1 or IB1 Derived Cargo Peptides According to any of SEQ ID NO:118, SEQ ID NO:119, and one of SEQ ID NO:121 to 200 in the Treatment of Chronic Obstructive Pulmonary Disease (COPD)

In order to determine the activity of the exemplary inventive transporter cargo conjugate molecules comprising TAT derived transporter constructs according to any of SEQ ID NOs: 1 to 116 and JNK1 or IB1 derived cargo peptides according to any of SEQ ID NO:118, SEQ ID NO:119, and one of SEQ ID NO:121 to 200 in the treatment of Chronic Obstructive Pulmonary Disease (COPD) these inventive transporter cargo conjugate molecules are used in an animal model of Bleomycin induced acute lung inflammation and fibrosis. The protocol of bleomycin induced inflammation and fibrosis has been described before in the literature. The aim of the Experiment is to investigate the effect of these inventive transporter cargo conjugate molecules by subcutaneous (s.c.) route on neutrophil recruitment in broncho alveolar lavage (BAL) and lung in bleomycin induced inflammation and fibrosis:

at 1 day after a single bleomycin administration (10 mg/kg)

and at day 10 with the development of fibrosis

1) Method and Experimental Approach

The test compounds selected from inventive transporter cargo conjugate molecules comprising TAT derived transporter constructs according to any of SEQ ID NOs: 1 to 116 and JNK1 or IB1 derived cargo peptides according to any of SEQ ID NO:118, SEQ ID NO:119, and one of SEQ ID NO:121 to 200 at two doses and vehicle control are given s.c. with a single intranasal administration of bleomycin and mice are analyzed after 1 and 10 days. The animals used in the model are 10 C57BU6 mice (8 weeks old) per group. The experimental groups include vehicle, 0.001 mg/kg of inventive transporter cargo conjugate molecules comprising TAT derived transporter constructs according to any of SEQ ID NOs: 1 to 116 and JNK1 or IB1 derived cargo peptides according to any of SEQ ID NO:118, SEQ ID NO:119, and one of SEQ ID NO:121 to 200 and 0.1 mg/kg of these inventive transporter cargo conjugate molecules, and the treatment consists of repeated sub-cutaneous administration of these inventive transporter cargo conjugate molecules prior to bleomycin administration every 3 days. Acute lung inflammation at 24 h is monitored by BAL lavage, cytology, cell counts, and lung myeloperoxidase activity. The effect of the compound is compared with vehicle controls. Lung fibrosis is assessed histologically using hematoxylin and eosin staining at day 10 after the single dose of bleomycin.

1.1) Bleomycin Administration

Bleomycin sulfate in saline (10 mg/kg body weight) from Bellon Laboratories (Montrouge, France) or saline are given through the airways by nasal instillation in a volume of 40 μL under light ketamine-xylasine anesthesia. The groups for Bleomycin administration for both bleomycin induced inflammation and fibrosis included: Vehicle, 0.001 mg/kg of the inventive transporter cargo conjugate molecules comprising TAT derived transporter constructs according to any of SEQ ID NOs: 1 to 116 and JNK1 or IB1 derived cargo peptides according to any of SEQ ID NO:118, SEQ ID NO:119, and one of SEQ ID NO:121 to 200 and 0.1 mg/kg of these inventive transporter cargo conjugate molecules. The route for bleomycin induced inflammation is subcutaneous (s.c.) route, and administration occurrs as a single dose. The route for bleomycin induced fibrosis is subcutaneous (s.c.) route, and administration occurred 3 times in 10 days.

1.2) Bronchoalveolar Lavage Fluid (BALF)

After incision of the trachea, a plastic cannula is inserted and airspaces are ished using 0.3 ml of PBS solution, heated to 37° C. The samples collected are dispatched in 2 fractions: the first one (1 ml corresponding to the 2 first lavages) is used for mediator measurement and the second one for the cell determination (4 ml). The first fraction is centrifuged (600 g for 10 min) and supernatant is fractionated and kept at −80° C. until mediator determination. The cell pellet is then resuspended in 0.4 ml sterile NaCl, 0.9%, and pooled with the second fraction and is used for cell counts.

1.3) Lung Homogenization

After BAL the whole lung is removed and placed inside a microtube (Lysing matrix D, Q Bio Gene, Illkrich, France) with 1 ml of PBS, total lung tissue extract is prepared using a Fastprep® system (FP120, Q Bio Gene, Illkrich, France), the extract is then centrifuged and the supernatant stored at −80° C. before mediator measurement and collagen assay with Sircol Collagen Assay (France Biochem Division, France).

1.4) Cell Count and Determination

Total cell count is determined in BAL fluid using a Malassez hemocytometer.

Differential cell counts are performed on cytospin preparations (Cytospin 3, Thermo Shandon) after staining with MGG Diff-quick (Dade Behring AG). Differential cell counts are made on 200 cells using standard morphological criteria.

1.5) TNF Measurement

TNF level in BALF is determined using ELISA assay kits (Mouse DuoSet, R&D system, Minneapolis, USA) according to manufacturer's instructions. Results are reported as pg/ml.

1.6) MPO-Measurement

MPO-levels are measured upon administration of inventive transporter cargo conjugate molecules comprising TAT derived transporter constructs according to any of SEQ ID NOs: 1 to 116 and JNK1 or IB1 derived cargo peptides according to any of SEQ ID NO:118, SEQ ID NO:119, and one of SEQ ID NO:121 to 200.

1.7) Histology

After BAL and lung perfusion, the large lobe is fixed in 4% buffered formaldehyde for standard microscopic analysis. 3-μm sections are stained with hematoxylin and eosin (H&E).

22. Determining the Activity of Inventive Transporter Cargo Conjugate Molecules Comprising TAT Derived Transporter Constructs According to any of SEQ ID NOs: 1 to 116 and JNK1 or IB1 Derived Cargo Peptides According to any of SEQ ID NO:118, SEQ ID NO:119, and one of SEQ ID NO:121 to 200 in the Treatment of Alzheimer's Disease In order to determine the activity of the exemplary inventive transporter cargo conjugate molecules comprising TAT derived transporter constructs according to any of SEQ ID NOs: 1 to 116 and JNK1 or IB1 derived cargo peptides according to any of SEQ ID NO:118, SEQ ID NO:119, and one of SEQ ID NO:121 to 200 in Alzheimer's disease, these peptides are evaluated in the hAPP-transgenic mice model overexpressing APP751 with London and Swedish mutations using the behavioral Morris Water Maze test as well as immunohistological tests measuring plaque load and ELISA tests measuring β-amyloid$_{1-40}$ and β-amyloid$_{1-42}$ levels in the brain of mice.

a) Methods i) Introduction

The study is designed to evaluate the efficacy of the inventive transporter cargo conjugate molecules comprising TAT derived transporter constructs according to any of SEQ ID NOs: 1 to 116 and JNK1 or IB1 derived cargo peptides according to any of SEQ ID NO:118, SEQ ID NO:119, and one of SEQ ID NO:121 to 200 on behavioral, biochemical and histological markers using 5 months (±2 weeks) old female hAPP Tg mice. Therefore, mice are treated every two or three weeks up to 4 months and in the end of the treatment period behavior is evaluated in the Morris Water Maze. At sacrifice brain, CSF and blood are collected. Aβ40 and Aβ42 levels are determined in four different brain homogenate fractions as well as in CSF of Tg mice. Plaque load is quantified in the cortex and the hippocampus of 8 Tg animals per treatment group.

ii) Animals

Female Tg mice with a C57BU6xDBA background and an age of 5 months (±2 week) are randomly assigned to treatment groups 1 to 3 (n=12). Animals are subjected to administration of vehicle or inventive transporter cargo conjugate molecules comprising TAT derived transporter constructs according to any of SEQ ID NOs: 1 to 116 and JNK1 or IB1 derived cargo peptides according to any of SEQ ID NO:118, SEQ ID NO:119, and one of SEQ ID NO:121 to 200 in two different concentrations beginning at 5 months of age and continued for up to 4 months with subcutaneous (s.c.) applications every second or third week. All animals which are used for the present study had dark eyes and are likely to perceive the landmarks outside the MWM pool. However, it had to be excluded that seeing abilities of an animal are poor, which is controlled in the visible platform training, the so called pretest, before treatment start for all animals including reserves enclosed to the study. In case a seeing handicap for a specific animal would have been affirmed, the mouse would have been excluded from the study.

iii) Animal Identification and Housing

Mice are individually identified by ear markings. They are housed in individual ventilated cages (IVCs) on standardized rodent bedding supplied by Rettenmaier®. Each cage contained a maximum of five mice. Mice are kept according to the JSW Standard Operating Procedures (SOP GEN011) written on the basis of international standards. Each cage is identified by a colored card indicating the study number, sex, the individual registration numbers (IRN) of the animals, date of birth, as well as the screening date and the treatment group allocation. The temperature during the study is maintained at approximately 24° C. and the relative humidity is maintained at approximately 40-70%. Animals are housed under a constant light-cycle (12 hours light/dark). Normal tap water is available to the animals ad libitum.

iv) Treatment

Forty female hAPP transgenic mice are treated with either 0.1 mg/kg b.w./every two weeks or 10 mg/kg b.w./every three weeks of inventive transporter cargo conjugate molecules comprising TAT derived transporter constructs according to any of SEQ ID NOs: 1 to 116 and JNK1 or IB1 derived cargo peptides according to any of SEQ ID NO:118, SEQ ID NO:119, and one of SEQ ID NO:121 to 200 in two different dosages (n=12/group) or treated with the vehicle (n=12) s.c. once every three weeks over four months.

v) Morris Water Maze (MWM)

The Morris Water Maze (MWM) task is conducted in a black circular pool of a diameter of 100 cm. Tap water is filled in with a temperature of 22±1° C. and the pool is virtually divided into four sectors. A transparent platform (8 cm diameter) is placed about 0.5 cm beneath the water surface. During the whole test session, except the pretest, the platform is located in the southwest quadrant of the pool. One day before the 4 days lasting training session animals had to perform a so called "pre-test" (two 60 sec lasting trials) to ensure that the seeing abilities of each animal are normal. Only animals that fulfilled this task are enclosed to the MWM testing. In the MWM task each mouse had to perform three trials on four consecutive days. A single trial lasted for a maximum of maximum one minute. During this time, the mouse had the chance to find the hidden, diaphanous target. If the animal could not find a "way" out of the water, the investigator guided to or placed the mouse on the platform. After each trial mice are allowed to rest on the platform for 10-15 sec. During this time, the mice had the possibility to orientate in the surrounding. Investigations took place under dimmed light conditions, to prevent the tracking system from negative influences (Kaminski; PCS, Biomedical Research Systems). On the walls surrounding the pool, posters with black, bold geometric symbols (e.g. a circle and a square) are fixed which the mice could use the symbols as landmarks for their orientation. One swimming group per trial consists of five to six mice, so that an intertrial time of about five to ten minutes is ensured. For the quantification of escape latency (the time [second]—the mouse needs to find the hidden platform and therefore to escape from the water), of pathway (the length of the trajectory [meter] to reach the target) and of the abidance in the goal quadrant a computerized tracking system is used. The computer is connected to a camera placed above the centre of the pool. The camera detected the signal of the light emitting diode (LED), which is fixed with a little hairgrip on the mouse's tail. One hour after the last trial on day 4 the mice had to fulfill a so-called probe trial. At this time, the platform is removed from the pool and during the one-minute probe trial; the experimentator counts the number of crossings over the former target position. Additionally the abidance in this quadrant as well as the three other quadrants is calculated. Through out this trial a mouse could not get any, howsoever-natured, clue from the platform.

vi) Tissue Sampling

At the end of the treatment period, and following all behavioral testing, all remaining mice (n=28) are sacrificed. Therefore, all mice are sedated by standard inhalation anesthesia (Isofluran, Baxter) as described in SOP MET030. Cerebrospinal fluid (CSF) is obtained by blunt dissection and exposure of the foramen magnum. Upon exposure, a Pasteur pipette is inserted to the approximate depth of 0.3-1 mm into the foramen magnum. CSF is collected by suctioning and capillary action until flow fully ceases. Two aliquots of each sample are immediately frozen and kept at −80° C. until ready for further analysis with ELISA technique. After CSF sampling, each mouse is placed in dorsal recumbence, thorax is opened and a 26-gauge needle attached to a 1 cc syringe is inserted into the right cardiac ventricular chamber. Light suction is applied to the needle and blood is collected into EDTA and consequently used to obtain plasma. To get plasma, blood samples from each mouse are spun at 1,750 rpm (700 g) for 10 minutes in a centrifuge (GS-6R Beckman) using a rotor with swing buckets (GH-3.8 Beckman). Plasma is frozen and stored at −20° C. until further analysis. After blood sampling transgenic mice are intracardially perfused with 0.9% sodium chloride. Brains are rapidly removed the cerebellum is cut off. The right hemispheres of all mice are immersion fixed in freshly produced 4% Paraformaldehyde/PBS (pH 7.4) for one hour at room temperature. Thereafter brains are transferred to a 15% sucrose PBS solution for 24 hours to ensure cryoprotection. On the next day brains are frozen in isopentane and stored at −80° C. until used for histological investigations (SOP MET042). The left hemispheres are weighed and frozen in liquid nitrogen and stored at −80° C. for biochemical analysis.

vii) Determination of $A\beta_{1-40}$ and $A\beta_{1-42}$

In four different brain homogenate fractions of each Tg mouse as well as in CSF samples the $A\beta_{1-40}$ and $A\beta_{1-42}$ levels are evaluated with ELISA technique. Highly sensitive $A\beta_{1-40}$ and $A\beta_{1-42}$ ELISA test kits are purchased from The Genetics Company™, Switzerland (SOP MET058). CSF is prepared as described above. For the brain homogenates frozen hemispheres are homogenized in TRIS buffered saline (TBS)-buffer (5 ml) containing protease inhibitor cocktail. 1.25 ml of this initial brain TBS homogenate is stored at −80° C., 1.25 ml have been further investigatated. The remaining brain homogenate (2.5 ml) is centrifuged and the resulting supernatant (=TBS fraction) is aliquoted and kept at −20° C. until ELISA determination. The pellet is suspended in Triton X-100 (2.5 ml), centrifuged and the supernatant (=Triton X-100 fraction) is aliquoted and kept at −20° C. These steps are repeated with SDS (2.5 ml). The pellet out of the SDS fraction is suspended in 70% formic acid (0.5 ml) prior to subsequent centrifugation. The obtained supernatant is neutralized with 1 M TRIS (9.5 ml) aliquoted and kept at −20° C. (=FA fraction). Samples of the four brain homogenate fraction (TBS, Triton X-100, SDS, and FA) are used for Aβ$_{1-40}$ and Aβ$_{1-42}$ determination with ELISA technique. ELISA test kits are purchased from The Genetics Company™, Switzerland (SOP MET062). It could be assumed that TBS and Triton X-100 solubilize monomeric to oligomeric structures. Polymers like protofibrils and water insoluble fibrils could be dissolved in SDS and FA. In this regard the investigation of all four fractions also provides insight in Aβ polymerization status.

viii) Evaluation of Brain Morphology

Brain tissues of all Tg animals investigated are handled in exactly the same way to avoid bias due to variation of this procedure. From brain halves of 24 Tg mice (8 of each group) 20 cryo-sections per layer (altogether 5 layers), each 10 μm thick (Leica CM 3050S) are sagittally cut and 5 (one from each layer) are processed and evaluated for quantification of plaque load. The five sagittal layers corresponded with the FIGS. 104 to 105, 107 to 108, 111 to 112, 115 to 116 and 118 to 119 according to the morphology atlas "The Mouse Brain" from Paxinos and Franklin (2nd edition). The first layer is specified by the requirement to include the whole hippocampus with it's regions CA1, CA2, CA3, GDIb and GDmb. Immunoreactivity is quantitatively evaluated in the hippocampus and in the cortex using the monoclonal human Aβ-specific antibody 6E10 (Signet) as well as ThioflavinS staining. Remaining brain hemispheres or tissue not used are saved and stored at JSW CNS until the end of the project.

b) EVALUATION i) Behavior In the Morris Water Maze trials length of swimming path, escape latencies, swimming speed and in the probe trial crossings over the former platform position and the time spent in each quadrant of the pool are measured for each Tg animal with a special computer software.

ii) Biochemical Evaluation

From all Tg mice CSF samples as well as samples from the brain preparations are analyzed with commercially available Aβ$_{1-40}$ and Aβ$_{1-42}$ ELISAs. Measurements of adequate standards are performed concurrently. Samples from brain preparations are analyzed in duplicates. Due to the small sample amount CSF samples are analyzed in a single measurement only.

iii) Histology i1) Measurement of Amyloid Depositions and Plaque Load

For 6E10 immunohistochemistry the following evaluation procedure is used:

aa) Contrasting the image for visualization of slice borders without applying the contrast on the image.

bb) Interactive drawing of the cortical outlines and the following measurement of the cortical area (=region area).

cc) Interactive drawing of the area of interest (AOI), in which stained objects are detected over a certain intensity based threshold level (the same for each image) and above a size of 8 μm$^2$.

dd) Measurement of the area of each object, the sum of stained area in the AOI as well as the number of objects after a smooth contrasting to enhance signal/noise ratio (the same for each image).

ee) Repetition of aa)-dd) for the hippocampus.

ff) Calculation of the mean plaque size (="sum area of plaques/number of plaques"), the relative plaque number and area (="number of plaques/region area" and "sum area of plaques/region area * 100").

gg) Automated data export into an Excel spread sheet, including the parameters "image title, region area, number of plaques, sum of plaque area, relative plaque number, relative plaque area and mean plaque size. A field for remarks is used to record image quality and exclusion criteria, respectively. Exclusion criteria are missing parts of the slice, many wrinkles, dominant flaws or staining inconsistencies (e.g. due to bulges, which can impede the full reaction of the blocking reagent).

hh) Closing the image without saving (to keep raw data raw).

23. Determining the Activity of Inventive Transporter Cargo Conjugate Molecules Comprising TAT Derived Transporter Constructs According to any of SEQ ID NOs: 1 to 116 and INK1 or IB1 Derived Cargo Peptides According to any of SEQ ID NO:118, SEQ ID NO:119, and one of SEQ ID NO:121 to 200 in the Treatment of Diabetes Type 2

This is designed to determine the activity of inventive transporter cargo conjugate molecules comprising TAT derived transporter constructs according to any of SEQ ID NOs: 1 to 116 and JNK1 or IB1 derived cargo peptides according to any of SEQ ID NO:118, SEQ ID NO:119, and one of SEQ ID NO:121 to 200 in the treatment of Diabetes Type 2, particularly to determine the effect of chronic treatment with these inventive transporter cargo conjugate molecules in the db/db mice model of type 2 diabetes by evaluating fasting blood glucose levels every third day (28 days)

a) Materials and Methods i) Animals

A total of twenty (20) male db/db mice (8 weeks old) are obtained from Charles River (Germany). Upon arrival, animals are group housed (n=6-7/group) and offered regular rodent chow (Altromin standard #1324 chow; C. Petersen, Ringsted, Denmark) and water ad libitum unless otherwise stated.

The mice are housed under a 12:12 UD cycle (lights on at 4:00 and lights off at 16:00) and in temperature and humidity controlled rooms.

ii) Groups and randomization

On day–4, mice are randomized according to blood glucose level (fasted; blood glucose measured on Biosen S line analyzer (EKF diagnostic, Germany) to participate in one of the following drug treatment groups (n=6):

1) Vehicle control, S.C. (physiological saline)

2) inventive transporter cargo conjugate molecules comprising TAT derived transporter constructs according to any of SEQ ID NOs: 1 to 116 and JNK1 or IB1 derived cargo peptides according to any of SEQ ID NOs: 117 to 200; 1 mg/kg; s.c.

3) inventive transporter cargo conjugate molecules comprising TAT derived transporter constructs according to any of SEQ ID NOs: 1 to 116 and JNK1 or IB1 derived cargo peptides according to any of SEQ ID NO:118, SEQ ID NO:119, and one of SEQ ID NO:121 to 200; 10 mg/kg; s.c All doses listed are calculated for the free-base. Drug purity: 95.28%, peptide content: 78.0%. All compounds are administered sub-cutaneously (s.c.) in a volume of 3 ml/kg. The formulation instructions for vehicle control and inventive transporter cargo conjugate molecules comprising TAT derived transporter constructs according to any of SEQ ID NOs: 1 to 116 and JNK1 or IB1 derived cargo peptides according to any of SEQ ID NO:118, SEQ ID NO:119, and one of SEQ ID NO:121 to 200 are as follows:

First, inventive transporter cargo conjugate molecules comprising TAT derived transporter constructs according to any of SEQ ID NOs: 1 to 116 and JNK1 or IB1 derived cargo peptides according to any of SEQ ID NO:118, SEQ ID NO:119, and one of SEQ ID NO:121 to 200 are dissolved in the vehicle. The formulations (concentrations of 0.33 and 3.3 mg/ml, corresponding to the doses of 1 and 10 mg/kg, respectively) are prepared according to the procedure detailed below. Concentrations are calculated and expressed taking into account test items purity and peptide content (multiplier coefficient is 1.346).

Preparation of a stock solution: the freeze-dried inventive transporter cargo conjugate molecules comprising TAT derived transporter constructs according to any of SEQ ID NOs: 1 to 116 and JNK1 or IB1 derived cargo peptides according to any of SEQ ID NO:118, SEQ ID NO:119, and one of SEQ ID NO:121 to 200 is thawed for one hour minimum and prepared as a stock solution in the vehicle at 1 mM. Aliquots are prepared for each treatment day and stored at approximately −80° C. Dilutions of this stock solution to the required concentrations are performed on each treatment day;

Storage of the stock solution: at approximately −80° C.;

Storage of the diluted preparations: at room temperature for 24 hours maximum.

Prior to solubilisation, the powder is stored at −20° C. The stability of the stock solution is 3 months at approximately −80° C.; the stability of the diluted formulations for animal dosing is 24 hours at room temperature. Unused diluted material could be stored for up to 7 days if kept at 4-8° C.

c) Experimental Procedure

Following 8 days of acclimatization the mice are treated daily at 08.00 AM for 21 days by SC dosing 8 hours prior to lights out at 04.00 PM according to the outline groups.

i) Blood Glucose

Blood glucose is measured from 7 hour fasted animals 6 hours post dosing by collection of 10 μl blood samples from the tail-vein in hematocrite tubes and subsequent analysis on a Biosen s-line analyzer (EKF-diagnostic; Germany).

ii) Metabolic Cages

Groups 1+3: Mice are placed in metabolic cages for the recording of 24-hour food and water intake as well as 24-hour urine and faeces production. Mice are stratified into two subteams of n=6-7 and subsequently the metabolic characterisation is performed.

iii) Adipokine Panel

Groups 1+3: On three occasions blood is collected from the tail vein using EDTA coated hematocrite tubes (100 μl). Following centrifugation of blood the plasma is collected and stored at −20° C. until measurement. Then, the following panel of adipokines/cytokines is determined using Luminex based 7-plex: leptin, resistin, MCP-1, PAI-1, TNFα, insulin and interleukin-6 (IL-6).

iv) Termination

Groups 1+3 (day 111): The following organs are excised and weighed: inguinal subcutaneous fat, epididymal fat, retroperitoneal fat, brain, liver, kidney, spleen and heart. All organs described above are samples in 4% PFA for possible future histo-pathological examination. Also, pancreas (en bloc) is sampled for possible stereological and imunohistochemical analysis, and eyes are sampled for possible later analysis of retinopathy. Group 2 (day 28): No tissues or plasma are collected.

24. TAT Derivatives Target Human Leukocyte Populations

Primary human white blood cells (WBC) were obtained from whole blood after red blood cell lysis. WBC were incubated with 1 uM of D-TAT (SEQ ID NO: 4)-FITC or r3-L-TAT (SEQ ID NO: 15)—FITC for 30 min at 37° C., washed in acid buffer and stained with fluorescent antibodies against cell type specific surface markers (CD14 for monocytes, CD15 for polymorphnuclears, CD3 for lymphocyte T, CD19 for lymphocyte B). Cells containing D-TAT-FITC and r3-L-TAT-FITC were finally analysed by flow cytometry to measure their respective transporter content. Both TAT derivatives target the human leukocyte populations. dTAT and r3LTAT binds to monocytes, neutrophils and lymphocyte T cells, and less efficiently to lymphocyte B cells. A minor difference between dTAT and r3-L-TAT specificity exists, D-TAT seeming to bind more efficiently to lymphocyte T than the r3-L-TAT.

25. Uptake of Selected Transporter Constructs According to the Present Invention by Different Cell Types Cells were plated in Poly-D-lysine pre-coated 96-well-plates at subconfluent density (which can vary depending on the cell type used). Different FITC-coupled transporters were then incubated with the cells for 15 h at 3 μM. Following this time, cells were kept on ice for the rest of the procedure. To remove cell-surface bound peptides, cells were first washed 2 times with an acid wash to remove plasma membrane-bound molecules. Subsequently, cells were washed 2 times with PBS and lysed in a standard lysis buffer for 30 min. Plates containing cell lysates were then centrifuged for 5 min at 1500 rpm at 4° c. Clear supernatant was then collected and transferred into a black 96-well-plate for the measure of intracellular FITC fluorescence. The following cells were used:

| | |
|---|---|
| Leucocyte cell lines: | Raw: Macrophage cells (mouse)<br>J77: Macrophage cells (mouse) |
| Primary purified leucocytes: | BMDM: Bone Marrow-Derived Macrophages (mouse) |

Results are expressed as percentage of D-TAT (SEQ ID NO: 4) (FIG. 17) or r3-L-TAT (SEQ ID NO: 15) (FIG. 18) uptake. All transporter constructs show uptake in the respective cells, albeit at different rates.

26. Immunohistochemistry on Paw from CFA-Induced Inflammation (4 h)

Male C57/Bl6 mice of 8 weeks were used in this study. Peripheral inflammation was induced by subcutaneous injection of Complete Freund Adjuvent (CFA) (Sigma, 20 μl) in the left hindpaw under brief anesthesia with isofluorane. XG-102 (SEQ ID NO: 233) treated animals received one single bolus i.v injection of XG-102 at 10 μg/kg one hour prior to CFA injection. Mice were sacrificed four hours after CFA injection by perfusion through the heart with 4% PFA in PBS. Hindpaws were cryoprotected in sucrose (30% in PBS) and were then frozen using liquid isopentane and kept for further cryostat sectioning. Sections were either stained with Hematoxylin and Eosin (H&E) or processed for XG-102 (SEQ ID NO:233) immunostaining. Sections were first quenched for 30 min with 0.3% $H_2O_2$ in methanol and rinsed 3 min in $H_2O$ followed by a 5 min PBS wash. Following this step, sections were pre-incubated for 45 min in PBS containing 15% serum and 0.3% triton followed by over-night incubation at RT with primary antibody (rabbit polyclonal anti-XG102, dilution 1/1000) diluted in 1.5% serum, 0.1% triton in PBS. Sections were then incubated for 2 h at RT with the appropriate biotinylated secondary antibody, washes 3 times in PBS and incubated for two hours at RT with streptavidin-biotin-peroxidase complex (ABC kit, Vectastain, Vector Laboratories). Immunolabeling was revealed after 3 washes in PBS using 2,3' diaminobenzidene as substrate diluted 1/10° in buffer according to manufacturer (Roche). Sections were finally dehydrated and mounted using Eukitt (Kindler GmBH). All animals were processed for immunostaining in the same experiment and were subjected to the same revelation time. HRP staining (lower panels) revealed the presence of XG-102 in infiltrating leucocytes in the CFA-XG-102 treated animals.

27. CD11b Staining

Male C57/B16 mice of 8 weeks were used in this study. Peripheral inflammation was induced by subcutaneous injection of Complete Freund Adjuvent (CFA) (Sigma, 20 μl) in the left hind paw under brief anesthesia with isofluorane. XG-102 (SEQ ID NO: 233) treated animals received one single bolus i.v injection of XG-102 at 10 μg/kg one hour prior to CFA injection. Mice were sacrificed four hours after CFA injection by perfusion through the heart with 4% PFA in PBS. Hind paws were cryoprotected in sucrose (30% in PBS) and were then frozen using liquid isopentane and kept for further cryostat sectioning. Sections were either stained with XG-102 antibodies or with CD11b used as leucocyte surface marker. Sections were first quenched for 30 min with 0.3% $H_2O_2$ in methanol and rinsed 3 min in $H_2O$ followed by a 5 min PBS wash. Following this step, sections were pre-incubated for 45 min in PBS containing 15% serum and 0.3% triton followed by overnight incubation at RT with primary antibody (rabbit polyclonal anti-XG102, dilution 1/1000) diluted in 1.5% serum, 0.1% triton in PBS. Sections were then incubated for 2 h at RT with the appropriate biotinylated secondary antibody, washes 3 times in PBS and incubated for two hours at RT with streptavidin-biotin-peroxidase complex (ABC kit, Vectastain, Vector Laboratories). Immunolabeling was revealed after 3 washes in PBS using 2,3' diaminobenzidene as substrate diluted 1/10° in buffer according to manufacturer (Roche). Sections were finally dehydrated and mounted using Eukitt (Kindler GmBH). All animals were processed for immunostaining in the same experiment and were subjected to the same revelation time.

28. Detection and Kinetic of XG-102 (SEQ ID NO:233) on Rat Whole Blood Cells

Male Sprague Dawley rat weighing 180-200 g were treated with one single bolus i.v injection of XG-102 (SEQ ID NO:233) at 0.1 mg/kg. Injection time is considered as the reference time for the following sampling. Rats were sacrificed after different injection time periods: 30 min, 24 h, 3 d, 7 d, 14 d and 27 days. Rats were sacrificed by exsanguination. Subsequently, mesenteric lymph node chain and (when possible cervical, axillaries, brachial, renal and lumbar lymph nodes) were removed for histological sections. Organs were rinsed in PBS 1× at 4° C. and fixed overnight in PAF4%/PBS 1× at 4° C. 24 h later, samples were rinsed 3×10 min with agitation in PBS 1× at 4° C. and immersed in sucrose 30%/PBS 1× until the LN sunk. The sample were then frozen in isopentane for 3 min at −(35-40)° C. using a vial on dry ice. After cryostat sectioning, slices were processed for XG-102 immunostaining. Sections from cryostat were first quenched for 30 min with 0.3% $H_2O_2$ in methanol and rinsed 3 min in $H_2O$ followed by a 5 min PBS wash. Sections were then pre-incubated for 45 min in PBS containing 15% serum and 0.3% triton followed by over-night incubation at RT with primary antibody (rabbit polyclonal anti-XG102, dilution 1/1000) diluted in 1.5% serum, 0.1% triton in PBS. Sections were incubated for 2 h at RT with the appropriate biotinylated secondary antibody. Following 3 washes in PBS, sections were incubated for 2 h at RT with streptavidin-biotin-peroxidase complex (ABC kit, Vectastain, Vector Laboratories). Immunolabeling was revealed after 3 washes in PBS using 2,3' diaminobenzidene as substrate diluted 1/10° in buffer according to manufacturer (Roche). Sections were then dehydrated and mounted using Eukitt (Kindler GmBH). All animals were processed for immunostaining in the same experiment and were subjected to the same revelation time.

29. FITC-XG-102 (SEQ ID NO:233) and FITC-D-TAT (SEQ ID NO:4) Localization in Liver and Lymph Nodes Female Sprague Dawley rat was injected i.v. in the tail with either 1 mg/kg of FITC-XG102 (SEQ ID NO:233) or 1 mg/kg FITC-D-TAT (SEQ ID NO:4). Rats were sacrified 6 h post-injection using a lethal dose of sodium pentobarbital (150 mg/kg i.p.). For histological analysis and during narcosis, rats were perfused through the heart with 4% paraformaldehyde (PFA) in PBS. Organs (liver and lymph nodes) were cryoprotected in sucrose (30% in PBS), frozen using liquid isopentane and kept for further cryostat sectioning. Sections of 14 μm were incubated for 5 min in PBS before Hoechst staining for 2 min at RT (1 μg/ml). After PBS wash, sections were mounted in Fluorsave mounting medium. Slices were visualized using epifluorescence microscope.

The invention claimed is:

1. A method of transporting a substance of interest (cargo molecule) into white blood cells, the method comprising contacting the white blood cells with a transporter cargo conjugate molecule, wherein the transporter cargo conjugate molecule comprises:

a) as component (A): a peptide selected from the group consisting of a peptide comprising SEQ ID NO:235, a peptide comprising one of SEQ ID NOs: 15 to 116, and a reverse sequence thereof, and b) as component (B): a cargo molecule.

2. The method of claim 1, wherein components (A) and (B) are covalently linked with each other.

3. The method of claim 1, wherein the cargo molecule (component (B)) is selected from the group consisting of:

a) a therapeutically active polypeptide,
b) a protein kinase inhibitor,
c) an antigen,
d) an antibody,
e) an apoptotic factor,
f) a protease,
g) a protein containing a B-cell lymphoma 2 (Bcl-2) homology 3 (BH3)-domain,
h) a c Jun N-terminal kinase (JNK) inhibitor,
i) a DNA molecule,
j) an RNA molecule,
k) a cytotoxic agent,
l) an organic compound,
m) a protease inhibitor,
n) a gold particle,
o) a fluorescent dye,
p) an antibiotic, and
q) an antiviral compound.

4. The method of claim 1, wherein the peptide is a chemical derivative of: one of SEQ ID NOs: 15 to 116, SEQ ID NO: 235, or a reverse sequence thereof, wherein the chemical derivative is derived from:

i. acetylation at the N-terminus,
ii. amidation at the C-terminus,
iii. glycosylation; or
iv. a label selected from the group consisting of a radioactive label, a colored dye, a fluorescent group, a chemoluminescent group, and a combination thereof, wherein formation of the chemical derivative does not comprise addition, substitution or deletion of amino acids in the sequence.

5. The method of claim 1, further comprising one or more components selected from the group consisting of a signal sequence or localization sequence, which directs the transporter cargo conjugate molecule to a particular intracellular target localization or to a particular cell type.

6. The method of claim 1, wherein the cargo is an inhibitor of the c-Jun amino terminal kinase (JNK inhibitor), wherein the JNK inhibitor is a peptide with an amino acid sequence selected from the group consisting of SEQ ID NO: 118, SEQ ID NO: 119, one of the amino acid sequences of SEQ ID NO: 121 to SEQ ID NO:200 and a fragment thereof.

7. The method of claim 1, wherein the white blood cells are primary cells, immortalized cells, or transgenic cells.

8. The method of claim 1, wherein the white blood cells are selected from the group consisting of granulocytes, lymphocytes, monocytes, macrophages, dendritic cells, microglial cells and mast cells.

9. The method of claim 8, wherein the granulocytes are selected from the group consisting of neutrophils, eosinophils and basophils.

10. The method of claim 8, wherein the lymphocytes are selected from the group consisting of NK cells, Helper T cells, cytotoxic T cells, γδ T cells, and B cells.

11. The method of claim 1, wherein the peptide is selected from the group consisting of a peptide comprising SEQ ID NO: 15, a peptide comprising SEQ ID NO: 16, and a reverse sequence thereof.

* * * * *